United States Patent
Choi et al.

(10) Patent No.: US 11,981,912 B2
(45) Date of Patent: May 14, 2024

(54) ADENO ASSOCIATED VIRUS VECTORS FOR THE TREATMENT OF HUNTER DISEASE

(71) Applicant: Takeda Pharmaceutical Company Limited, Osaka (JP)

(72) Inventors: Vivian Choi, Lexington, MA (US); Xing Li, Lexington, MA (US)

(73) Assignee: Takeda Pharma ceutical Company Limited, Osaka (JP)

( * ) Notice: Subject to any disclaimer, the term of this patent is extended or adjusted under 35 U.S.C. 154(b) by 194 days.

(21) Appl. No.: 17/116,098

(22) Filed: Dec. 9, 2020

(65) Prior Publication Data

US 2021/0332383 A1    Oct. 28, 2021

Related U.S. Application Data

(60) Provisional application No. 62/945,920, filed on Dec. 10, 2019.

(51) Int. Cl.
| | |
|---|---|
| *C12N 15/86* | (2006.01) |
| *A61K 9/00* | (2006.01) |
| *A61K 48/00* | (2006.01) |
| *C12N 9/16* | (2006.01) |

(52) U.S. Cl.
CPC ............ *C12N 15/86* (2013.01); *A61K 9/0019* (2013.01); *C12N 9/16* (2013.01); *C12N 2750/14132* (2013.01); *C12N 2750/14143* (2013.01); *C12N 2800/22* (2013.01); *C12N 2830/008* (2013.01); *C12N 2830/48* (2013.01); *C12Y 301/06013* (2013.01)

(58) Field of Classification Search
CPC ................ A61K 9/0019; A61K 48/005; A61K 48/0058; C12N 15/86; C12N 2750/14132; C12N 2750/14143; C12N 2800/22; C12N 2830/008; C12N 2830/42; C12N 2830/48; C12Y 301/06013

See application file for complete search history.

(56) References Cited

U.S. PATENT DOCUMENTS

| | | |
|---|---|---|
| 9,127,074 B2 | 9/2015 | Ballabio et al. |
| 9,193,755 B1 | 11/2015 | Ballabio et al. |
| 9,206,401 B2 | 12/2015 | Ballabio et al. |
| 9,249,424 B2 | 2/2016 | Wolf et al. |
| 9,487,766 B2 | 11/2016 | Ballabio et al. |
| 9,700,587 B2 | 7/2017 | Gill et al. |
| 9,827,295 B2 | 11/2017 | McIvor et al. |
| 2013/0302308 A1 | 11/2013 | Ballabio et al. |
| 2014/0038897 A1 | 2/2014 | Ballabio et al. |
| 2014/0196176 A1* | 7/2014 | Heintz ............... C12N 15/1003 536/25.4 |
| 2015/0079051 A1 | 3/2015 | Brunetti-Pierri et al. |
| 2015/0151007 A1 | 6/2015 | Dodge et al. |
| 2015/0273016 A1 | 10/2015 | Parenti et al. |
| 2016/0120960 A1 | 5/2016 | McIvor et al. |
| 2016/0122731 A1 | 5/2016 | Ballabio et al. |
| 2016/0143966 A1 | 5/2016 | Gill et al. |
| 2016/0243260 A1 | 8/2016 | Blits |
| 2018/0071373 A1 | 3/2018 | McIvor et al. |
| 2018/0099030 A1 | 4/2018 | McIvor et al. |
| 2018/0169272 A1* | 6/2018 | Bosch Tubert .... A61K 48/0016 |

FOREIGN PATENT DOCUMENTS

| | | | |
|---|---|---|---|
| WO | WO 2017181113 A1 | | 10/2017 |
| WO | WO 18/093925 | * | 5/2018 |
| WO | WO 2019/060662 A1 | | 3/2019 |

OTHER PUBLICATIONS

GenBank XM_031005854.1, gorilla iduronate-2-sulfatase (2019).*
GenBank XP_030861714.1 gorilla iduronate-2-sulfatase (2019).*
GenBank KAI2601037, human iduronate-2-sulfatase, 2022.*
GenBank AAB33747.1, Human Hunter Syndrome mutation, 1995.*
GenBank 5FQLA, Human Hunter Syndrome mutation, 2020.*
Pimentel et al, Production and characterization of a human lysosomal recombinant iduronate-2-sulfatase produced in Pichia pastoris, Biotechnol. & Applied Biochem. 65(5): 655-664, published online Apr. 23, 2018.*
Hinderer et al, Delivery of an Adeno-Associated Virus Vector into Cerebrospinal Fluid Attenuates Central Nervous System Disease in Mucopolysaccharidosis Type II Mice, Human Gene Therapy 27(11): 906-915, 2016.*
Chuah et al, Liver-Specific Transcriptional Modules Identified by Genome-Wide In Silico Analysis Enable Efficient Gene Therapy in Mice and Non-Human Primates, Molecular Therapy 22(9): 1605-1613, 2014.*
Domenger et al, Next-generation AAV vectors—do not judge a virus (only) by its cover, Human Molecular Genetics 28(R1): R3-R14, 2019; available online Jul. 2, 2019.*
Quax et al, Codon Bias as a Means to Fine-Tune Gene Expression, Molecular Cell 59(2): 149-161, 2015.*
Grote et al, JCat: a novel tool to adapt codon usage of a target gene to its potential expression host, Nucleic Acids Research 33: W526-W531; doi:10.1093/nar/gki376, 2005.*
Daniel et al, ATGme: Open-source web application for rare codon identification and custom DNA sequence optimization, BMC Bioinformatics 16: 303, 6 pages, doi.10.1186/s12859-015-0743-5; 2015.*

(Continued)

*Primary Examiner* — Kevin K Hill
(74) *Attorney, Agent, or Firm* — Sterne, Kessler, Goldstein & Fox P.L.L.C.

(57) ABSTRACT

The present disclosure provides, among other things, a recombinant adeno-associated virus (rAAV) vector comprising an AAV8 or AAV9 capsid and a codon-optimized sequence encoding a human iduronate-2-sulfatase (I2S) enzyme. The disclosure also provides a method of treating a subject having Hunter syndrome (MPS II), comprising administering to the subject in need thereof a recombinant adeno-associated virus (rAAV) vector comprising an AAV8 or AAV9 capsid, and a promoter operably linked to a nucleic acid sequence that encodes iduronate-2-sulfatase (I2S), and wherein administering results in an increase in I2S enzymatic activity in the subject.

17 Claims, 24 Drawing Sheets

Specification includes a Sequence Listing.

(56) References Cited

OTHER PUBLICATIONS

International Search Report and Written Opinion dated May 3, 2021 for International Patent Application No. PCT/US2020/063887, 20 pages.
Jung et al: "Characterization of a novel mucopolysaccharidosis type II mouse model and recombinant AAV2/8 vector-mediated gene therapy", Molecules and Cells, vol. 30, No. 1, Jul. 1, 2010 (Jul. 1, 2010), pp. 13-18.
Laoharawee et al: "Prevention of Neurocognitive Deficiency in Mucopolysaccharidosis Type II Mice by Central Nervous System-Directed, AAV9-Mediated Iduronate Sulfatase Gene Transfer", Human Gene Therapy, vol. 28, No. 8, Aug. 1, 2017 (Aug. 1, 2017), pp. 626-638.
Motas et al: "CNS-directed gene therapy for the treatment of neurologic and somatic mucopolysaccharidosis type II (Hunter syndrome)", JCI Insight, vol. 1, No. 9, Jun. 16, 2016 (Jun. 16, 2016).
Sharma et al: "In vivo genome editing of the albumin locus as a platform for protein replacement therapy", Blood, vol. 126, No. 15, Oct. 8, 2015 (Oct. 8, 2015), pp. 1777-1784.
Wu et al: "Adeno-associated Virus Serotypes: Vector Toolkit for Human Gene Therapy", Molecular Therapy, No Longer Published by Elsevier, vol. 14, No. 3, Aug. 12, 2006 (Aug. 12, 2006), pp. 316-327.
Auricchio et al. "Isolation of Highly Infectious and Pure Adeno-Associated Virus Type 2 Vectors with a Single-Step Gravity-Flow Column." Human Gene Therapy 12:71-76. Jan. 1, 2001.
Boado et al. "Blood-Brain Barrier Molecular Trojan Horse Enables Imaging of Brain Uptake off Radioiodinated Recombinant Protein in the Rhesus Monkey." Bioconjugate Chemistry 2013, 24, 1741-1749. Sep. 23, 2013.
Braun et al. "Preclinical Studies of Lymphocyte Gene Therapy for Mild Hunter Syndrome (Mucopolysaccharidosis Type II)." Human Gene Therapy 7:283-290. Feb. 10, 1996.
Calias et al. "CNS Penetration of Intrathecal-Lumbar Idursulfase in the Monkey, Dog and Mouse: Implications for Neurological Outcomes of Lysosomal Storage Disorder." PLoS One 7(1): e30341. doi:10.1371/journal.pone.0030341. Jan. 18, 2012.
Cardone et al. "Correction of Hunter syndrome in the MPSII mouse model by AAV2/8-mediated gene delivery." Human Molecular Genetics, 2006, vol. 15, No. 7 1225-1236. Feb. 27, 2006.
Cho et al. "Effect of systemic high dose enzyme replacement therapy on the improvement of CNS defects in a mouse model of mucopolysaccharidosis type II." Orphanet Journal of Rare Diseases (2015) 10:141. DOI 10.1186/s13023-015-0356-0. Oct. 31, 2015.
Da Silva et al. "Enzyme replacement therapy with idursulfase for mucopolysaccharidosis type II (Hunter syndrome)." Cochrane Database of Systematic Reviews 2014, Issue 1. Art. No. CD008185. DOI: 10.1002/14651858.CD008185.pub3. Nov. 6, 2013.
Fraldi et al. "SUMF1 enhances sulfatase activities in vivo in five sulfatase deficiencies." Biochem. J. (2007) 403, 305-312 (Printed in Great Britain) doi:10.1042/BJ20061783.
Friso et al. "Gene therapy of Hunter syndrome: Evaluation of the efficiency of muscle electro gene transfer for the production and release of recombinant iduronate-2-sulfatase (IDS)." Biochimica et Biophysica Acta 1782 (2008) 574-580.
Fu et al. "Targeting Root Cause by Systemic scAAV9-h/DS Gene Delivery: Functional Correction and Reversal of Severe MPS II in Mice." Molecular Therapy: Methods & Clinical Development. vol. 10. Sep. 2018.
Futerman et al. "The Cell Biology of Lysosomal Storage Disorders." Nature Publishing Group. Jul. 2005. vol. 5. 554-565.
Garcia et al. "Preclinical dose ranging studies for enzyme replacement therapy with idursulfase in a knock-out mouse model of MPS II." Molecular Genetics and Metabolism 91 (2007) 183-190. Mar. 9, 2007.
Gleitz et al. "Identification of age-dependent motor and neuropsychological behavioural abnormalities in a mouse model of Mucopolysaccharidosis Type II." PLoS One 12(2): e0172435. doi:10.1371/journal.pone.0172435. Feb. 16, 2017.
Gleitz et al. "Brain-targeted stem cell gene therapy corrects mucopolysaccharidosis type II via multiple mechanisms." EMBO Molecular Medicine. DOI 10.15252. emmm.201708730. Jun. 8, 2018.
Motas et al. "CNS-directed gene therapy for the treatment of neurologic and somatic mucopolysaccharidosis type II (Hunter syndrome)." JCI Insight. 2016;1(9):e86696. Jun. 19, 2016.
Okuyama et al., A Phase ⅔ Trial of Pabinafusp Alfa, IDS Fused with Anti-Human Transferrin Receptor Antibody, Targeting Neurodegeneration in MPS-II, Molecular Therapy (2020), https://doi.org/10.1016/j.ymthe.2020.09.039.
Parkinson et al. "Iduronate-2-sulphatase protein detection in plasma from mucopolysaccharidosis type II patients." Molecular Genetics and Metabolism 81 (2004) 58-164. Nov. 13, 2003.
Voznyi et al. "A fluorimetric enzyme assay for diagnosis of MPS II (Hunter disease)." J. Inherit. Metab. Dis. 24 (2001) 675-680.
Wraith et al. "Mucopolysaccharidosis type II (Hunter syndrome): a clinical review and recommendations for treatment in the era of enzyme replacement therapy." Eur J Pediatr (2008) 167:267-277. Nov. 23, 2007.
Hinderer, C., et al., "Delivery of an Adeno-Associated Virus Vector into Cerebrospinal Fluid Attenuates Central Nervous System Disease in Mucopolysaccharidosis Type II Mice," Human Gene Therapy 27(11): 906-915, Mary Ann Liebert, Inc., United States (Nov. 2016).
Hinderer, C., et al., "Evaluation of Intrathecal Routes of Administration for Adeno-Associated Viral Vectors in Large Animals," Human Gene Therapy 29(1):1-24, Mary Ann Liebert, Inc., United States (Aug. 2017).
Holley, R.J., et al., "Macrophage enzyme and reduced inflammation drive brain correction of mucopolysaccharidosis IIIB by stem cell gene therapy," Brain 141:99-116, Oxford Academic Press, United Kingdom (Jan. 2018).
Hordeaux, J., et al., "Toxicology Study of Intra-Cisterna Magna Adeno-Associated Virus 9 Expressing Human Alpha-L-Iduronidase in Rhesus Macaques," Molecular Therapy: Methods & Clinical Development 10:79-88, Cell Press, United States (Sep. 2018).
Kariolis, M.S., et al., "Brain delivery of therapeutic proteins using an Fc fragment blood-brain barrier transport vehicle in mice and monkeys," Sci. Transl. Med. 12(545):eaay 1359, American Association for the Advancement of Science, United States (May 2020).
Laoharawee, K., et al., "Prevention of Neurocognitive Deficiency in Mucopolysaccharidosis Type II Mice by Central Nervous System-Directed, AAV9-Mediated Iduronate Sulfatase Gene Transfer," Human Gene Therapy 28(8):626-638, Mary Ann Liebert, Inc., United States (Aug. 2017).
Laoharawee, K., et al., "Dose-Dependent Prevention of Metabolic and Neurologic Disease in Murine MPS II by ZFN-Mediated In Vivo Genome Editing," Molecular Therapy 26(4): 1127-1136, Cell Press, United States (Apr. 2018).
Lowe, D., "Sangamo's Gene Therapy Results," published Sep. 5, 2018, accessed https://www.science.org/content/blog-post/sangamos-gene-therapy-results, accessed on Jun. 29, 2023.
Okuyama, T., et al., "Iduronate-2-Sulfatase with Anti-human Transferrin Receptor Antibody for Neuropathic Mucopolysaccharidosis Ii: A Phase ½ Trial," Molecular Therapy 27(2):456-464, Cell Press, United States (Feb. 2019).
Sangamo Therapeutics Inc., "Sangamo Announces 16 Week Clinical Results Including Reductions in Glycosaminoglycans in Phase 1/2 Trial Evaluating SB-913, A Zinc Finger Nuclease Genome Editing Treatment for MPS II (Hunter Syndrome)," released Sep. 5, 2018, accessed at https://investor.sangamo.com/node/14036/pdf, accessed on Jun. 29, 2023.
Azadeh, M., et al., "A Rapid Two-Step Iduronate-2-Sulfatatse Enzymatic Activity Assay for MPSII Pharmacokinetic Assessment," in *JIMD Reports*, vol. 38, pp. 89-95, Morava, E., et al., eds., Springer, Berlin, Germany (Jun. 2017).
Bragge, T., et al., "Principal Component Analysis (PCA) Based Data Fusion Approach for a Mouse Model of CLN6 Batten Disease," *Molecular Genetics and Metabolism*, vol. 129(2), Page S119, Elsevier BV, Amsterdam, Netherlands (Feb. 2020); accessed at https://www.criver.com/sites/default/files/SH-SFN-18-principal-component-analysis-PCA-based-data-fusion-approach-for-a-mouse-model-of-CLN6-batten-disease.pdf; accessed on Jun. 29, 2023.

(56) References Cited

OTHER PUBLICATIONS

Lehtimäki, K., et al., "Fine Motor Performance, Brain Volumetry and Metabolism in Cln2R2$^{07X/R207X}$ Nonsense Point Mutation Model for CLN2 Batten Disease," poster presented on Nov. 3, 2018 at the Society for Neuroscience annual meeting, San Diego, California; accessed at https://www.criver.com/sites/default/files/resource-files/SH-SFN-18-fine-motor-performance-brain-volumetry-and-metabolism-in-Cln2R207X-R207X-nonsense-point-mutation-model-for-CLN2-Batten-disease.pdf; accessed on Jun. 29, 2023; 1 page.

Lehtimäki, K., et al., "Longitudinal Characterization of the Cln6$^{nclf}$ Mouse Model of CLN6 Batten Disease—Characterization of Fine Motor Performance, Brain Pathology and Metabolic Changes," poster presented on Nov. 3, 2018 at the Society for Neuroscience annual meeting, San Diego, California; accessed at https://www.criver.com/sites/default/files/resource-files/SH-SFN-18-longitudinal-characterization-of-the-Clnonolf-mouse-model-of-CLN6-batten-disease.pdf; accessed on Jun. 29, 2023; 1 page.

* cited by examiner hIDS-WPRE:
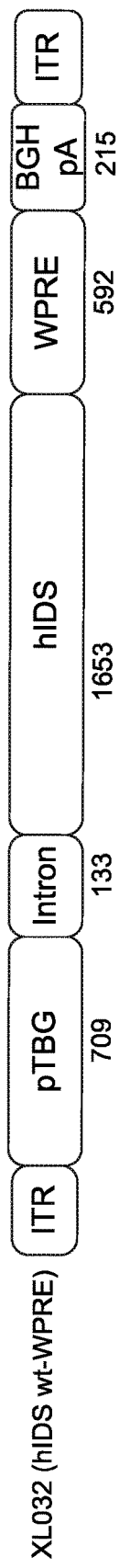 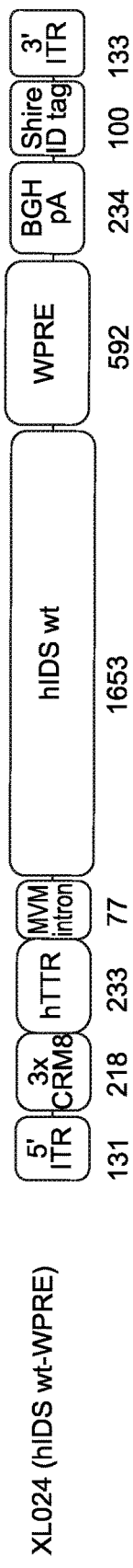 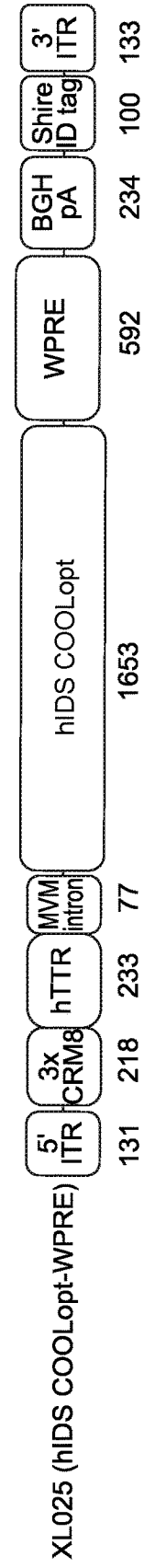 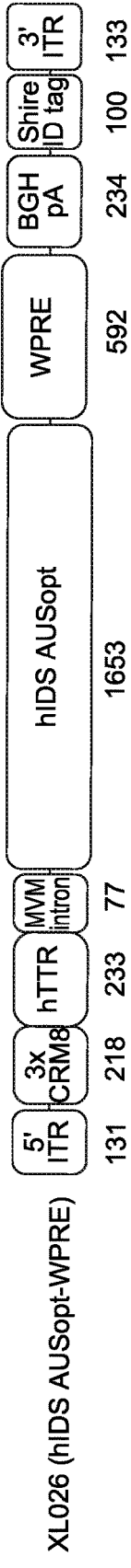
FIG. 1A
FIG. 1B hIDS-IRES-SUMF1:

XL027 (hIDS wt-IRES-SUMF1 wt)

| 5' ITR | 3x CRM8 | hTTR | MVM intron | hIDS wt | IRES | SUMF1 wt | BGH pA | Shire ID tag | 3' ITR |
|---|---|---|---|---|---|---|---|---|---|
| 131 | 218 | 233 | 77 | 1653 | 575 | 1125 | 234 | 100 | 133 |

XL028 hIDS COOLopt-IRES-SUMF1COOLopt)

| 5' ITR | 3x CRM8 | hTTR | MVM intron | hIDS COOLopt | IRES | SUMF1 COOLopt | BGH pA | Shire ID tag | 3' ITR |
|---|---|---|---|---|---|---|---|---|---|
| 131 | 218 | 233 | 77 | 1653 | 575 | 1125 | 234 | 100 | 133 |

XL029 (hIDS AUSopt-IRES-SUMF1AUSopt)

| 5' ITR | 3x CRM8 | hTTR | MVM intron | hIDS AUSopt | IRES | SUMF1 AUSopt | BGH pA | Shire ID tag | 3' ITR |
|---|---|---|---|---|---|---|---|---|---|
| 131 | 218 | 233 | 77 | 1653 | 575 | 1125 | 234 | 100 | 133 |

Control:

XL030 (SUMF1 wt)

| 5' ITR | 3x CRM8 | hTTR | MVM intron | SUMF1 wt | BGH pA | Shire ID tag | 3' ITR |
|---|---|---|---|---|---|---|---|
| 131 | 218 | 233 | 77 | 1125 | 234 | 100 | 133 |

FIG. 2

SEQUENCE LISTING

<160> NUMBER OF SEQ ID NOS: 24

<210> SEQ ID NO 1
<211> LENGTH: 525
<212> TYPE: PRT
<213> ORGANISM: Homo sapiens

<400> SEQUENCE: 1

```
Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255

Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335
```

```
Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
            355                 360                 365

Gly Arg Gln Ser Met Asp Leu Val Glu Leu Val Ser Leu Phe Pro Thr
        370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
            405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
            435                 440                 445

Gln Trp Asn Ser Asp Lys Pro Ser Leu Lys Asp Ile Lys Ile Met Gly
            450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
            485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
            515                 520                 525

<210> SEQ ID NO 2
<211> LENGTH: 550
<212> TYPE: PRT
<213> ORGANISM: Homo sapiens

<400> SEQUENCE: 2

Met Pro Pro Pro Arg Thr Gly Arg Gly Leu Leu Trp Leu Gly Leu Val
1               5                   10                  15

Leu Ser Ser Val Cys Val Ala Leu Gly Ser Glu Thr Gln Ala Asn Ser
            20                  25                  30

Thr Thr Asp Ala Leu Asn Val Leu Leu Ile Ile Val Asp Asp Leu Arg
        35                  40                  45

Pro Ser Leu Gly Cys Tyr Gly Asp Lys Leu Val Arg Ser Pro Asn Ile
    50                  55                  60

Asp Gln Leu Ala Ser His Ser Leu Leu Phe Gln Asn Ala Phe Ala Gln
65                  70                  75                  80

Gln Ala Val Cys Ala Pro Ser Arg Val Ser Phe Leu Thr Gly Arg Arg
                85                  90                  95

Pro Asp Thr Thr Arg Leu Tyr Asp Phe Asn Ser Tyr Trp Arg Val His
            100                 105                 110

Ala Gly Asn Phe Ser Thr Ile Pro Gln Tyr Phe Lys Glu Asn Gly Tyr
        115                 120                 125

Val Thr Met Ser Val Gly Lys Val Phe His Pro Gly Ile Ser Ser Asn
    130                 135                 140

His Thr Asp Asp Ser Pro Tyr Ser Trp Ser Phe Pro Pro Tyr His Pro
145                 150                 155                 160

Ser Ser Glu Lys Tyr Glu Asn Thr Lys Thr Cys Arg Gly Pro Asp Gly
                165                 170                 175

Glu Leu His Ala Asn Leu Leu Cys Pro Val Asp Val Leu Asp Val Pro
            180                 185                 190
```

Glu Gly Thr Leu Pro Asp Lys Gln Ser Thr Glu Gln Ala Ile Gln Leu
            195                 200                 205

Leu Glu Lys Met Lys Thr Ser Ala Ser Pro Phe Phe Leu Ala Val Gly
210                 215                 220

Tyr His Lys Pro His Ile Pro Phe Arg Tyr Pro Lys Glu Phe Gln Lys
225                 230                 235                 240

Leu Tyr Pro Leu Glu Asn Ile Thr Leu Ala Pro Asp Pro Glu Val Pro
                245                 250                 255

Asp Gly Leu Pro Pro Val Ala Tyr Asn Pro Trp Met Asp Ile Arg Gln
                260                 265                 270

Arg Glu Asp Val Gln Ala Leu Asn Ile Ser Val Pro Tyr Gly Pro Ile
            275                 280                 285

Pro Val Asp Phe Gln Arg Lys Ile Arg Gln Ser Tyr Phe Ala Ser Val
            290                 295                 300

Ser Tyr Leu Asp Thr Gln Val Gly Arg Leu Leu Ser Ala Leu Asp Asp
305                 310                 315                 320

Leu Gln Leu Ala Asn Ser Thr Ile Ile Ala Phe Thr Ser Asp His Gly
                325                 330                 335

Trp Ala Leu Gly Glu His Gly Glu Trp Ala Lys Tyr Ser Asn Phe Asp
            340                 345                 350

Val Ala Thr His Val Pro Leu Ile Phe Tyr Val Pro Gly Arg Thr Ala
            355                 360                 365

Ser Leu Pro Glu Ala Gly Glu Lys Leu Phe Pro Tyr Leu Asp Pro Phe
370                 375                 380

Asp Ser Ala Ser Gln Leu Met Glu Pro Gly Arg Gln Ser Met Asp Leu
385                 390                 395                 400

Val Glu Leu Val Ser Leu Phe Pro Thr Leu Ala Gly Leu Ala Gly Leu
                405                 410                 415

Gln Val Pro Pro Arg Cys Pro Val Pro Ser Phe His Val Glu Leu Cys
            420                 425                 430

Arg Glu Gly Lys Asn Leu Leu Lys His Phe Arg Phe Arg Asp Leu Glu
            435                 440                 445

Glu Asp Pro Tyr Leu Pro Gly Asn Pro Arg Glu Leu Ile Ala Tyr Ser
    450                 455                 460

Gln Tyr Pro Arg Pro Ser Asp Ile Pro Gln Trp Asn Ser Asp Lys Pro
465                 470                 475                 480

Ser Leu Lys Asp Ile Lys Ile Met Gly Tyr Ser Ile Arg Thr Ile Asp
                485                 490                 495

Tyr Arg Tyr Thr Val Trp Val Gly Phe Asn Pro Asp Glu Phe Leu Ala
            500                 505                 510

Asn Phe Ser Asp Ile His Ala Gly Glu Leu Tyr Phe Val Asp Ser Asp
            515                 520                 525

Pro Leu Gln Asp His Asn Met Tyr Asn Asp Ser Gln Gly Gly Asp Leu
530                 535                 540

Phe Gln Leu Leu Met Pro
545                 550

<210> SEQ ID NO 3
<211> LENGTH: 218
<212> TYPE: DNA
<213> ORGANISM: Homo sapiens

<400> SEQUENCE: 3
gggggaggct gctggtgaat attaaccaag gtcaccccag ttatcggagg agcaaacagg      60
ggctaagtcc accggggag gctgctggtg aatattaacc aaggtcaccc cagttatcgg    120
aggagcaaac aggggctaag tccaccgggg gaggctgctg gtgaatatta accaaggtca    180
ccccagttat cggaggagca aacagggct aagtccac                             218

<210> SEQ ID NO 4
<211> LENGTH: 233
<212> TYPE: DNA
<213> ORGANISM: Homo sapiens

<400> SEQUENCE: 4
aaatgaccta ttaagaatat ttcatagaac gaatgttccg atgctctaat ctctctagac    60
aaggttcata tttgtatggg ttacttattc tctctttgtt gactaagtca ataatcagaa    120
tcagcaggtt tgcagtcaga ttggcaggga taagcagcct agctcaggag aagtgagtat    180
aaaagcccca ggctgggagc agccatcaca gaagtccact cattcttggc agg           233

<210> SEQ ID NO 5
<211> LENGTH: 77
<212> TYPE: DNA
<213> ORGANISM: Homo sapiens

<400> SEQUENCE: 5
ctaaggtaag ttggcgccgt ttaagggatg gttggttggt ggggtattaa tgtttaatta    60 cctttttac aggcctg                                                    77

<210> SEQ ID NO 6
<211> LENGTH: 1653
<212> TYPE: DNA
<213> ORGANISM: Homo sapiens

<400> SEQUENCE: 6
atgccgccac cccggaccgg ccgaggcctt ctctggctgg gtctggttct gagctccgtc    60
tgcgtcgccc tcggatccga aacgcaggcc aactcgacca cagatgctct gaacgttctt    120
ctcatcatcg tggatgacct gcgcccctcc ctgggctgtt atggggataa gctggtgagg    180
tccccaaata ttgaccaact ggcatcccac agcctcctct tccagaatgc ctttgcgcag    240
caagcagtgt gcgccccgag ccgcgttttct ttcctcactg gcaggagacc tgacaccacc    300
cgcctgtacg acttcaactc ctactggagg gtgcacgctg aaacttctc caccatcccc    360 cagtacttca ggagaatgg ctatgtgacc atgtcggtgg aaaagtctt tcaccctggg    420 atatcttcta accataccga tgattctccg tatagctggt cttttccacc ttatcatcct    480
tcctctgaga agtatgaaaa cactaagaca tgtcgagggc cagatggaga actccatgcc    540
aacctgcttt gcctgtgga tgtgctggat gttcccgagg gcaccttgcc tgacaaacag    600
agcactgagc aagccataca gttgttggaa aagatgaaaa cgtcagccag tccttctctc    660
ctggccgttg ggtatcataa gccacacatc cccttcagat accccaagga atttcagaag    720 ttgtatcct tggagaacat caccctggcc ccgatcccg aggtccctga tggcctaccc    780
cctgtggcct acaaccctg gatggacatc aggcaacggg aagacgtcca agccttaaac    840
atcagtgtgc cgtatggtcc aattcctgtg gactttcagc ggaaaatccg ccagagctac    900
tttgcctctg tgtcatattt ggatacacag gtcggccgcc tcttgagtgc tttggacgat    960
cttcagctgg ccaacagcac catcattgca tttacctcgg atcatgggtg ggctctaggt    1020
gaacatggag aatgggccaa atacagcaat tttgatgttg ctacccatgt tccccctgata    1080

```
ttctatgttc ctggaaggac ggcttcactt ccggaggcag gcgagaagct tttcccttac    1140 ctcgacccett ttgattccgc ctcacagttg atggagccag gcaggcaatc catggacctt    1200
gtggaacttg tgtctcttt tcccacgctg gctggacttg caggactgca ggttccacct    1260
cgctgccccg ttccttcatt tcacgttgag ctgtgcagag aaggcaagaa ccttctgaag    1320
cattttcgat tccgtgactt ggaagaggat ccgtacctcc ctggtaatcc ccgtgaactg    1380
attgcctata gccagtatcc ccggccttca gacatccctc agtggaattc tgacaagccg    1440
agtttaaaag atataaagat catgggctat tccatacgca ccatagacta taggtatact    1500
gtgtgggttg gcttcaatcc tgatgaattt ctagctaact tttctgacat ccatgcaggg    1560
gaactgtatt ttgtggattc tgacccattg caggatcaca atatgtataa tgattcccaa    1620
ggtggagatc ttttccagtt gttgatgcct tga                                 1653

<210> SEQ ID NO 7
<211> LENGTH: 592
<212> TYPE: DNA
<213> ORGANISM: Homo sapiens

<400> SEQUENCE: 7
aatcaacctc tggattacaa aatttgtgaa agattgactg gtattcttaa ctttgttgct    60
ccttttacgc tttgtggata cgctgcttta ttgcctttgt atcttgctat tgcttcccgt    120
ttggctttca ttttctcctc cttgtataaa tcctggttgc tgtctctttt tgaggagttg    180
tggcccgttg tcaggcaacg tggcgtggtg tgcactgtgt ttgctgacgc aaccccccact    240 ggttggggca ttgccaccac ctgtcagctc ctttccggga cttttcgcttt ccccctccct    300 attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgca tc            592

<210> SEQ ID NO 8
<211> LENGTH: 234
<212> TYPE: DNA
<213> ORGANISM: Homo sapiens

<400> SEQUENCE: 8
cctagagctc gctgatcagc ctcgactgtg ccttctagtt gccagccatc tgttgtttgc    60 ccctccccg tgccttcctt gaccctggaa ggtgccactc ccactgtcct ttcctaataa    120
aatgaggaaa ttgcatcgca ttgtctgagt aggtgtcatt ctattctggg ggtgggggtg    180
gggcaggaca gcaaggggga ggattgggaa gacaatagca ggcatgctgg ggaa          234

<210> SEQ ID NO 9
<211> LENGTH: 133
<212> TYPE: DNA
<213> ORGANISM: Homo sapiens

<400> SEQUENCE: 9
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc    120
gagcgcgcag aga                                                        133
```

```
<210> SEQ ID NO 10
<211> LENGTH: 130
<212> TYPE: DNA
<213> ORGANISM: Homo sapiens

<400> SEQUENCE: 10
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct                                                             130

<210> SEQ ID NO 11
<211> LENGTH: 1653
<212> TYPE: DNA
<213> ORGANISM: Homo sapiens

<400> SEQUENCE: 11
atgccaccac ctaggacagg caggggcctg ctttggcttg gactggtgct gagctctgtc      60
tgtgttgccc tgggctccga gacccaagcc aactctacaa ccgatgctct caatgttctg     120
ctcatcatag tggatgacct gcggccctct ctaggctgct atggagacaa gttggtgcgg     180
agccccaaca tagaccagct agcctctcac tccctgctgt tccagaatgc cttcgcccag     240
caagctgtgt gcgcccctc tagagtgtct ttcctgaccg ggagaaggcc tgatacaaca      300
aggctgtatg actttaacag ctactggagg gtgcacgcag caacttctc cactatcccc      360 caatacttca aggagaatgg ctatgtgacc atgagcgtgg gcaaggtctt ccaccctgga     420
atctcctcca accacactga tgatagtccc tactcttggt cttttcctcc ctatcaccct     480
agcagtgaga agtatgagaa caccaaaacc tgcagaggcc ctgatgggga gctgcatgct     540
aacctcctgt gtcctgtaga tgtgctggac gtcccagagg gcaccttgcc agataagcag     600
tctactgagc aggctatcca gctgcttgag aaaatgaaga cttctgcatc tcccttcttt     660
ctggctgttg ctaccacaa gcctcacatc cccttcaggt accctaagga gttccaaaag     720
ctctatcctc tggaaaacat cacacttgcc cccgatcctg aggtccctga cggcctccca     780
ccagtagcct acaatccttg gatggacatt aggcagagag aggatgtcca ggctctgaat     840
atttctgtgc cctatgggcc catcccggtg gacttccagc gcaaaatcag acagtcctac     900
tttgcctctg tgagctatct ggacacccag gttgggaggc tcctctccgc ccttgacgac     960
ctccagttgg ccaacagcac cattatagcc ttcacctctg accacggctg ggcactgggg    1020
gaacacgggg agtgggctaa gtactctaac tttgatgtgg ccacccacgt gcccctcatc    1080
ttttatgtgc ctggcaggac tgccagcctg cccgaagctg gggaaaaact gtttccatac    1140
ctggaccctt ttgacagtgc ttctcagctc atggaacctg gccgtcagag catggatctg    1200
gtggagctag tgtccctctt cccaaccttg gctggcttg ctggtctcca ggtgcctcct    1260
agatgcccag tcccctcctt ccatgttgaa ctctgccgtg aggggaagaa tctgctgaag    1320
cacttcagat tcagagactt ggaggaggac ccctaccttc tgggaaccc agggagttg     1380 attgcatact cccagtatcc caggccaagt gacattcccc agtggaactc cgacaaacca    1440
agtctgaagg acatcaagat catggggtac agcatcagga ccattgacta cagatacaca    1500
gtgtgggttg gatttaaccc agatgagttc ttggcaaact ttctgacat ccatgcaagt    1560 cagttgtatt tgtggacag cgaccctctg caggatcaca acatgtacaa tgacagccag    1620
ggtggggacc tctttcaact cctcatgcca tag                                 1653

<210> SEQ ID NO 12
```

<211> LENGTH: 1653
<212> TYPE: DNA
<213> ORGANISM: Homo sapiens

<400> SEQUENCE: 12

```
atgccacccc cccggaccgg gagaggcctc ttgtggttgg gcctggtgct gagcagcgtg      60
tgcgtggccc tgggcagtga gacccaggct aactctacaa cagatgcctt gaatgtgctg     120
ctgatcattg tggatgacct gaggccaagt ctgggctgct atggggacaa attggtgagg     180
tcccccaaca tcgaccagtt ggcctcccac tctctcctat ccaaaatgc tttcgcccag      240
caggcagttt gtgcccccetc tagggtgagc ttcctcactg gcaggcgccc tgacaccact     300
agactgtatg actttaacag ctattggagg gtgcacgcag gaaacttctc cacaatccct     360
caatacttca aggagaatgg ttatgtgaca atgtctgtgg gcaaggtgtt ccaccctggc     420
atcagcagca accacaccga tgactcaccc tatagttggt cttttccccc ctaccatcct     480
tcatctgaga aatatgaaaa cacaaaaacc tgccgaggcc cagacgggga actgcatgcc     540
aacctactct gtcctgttga tgtactggac gtgcccgagg gcaccctccc tgataagcag     600
tccacagaac aggccattca gctgcttgaa aagatgaaga cctccgcatc cccttcttc      660
ttggctgtcg gctaccacaa gccccatatc ccctttagat accccaagga attccagaaa     720
ctgtacccac tggagaacat cacacttgct cctgaccctg aagtgcctga cggactgcct     780
ccagtggcct ataaccttg gatggacatc cggcagcgcg aggatgtgca ggctctgaac     840
attagtgtgc cttatgggcc catccctgtg actttcaga ggaagattcg ccagtcctac      900
tttgcctctg tatcctacct ggacacacag gtggacgcc tgctgtctgc ccttgatgat     960
ctgcaactgg ccaacagcac cattatagct ttcacatcag accatgggtg ggctcttggg    1020
gagcatggtg aatgggctaa gtactccaac ttcgatgtgg caacccatgt cccctctgatc   1080
ttctatgtgc caggaaggac cgcctctctg ccagaggcag gtgagaagct gttcccctat    1140
ctggacccctt tgactccgc cagccagctg atggagcctg ccgacagtc tatggacctg    1200
gttgagctgg tcagcctgtt tcccacactc gctggactgg ctggcctgca agtaccccca    1260
cgctgcccag tgccctcctt ccatgtggag ctttgcaggg aggggaagaa cctcctcaag    1320
cacttcaggt tcagggacct agaggaggat ccttatctgc ctggaaaccc cagagagctt    1380
attgcttact cccagtatcc aaggcctagt gacattcccc aatggaactc agacaaacca    1440
agcctgaaag acatcaagat catgggatac tctatcagga ccattgacta caggtacact    1500
gtgtgggttg gcttcaaccc ggatgagttc ctggctaatt tctctgacat acatgctggc    1560
gagctgtact tcgtggacag tgaccccctg caggatcaca acatgtacaa tgattcccag    1620
gggggtgacc tcttccagct tctgatgccc taa                                 1653
```

<210> SEQ ID NO 13
<211> LENGTH: 575
<212> TYPE: DNA
<213> ORGANISM: Homo sapiens

<400> SEQUENCE: 13

```
gcccctctcc ctccccccc cctaacgtta ctggccgaag ccgcttggaa taaggccggt      60
gtgcgtttgt ctatatgtta ttttccacca tattgccgtc ttttggcaat gtgagggccc    120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc cccacctggc gacaggtgcc    300
```

```
tctgcggcca aaagccacgt gtataagata cacctgcaaa ggcggcacaa ccccagtgcc    360
acgttgtgag ttggatagtt gtggaaagag tcaaatggct cacctcaagc gtattcaaca    420
aggggctgaa ggatgcccag aaggtacccc attgtatggg atctgatctg gggcctcggt    480
gcacatgctt tacatgtgtt tagtcgaggt taaaaaacgt ctaggccccc cgaaccacgg    540
ggacgtggtt ttcctttgaa aaacacgatg ataat                              575
```

<210> SEQ ID NO 14
<211> LENGTH: 1125
<212> TYPE: DNA
<213> ORGANISM: Homo sapiens

<400> SEQUENCE: 14

```
atggctgcgc ccgcactagg gctggtgtgt ggacgttgcc ctgagctggg tctcgtcctc     60
ttgctgctgc tgctctcgct gctgtgtgga gcggcaggga gccaggaggc cgggaccggt    120
gcgggcgcgg ggtcccttgc gggttcttgc ggctgcggca cgcccagcg gcctggcgcc     180 catggcagtt cggcagccgc tcaccgatac tcgcgggagg ctaacgctcc gggccccgta    240
cccggagagc ggcaactcgc gcactcaaag atggtcccca tccctgctgg agtatttaca    300
atgggcacag atgatcctca gataaagcag gatggggaag cacctgcgag gagagttact    360
attgatgcct tttacatgga tgcctatgaa gtcagtaata ctgaatttga aagtttgtg     420 aactcaactg gctatttgac agaggctgag aagtttggcg actcctttgt ctttgaaggc    480
atgttgagtg agcaagtgaa gaccaatatt caacaggcag ttgcagctgc tcccctggtgg   540 ttacctgtga aaggcgctaa ctggagacac ccagaagggc ctgactctac tattctgcac    600
aggccggatc atccagttct ccatgtgtcc tggaatgatg cggttgccta ctgcacttgg    660
gcagggaagc ggctgcccac ggaagctgag tgggaataca gctgtcgagg aggcctgcat    720
aatagacttt ccccctgggg caacaaactg cagcccaaag ccagcatta tgccaacatt     780 tggcagggcg agtttccggt gaccaacact ggtgaggatg gcttccaagg aactgcgcct    840
gttgatgcct ccctcccaa tggttatggc ttatacaaca tagtgggaa cgcatgggaa      900 tggacttcag actggtggac tgttcatcat tctgttgaag aaacgcttaa cccaaaaggt    960
cccccttctg ggaaagaccg agtgaagaaa ggtggatcct acatgtgcca taggtcttat   1020
tgttacaggt atcgctgtgc tgctcggagc cagaacacac ctgatagctc tgcttcgaat   1080
ctgggattcc gctgtgcagc cgaccgcctg cccactatgg actga                   1125
```

<210> SEQ ID NO 15
<211> LENGTH: 1125
<212> TYPE: DNA
<213> ORGANISM: Homo sapiens

<400> SEQUENCE: 15

```
atggctgctc ctgccctggg gctggtgtgt ggaagatgtc ctgaactggg cctggttctg     60
ttactgcttc tgctcagcct gctctgtggt gctgccggca gccaagaggc aggcactggc    120
gctggagctg gaagcctggc tgggtcttgt ggatgtggca caccacagag gccaggggct    180 catgctcct ctgctgcagc tcataggtac agcagagaag ccaatgctcc aggcccagtg     240
cctggagaga cagctggc tcacagcaag atggtgccca tccctgctgg ggtgttcaca      300
atgggaacag atgatcccca gatcaagcag gatggggagg cgcctgccag gagggtgacc    360
attgatgcat tctatatgga tgcctatgag gtgagcaata cagaatttga aagtttgtg    420
```

-continued

| | |
|---|---|
| aactctactg gctacctgac tgaggctgaa aaatttggag actcttttgt gtttgaagga | 480 |
| atgcttagtg aacaggttaa gaccaacatc cagcaggctg ttgcagcagc ccctggtgg | 540 |
| ttgcctgtca agggagctaa ctggaggcac cctgagggac cagattctac aatcctgcat | 600 |
| agacctgatc atcctgttct gcatgtgtct tggaatgatg ctgtggctta ctgtacctgg | 660 |
| gcaggaaaaa ggctgccaac agaagctgag tgggaatact cttgcagagg aggcctgcac | 720 |
| aatagactgt tcccatgggg caacaagctg caacccaagg ccagcacta tgctaacatc | 780 |
| tggcagggag aattccctgt gacaaacaca ggagaggacg gcttccaggg aactgcccct | 840 |
| gtagatgctt tccctcctaa tggctatggc ctgtataaca ttgttggcaa cgcctgggag | 900 |
| tggacttctg attggtggac agtgcaccac tctgttgagg agacactgaa tcctaagggg | 960 |
| ccaccttctg gaaaggatag agtgaagaag gggggaagct acatgtgcca caggtcttat | 1020 |
| tgttacagat acaggtgcgc tgctaggtct cagaacaccc ctgatagcag tgctagcaat | 1080 |
| ctgggcttca ggtgtgccgc tgacagactg cctaccatgg attaa | 1125 |

<210> SEQ ID NO 16
<211> LENGTH: 1125
<212> TYPE: DNA
<213> ORGANISM: Homo sapiens

<400> SEQUENCE: 16

| | |
|---|---|
| atggctgccc ctgctctggg attggtttgt ggcagatgtc ctgagcttgg tctggtgctg | 60 |
| ttgctccttc tgttgtctct gctgtgtgga gcagctgggt ctcaggaagc tggcacaggc | 120 |
| gctggggctg gctctctggc cgggtcatgt ggctgtggaa ctccccagcg gcctggagcc | 180 |
| catggcagct ctgccgcagc acacaggtat tctaggaag ccaatgcccc aggccctgtg | 240 |
| cctggggaga gacagctagc tcattctaag atggtgccta tcccagccgg ggttttaca | 300 |
| atgggcactg atgatcctca gattaagcag gatggagagg cccccgccag aagagtgacc | 360 |
| attgatgctt tctacatgga tgcatatgaa gtgtccaaca cagagtttga gaaatttgtg | 420 |
| aactctactg gatacttgac cgaggctgag aagtttggag attcctttgt ctttgaaggc | 480 |
| atgctgtctg agcaggtcaa gaccaacatt cagcaagcag tggccgctgc accttggtgg | 540 |
| cttcctgtga agggcgccaa ctggagacat ccagaggggc cagatagtac catcctccac | 600 |
| agacctgatc acccagtcct tcatgttttcc tggaatgatg cagttgctta ctgcacttgg | 660 |
| gccggcaaga ggctccctac tgaggcagag tgggaatact cctgcagagg aggcctgcac | 720 |
| aacagactgt tcccttgggg gaacaagctt cagcccaaag ccagcactaa tgctaacatc | 780 |
| tggcagggtg agtttccagt caccaataca ggggaggacg gattccaggg aaccgcacca | 840 |
| gtagatgcct tccctcctaa tggctatggc ctgtataata ttgtgggcaa tgcatgggag | 900 |
| tggacctctg actggtggac tgtgcaccac tcagtggagg aaaccctgaa ccctaaggga | 960 |
| cccccttcag gcaaagatag agtcaaaaag ggagggagct atatgtgtca cagatcctat | 1020 |
| tgctacagat atagatgtgc agccaggtcc cagaacaccc ctgactcttc tgctagcaac | 1080 |
| ctgggctttc ggtgtgctgc tgatagactg cccaccatgg actaa | 1125 |

<210> SEQ ID NO 17
<211> LENGTH: 9856
<212> TYPE: DNA
<213> ORGANISM: Homo sapiens
<220> FEATURE:
<221> NAME/KEY: n
<222> LOCATION: (3202)..(3202)
<223> OTHER INFORMATION: Any nucleic acid

```
<220> FEATURE:
<221> NAME/KEY: misc_feature
<222> LOCATION: (3202)..(3203)
<223> OTHER INFORMATION: n is a, c, g, or t

<400> SEQUENCE: 17
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct ttaattaaac gcgtgggggga ggctgctggt gaatattaac caaggtcacc    180
ccagttatcg gaggagcaaa caggggctaa gtccaccggg ggaggctgct ggtgaatatt     240
aaccaaggtc accccagtta tcggaggagc aaacaggggc taagtccacc ggggaggct     300 gctggtgaat attaaccaag gtcaccccag ttatcggagg agcaaacagg ggctaagtcc     360
acactagtaa atgacctatt aagaatattt catagaacga atgttccgat gctctaatct    420
ctctagacaa ggttcatatt tgtatgggtt acttattctc tctttgttga ctaagtcaat    480
aatcagaatc agcaggtttg cagtcagatt ggcagggata agcagcctag ctcaggagaa    540
gtgagtataa aagccccagg ctgggagcag ccatcacaga agtccactca ttcttggcag    600
gccgcggcta aggtaagttg cgccgtttta agggatggtt ggttggtggg gtattaatgt    660
ttaattacct tttttacagg cctgggcgcg ccgccaccat gccgccaccc cggaccggcc    720
gaggccttct ctggctgggt ctggttctga gctccgtctg cgtcgccctc ggatccgaaa    780
cgcaggccaa ctcgaccaca gatgctctga acgttcttct catcatcgtg gatgacctgc    840
gcccctccct gggctgttat ggggataagc tggtgaggtc cccaaatatt gaccaactgg    900
catcccacag cctcctcttc cagaatgcct tgcgcagca agcagtgtgc gccccgagcc     960
gcgtttcttt cctcactggc aggagacctg acaccaccccg cctgtacgac ttcaactcct   1020
actggagggt gcacgctgga aacttctcca ccatccccca gtacttcaag gagaatggct   1080
atgtgaccat gtcggtggga aaagtctttc accctgggat atcttctaac catccgatg   1140 attctccgta tagctggtct tttccacctt atcatccttc ctctgagaag tatgaaaaca   1200
ctaagacatg tcgagggcca gatggagaac tccatgccaa cctgctttgc cctgtggatg   1260
tgctggatgt tcccgagggc accttgcctg acaaacagag cactgagcaa gccatacagt   1320
tgttggaaaa gatgaaaacg tcagccagtc ctttcttcct ggccgttggg tatcataagc   1380
cacacatccc cttcagatac cccaaggaat ttcagaagtt gtatcccttg agaacatca   1440 ccctggcccc cgatcccgag gtccctgatg gcctaccccc tgtggcctac aaccccctgga   1500 tggacatcag gcaacgggaa gacgtccaag ccttaaacat cagtgtgccg tatggtccaa   1560
ttcctgtgga ctttcagcgg aaaatccgcc agagctactt tgcctctgtg tcatatttgg   1620
atacacaggt cggccgcctc ttgagtgctt tggacgatct tcagctggcc aacagcacca   1680
tcattgcatt tacctcggat catgggtggg ctctaggtga acatggagaa tgggccaaat   1740
acagcaattt tgatgttgct acccatgttc cctgatatt ctatgttcct ggaaggacgg    1800
cttcacttcc ggaggcaggc gagaagcttt tcccttacct cgaccctttt gattccgcct   1860
cacagttgat ggagccaggc aggcaatcca tggaccttgt ggaacttgtg tctctttttc    1920
ccacgctggc tggacttgca ggactgcagg ttccacctcg ctgccccgtt ccttcatttc   1980
acgttgagct gtgcagagaa ggcaagaacc ttctgaagca ttttcgattc cgtgacttgg   2040
aagaggatcc gtacctcccc cggtaatccccc gtgaactgat tgcctatagc cagtatcccc   2100
ggccttcaga catccctcag tggaattctg acaagccgag tttaaaagat ataaagatca   2160
```

```
tgggctattc catacgcacc atagactata ggtatactgt gtgggttggc ttcaatcctg    2220
atgaatttct agctaacttt tctgacatcc atgcagggga actgtatttt gtggattctg    2280
acccattgca ggatcacaat atgtataatg attcccaagg tggagatctt ttccagttgt    2340
tgatgccttg aggtaccaat caacctctgg attacaaaat ttgtgaaaga ttgactggta    2400
ttcttaactt tgttgctcct tttacgcttt gtggatacgc tgctttattg cctttgtatc    2460
ttgctattgc ttcccgtttg gctttcattt tctcctcctt gtataaatcc tggttgctgt    2520
ctcttttga ggagttgtgg cccgttgtca ggcaacgtgg cgtggtgtgc actgtgtttg    2580
ctgacgcaac ccccactggt tggggcattg ccaccacctg tcagctcctt tccgggactt    2640
tcgctttccc cctccctatt gccacggcgg aactcatcgc cgcctgcctt gcccgctgct    2700
ggacaggggc tcggctgttg ggcactgaca attccgtggt gttgtcgggg aaatcatcgt    2760
cctttccttg gctgctcgcc tgtgttgcca cctggattct gcgcgggacg tccttctgct    2820
acgtcccttc ggccctcaat ccagcggacc ttccttcccg cggcctgctg ccggctctgc    2880
ggcctcttcc gcgtcttcgc cttcgccctc agacgagtcg gatctccctt tgggccgcct    2940
ccccgcatcg gtaccgtcga ccctagagct cgctgatcag cctcgactgt gccttctagt    3000
tgccagccat ctgttgtttg cccctccccc gtgccttcct tgaccctgga aggtgccact    3060
cccactgtcc tttcctaata aaatgaggaa attgcatcgc attgtctgag taggtgtcat    3120
tctattctgg ggggtgggggt ggggcaggac agcaaggggg aggattggga agacaatagc    3180
aggcatgctg gggaatctag anngtttaaa catttaaata ggaacccta gtgatggagt    3240
tggccactcc ctctctgcgc gctcgctcgc tcactgaggc cgggcgacca aaggtcgccc    3300
gacgcccggg ctttgcccgg gcggcctcag tgagcgagcg agcgcgcaga gagtatacat    3360
cgatgtgagt tcgcgggtgg ctgggggggcc ctggctgcg accgccccg aaccgcgtct    3420
acgagccttg cgggctccgg gtctttgcag tcgtatgggg gcagggtagc tgttccccgc    3480
aaggagagct caaggtcagc gctcggacct ggcggagccc cgcacccagg ctgtggcgcc    3540
ctgtgcagct ccgccttgc ggcgccatct gcccggagcc tccttcccct agtccccaga    3600
aacaggaggt ccctactccc gcccgagatc ccgacccgga ccctaggtg ggggacgctt    3660
tctttccttt cgcgctctgc ggggtcacgt gtcgcagagg agccctcccc cacggcctc    3720
cggcaccgca ggccccggga tgctagtgcg cagcgggtgc atccctgtcc ggatgctgcg    3780
cctgcggtag agcggccgcc atgttgcaac cgggaaggaa atgaatgggc agccgttagg    3840
aaagcctgcc ggtgactaac cctgcgctcc tgcctcgatg ggtggagtcg cgtgtggcgg    3900
ggaagtcagg tggagcgagg ctagctggcc cgatttctcc tccgggtgat gcttttccta    3960
gattattctc tggtaaatca agaagtggg tttatggagg tcctcttgtg tcccctcccc    4020
gcagaggtgt ggtggctgtg gcatggtgcc aagccgggag aagctgagtc atgggtagtt    4080
ggaaaaggac atttccaccg caaaatggcc cctctggtgg tggccccttc ctgcagcgcc    4140
ggctcacctc acgccccgc ccttcccctg ccagcctagc gttgacccga ccccaaaggc    4200
caggctgtaa atgtcaccgg gaggattggg tgtctgggcg cctcggggaa cctgcccttc    4260
tccccattcc gtcttccgga aaccagatct cccaccgcac cctggtctga ggttaaatat    4320
agctgctgac ctttctgtag ctgggggcct gggctggggc tctctcccat ccttctccc    4380
cacacacatg cacttacctg tgctcccact cctgatttct ggaaaagagc taggaaggac    4440
aggcaacttg gcaaatcaaa gccctgggac taggggggtta aaatacagct tcccctcttc    4500
ccacccgccc cagtctctgt cccttttgta ggagggactt agagaagggg tgggcttgcc    4560
```

```
ctgtccagtt aatttctgac ctttactcct gcccttttgag tttgatgatg ctgagtgtac    4620
aagcgttttc tccctaaagg gtgcagctga gctaggcagc agcaagcatt cctggggtgg    4680
catagtgggg tggtgaatac catgtacaaa gcttgtgccc agactgtggg tggcagtgcc    4740
ccacatggcc gcttctcctg gaagggcttc gtatgactgg gggtgttggg cagccctgga    4800
gccttcagtt gcagccatgc cttaagccag gccagcctgg cagggaagct caagggagat    4860
aaaattcaac ctcttgggcc ctcctggggg taaggagatg ctgcattcgc cctcttaatg    4920
gggaggtggc ctagggctgc tcacatattc tggaggagcc tcccctcctc atgccttctt    4980
gcctcttgtc tcttaggcat gcaaaagagt cgaataaggg cgacacaaaa tttattctaa    5040
atgcataata aatactgata acatcttata gtttgtatta tattttgtat tatcgttgac    5100
atgtataatt ttgatatcaa aaactgattt tcccttttatt attttcgaga tttatttttct    5160 taattctctt taacaaacta gaaatattgt atatacaaaa aatcataaat aatagatgaa    5220
tagtttaatt ataggtgttc atcaatcgaa aaagcaacgt atcttattta aagtgcgttg    5280
cttttttctc atttataagg ttaaataatt ctcatatatc aagcaaagtg acaggcgccc    5340
ttaaatattc tgacaaatgc tctttcccta aactcccccc ataaaaaaac ccgccgaagc    5400 gggttttttac gttatttgcg gattaacgat tactcgttat cagaaccgcc caggggggccc    5460 gagcttaaga ctggccgtcg ttttacaaca cagaaagagt ttgtagaaac gcaaaaaggc    5520
catccgtcag gggccttctg cttagtttga tgcctggcag ttccctactc tcgccttccg    5580
cttcctcgct cactgactcg ctgcgctcgg tcgttcggct gcggcgagcg gtatcagctc    5640
actcaaaggc ggtaatacgg ttatccacag aatcagggga taacgcagga aagaacatgt    5700
gagcaaaagg ccagcaaaag gccaggaacc gtaaaaaggc cgcgttgctg gcgttttttcc    5760 ataggctccg ccccctgac gagcatcaca aaaatcgacg ctcaagtcag aggtggcgaa    5820
acccgacagg actataaaga taccaggcgt ttccccctgg aagctccctc gtgcgctctc    5880
ctgttccgac cctgccgctt accggatacc tgtccgcctt tctcccttcg ggaagcgtgg    5940
cgctttctca tagctcacgc tgtaggtatc tcagttcggt gtaggtcgtt cgctccaagc    6000
tgggctgtgt gcacgaaccc cccgttcagc ccgaccgctg cgccttatcc ggtaactatc    6060
gtcttgagtc caacccggta agacacgact tatcgccact ggcagcagcc actggtaaca    6120
ggattagcag agcgaggtat gtaggcggtg ctacagagtt cttgaagtgg tgggctaact    6180
acggctacac tagaagaaca gtatttggta tctgcgctct gctgaagcca gttaccttcg    6240
gaaaaagagt tggtagctct tgatccggca acaaaccac cgctggtagc ggtggttttt    6300
ttgtttgcaa gcagcagatt acgcgcagaa aaaaggatc tcaagaagat cctttgatct    6360
tttctacggg gtctgacgct cagtggaacg acgcgcgcgt aactcacgtt aagggatttt    6420
ggtcatgagc ttgcgccgtc ccgtcaagtc agcgtaatgc tctgcttagg tggcggtact    6480
tgggtcgata tcaaagtgca tcacttcttc ccgtatgccc aactttgtat agagagccac    6540
tgcgggatcg tcaccgtaat ctgcttgcac gtagatcaca taagcaccaa gcgcgttggc    6600
ctcatgcttg aggagattga tgagcgcggt ggcaatgccc tgcctccggt gctcgccgga    6660
gactgcgaga tcatagatat agatctcact acgcggctgc tcaaacttgg gcagaacgta    6720
agccgcgaga gcgccaacaa ccgcttcttg gtcgaaggca gcaagcgcga tgaatgtctt    6780 actacgagc aagttcccga ggtaatcgga gtccggctga tgttgggagt aggtggctac    6840
gtcaccgaac tcacgaccga aaagatcaag agcagcccgc atggatttga cttggtcagg    6900
```

-continued

```
gccgagccta catgtgcgaa tgatgccat  acttgagcca cctaactttg tttagggcg   6960
actgccctgc tgcgtaacat cgttgctgct ccataacatc aaacatcgac ccacggcgta  7020
acgcgcttgc tgcttggatg cccgaggcat agactgtaca aaaaacagt  cataacaagc  7080
catgaaaacc gccactgcgc cgttaccacc gctgcgttcg gtcaaggttc tggaccagtt  7140
gcgtgagcgc attttttttt cctcctcggc gtttacgccc cgccctgcca ctcatcgcag  7200
tactgttgta attcattaag cattctgccg acatggaagc catcacagac ggcatgatga  7260
acctgaatcg ccagcggcat cagcaccttg tcgccttgcg tataatattt gcccatagtg  7320
aaaacggggg cgaagaagtt gtccatattg gccacgttta atcaaaaact ggtgaaactc  7380
acccagggat tggcgctgac gaaaaacata ttctcaataa acccttagg  gaataggcc   7440
aggttttcac cgtaacacgc cacatcttgc gaatatatgt gtagaaactg ccggaaatcg  7500
tcgtgtgcac tcatggaaaa cggtgtaaca agggtgaaca ctatcccata tcaccagctc  7560
accgtctttc attgccatac ggaactccgg atgagcattc atcaggcggg caagaatgtg  7620
aataaaggcc ggataaaact tgtgcttatt tttctttacg gtctttaaaa aggccgtaat  7680
atccagctga acgtctggt  tataggtaca ttgagcaact gactgaaatg cctcaaaatg  7740
ttctttacga tgccattggg atatatcaac ggtggtatat ccagtgattt ttttctccat  7800
ttttttttcc tcctttagaa aaactcatcg agcatcaaat gaaactgcaa tttattcata  7860
tcaggattat caataccata ttttgaaaa  agccgtttct gtaatgaagg agaaaactca  7920
ccgaggcagt tccataggat ggcaagatcc tggtatcggt ctgcgattcc gactcgtcca  7980
acatcaatac aacctattaa tttcccctcg tcaaaaataa ggttatcaag tgagaaatca  8040
ccatgagtga cgactgaatc cggtgagaat ggcaaaagtt tatgcatttc tttccagact  8100
tgttcaacag gccagccatt acgctcgtca tcaaaatcac tcgcatcaac caaaccgtta  8160
ttcattcgtg attgcgcctg agcgaggcga atacgcgat  cgctgttaaa aggacaatta  8220
caaacaggaa tcgagtgcaa ccggcgcagg aacactgcca gcgcatcaac aatattttca  8280
cctgaatcag gatattcttc taatacctgg aacgctgttt ttccggggat cgcagtggtg  8340
agtaaccatg catcatcagg agtacggata aaatgcttga tggtcggaag tggcataaat  8400
tccgtcagcc agtttagtct gaccatctca tctgtaacat cattggcaac gctacctttg  8460
ccatgtttca gaaacaactc tggcgcatcg ggcttcccat acaagcgata gattgtcgca  8520
cctgattgcc cgacattatc gcgagcccat ttatacccat ataaatcagc atccatgttg  8580
gaatttaatc gcggcctcga cgtttcccgt tgaatatggc tcattttttt ttcctccttt  8640
accaatgctt aatcagtgag gcacctatct cagcgatctg tctatttcgt tcatccatag  8700
ttgcctgact ccccgtcgtg tagataacta cgatacggga gggcttacca tctggcccca  8760
gcgctgcgat gataccgcga gaaccacgct caccggctcc ggatttatca gcaataaacc  8820
agccagccgg aagggccgag cgcagaagtg gtcctgcaac tttatccgcc tccatccagt  8880
ctattaattg ttgccgggaa gctagagtaa gtagttcgcc agttaatagt ttgcgcaacg  8940
ttgttgccat cgctacaggc atcgtggtgt cacgctcgtc gtttggtatg gcttcattca  9000
gctccggttc ccaacgatca aggcgagtta catgatcccc catgttgtgc acgttgtcag  9060
aagtaagttg gccgcagtgt tatcactcat ggttatggca gcactgcata attctcttac  9120
tgtcatgcca tccgtaagat gcttttctgt gactggtgag tactcaacca agtcattctg  9180
agaatagtgt atgcggcgac cgagttgctc ttgcccggcg tcaatacggg ataataccgc  9240
gccacatagc agaactttaa aagtgctcat cattggaaaa cgttcttcgg ggcgaaaact  9300
```

-continued

```
ctcaaggatc ttaccgctgt tgagatccag ttcgatgtaa cccactcgtg cacccaactg      9360
atcttcagca tcttttactt tcaccagcgt ttctgggtga gcaaaaacag gaaggcaaaa      9420
tgccgcaaaa aagggaataa gggcgacacg gaaatgttga atactcatat tcttcctttt      9480
tcaatattat tgaagcattt atcagggtta ttgtctcatg agcggataca tatttgaatg      9540
tatttagaaa aataaacaaa taggggtcag tgttacaacc aattaaccaa ttctgaacat      9600
tatcgcgagc ccatttatac ctgaatatgg ctcataacac cccttgtttg cctggcggca      9660
gtagcgcggt ggtcccacct gaccccatgc cgaactcaga agtgaaacgc cgtagcgccg      9720
atggtagtgt ggggactccc catgcgagag tagggaactg ccaggcatca aataaaacga      9780
aaggctcagt cgaaagactg ggcctttcgc ccgggctaat tgagggtgtg cgcccttatt      9840
cgactcgggg ctcgag                                                      9856
```

<210> SEQ ID NO 18
<211> LENGTH: 9856
<212> TYPE: DNA
<213> ORGANISM: Homo sapiens
<220> FEATURE:
<221> NAME/KEY: misc_feature
<222> LOCATION: (3202)..(3203)
<223> OTHER INFORMATION: n is a, c, g, or t

<400> SEQUENCE: 18

```
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct ttaattaaac gcgtggggga ggctgctggt gaatattaac caaggtcacc       180
ccagttatcg gaggagcaaa caggggctaa gtccaccggg ggaggctgct ggtgaatatt       240
aaccaaggtc accccagtta tcggaggagc aaacaggggc taagtccacc ggggaggct        300 gctggtgaat attaaccaag gtcaccccag ttatcggagg agcaaacagg ggctaagtcc       360
acactagtaa atgacctatt aagaatattt catagaacga atgttccgat gctctaatct       420
ctctagacaa ggttcatatt tgtatgggtt acttattctc tctttgttga ctaagtcaat       480
aatcagaatc agcaggtttg cagtcagatt ggcaggata agcagcctag ctcaggagaa        540
gtgagtataa aagccccagg ctgggagcag ccatcacaga agtccactca ttcttggcag       600
gccgcggcta aggtaagttg gcgccgttta agggatggtt ggttggtggg gtattaatgt       660
ttaattacct ttttttacagg cctgggcgcg ccgccaccat gccaccccc cggaccggga       720 gaggcctctt gtggttgggc ctggtgctga gcagcgtgtg cgtggccctg gcagtgaga       780 cccaggctaa ctctacaaca gatgccttga atgtgctgct gatcattgtg gatgacctga       840
ggccaagtct gggctgctat ggggacaaat tggtgaggtc ccccaacatc gaccagttgg       900
cctcccactc tctcctattc caaaatgctt tcgcccagca ggcagtttgt gccccctcta       960
gggtgagctt cctcactggc aggcgccctg acaccactag actgtatgac tttaacagct      1020
attggagggt gcacgcagga aacttctcca caatccctca atacttcaag gagaatggtt      1080
atgtgacaat gtctgtgggc aaggtgttcc accctggcat cagcagcaac cacaccgatg      1140
actcacccta tagttggtct ttttccccct accatccttc atctgagaaa tatgaaaaca      1200
caaaaacctg ccgaggccca gacgggggaac tgcatgccaa cctactctgt cctgttgatg      1260
tactggacgt gcccgagggc accctccctg ataagcagtc cacagaacag gccattcagc      1320
tgcttgaaaa gatgaagacc tccgcatccc ccttcttctt ggctgtcggc taccacaagc      1380
```

```
cccatatccc ctttagatac cccaaggaat tccagaaact gtacccactg gagaacatca   1440
cacttgctcc tgaccctgaa gtgcctgacg gactgcctcc agtggcctat aacccttgga   1500
tggacatccg gcagcgcgag gatgtgcagg ctctgaacat tagtgtgcct tatgggccca   1560
tccctgtgga ctttcagagg aagattcgcc agtcctactt tgcctctgta tcctacctgg   1620
acacacaggt gggacgcctg ctgtctgccc ttgatgatct gcaactggcc aacagcacca   1680
ttatagcttt cacatcagac catggtgggg ctcttgggga gcatggtgaa tgggctaagt   1740
actccaactt cgatgtggca acccatgtcc ctctgatctt ctatgtgcca ggaaggaccg   1800
cctctctgcc agaggcaggt gagaagctgt tccctatct ggacccttt gactccgcca   1860 gccagctgat ggagcctggc cgacagtcta tggacctggt tgagctggtc agcctgtttc   1920
ccacactcgc tggactggct ggcctgcaag tacccccacg ctgcccagtg ccctccttcc   1980
atgtggagct ttgcagggag gggaagaacc tcctcaagca cttcaggttc agggacctag   2040
aggaggatcc ttatctgcct ggaaaccccca gagagcttat tgcttactcc cagtatccaa   2100
ggcctagtga cattccccaa tggaactcag acaaaccaag cctgaaagac atcaagatca   2160
tgggatactc tatcaggacc attgactaca ggtacactgt gtgggttggc ttcaacccgg   2220
atgagttcct ggctaatttc tctgacatac atgctggcga gctgtacttc gtggacagtg   2280
accccctgca ggatcacaac atgtacaatg attcccaggg gggtgacctc ttccagcttc   2340
tgatgcccta aggtaccaat caacctctgg attacaaaat ttgtgaaaga ttgactggta   2400
ttcttaactt tgttgctcct tttacgcttt gtggatacgc tgctttattg cctttgtatc   2460
ttgctattgc ttcccgtttg gctttcattt tctcctcctt gtataaatcc tggttgctgt   2520
ctctttttga ggagttgtgg cccgttgtca ggcaacgtgg cgtggtgtgc actgtgtttg   2580
ctgacgcaac ccccactggt tggggcattg ccaccacctg tcagctcctt tccgggactt   2640
tcgctttccc cctccctatt gccacggcgg aactcatcgc cgcctgcctt gcccgctgct   2700
ggacaggggc tcggctgttg ggcactgaca attccgtggt gttgtcgggg aaatcatcgt   2760
cctttccttg gctgctcgcc tgtgttgcca cctggattct gcgcgggacg tccttctgct   2820
acgtcccttc ggccctcaat ccagcggacc ttccttcccg cggcctgctg ccggctctgc   2880
ggcctcttcc gcgtcttcgc cttcgccctc agacgagtcg gatctcccct tgggccgcct   2940
ccccgcatcg gtaccgtcga ccctagagct cgctgatcag cctcgactgt gccttctagt   3000
tgccagccat ctgttgtttg cccctccccc gtgccttcct tgaccctgga aggtgccact   3060
cccactgtcc tttcctaata aaatgaggaa attgcatcgc attgtctgag taggtgtcat   3120
tctattctgg ggggtggggt ggggcaggac agcaagggg aggattggga agacaatagc   3180
aggcatgctg gggaatctag anngtttaaa catttaaata ggaaccccta gtgatggagt   3240
tggccactcc ctctctgcgc gctcgctcgc tcactgaggc cgggcgacca aggtcgccc   3300 gacgcccggg ctttgcccgg gcggcctcag tgagcgagcg agcgcgcaga gagtatacat   3360
cgatgtgagt tcgcgggtgg ctgggggggcc ctgggctgcg accgccccg aaccgcgtct   3420 acgagccttg cgggctccgg gtctttgcag tcgtatgggg gcagggtagc tgttccccgc   3480
aaggagagct caaggtcagc gctcggacct ggcggagccc cgcacccagg ctgtggcgcc   3540
ctgtgcagct ccgccttgc ggcgccatct gcccggagcc tccttcccct agtccccaga   3600
aacaggaggt ccctactccc gcccgagatc ccgaccccga ccctaggtg ggggacgctt   3660 tctttccttt cgcgctctgc ggggtcacgt gtcgcagagg agcccctccc ccacggcctc   3720
cggcaccgca ggccccggga tgctagtgcg cagcgggtgc atccctgtcc ggatgctgcg   3780
```

```
cctgcggtag agcggccgcc atgttgcaac cgggaaggaa atgaatgggc agccgttagg    3840
aaagcctgcc ggtgactaac cctgcgctcc tgcctcgatg ggtggagtcg cgtgtggcgg    3900
ggaagtcagg tggagcgagg ctagctggcc cgatttctcc tccgggtgat gcttttccta    3960
gattattctc tggtaaatca aagaagtggg tttatggagg tcctcttgtg tcccctcccc    4020
gcagaggtgt ggtggctgtg gcatggtgcc aagccgggag aagctgagtc atgggtagtt    4080
ggaaaaggac atttccaccg caaaatggcc cctctggtgg tggcccccttc ctgcagcgcc    4140 ggctcacctc acggcccccgc ccttcccctg ccagcctagc gttgacccga ccccaaaggc    4200
caggctgtaa atgtcaccgg gaggattggg tgtctgggcg cctcggggaa cctgcccttc    4260
tccccattcc gtcttccgga aaccagatct cccaccgcac cctggtctga ggttaaatat    4320
agctgctgac ctttctgtag ctgggggcct gggctgggc tctctcccat cccttctccc    4380
cacacacatg cacttacctg tgctcccact cctgatttct ggaaaagagc taggaaggac    4440
aggcaacttg gcaaatcaaa gccctgggac taggggtta aatacagct tcccctcttc    4500 ccacccgccc cagtctctgt ccctttgta ggagggactt agagaagggg tgggcttgcc    4560
ctgtccagtt aatttctgac ctttactcct gcccctttgag tttgatgatg ctgagtgtac    4620
aagcgttttc tccctaaagg gtgcagctga gctaggcagc agcaagcatt cctggggtgg    4680
catagtgggg tggtgaatac catgtacaaa gcttgtgccc agactgtggg tggcagtgcc    4740
ccacatggcc gcttctcctg gaagggcttc gtatgactgg gggtgttggg cagccctgga    4800
gccttcagtt gcagccatgc cttaagccag gccagcctgg cagggaagct caagggagat    4860
aaaattcaac ctcttgggcc ctcctggggg taaggagatg ctgcattcgc cctcttaatg    4920
gggaggtggc ctagggctgc tcacatattc tggaggagcc tcccctcctc atgccttctt    4980
gcctcttgtc tcttaggcat gcaaaagagt cgaataaggg cgacacaaaa tttattctaa    5040
atgcataata aatactgata acatcttata gtttgtatta tattttgtat tatcgttgac    5100
atgtataatt ttgatatcaa aaactgattt tccctttatt atttttcgaga tttattttct    5160 taattctctt taacaaacta gaaatattgt atatacaaaa aatcataaat aatagatgaa    5220
tagtttaatt ataggtgttc atcaatcgaa aaagcaacgt atcttattta aagtgcgttg    5280
cttttttctc atttataagg ttaaataatt ctcatatatc aagcaaagtg acaggcgccc    5340
ttaaatattc tgacaaatgc tcttttcccta aactcccccc ataaaaaaac ccgccgaagc    5400 gggttttttac gttatttgcg gattaacgat tactcgttat cagaaccgcc caggggggccc    5460 gagcttaaga ctggccgtcg ttttacaaca cagaaagagt tgtagaaac gcaaaaaggc    5520 catccgtcag gggccttctg cttagtttga tgcctggcag ttccctactc tcgccttccg    5580
cttcctcgct cactgactcg ctgcgctcgg tcgttcggct gcggcgagcg gtatcagctc    5640
actcaaaggc ggtaatacgg ttatccacag aatcagggga taacgcagga aagaacatgt    5700
gagcaaaagg ccagcaaaag gccaggaacc gtaaaaaggc cgcgttgctg gcgtttttcc    5760
ataggctccg cccccctgac gagcatcaca aaaatcgacg ctcaagtcag aggtggcgaa    5820
acccgacagg actataaaga taccaggcgt ttccccctgg aagctccctc gtgcgctctc    5880
ctgttccgac cctgccgctt accggatacc tgtccgcctt tctcccttcg ggaagcgtgg    5940
cgctttctca tagctcacgc tgtaggtatc tcagttcggt gtaggtcgtt cgctccaagc    6000
tgggctgtgt gcacgaaccc cccgttcagc ccgaccgctg cgccttatcc ggtaactatc    6060
gtcttgagtc caacccggta agacacgact tatcgccact ggcagcagcc actggtaaca    6120
```

```
ggattagcag agcgaggtat gtaggcggtg ctacagagtt cttgaagtgg tgggctaact    6180
acggctacac tagaagaaca gtatttggta tctgcgctct gctgaagcca gttaccttcg    6240
gaaaaagagt tggtagctct tgatccggca aacaaaccac cgctggtagc ggtggttttt    6300
ttgtttgcaa gcagcagatt acgcgcagaa aaaaaggatc tcaagaagat cctttgatct    6360
tttctacggg gtctgacgct cagtggaacg acgcgcgcgt aactcacgtt aagggatttt    6420
ggtcatgagc ttgcgccgtc ccgtcaagtc agcgtaatgc tctgcttagg tggcggtact    6480
tgggtcgata tcaaagtgca tcacttcttc ccgtatgccc aactttgtat agagagccac    6540
tgcgggatcg tcaccgtaat ctgcttgcac gtagatcaca taagcaccaa gcgcgttggc    6600
ctcatgcttg aggagattga tgagcgcggt ggcaatgccc tgcctccggt gctcgccgga    6660
gactgcgaga tcatagatat agatctcact acgcggctgc tcaaacttgg gcagaacgta    6720
agccgcgaga gcgccaacaa ccgcttcttg gtcgaaggca gcaagcgcga tgaatgtctt    6780
actacggagc aagttcccga ggtaatcgga gtccggctga tgttgggagt aggtggctac    6840
gtcaccgaac tcacgaccga aaagatcaag agcagcccgc atggatttga cttggtcagg    6900
gccgagccta catgtgcgaa tgatgcccat acttgagcca cctaactttg ttttagggcg    6960
actgccctgc tgcgtaacat cgttgctgct ccataacatc aaacatcgac ccacggcgta    7020
acgcgcttgc tgcttggatg cccgaggcat agactgtaca aaaaaacagt cataacaagc    7080
catgaaaacc gccactgcgc cgttaccacc gctgcgttcg gtcaaggttc tggaccagtt    7140
gcgtgagcgc atttttttt cctcctcggc gtttacgccc cgccctgcca ctcatcgcag    7200
tactgttgta attcattaag cattctgccg acatggaagc catcacagac ggcatgatga    7260
acctgaatcg ccagcggcat cagcaccttg tcgccttgcg tataatattt gcccatagtg    7320
aaaacggggg cgaagaagtt gtccatattg gccacgttta atcaaaaact ggtgaaactc    7380
acccagggat tggcgctgac gaaaaacata ttctcaataa accctttagg gaaataggcc    7440
aggttttcac cgtaacacgc cacatcttgc gaatatatgt gtagaaactg ccggaaatcg    7500
tcgtgtgcac tcatggaaaa cggtgtaaca agggtgaaca ctatcccata tcaccagctc    7560
accgtctttc attgccatac ggaactccgg atgagcattc atcaggcggg caagaatgtg    7620
aataaaggcc ggataaaact tgtgcttatt tttctttacg gtctttaaaa aggccgtaat    7680
atccagctga acggtctggt tataggtaca ttgagcaact gactgaaatg cctcaaaatg    7740
ttctttacga tgccattggg atatatcaac ggtggtatat ccagtgattt ttttctccat    7800
ttttttttcc tcctttagaa aaactcatcg agcatcaaat gaaactgcaa tttattcata    7860
tcaggattat caataccata ttttgaaaa agccgtttct gtaatgaagg agaaaactca    7920
ccgaggcagt tccataggat ggcaagatcc tggtatcggt ctgcgattcc gactcgtcca    7980
acatcaatac aacctattaa tttcccctcg tcaaaaataa ggttatcaag tgagaaatca    8040
ccatgagtga cgactgaatc cggtgagaat ggcaaaagtt tatgcatttc tttccagact    8100
tgttcaacag gccagccatt acgctcgtca tcaaaatcac tcgcatcaac caaaccgtta    8160
ttcattcgtg attgcgcctg agcgaggcga atacgcgat cgctgttaaa aggacaatta    8220
caaacaggaa tcgagtgcaa ccggcgcagg aacactgcca gcgcatcaac aatatttca    8280
cctgaatcag gatattcttc taatacctgg aacgctgttt ttccggggat cgcagtggtg    8340
agtaaccatg catcatcagg agtacggata aaatgcttga tggtcggaag tggcataaat    8400
tccgtcagcc agtttagtct gaccatctca tctgtaacat cattggcaac gctacctttg    8460
ccatgtttca gaaacaactc tggcgcatcg ggcttcccat acaagcgata gattgtcgca    8520
```

| | |
|---|---|
| cctgattgcc cgacattatc gcgagcccat ttatacccat ataaatcagc atccatgttg | 8580 |
| gaatttaatc gcggcctcga cgtttcccgt tgaatatggc tcattttttt ttcctccttt | 8640 |
| accaatgctt aatcagtgag gcacctatct cagcgatctg tctatttcgt tcatccatag | 8700 |
| ttgcctgact ccccgtcgtg tagataacta cgatacggga gggcttacca tctggcccca | 8760 |
| gcgctgcgat gataccgcga gaaccacgct caccggctcc ggatttatca gcaataaacc | 8820 |
| agccagccgg aagggccgag cgcagaagtg gtcctgcaac tttatccgcc tccatccagt | 8880 |
| ctattaattg ttgccgggaa gctagagtaa gtagttcgcc agttaatagt ttgcgcaacg | 8940 |
| ttgttgccat cgctacaggc atcgtggtgt cacgctcgtc gtttggtatg gcttcattca | 9000 |
| gctccggttc ccaacgatca aggcgagtta catgatcccc catgttgtgc acgttgtcag | 9060 |
| aagtaagttg gccgcagtgt tatcactcat ggttatggca gcactgcata attctcttac | 9120 |
| tgtcatgcca tccgtaagat gcttttctgt gactggtgag tactcaacca agtcattctg | 9180 |
| agaatagtgt atgcggcgac cgagttgctc ttgcccggcg tcaatacggg ataataccgc | 9240 |
| gccacatagc agaactttaa aagtgctcat cattggaaaa cgttcttcgg ggcgaaaact | 9300 |
| ctcaaggatc ttaccgctgt tgagatccag ttcgatgtaa cccactcgtg cacccaactg | 9360 |
| atcttcagca tcttttactt tcaccagcgt ttctgggtga gcaaaaacag gaaggcaaaa | 9420 |
| tgccgcaaaa aagggaataa gggcgacacg gaaatgttga atactcatat tcttcctttt | 9480 |
| tcaatattat tgaagcattt atcagggtta ttgtctcatg agcggataca tatttgaatg | 9540 |
| tatttagaaa aataaacaaa tagggggtcag tgttacaacc aattaaccaa ttctgaacat | 9600 |
| tatcgcgagc ccatttatac ctgaatatgg ctcataacac cccttgtttg cctggcggca | 9660 |
| gtagcgcggt ggtcccacct gacccccatgc cgaactcaga agtgaaacgc cgtagcgccg | 9720 |
| atggtagtgt ggggactccc catgcgagag tagggaactg ccaggcatca aataaaacga | 9780 |
| aaggctcagt cgaaagactg ggcctttcgc ccgggctaat tgaggggtgt cgcccttatt | 9840 |
| cgactcgggg ctcgag | 9856 |

<210> SEQ ID NO 19
<211> LENGTH: 10970
<212> TYPE: DNA
<213> ORGANISM: Homo sapiens
<220> FEATURE:
<221> NAME/KEY: misc_feature
<222> LOCATION: (4316)..(4317)
<223> OTHER INFORMATION: n is a, c, g, or t

<400> SEQUENCE: 19

| | |
|---|---|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct ttaattaaac gcgtggggga ggctgctggt gaatattaac caaggtcacc | 180 |
| ccagttatcg gaggagcaaa caggggctaa gtccaccggg ggaggctgct ggtgaatatt | 240 |
| aaccaaggtc accccagtta tcggaggagc aaacaggggc taagtccacc ggggaggct | 300 |
| gctggtgaat attaaccaag gtcaccccag ttatcggagg agcaaacagg ggctaagtcc | 360 |
| acactagtaa atgacctatt aagaatattt catagaacga atgttccgat gctctaatct | 420 |
| ctctagacaa ggttcatatt tgtatgggtt acttattctc tctttgttga ctaagtcaat | 480 |
| aatcagaatc agcaggtttg cagtcagatt ggcaggaata gcagcctag ctcaggagaa | 540 |
| gtgagtataa aagccccagg ctgggagcag ccatcacaga agtccactca ttcttggcag | 600 |

```
gccgcggcta aggtaagttg gcgccgttta agggatggtt ggttggtggg gtattaatgt      660
ttaattacct tttttacagg cctgggcgcg ccgccaccat gccgccaccc cggaccggcc      720
gaggccttct ctggctgggt ctggttctga gctccgtctg cgtcgccctc ggatccgaaa      780
cgcaggccaa ctcgaccaca gatgctctga acgttcttct catcatcgtg gatgacctgc      840
gccctccct gggctgttat ggggataagc tggtgaggtc cccaaatatt gaccaactgg       900
catcccacag cctcctcttc cagaatgcct ttgcgcagca agcagtgtgc gccccgagcc      960
gcgtttcttt cctcactggc aggagacctg acaccacccg cctgtacgac ttcaactcct     1020
actggagggt gcacgctgga aacttctcca ccatccccca gtacttcaag gagaatggct     1080
atgtgaccat gtcggtggga aaagtctttc accctgggat atcttctaac cataccgatg     1140
attctccgta tagctggtct tttccacctt atcatccttc ctctgagaag tatgaaaaca     1200
ctaagacatg tcgagggcca gatggagaac tccatgccaa cctgctttgc cctgtggatg     1260
tgctggatgt tcccgagggc accttgcctg acaaacagag cactgagcaa gccatacagt     1320
tgttggaaaa gatgaaaacg tcagccagtc ctttcttcct ggccgttggg tatcataagc     1380
cacacatccc cttcagatac cccaaggaat tcagaagtt gtatcccttg gagaacatca      1440
ccctggcccc cgatcccgag gtccctgatg cctaccccc tgtggcctac aaccctggaa      1500
tggacatcag gcaacgggaa gacgtccaag ccttaaacat cagtgtgccg tatggtccaa     1560
ttcctgtgga ctttcagcgg aaaatccgcc agagctactt gcctctgtg tcatatttgg      1620
atacacaggt cggccgcctc ttgagtgctt tggacgatct tcagctggcc aacagcacca     1680
tcattgcatt tacctcggat catgggtggg ctctaggtga acatggagaa tgggccaaat     1740
acagcaattt tgatgttgct acccatgttc ccctgatatt ctatgttcct ggaaggacgg     1800
cttcacttcc ggaggcaggc gagaagcttt tcccttacct cgaccctttt gattccgcct     1860
cacagttgat ggagccaggc aggcaatcca tggaccttgt ggaacttgtg tctctttttc     1920
ccacgctggc tggacttgca ggactgcagg ttccacctcg ctgccccgtt ccttcatttc     1980
acgttgagct gtgcagagaa ggcaagaacc ttctgaagca ttttcgattc cgtgacttgg     2040
aagaggatcc gtacctccct ggtaatcccc gtgaactgat tgcctatagc cagtatcccc     2100
ggccttcaga catccctcag tggaattctg acaagccgag tttaaaagat ataaagatca     2160
tgggctattc catacgcacc atagactata ggtatactgt gtgggttggc ttcaatcctg     2220
atgaatttct agctaacttt tctgacatcc atgcagggga actgtatttt gtggattctg     2280
acccattgca ggatcacaat atgtataatg attcccaagg tggagatctt ttccagttgt     2340
tgatgccttg acaattggcc cctctccctc ccccccccct aacgttactg gccgaagccg     2400
cttggaataa ggccggtgtg cgtttgtcta tatgttattt tccaccatat tgccgtcttt     2460
tggcaatgtg agggcccgga aacctggccc tgtcttcttg acgagcattc ctagggtct     2520
ttcccctctc gccaaaggaa tgcaaggtct gttgaatgtc gtgaaggaag cagttcctct     2580
ggaagcttct tgaagacaaa caacgtctgt agcgaccctt gcaggcagc ggaaccccc      2640
acctggcgac aggtgcctct gcggccaaaa gccacgtgta agatacac ctgcaaaggc      2700
ggcacaaccc cagtgccacg ttgtgagttg atagttgtg gaaagagtca atggctcac      2760
ctcaagcgta ttcaacaagg ggctgaagga tgcccagaag gtaccccatt gtatgggatc     2820
tgatctgggg cctcggtgca catgctttac atgtgtttag tcgaggttaa aaaacgtcta     2880
ggcccccga accacgggga cgtggttttc ctttgaaaaa cacgatgata atcatatggc     2940
caccatggct gcgcccgcac tagggctggt gtgtggacgt tgccctgagc tgggtctcgt     3000
```

```
cctcttgctg ctgctgctct cgctgctgtg tggagcggca gggagccagg aggccgggac    3060
cggtgcgggc gcggggtccc ttgcgggttc ttgcggctgc ggcacgcccc agcggcctgg    3120
cgcccatggc agttcggcag ccgctcaccg atactcgcgg gaggctaacg ctccgggccc    3180
cgtacccgga gagcggcaac tcgcgcactc aaagatggtc cccatccctg ctggagtatt    3240
tacaatgggc acagatgatc ctcagataaa gcaggatggg gaagcacctg cgaggagagt    3300
tactattgat gccttttaca tggatgccta tgaagtcagt aatactgaat tgagaagtt     3360 tgtgaactca actggctatt tgacagaggc tgagaagttt ggcgactcct ttgtctttga    3420
aggcatgttg agtgagcaag tgaagaccaa tattcaacag gcagttgcag ctgctccctg    3480
gtggttacct gtgaaaggcg ctaactggag acacccagaa gggcctgact ctactattct    3540
gcacaggccg gatcatccag ttctccatgt gtcctggaat gatgcggttg cctactgcac    3600
ttgggcaggg aagcggctgc ccacggaagc tgagtgggaa tacagctgtc gaggaggcct    3660
gcataataga cttttcccct ggggcaacaa actgcagccc aaaggccagc attatgccaa    3720
catttggcag ggcgagtttc cggtgaccaa cactggtgag gatggcttcc aaggaactgc    3780
gcctgttgat gccttccctc ccaatggtta tggcttatac aacatagtgg ggaacgcatg    3840
ggaatggact tcagactggt ggactgttca tcattctgtt gaagaaacgc ttaacccaaa    3900
aggtccccct tctgggaaag accgagtgaa gaaggtgga tcctacatgt gccataggtc     3960
ttattgttac aggtatcgct gtgctgctcg gagccagaac acacctgata gctctgcttc    4020
gaatctggga ttccgctgtg cagccgaccg cctgcccact atggactgag tcgaccctag    4080
agctcgctga tcagcctcga ctgtgccttc tagttgccag ccatctgttg tttgcccctc    4140
ccccgtgcct tccttgaccc tggaaggtgc cactcccact gtcctttcct aataaaatga    4200
ggaaattgca tcgcattgtc tgagtaggtg tcattctatt ctgggggtg gggtggggca     4260 ggacagcaag gggaggatt gggaagacaa tagcaggcat gctggggaat ctaganngtt     4320
taaacattta aataggaacc cctagtgatg gagttggcca ctccctctct gcgcgctcgc    4380
tcgctcactg aggccgggcg accaaaggtc gcccgacgcc cgggctttgc ccgggcggcc    4440
tcagtgagcg agcgagcgcg cagagagtat acatcgatgt gagttcgcgg gtggctgggg    4500
ggccctgggc tgcgaccgcc cccgaaccgc gtctacgagc cttgcgggct ccgggtcttt    4560
gcagtcgtat gggggcaggg tagctgttcc ccgcaaggag agctcaaggt cagcgctcgg    4620
acctggcgga gccccgcacc caggctgtgg cgccctgtgc agctccgccc ttgcggcgcc    4680
atctgcccga gcctccttc ccctagtccc cagaaacagg aggtccctac tcccgcccga     4740
gatcccgacc cggacccta ggtgggggac gctttctttc ctttcgcgct ctgcggggtc     4800
acgtgtcgca gaggagcccc tcccccacgg cctccggcac cgcaggcccc gggatgctag    4860
tgcgcagcgg gtgcatccct gtccggatgc tgcgcctgcg gtagagcggc cgccatgttg    4920
caaccgggaa ggaaatgaat gggcagccgt taggaaagcc tgccggtgac taaccctgcg    4980
ctcctgcctc gatgggtgga gtcgcgtgtg gcggggaagt caggtggagc gaggctagct    5040
ggcccgattt ctcctccggg tgatgctttt cctagattat tctctggtaa atcaaagaag    5100
tgggtttatg gaggtcctct tgtgtcccct ccccgcagag gtgtggtggc tgtggcatgg    5160
tgccaagccg ggagaagctg agtcatgggt agttggaaaa ggacatttcc accgcaaaat    5220
ggcccctctg gtggtggccc cttcctgcag cgccggctca cctcacgccc cgcccttcc     5280 cctgccagcc tagcgttgac ccgaccccaa aggccaggct gtaaatgtca ccgggaggat    5340
```

```
tgggtgtctg gcgcctcgg ggaacctgcc cttctcccca ttccgtcttc cggaaaccag    5400
atctcccacc gcaccctggt ctgaggttaa atatagctgc tgacctttct gtagctgggg    5460
gcctgggctg gggctctctc ccatcccttc tccccacaca catgcactta cctgtgctcc    5520
cactcctgat ttctggaaaa gagctaggaa ggacaggcaa cttggcaaat caaagccctg    5580
ggactagggg gttaaaatac agcttcccct cttcccaccc gccccagtct ctgtcccttt    5640
tgtaggaggg acttagagaa ggggtgggct tgccctgtcc agttaatttc tgaccttttac   5700 tcctgccctt tgagtttgat gatgctgagt gtacaagcgt tttctcccta aagggtgcag    5760
ctgagctagg cagcagcaag cattcctggg gtggcatagt ggggtggtga ataccatgta    5820
caaagcttgt gcccagactg tgggtggcag tgccccacat ggccgcttct cctggaaggg    5880
cttcgtatga ctgggggtgt tgggcagccc tggagcctcc agttgcagcc atgccttaag    5940
ccaggccagc ctggcaggga agctcaaggg agataaaatt caacctcttg ggccctcctg    6000
ggggtaagga gatgctgcat tcgccctctt aatgggagg tggcctaggg ctgctcacat     6060
attctggagg agcctcccct cctcatgcct tcttgcctct tgtctcttag gcatgcaaaa    6120
gagtcgaata agggcgacac aaaatttatt ctaaatgcat aataaatact gataacatct    6180
tatagtttgt attatattt gtattatcgt tgacatgtat aattttgata tcaaaaactg     6240
attttccctt tattattttc gagatttatt ttcttaattc tctttaacaa actagaaata    6300
ttgtatatac aaaaaatcat aaataataga tgaatagttt aattataggt gttcatcaat    6360
cgaaaaagca acgtatctta tttaaagtgc gttgcttttt tctcatttat aaggttaaat    6420
aattctcata tatcaagcaa agtgacaggc gcccttaaat attctgacaa atgctctttc    6480
cctaaactcc ccccataaaa aaacccgccg aagcgggttt ttacgttatt tgcggattaa    6540
cgattactcg ttatcagaac cgcccagggg gcccgagctc aagactggcc gtcgttttac    6600
aacacagaaa gagtttgtag aaacgcaaaa aggccatccg tcagggggcct tctgcttagt   6660 ttgatgcctg gcagttccct actctcgcct tccgcttcct cgctcactga ctcgctgcgc    6720
tcggtcgttc ggctgcggcg agcggtatca gctcactcaa aggcggtaat acggttatcc    6780
acagaatcag gggataacgc aggaaagaac atgtgagcaa aaggccagca aaaggccagg    6840
aaccgtaaaa aggccgcgtt gctggcgttt ttccataggc tccgcccccc tgacgagcat    6900
cacaaaaatc gacgctcaag tcagaggtgg cgaaacccga caggactata aagataccag    6960
gcgtttcccc ctggaagctc cctcgtgcgc tctcctgttc cgaccctgcc gcttaccgga    7020
tacctgtccg cctttctccc ttcgggaagc gtggcgcttt ctcatagctc acgctgtagg    7080
tatctcagtt cggtgtaggt cgttcgctcc aagctgggct gtgtgcacga accccccgtt    7140
cagcccgacc gctgcgcctt atccggtaac tatcgtcttg agtccaaccc ggtaagacac    7200
gacttatcgc cactggcagc agccactggt aacaggatta gcagagcgag gtatgtaggc    7260
ggtgctacag agttcttgaa gtggtgggct aactacggct acactagaag aacagtattt    7320
ggtatctgcg ctctgctgaa gccagttacc ttcggaaaaa gagttggtag ctcttgatcc    7380
ggcaaacaaa ccaccgctgg tagcggtggt ttttttgttt gcaagcagca gattacgcgc    7440
agaaaaaaag gatctcaaga agatcctttg atcttttcta cggggtctga cgctcagtgg    7500
aacgacgcgc gcgtaactca cgttaaggga ttttggtcat gagcttgcgc cgtcccgtca    7560
agtcagcgta atgctctgct taggtggcgg tacttgggtc gatatcaaag tgcatcactt    7620
cttcccgtat gcccaacttt gtatagagag ccactgcggg atcgtcaccg taatctgctt    7680
gcacgtagat cacataagca ccaagcgcgt tggcctcatg cttgaggaga ttgatgagcg    7740
```

```
cggtggcaat gccctgcctc cggtgctcgc cggagactgc gagatcatag atatagatct    7800
cactacgcgg ctgctcaaac ttgggcagaa cgtaagccgc gagagcgcca acaaccgctt    7860
cttggtcgaa ggcagcaagc gcgatgaatg tcttactacg gagcaagttc ccgaggtaat    7920
cggagtccgg ctgatgttgg gagtaggtgg ctacgtcacc gaactcacga ccgaaaagat    7980
caagagcagc ccgcatggat ttgacttggt cagggccgag cctacatgtg cgaatgatgc    8040
ccatacttga gccacctaac tttgttttag ggcgactgcc ctgctgcgta acatcgttgc    8100
tgctccataa catcaaacat cgacccacgg cgtaacgcgc ttgctgcttg gatgcccgag    8160
gcatagactg tacaaaaaaa cagtcataac aagccatgaa aaccgccact gcgccgttac    8220
caccgctgcg ttcggtcaag gttctggacc agttgcgtga gcgcattttt ttttcctcct    8280
cggcgtttac gccccgccct gccactcatc gcagtactgt tgtaattcat taagcattct    8340
gccgacatgg aagccatcac agacggcatg atgaacctga atcgccagcg gcatcagcac    8400
cttgtcgcct tgcgtataat atttgcccat agtgaaaacg ggggcgaaga agttgtccat    8460
attggccacg tttaaatcaa aactggtgaa actcacccag ggattggcgc tgacgaaaaa    8520
catattctca ataaaccctt tagggaaata ggccaggttt tcaccgtaac acgccacatc    8580
ttgcgaatat atgtgtagaa actgccggaa atcgtcgtgt gcactcatgg aaaacggtgt    8640
aacaagggtg aacactatcc catatccacca gctcaccgtc tttcattgcc atacggaact    8700
ccggatgagc attcatcagg cgggcaagaa tgtgaataaa ggccggataa aacttgtgct    8760
tatttttctt tacggtcttt aaaaaggccg taatatccag ctgaacggtc tggttatagg    8820
tacattgagc aactgactga aatgcctcaa aatgttcttt acgatgccat tgggatatat    8880
caacggtggt atatccagtg atttttttct ccatttttt ttcctccttt agaaaaactc    8940
atcgagcatc aaatgaaact gcaatttatt catatcagga ttatcaatac catattttg    9000 aaaaagccgt ttctgtaatg aaggagaaaa ctcaccgagg cagttccata ggatggcaag    9060
atcctggtat cggtctgcga ttccgactcg tccaacatca atacaaccta ttaatttccc    9120
ctcgtcaaaa ataaggttat caagtgagaa atcaccatga gtgacgactg aatccggtga    9180
gaatggcaaa agtttatgca tttctttcca gacttgttca acaggccagc cattacgctc    9240
gtcatcaaaa tcactcgcat caaccaaacc gttattcatt cgtgattgcg cctgagcgag    9300
gcgaaatacg cgatcgctgt taaaaggaca attacaaaca ggaatcgagt gcaaccggcg    9360
caggaacact gccagcgcat caacaatatt ttcacctgaa tcaggatatt cttctaatac    9420
ctggaacgct gtttttccgg ggatcgcagt ggtgagtaac catgcatcat caggagtacg    9480
gataaaatgc ttgatggtcg gaagtggcat aaattccgtc agccagttta gtctgaccat    9540
ctcatctgta acatcattgg caacgctacc tttgccatgt tcagaaaca actctggcgc    9600 atcgggcttc ccatacaagc gatagattgt cgcacctgat tgcccgacat tatcgcgagc    9660
ccatttatac ccatataaat cagcatccat gttggaattt aatcgcggcc tcgacgtttc    9720
ccgttgaata tggctcattt ttttttcctc ctttaccaat gcttaatcag tgaggcacct    9780
atctcagcga tctgtctatt tcgttcatcc atagttgcct gactccccgt cgtgtagata    9840
actacgatac gggagggctt accatctggc cccagcgctg cgatgatacc gcgagaacca    9900
cgctcaccgg ctccggattt atcagcaata aaccagccag ccggaagggc cgagcgcaga    9960
agtggtcctg caactttatc cgcctccatc cagtctatta attgttgccg ggaagctaga    10020
gtaagtagtt cgccagttaa tagtttgcgc aacgttgttg ccatcgctac aggcatcgtg    10080
```

```
gtgtcacgct cgtcgtttgg tatggcttca ttcagctccg gttcccaacg atcaaggcga    10140
gttacatgat cccccatgtt gtgcacgttg tcagaagtaa gttggccgca gtgttatcac    10200
tcatggttat ggcagcactg cataattctc ttactgtcat gccatccgta agatgctttt    10260
ctgtgactgg tgagtactca accaagtcat tctgagaata gtgtatgcgg cgaccgagtt    10320
gctcttgccc ggcgtcaata cgggataata ccgcgccaca tagcagaact ttaaaagtgc    10380
tcatcattgg aaaacgttct tcggggcgaa aactctcaag gatcttaccg ctgttgagat    10440
ccagttcgat gtaacccact cgtgcaccca actgatcttc agcatctttt actttcacca    10500
gcgtttctgg gtgagcaaaa acaggaaggc aaaatgccgc aaaaaaggga ataagggcga    10560
cacggaaatg ttgaatactc atattcttcc ttttcaata ttattgaagc atttatcagg    10620
gttattgtct catgagcgga tacatatttg aatgtattta aaaaataaa caaatagggg    10680 tcagtgttac aaccaattaa ccaattctga acattatcgc gagcccattt atacctgaat    10740
atggctcata cacccttg tttgcctggc ggcagtagcg cggtggtccc acctgacccc    10800
atgccgaact cagaagtgaa acgccgtagc gccgatggta gtgtggggac tccccatgcg    10860
agagtaggga actgccaggc atcaaataaa acgaaaggct cagtcgaaag actgggcctt    10920
tcgccccggg taattgaggg gtgtcgccct tattcgactc ggggctcgag              10970

<210> SEQ ID NO 20
<211> LENGTH: 10970
<212> TYPE: DNA
<213> ORGANISM: Homo sapiens
<220> FEATURE:
<221> NAME/KEY: misc_feature
<222> LOCATION: (4316)..(4317)
<223> OTHER INFORMATION: n is a, c, g, or t

<400> SEQUENCE: 20
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct ttaattaaac gcgtggggga ggctgctggt gaatattaac caaggtcacc     180
ccagttatcg gaggagcaaa caggggctaa gtccaccggg ggaggctgct ggtgaatatt     240
aaccaaggtc accccagtta tcggaggagc aaacaggggc taagtccacc ggggaggct     300 gctggtgaat attaaccaag gtcacccag ttatcggagg agcaaacagg ggctaagtcc     360
acactagtaa atgacctatt aagaatattt catagaacga atgttccgat gctctaatct     420
ctctagacaa ggttcatatt tgtatgggtt acttattctc tctttgttga ctaagtcaat     480
aatcagaatc agcaggtttg cagtcagatt ggcagggata agcagcctag ctcaggagaa     540
gtgagtataa agcccccagg ctgggagcag ccatcacaga agtccactca ttcttggcag     600
gccgcggcta aggtaagttg gcgccgttta agggatggtt ggttggtggg gtattaatgt     660 ttaattaccct ttttttacagg cctgggcgcg ccgccaccat gccaccacct aggacaggca     720
ggggcctgct ttggcttgga ctggtgctga gctctgtctg tgttgccctg ggctccgaga     780
cccaagccaa ctctacaacc gatgctctca atgttctgct catcatagtg gatgacctgc     840 ggcccctctct aggctgctat ggagacaagt tggtgcggag ccccaacata gaccagctag     900
cctctcactc cctgctgttc cagaatgcct tcgcccagca agctgtgtgc gcccctctca     960
gagtgtcttt cctgaccggg agaaggcctg atacaacaag gctgtatgac tttaacagct    1020 actgagggt gcacgcaggc aacttctcca ctatccccca atacttcaag agaatggct    1080 atgtgaccat gagcgtgggc aaggtcttcc accctggaat ctcctccaac cacactgatg    1140
```

```
atagtccta ctcttggtct tttcctccct atcaccctag cagtgagaag tatgagaaca    1200
ccaaaacctg cagaggccct gatggggagc tgcatgctaa cctcctgtgt cctgtagatg    1260
tgctggacgt cccagagggc accttgccag ataagcagtc tactgagcag gctatccagc    1320
tgcttgagaa aatgaagact tctgcatctc ccttctttct ggctgttggc taccacaagc    1380
ctcacatccc cttcaggtac cctaaggagt tccaaaagct ctatcctctg gaaaacatca    1440
cacttgcccc cgatcctgag gtccctgacg gcctcccacc agtagcctac aatccttgga    1500
tggacattag gcagagagag gatgtccagg ctctgaatat ttctgtgccc tatgggccca    1560
tcccggtgga cttccagcgc aaaatcagac agtcctactt tgcctctgtg agctatctgg    1620
acacccaggt tgggaggctc ctctccgccc ttgacgacct ccagttggcc aacagcacca    1680
ttatagcctt cacctctgac cacgctggg cactgggggA acacggggag tgggctaagt    1740
actctaactt tgatgtggcc acccacgtgc ccctcatctt ttatgtgcct ggcaggactg    1800
ccagcctgcc cgaagctggg gaaaaactgt ttccatacct ggacccttt gacagtgctt    1860 ctcagctcat ggaacctggc cgtcagagca tggatctggt ggagctagtg tccctcttcc    1920
caaccttggc tggccttgct ggtctccagg tgcctcctag atgcccagtc ccctccttcc    1980
atgttgaact ctgccgtgag gggaagaatc tgctgaagca cttcagattc agagacttgg    2040
aggaggaccc ctaccttcct gggaacccca gggagttgat tgcatactcc cagtatccca    2100
ggccaagtga cattccccag tggaactccg acaaaccaag tctgaaggac atcaagatca    2160
tggggtacag catcaggacc attgactaca gatacacagt gtgggttgga tttaacccag    2220
atgagttctt ggcaaacttt tctgacatcc atgcaagtca gttgtatttt gtggacagcg    2280
accctctgca ggatcacaac atgtacaatg acagccaggg tggggacctc tttcaactcc    2340
tcatgccata gcaattggcc cctctccctc ccccccccct aacgttactg gccgaagccg    2400
cttggaataa ggccggtgtg cgtttgtcta tatgttattt tccaccatat tgccgtcttt    2460
tggcaatgtg agggcccgga aacctggccc tgtcttcttg acgagcattc ctaggggtct    2520
ttcccctctc gccaaaggaa tgcaaggtct gttgaatgtc gtgaaggaag cagttcctct    2580
ggaagcttct tgaagacaaa caacgtctgt agcgaccctt tgcaggcagc ggaacccccc    2640
acctggcgac aggtgcctct gcggccaaaa gccacgtgta taagatacac ctgcaaaggc    2700
ggcacaaccc cagtgccacg ttgtgagttg gatagttgtg gaaagagtca aatggctcac    2760
ctcaagcgta ttcaacaagg ggctgaagga tgcccagaag gtaccccatt gtatgggatc    2820
tgatctgggg cctcggtgca catgctttac atgtgtttag tcgaggttaa aaaacgtcta    2880
ggccccccga accacgggga cgtggttttc ctttgaaaaa cacgatgata atcatatggc    2940
caccatggct gctcctgccc tggggctggt gtgtggaaga tgtcctgaac tgggcctggt    3000
tctgttactg cttctgctca gcctgctctg tggtgctgcc ggcagccaag aggcaggcac    3060
tggcgctgga gctggaagcc tggctgggtc ttgtggatgt ggcacaccac agaggccagg    3120
ggctcatggc tcctctgctg cagctcatag gtacagcaga aagccaatg ctccaggccc    3180 agtgcctgga gagagacagc tggctcacag caagatggtg cccatccctg ctggggtgtt    3240
cacaatggga acagatgatc cccagatcaa gcaggatggg gaggcgcctg ccaggagggt    3300
gaccattgat gcattctata tggatgccta tgaggtgagc aatacagaat tgagaagtt    3360 tgtgaactct actggctacc tgactgaggc tgaaaaattt ggagactctt ttgtgtttga    3420
aggaatgctt agtgaacagg ttaagaccaa catccagcag gctgttgcag cagcccctg    3480
```

```
gtggttgcct gtcaagggag ctaactggag gcaccctgag ggaccagatt ctacaatcct    3540
gcatagacct gatcatcctg ttctgcatgt gtcttggaat gatgctgtgg cttactgtac    3600
ctgggcagga aaaggctgc caacagaagc tgagtgggaa tactcttgca gaggaggcct     3660
gcacaataga ctgttcccat ggggcaacaa gctgcaaccc aagggccagc actatgctaa    3720
catctggcag ggagaattcc ctgtgacaaa cacaggagag gacggcttcc agggaactgc    3780
ccctgtagat gctttccctc ctaatggcta tggcctgtat aacattgttg gcaacgcctg    3840
ggagtggact tctgattggt ggacagtgca ccactctgtt gaggagacac tgaatcctaa    3900
ggggccacct tctggaaagg atagagtgaa aagggggga agctacatgt gccacaggtc     3960
ttattgttac agatacaggt gcgctgctag gtctcagaac ccccctgata gcagtgctag    4020
caatctgggc ttcaggtgtg ccgctgacag actgcctacc atggattaag tcgaccctag    4080
agctcgctga tcagcctcga ctgtgccttc tagttgccag ccatctgttg tttgcccctc    4140
ccccgtgcct tccttgaccc tggaaggtgc cactcccact gtcctttcct aataaaatga    4200
ggaaattgca tcgcattgtc tgagtaggtg tcattctatt ctgggggtg gggtggggca     4260 ggacagcaag ggggaggatt gggaagacaa tagcaggcat gctggggaat ctaganngtt    4320
taaacattta aataggaacc cctagtgatg gagttggcca ctccctctct gcgcgctcgc    4380
tcgctcactg aggccgggcg accaaaggtc gcccgacgcc cgggctttgc ccgggcggcc    4440
tcagtgagcg agcgagcgcg cagagagtat acatcgatgt gagttcgcgg gtggctgggg    4500
ggccctgggc tgcgaccgcc ccgaaccgc gtctacgagc cttgcgggct ccgggtcttt     4560
gcagtcgtat gggggcaggg tagctgttcc ccgcaaggag agctcaaggt cagcgctcgg    4620
acctggcgga gccccgcacc caggctgtgg cgccctgtgc agctccgccc ttgcggcgcc    4680
atctgcccgg agcctccttc ccctagtccc cagaaacagg aggtccctac tcccgcccga    4740
gatcccgacc cggaccccta ggtggggac gctttctttc ctttcgcgct ctgcggggtc     4800
acgtgtcgca gaggagcccc tcccccacgg cctccggcac cgcaggcccc gggatgctag    4860
tgcgcagcgg gtgcatccct gtccggatgc tgcgcctgcg gtagagcggc cgccatgttg    4920
caaccgggaa ggaaatgaat gggcagccgt taggaaagcc tgccggtgac taaccctgcg    4980
ctcctgcctc gatgggtgga gtcgcgtgtg gcggggaagt caggtggagc gaggctagct    5040
ggcccgattt ctcctccggg tgatgctttt cctagattat tctctggtaa atcaaagaag    5100
tgggtttatg gaggtcctct gtgtcccct ccccgcagag gtgtggtggc tgtggcatgg     5160
tgccaagccg ggagaagctg agtcatgggt agttggaaaa ggacatttcc accgcaaaat    5220
ggcccctctg gtggtggccc cttcctgcag cgccggctca cctcacggcc ccgcccttcc    5280
cctgccagcc tagcgttgac ccgaccccaa aggccaggct gtaaatgtca ccgggaggat    5340
tgggtgtctg ggcgcctcgg ggaacctgcc cttctcccca ttccgtcttc cggaaaccag    5400
atctcccacc gcaccctggt ctgaggttaa atatagctgc tgacctttct gtagctgggg    5460
gcctgggctg gggctctctc ccatcccttc tccccacaca catgcactta cctgtgctcc    5520
cactcctgat ttctggaaaa gagctaggaa ggacaggcaa cttggcaaat caaagccctg    5580
ggactagggg gttaaaatac agcttcccct cttcccaccc gccccagtct ctgtcccttt    5640
tgtaggaggg acttagagaa ggggtgggct tgccctgtcc agttaatttc tgacctttac    5700
tcctgccctt tgagtttgat gatgctgagt gtacaagcgt tttctcccta aagggtgcag    5760
ctgagctagg cagcagcaag cattcctggg gtggcatagt ggggtggtga ataccatgta    5820
caaagcttgt gcccagactg tgggtggcag tgccccacat ggccgcttct cctggaaggg    5880
```

```
cttcgtatga ctgggggtgt tgggcagccc tggagccttc agttgcagcc atgccttaag   5940
ccaggccagc ctggcaggga agctcaaggg agataaaatt caacctcttg ggccctcctg   6000
ggggtaagga gatgctgcat tcgccctctt aatggggagg tggcctaggg ctgctcacat   6060
attctggagg agcctcccct cctcatgcct tcttgcctct tgtctcttag gcatgcaaaa   6120
gagtcgaata agggcgacac aaaatttatt ctaaatgcat aataaatact gataacatct   6180
tatagtttgt attatatttt gtattatcgt tgacatgtat aattttgata tcaaaaactg   6240
attttccctt tattattttc gagatttatt ttcttaattc tctttaacaa actagaaata   6300
ttgtatatac aaaaaatcat aaataataga tgaatagttt aattataggt gttcatcaat   6360
cgaaaaagca acgtatctta tttaaagtgc gttgcttttt tctcatttat aaggttaaat   6420
aattctcata tatcaagcaa agtgacaggc gcccttaaat attctgacaa atgctctttc   6480
cctaaactcc ccccataaaa aaacccgccg aagcgggttt ttacgttatt tgcggattaa   6540
cgattactcg ttatcagaac cgcccagggg gcccgagctt aagactggcc gtcgttttac   6600
aacacagaaa gagtttgtag aaacgcaaaa aggccatccg tcaggggcct tctgcttagt   6660
ttgatgcctg gcagttccct actctcgcct tccgcttcct cgctcactga ctcgctgcgc   6720
tcggtcgttc ggctgcggcg agcggtatca gctcactcaa aggcggtaat acggttatcc   6780
acagaatcag gggataacgc aggaaagaac atgtgagcaa aaggccagca aaaggccagg   6840
aaccgtaaaa aggccgcgtt gctggcgttt ttccataggc tccgcccccc tgacgagcat   6900
cacaaaaatc gacgctcaag tcagaggtgg cgaaacccga caggactata agataccag    6960
gcgtttcccc ctggaagctc cctcgtgcgc tctcctgttc cgaccctgcc gcttaccgga   7020
tacctgtccg cctttctccc ttcgggaagc gtggcgcttt ctcatagctc acgctgtagg   7080
tatctcagtt cggtgtaggt cgttcgctcc aagctgggct gtgtgcacga accccccgtt   7140
cagcccgacc gctgcgcctt atccggtaac tatcgtcttg agtccaaccc ggtaagacac   7200
gacttatcgc cactggcagc agccactggt aacaggatta gcagagcgag gtatgtaggc   7260
ggtgctacag agttcttgaa gtggtgggct aactacggct acactagaag aacagtattt   7320
ggtatctgcg ctctgctgaa gccagttacc ttcggaaaaa gagttggtag ctcttgatcc   7380
ggcaaacaaa ccaccgctgg tagcggtggt ttttttgttt gcaagcagca gattacgcgc   7440
agaaaaaaag gatctcaaga agatcctttg atcttttcta cggggtctga cgctcagtgg   7500
aacgacgcgc gcgtaactca cgttaaggga ttttggtcat gagcttgcgc cgtcccgtca   7560
agtcagcgta atgctctgct taggtggcgg tacttgggtc gatatcaaag tgcatcactt   7620
cttcccgtat gcccaacttt gtatagagag ccactgcggg atcgtcaccg taatctgctt   7680
gcacgtagat cacataagca ccaagcgcgt tggcctcatg cttgaggaga ttgatgagcg   7740
cggtggcaat gccctgcctc cggtgctcgc cggagactgc gagatcatag atatagatct   7800
cactacgcgg ctgctcaaac ttgggcagaa cgtaagccgc gagagcgcca acaaccgctt   7860
cttggtcgaa ggcagcaagc gcgatgaatg tcttactacg gagcaagttc ccgaggtaat   7920
cggagtccgg ctgatgttgg gagtaggtgg ctacgtcacc gaactcacga ccgaaaagat   7980
caagagcagc ccgcatggat ttgacttggt cagggccgag cctacatgtg cgaatgatgc   8040
ccatacttga gccacctaac tttgttttag ggcgactgcc ctgctgcgta acatcgttgc   8100
tgctccataa catcaaacat cgacccacgg cgtaacgcgc ttgctgcttg gatgcccgag   8160
gcatagactg tacaaaaaaa cagtcataac aagccatgaa aaccgccact gcgccgttac   8220
```

```
caccgctgcg ttcggtcaag gttctggacc agttgcgtga gcgcattttt ttttcctcct    8280
cggcgtttac gccccgccct gccactcatc gcagtactgt tgtaattcat taagcattct    8340
gccgacatgg aagccatcac agacggcatg atgaacctga atcgccagcg gcatcagcac    8400
cttgtcgcct tgcgtataat atttgcccat agtgaaaacg ggggcgaaga agttgtccat    8460
attggccacg tttaaatcaa aactggtgaa actcacccag ggattggcgc tgacgaaaaa    8520
catattctca ataaaccctt tagggaaata ggccaggttt tcaccgtaac acgccacatc    8580
ttgcgaatat atgtgtagaa actgccggaa atcgtcgtgt gcactcatgg aaaacggtgt    8640
aacaagggtg aacactatcc catatccacca gctcaccgtc tttcattgcc atacggaact    8700
ccggatgagc attcatcagg cgggcaagaa tgtgaataaa ggccggataa aacttgtgct    8760
tattttctt tacggtcttt aaaaaggccg taatatccag ctgaacggtc tggttatagg    8820
tacattgagc aactgactga aatgcctcaa aatgttcttt acgatgccat gggatatat    8880
caacggtggt atatccagtg atttttttct ccattttttt ttcctccttt agaaaaactc    8940
atcgagcatc aaatgaaact gcaatttatt catatcagga ttatcaatac catattttg    9000
aaaaagccgt ttctgtaatg aaggagaaaa ctcaccgagg cagttccata ggatggcaag    9060
atcctggtat cggtctgcga ttccgactcg tccaacatca atacaaccta ttaatttccc    9120
ctcgtcaaaa ataaggttat caagtgagaa atcaccatga gtgacgactg aatccggtga    9180
gaatggcaaa agtttatgca tttctttcca gacttgttca acaggccagc cattacgctc    9240
gtcatcaaaa tcactcgcat caaccaaacc gttattcatt cgtgattgcg cctgagcgag    9300
gcgaaatacg cgatcgctgt taaaaggaca attacaaaca ggaatcgagt gcaaccggcg    9360
caggaacact gccagcgcat caacaatatt ttcacctgaa tcaggatatt cttctaatac    9420
ctggaacgct gttttccgg ggatcgcagt ggtgagtaac catgcatcat caggagtacg    9480
gataaaatgc ttgatggtcg gaagtggcat aaattccgtc agccagttta gtctgaccat    9540
ctcatctgta acatcattgg caacgctacc tttgccatgt ttcagaaaca actctggcgc    9600
atcgggcttc ccatacaagc gatagattgt cgcacctgat tgcccgacat tatcgcgagc    9660
ccatttatac ccatataaat cagcatccat gttggaattt aatcgcggcc tcgacgtttc    9720
ccgttgaata tggctcattt tttttcctc ctttaccaat gcttaatcag tgaggcacct    9780
atctcagcga tctgtctatt tcgttcatcc atagttgcct gactccccgt cgtgtagata    9840
actacgatac gggagggctt accatctggc cccagcgctg cgatgatacc gcgagaacca    9900
cgctcaccgg ctccggattt atcagcaata aaccagccag ccggaagggc cgagcgcaga    9960
agtggtcctg caactttatc cgcctccatc cagtctatta attgttgccg ggaagctaga   10020
gtaagtagtt cgccagttaa tagtttgcgc aacgttgttg ccatcgctac aggcatcgtg   10080
gtgtcacgct cgtcgtttgg tatggcttca ttcagctccg gttcccaacg atcaaggcga   10140
gttacatgat cccccatgtt gtgcacgttg tcagaagtaa gttggccgca gtgttatcac   10200
tcatggttat ggcagcactg cataattctc ttactgtcat gccatccgta agatgctttt   10260
ctgtgactgg tgagtactca accaagtcat tctgagaata gtgtatgcgg cgaccgagtt   10320
gctcttgccc ggcgtcaata cgggataata ccgcgccaca tagcagaact ttaaaagtgc   10380
tcatcattgg aaaacgttct tcggggcgaa aactctcaag gatcttaccg ctgttgagat   10440
ccagttcgat gtaacccact cgtgcaccca actgatcttc agcatctttt actttcacca   10500
gcgtttctgg gtgagcaaaa acaggaaggc aaaatgccgc aaaaaaggga ataagggcga   10560
cacggaaatg ttgaatactc atattcttcc tttttcaata ttattgaagc atttatcagg   10620
```

| | | | | |
|---|---|---|---|---|
| gttattgtct | catgagcgga | tacatatttg | aatgtattta | gaaaaataaa | caaatagggg | 10680 |
| tcagtgttac | aaccaattaa | ccaattctga | acattatcgc | gagcccattt | atacctgaat | 10740 |
| atggctcata | acaccccttg | tttgcctggc | ggcagtagcg | cggtggtccc | acctgacccc | 10800 |
| atgccgaact | cagaagtgaa | acgccgtagc | gccgatggta | gtgtggggac | tccccatgcg | 10860 |
| agagtaggga | actgccaggc | atcaaataaa | acgaaaggct | cagtcgaaag | actgggcctt | 10920 |
| tcgcccgggc | taattgaggg | gtgtcgccct | tattcgactc | ggggctcgag | | 10970 |

<210> SEQ ID NO 21
<211> LENGTH: 10970
<212> TYPE: DNA
<213> ORGANISM: Homo sapiens
<220> FEATURE:
<221> NAME/KEY: misc_feature
<222> LOCATION: (4316)..(4317)
<223> OTHER INFORMATION: n is a, c, g, or t
<400> SEQUENCE: 21

| | | | | | | |
|---|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | ttaattaaac | gcgtggggga | ggctgctggt | gaatattaac | caaggtcacc | 180 |
| ccagttatcg | gaggagcaaa | caggggctaa | gtccaccggg | ggaggctgct | ggtgaatatt | 240 |
| aaccaaggtc | accccagtta | tcggaggagc | aaacaggggc | taagtccacc | ggggaggct | 300 |
| gctggtgaat | attaaccaag | gtcaccccag | ttatcggagg | agcaaacagg | ggctaagtcc | 360 |
| acactagtaa | atgacctatt | aagaatattt | catgaacga | atgttccgat | gctctaatct | 420 |
| ctctagacaa | ggttcatatt | tgtatgggtt | acttattctc | tctttgttga | ctaagtcaat | 480 |
| aatcagaatc | agcaggtttg | cagtcagatt | ggcagggata | agcagcctag | ctcaggagaa | 540 |
| gtgagtataa | aagccccagg | ctgggagcag | ccatcacaga | agtccactca | ttcttggcag | 600 |
| gccgcggcta | aggtaagttg | gcgccgttta | agggatggtt | ggttggtggg | gtattaatgt | 660 |
| ttaattacct | tttttacagg | cctgggcgcg | ccgccaccat | gccaccccc | cggaccggga | 720 |
| gaggcctctt | gtggttgggc | ctggtgctga | gcagcgtgtg | cgtggccctg | ggcagtgaga | 780 |
| cccaggctaa | ctctacaaca | gatgccttga | atgtgctgct | gatcattgtg | gatgacctga | 840 |
| ggccaagtct | gggctgctat | ggggacaaat | tggtgaggtc | ccccaacatc | gaccagttgg | 900 |
| cctcccactc | tctcctattc | caaaatgctt | tcgcccagca | ggcagtttgt | gcccctcta | 960 |
| gggtgagctt | cctcactggc | aggcgccctg | acaccactag | actgtatgac | tttaacagct | 1020 |
| attggagggt | gcacgcagga | aacttctcca | caatccctca | atacttcaag | gagaatggtt | 1080 |
| atgtgacaat | gtctgtgggc | aaggtgttcc | accctggcat | cagcagcaac | cacaccgatg | 1140 |
| actcacccta | tagttggtct | tttccccct | accatccttc | atctgagaaa | tatgaaaaca | 1200 |
| caaaaacctg | ccgaggccca | gacggggaac | tgcatgccaa | cctactctgt | cctgttgatg | 1260 |
| tactggacgt | gcccgagggc | accctccctg | ataagcagtc | cacagaacag | gccattcagc | 1320 |
| tgcttgaaaa | gatgaagacc | tccgcatccc | ccttcttctt | ggctgtcggc | taccacaagc | 1380 |
| cccatatccc | ctttagatac | cccaaggaat | tccagaaact | gtaccactg | gagaacatca | 1440 |
| cacttgctcc | tgaccctgaa | gtgcctgacg | gactgcctcc | agtggcctat | aacccttgga | 1500 |
| tggacatccg | gcagcgcgag | gatgtgcagg | ctctgaacat | tagtgtgcct | tatgggccca | 1560 |
| tccctgtgga | ctttcagagg | aagattcgcc | agtcctactt | tgcctctgta | tcctacctgg | 1620 |

-continued

```
acacacaggt gggacgcctg ctgtctgccc ttgatgatct gcaactggcc aacagcacca    1680
ttatagcttt cacatcagac catgggtggg ctcttgggga gcatggtgaa tgggctaagt    1740
actccaactt cgatgtggca acccatgtcc ctctgatctt ctatgtgcca ggaaggaccg    1800
cctctctgcc agaggcaggt gagaagctgt tccctatct ggaccttttt gactccgcca     1860
gccagctgat ggagcctggc cgacagtcta tggacctggt tgagctggtc agcctgtttc    1920
ccacactcgc tggactggct ggcctgcaag taccccacg ctgcccagtg ccctccttcc     1980
atgtggagct ttgcagggag gggaagaacc tcctcaagca cttcaggttc agggacctag    2040
aggaggatcc ttatctgcct ggaaacccca gagagcttat tgcttactcc cagtatccaa    2100
ggcctagtga cattccccaa tggaactcag acaaaccaag cctgaaagac atcaagatca    2160
tgggatactc tatcaggacc attgactaca ggtacactgt gtgggttggc ttcaacccgg    2220
atgagttcct ggctaatttc tctgacatac atgctggcga gctgtacttc gtggacagtg    2280
accccctgca ggatcacaac atgtacaatg attcccaggg gggtgacctc ttccagcttc    2340
tgatgcccta acaattggcc cctctccctc ccccccct aacgttactg gccgaagccg      2400
cttggaataa ggccggtgtg cgtttgtcta tatgttattt tccaccatat tgccgtcttt    2460
tggcaatgtg agggcccgga aacctggccc tgtcttcttg acgagcattc ctaggggtct    2520
ttcccctctc gccaaaggaa tgcaaggtct gttgaatgtc gtgaaggaag cagttcctct    2580
ggaagcttct tgaagacaaa caacgtctgt agcgaccctt tgcaggcagc ggaaccccc    2640 acctggcgac aggtgcctct gcggccaaaa gccacgtgta taagatacac ctgcaaaggc    2700
ggcacaaccc cagtgccacg ttgtgagttg gatagttgtg gaaagagtca aatggctcac    2760
ctcaagcgta ttcaacaagg ggctgaagga tgcccagaag gtaccccatt gtatgggatc    2820
tgatctgggg cctcggtgca catgctttac atgtgtttag tcgaggttaa aaaacgtcta    2880 ggcccccga accacgggga cgtggttttc ctttgaaaaa cacgatgata ataccggtgc     2940
caccatggct gcccctgctc tgggattggt ttgtggcaga tgtcctgagc ttggtctggt    3000
gctgttgctc cttctgttgt ctctgctgtg tggagcagct gggtctcagg aagctggcac    3060
aggcgctggg gctggctctc tggccgggtc atgtggctgt ggaactcccc agcggcctgg    3120
agcccatggc agctctgccg cagcacacag gtattctagg gaagccaatg ccccaggccc    3180
tgtgcctggg gagagacagc tagctcattc taagatggtg cctatcccag ccggggtttt    3240
tacaatgggc actgatgatc ctcagattaa gcaggatgga gaggcccccg ccagaagagt    3300
gaccattgat gctttctaca tggatgcata tgaagtgtcc aacacagagt ttgagaaatt    3360
tgtgaactct actggatact tgaccgaggc tgagaagttt ggagattcct ttgtctttga    3420
aggcatgctg tctgagcagg tcaagaccaa cattcagcaa gcagtggccg ctgcaccttg    3480
gtggcttcct gtgaagggcg ccaactggag acatccagag gggccagata gtaccatcct    3540
ccacagacct gatcacccag tccttcatgt ttcctggaat gatgcagttg cttactgcac    3600
ttgggccggc aagaggctcc ctactgaggc agagtggaaa tactcctgca gaggaggcct    3660
gcacaacaga ctgttcccct tggggaacaa gcttcagccc aaaggccagc actatgctaa    3720
catctggcag ggtgagtttc cagtcaccaa tacaggggag gacggattcc agggaaccgc    3780
accagtagat gccttccctc ctaatggcta tggcctgtat aatattgtgg gcaatgcatg    3840
ggagtggacc tctgactggt ggactgtgca ccactcagtg gaggaaaccc tgaaccctaa    3900
gggaccccct tcaggcaaag atagagtcaa aaagggaggg agctatatgt gtcacagatc    3960
ctattgctac agatatagat gtgcagccag gtcccagaac accccctgact cttctgctag    4020
```

```
caacctgggc tttcggtgtg ctgctgatag actgcccacc atggactaag tcgaccctag   4080
agctcgctga tcagcctcga ctgtgccttc tagttgccag ccatctgttg tttgcccctc   4140
ccccgtgcct tccttgaccc tggaaggtgc cactcccact gtcctttcct aataaaatga   4200
ggaaattgca tcgcattgtc tgagtaggtg tcattctatt ctgggggtg gggtggggca    4260 ggacagcaag ggggaggatt gggaagacaa tagcaggcat gctggggaat ctaganngtt   4320
taaacattta aataggaacc cctagtgatg gagttggcca ctccctctct gcgcgctcgc   4380
tcgctcactg aggccgggcg accaaaggtc gcccgacgcc cgggctttgc ccgggcggcc   4440
tcagtgagcg agcgagcgcg cagagagtat acatcgatgt gagttcgcgg gtggctgggg   4500
ggccctgggc tgcgaccgcc cccgaaccgc gtctacgagc cttgcgggct ccgggtcttt   4560
gcagtcgtat gggggcaggg tagctgttcc ccgcaaggag agctcaaggt cagcgctcgg   4620
acctggcgga gccccgcacc caggctgtgg cgccctgtgc agctccgccc ttgcggcgcc   4680
atctgcccgg agcctccttc ccctagtccc cagaaacagg aggtccctac tcccgcccga   4740
gatcccgacc cggaccccta ggtggggac gctttctttc ctttcgcgct ctgcggggtc    4800
acgtgtcgca gaggagcccc tcccccacgg cctccggcac cgcaggcccc gggatgctag   4860
tgcgcagcgg gtgcatccct gtccggatgc tgcgcctgcg gtagagcggc cgccatgttg   4920
caaccgggaa ggaaatgaat gggcagccgt taggaaagcc tgccggtgac taaccctgcg   4980
ctcctgcctc gatgggtgga gtcgcgtgtg gcggggaagt caggtggagc gaggctagct   5040
ggcccgattt ctcctccggg tgatgctttt cctagattat tctctggtaa atcaaagaag   5100
tgggtttatg gaggtcctct tgtgtcccct ccccgcagag gtgtggtggc tgtggcatgg   5160
tgccaagccg ggagaagctg agtcatgggt agttggaaaa ggacatttcc accgcaaaat   5220
ggcccctctg gtggtggccc cttcctgcag cgccggctca cctcacggcc ccgcccttcc   5280
cctgccagcc tagcgttgac ccgaccccaa aggccaggct gtaaatgtca ccggaggat    5340 tgggtgtctg ggcgcctcgg ggaacctgcc cttctcccca ttccgtcttc cggaaaccag   5400
atctcccacc gcaccctggt ctgaggttaa atatagctgc tgacctttct gtagctgggg   5460
gcctgggctg gggctctctc ccatcccttc tccccacaca catgcactta cctgtgctcc   5520
cactcctgat ttctggaaaa gagctaggaa ggacaggcaa cttggcaaat caaagccctg   5580
ggactagggg gttaaaatac agcttcccct cttcccaccc gccccagtct ctgtcccttt   5640
tgtaggaggg acttagagaa ggggtgggct tgccctgtcc agttaatttc tgacctttac   5700
tcctgccctt tgagtttgat gatgctgagt gtacaagcgt tttctcccta aagggtgcag   5760
ctgagctagg cagcagcaag cattcctggg gtggcatagt ggggtggtga ataccatgta   5820
caaagcttgt gcccagactg tgggtggcag tgccccacat ggccgcttct cctggaaggg   5880
cttcgtatga ctgggggtgt tgggcagccc tggagccttc agttgcagcc atgccttaag   5940
ccaggccagc ctggcaggga agctcaaggg agataaaatt caacctcttg ggccctcctg   6000
ggggtaagga gatgctgcat tcgccctctt aatggggagg tggcctaggg ctgctcacat   6060
attctggagg agcctcccct cctcatgcct tcttgcctct tgtctcttag gcatgcaaaa   6120
gagtcgaata agggcgacac aaaatttatt ctaaatgcat aataaatact gataacatct   6180
tatagtttgt attatatttt gtattatcgt tgacatgtat aattttgata tcaaaaactg   6240
attttccctt tattattttc gagatttatt ttcttaattc tctttaacaa actagaaata   6300
ttgtatatac aaaaaatcat aaataataga tgaatagttt aattataggt gttcatcaat   6360
```

```
cgaaaaagca acgtatctta tttaaagtgc gttgcttttt tctcatttat aaggttaaat    6420
aattctcata tatcaagcaa agtgacaggc gcccttaaat attctgacaa atgctctttc    6480
cctaaactcc ccccataaaa aaacccgccg aagcgggttt ttacgttatt tgcggattaa    6540
cgattactcg ttatcagaac cgcccagggg gcccgagctt aagactggcc gtcgttttac    6600
aacacagaaa gagtttgtag aaacgcaaaa aggccatccg tcaggggcct tctgcttagt    6660
ttgatgcctg gcagttccct actctcgcct tccgcttcct cgctcactga ctcgctgcgc    6720
tcggtcgttc ggctgcggcg agcggtatca gctcactcaa aggcggtaat acggttatcc    6780
acagaatcag gggataacgc aggaaagaac atgtgagcaa aaggccagca aaaggccagg    6840
aaccgtaaaa aggccgcgtt gctggcgttt ttccataggc tccgcccccc tgacgagcat    6900
cacaaaaatc gacgctcaag tcagaggtgg cgaaacccga caggactata agataccag    6960
gcgtttcccc ctggaagctc cctcgtgcgc tctcctgttc cgaccctgcc gcttaccgga    7020
tacctgtccg cctttctccc ttcgggaagc gtggcgcttt ctcatagctc acgctgtagg    7080
tatctcagtt cggtgtaggt cgttcgctcc aagctgggct gtgtgcacga accccccgtt    7140
cagcccgacc gctgcgcctt atccggtaac tatcgtcttg agtccaaccc ggtaagacac    7200
gacttatcgc cactggcagc agccactggt aacaggatta gcagagcgag gtatgtaggc    7260
ggtgctacag agttcttgaa gtggtgggct aactacggct acactagaag aacagtattt    7320
ggtatctgcg ctctgctgaa gccagttacc ttcggaaaaa gagttggtag ctcttgatcc    7380
ggcaaacaaa ccaccgctgg tagcggtggt ttttttgttt gcaagcagca gattacgcgc    7440
agaaaaaaag gatctcaaga agatcctttg atcttttcta cggggtctga cgctcagtgg    7500
aacgacgcgc gcgtaactca cgttaaggga ttttggtcat gagcttgcgc cgtcccgtca    7560
agtcagcgta atgctctgct taggtggcgg tacttgggtc gatatcaaag tgcatcactt    7620
cttcccgtat gcccaacttt gtatagagag ccactgcggg atcgtcaccg taatctgctt    7680
gcacgtagat cacataagca ccaagcgcgt tggcctcatg cttgaggaga ttgatgagcg    7740
cggtggcaat gccctgcctc cggtgctcgc cggagactgc gagatcatag atatagatct    7800
cactacgcgg ctgctcaaac ttgggcagaa cgtaagccgc gagagcgcca acaaccgctt    7860
cttggtcgaa ggcagcaagc gcgatgaatg tcttactacg gagcaagttc ccgaggtaat    7920
cggagtccgg ctgatgttgg gagtaggtgg ctacgtcacc gaactcacga ccgaaaagat    7980
caagagcagc ccgcatggat ttgacttggt cagggccgag cctacatgtg cgaatgatgc    8040
ccatacttga gccacctaac tttgttttag gcgactgcc ctgctgcgta acatcgttgc    8100
tgctccataa catcaaacat cgacccacgg cgtaacgcgc ttgctgcttg gatgcccgag    8160
gcatagactg tacaaaaaaa cagtcataac aagccatgaa aaccgccact gcgccgttac    8220
caccgctgcg ttcggtcaag gttctggacc agttgcgtga gcgcattttt ttttcctcct    8280
cggcgtttac gccccgccct gccactcatc gcagtactgt tgtaattcat taagcattct    8340
gccgacatgg aagccatcac agacggcatg atgaacctga atcgccagcg gcatcagcac    8400
cttgtcgcct tgcgtataat atttgcccat agtgaaaacg ggggcgaaga agttgtccat    8460
attggccacg tttaaatcaa aactggtgaa actcacccag ggattggcgc tgacgaaaaa    8520
catattctca ataaacccct tagggaaata ggccaggttt tcaccgtaac acgccacatc    8580
ttgcgaatat atgtgtagaa actgccggaa atcgtcgtgt gcactcatgg aaaacggtgt    8640
aacaagggtg aacactatcc catatcacca gctcaccgtc tttcattgcc atacggaact    8700
ccggatgagc attcatcagg cgggcaagaa tgtgaataaa ggccggataa aacttgtgct    8760
```

```
tatttttctt tacggtctttt aaaaaggccg taatatccag ctgaacggtc tggttatagg    8820
tacattgagc aactgactga aatgcctcaa aatgttcttt acgatgccat tgggatatat    8880
caacggtggt atatccagtg attttttct ccatttttt ttcctccttt agaaaaactc     8940
atcgagcatc aaatgaaact gcaatttatt catatcagga ttatcaatac catatttttg   9000
aaaaagccgt ttctgtaatg aaggagaaaa ctcaccgagg cagttccata ggatggcaag   9060
atcctggtat cggtctgcga ttccgactcg tccaacatca atacaaccta ttaatttccc   9120
ctcgtcaaaa ataaggttat caagtgagaa atcaccatga gtgacgactg aatccggtga   9180
gaatggcaaa agtttatgca tttctttcca gacttgttca acaggccagc cattacgctc   9240
gtcatcaaaa tcactcgcat caaccaaacc gttattcatt cgtgattgcg cctgagcgag   9300
gcgaaatacg cgatcgctgt taaaaggaca attacaaaca ggaatcgagt gcaaccggcg   9360
caggaacact gccagcgcat caacaatatt ttcacctgaa tcaggatatt cttctaatac   9420
ctggaacgct gttttccgg ggatcgcagt ggtgagtaac catgcatcat caggagtacg    9480
gataaaatgc ttgatggtcg gaagtggcat aaattccgtc agccagttta gtctgaccat   9540
ctcatctgta acatcattgg caacgctacc tttgccatgt ttcagaaaca actctggcgc   9600
atcgggcttc ccatacaagc gatagattgt cgcacctgat tgcccgacat tatcgcgagc   9660
ccatttatac ccatataaat cagcatccat gttggaattt aatcgcggcc tcgacgtttc   9720
ccgttgaata tggctcattt ttttttcctc ctttaccaat gcttaatcag tgaggcacct   9780
atctcagcga tctgtctatt tcgttcatcc atagttgcct gactccccgt cgtgtagata   9840
actacgatac gggagggctt accatctggc cccagcgctg cgatgatacc gcgagaacca   9900
cgctcaccgg ctccggattt atcagcaata aaccagccag ccggaagggc cgagcgcaga   9960
agtggtcctg caactttatc cgcctccatc cagtctatta attgttgccg ggaagctaga  10020
gtaagtagtt cgccagttaa tagtttgcgc aacgttgttg ccatcgctac aggcatcgtg  10080
gtgtcacgct cgtcgtttgg tatggcttca ttcagctccg gttcccaacg atcaaggcga  10140
gttacatgat cccccatgtt gtgcacgttg tcagaagtaa gttggccgca gtgttatcac  10200
tcatggttat ggcagcactg cataattctc ttactgtcat gccatccgta agatgctttt  10260
ctgtgactgg tgagtactca accaagtcat tctgagaata gtgtatgcgg cgaccgagtt  10320
gctcttgccc ggcgtcaata cgggataata ccgcgccaca tagcagaact ttaaaagtgc  10380
tcatcattgg aaaacgttct tcggggcgaa aactctcaag gatcttaccg ctgttgagat  10440
ccagttcgat gtaacccact cgtgcaccca actgatcttc agcatctttt actttcacca  10500
gcgtttctgg gtgagcaaaa acaggaaggc aaaatgccgc aaaaaaggga ataagggcga  10560
cacgaaaatg ttgaatactc atattcttcc tttttcaata ttattgaagc atttatcagg  10620
gttattgtct catgagcgga tacatatttg aatgtattta gaaaaataaa caaatagggg  10680
tcagtgttac aaccaattaa ccaattctga acattatcgc gagcccattt atacctgaat  10740
atggctcata cacccccttg tttgcctggc ggcagtagcg cggtggtccc acctgacccc  10800
atgccgaact cagaagtgaa acgccgtagc gccgatggta gtgtggggac tccccatgcg  10860
agagtaggga actgccaggc atcaaataaa acgaaaggct cagtcgaaag actgggcctt  10920
tcgcccgggc taattgaggg gtgtcgccct tattcgactc ggggctcgag              10970
```

<210> SEQ ID NO 22
<211> LENGTH: 8724
<212> TYPE: DNA

<213> ORGANISM: Homo sapiens
<220> FEATURE:
<221> NAME/KEY: misc_feature
<222> LOCATION: (2070)..(2071)
<223> OTHER INFORMATION: n is a, c, g, or t

<400> SEQUENCE: 22

| | | | | | |
|---|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | ttaattaaac | gcgtggggga | ggctgctggt | gaatattaac | caaggtcacc | 180 |
| ccagttatcg | gaggagcaaa | caggggctaa | gtccaccggg | ggaggctgct | ggtgaatatt | 240 |
| aaccaaggtc | accccagtta | tcggaggagc | aaacaggggc | taagtccacc | ggggaggct | 300 |
| gctggtgaat | attaaccaag | gtcaccccag | ttatcggagg | agcaaacagg | ggctaagtcc | 360 |
| acactagtaa | atgacctatt | aagaatattt | catagaacga | atgttccgat | gctctaatct | 420 |
| ctctagacaa | ggttcatatt | tgtatgggtt | acttattctc | tctttgttga | ctaagtcaat | 480 |
| aatcagaatc | agcaggtttg | cagtcagatt | ggcaggata | agcagcctag | ctcaggagaa | 540 |
| gtgagtataa | aagccccagg | ctgggagcag | ccatcacaga | agtccactca | ttcttggcag | 600 |
| gccgcggcta | aggtaagttg | gcgccgttta | agggatggtt | ggttggtggg | gtattaatgt | 660 |
| ttaattacct | tttttacagg | cctgggcgcg | ccgccaccat | ggctgcgccc | gcactagggc | 720 |
| tggtgtgtgg | acgttgccct | gagctgggtc | tcgtcctctt | gctgctgctg | ctctcgctgc | 780 |
| tgtgtggagc | ggcagggagc | caggaggccg | ggaccggtgc | gggcgcgggg | tcccttgcgg | 840 |
| gttcttgcgg | ctgcggcacg | ccccagcggc | ctggcgccca | tggcagttcg | gcagccgctc | 900 |
| accgatactc | gcgggaggct | aacgctccgg | gccccgtacc | cggagagcgg | caactcgcgc | 960 |
| actcaaagat | ggtccccatc | cctgctggag | tatttacaat | gggcacagat | gatcctcaga | 1020 |
| taaagcagga | tggggaagca | cctgcgagga | gagttactat | tgatgccttt | tacatggatg | 1080 |
| cctatgaagt | cagtaatact | gaatttgaga | agtttgtgaa | ctcaactggc | tatttgacag | 1140 |
| aggctgagaa | gtttggcgac | tcctttgtct | ttgaaggcat | gttgagtgag | caagtgaaga | 1200 |
| ccaatattca | acaggcagtt | gcagctgctc | cctggtggtt | acctgtgaaa | ggcgctaact | 1260 |
| ggagacaccc | agaagggcct | gactctacta | ttctgcacag | gccggatcat | ccagttctcc | 1320 |
| atgtgtcctg | gaatgatgcg | gttgcctact | gcacttgggc | agggaagcgg | ctgcccacgg | 1380 |
| aagctgagtg | ggaatacagc | tgtcgaggag | gcctgcataa | tagactttc | ccctggggca | 1440 |
| acaaactgca | gcccaaaggc | cagcattatg | ccaacatttg | gcagggcgag | tttccggtga | 1500 |
| ccaacactgg | tgaggatggc | ttccaaggaa | ctgcgcctgt | tgatgccttc | cctcccaatg | 1560 |
| gttatggctt | atacaacata | gtggggaacg | catgggaatg | gacttcagac | tggtggactg | 1620 |
| ttcatcattc | tgttgaagaa | acgcttaacc | caaaaggtcc | cccttctggg | aaagaccgag | 1680 |
| tgaagaaagg | tggatcctac | atgtgccata | ggtcttattg | ttacaggtat | cgctgtgctg | 1740 |
| ctcggagcca | gaacacacct | gatagctctg | cttcgaatct | gggattccgc | tgtgcagccg | 1800 |
| accgcctgcc | cactatggac | tgagtcgacc | ctagagctcg | ctgatcagcc | tcgactgtgc | 1860 |
| cttctagttg | ccagccatct | gttgtttgcc | cctcccccgt | gccttccttg | acctggaag | 1920 |
| gtgccactcc | cactgtcctt | tcctaataaa | atgaggaaat | tgcatcgcat | tgtctgagta | 1980 |
| ggtgtcattc | tattctgggg | ggtggggtgg | ggcaggacag | caaggggag | gattgggaag | 2040 |
| acaatagcag | gcatgctggg | gaatctagan | ngtttaaaca | tttaaatagg | aacccctagt | 2100 |
| gatggagttg | gccactccct | ctctgcgcgc | tcgctcgctc | actgaggccg | ggcgaccaaa | 2160 |

```
ggtcgcccga cgcccgggct tgcccgggc ggcctcagtg agcgagcgag cgcgcagaga   2220
gtatacatcg atgtgagttc gcgggtggct gggggggcccct gggctgcgac cgcccccgaa   2280
ccgcgtctac gagccttgcg ggctccgggt ctttgcagtc gtatggggc agggtagctg   2340 ttccccgcaa ggagagctca aggtcagcgc tcggacctgg cggagccccg cacccaggct   2400
gtggcgccct gtgcagctcc gcccttgcgg cgccatctgc ccggagcctc cttcccctag   2460
tccccagaaa caggaggtcc ctactcccgc ccgagatccc gacccggacc cctaggtggg   2520
ggacgctttc tttcctttcg cgctctgcgg ggtcacgtgt cgcagaggag cccctccccc   2580
acggcctccg gcaccgcagg ccccgggatg ctagtgcgca gcgggtgcat ccctgtccgg   2640
atgctgcgcc tgcggtagag cggccgccat gttgcaaccg ggaaggaaat gaatgggcag   2700
ccgttaggaa agcctgccgg tgactaaccc tgcgctcctg cctcgatggg tggagtcgcg   2760
tgtggcgggg aagtcaggtg gagcgaggct agctggcccg atttctcctc cgggtgatgc   2820
ttttcctaga ttattctctg gtaaatcaaa gaagtgggtt tatggaggtc ctcttgtgtc   2880
ccctccccgc agaggtgtgg tggctgtggc atggtgccaa gccgggagaa gctgagtcat   2940
gggtagttgg aaaaggacat tccaccgca aaatggcccc tctggtggtg gccccttcct   3000
gcagcgccgg ctcacctcac ggccccgccc ttcccctgcc agcctagcgt tgacccgacc   3060
ccaaaggcca ggctgtaaat gtcaccggga ggattgggtg tctgggcgcc tcggggaacc   3120
tgcccttctc cccattccgt cttccggaaa ccagatctcc caccgcaccc tggtctgagg   3180
ttaaatatag ctgctgacct ttctgtagct ggggcctgg gctggggctc tctcccatcc   3240
cttctcccca cacacatgca cttacctgtg ctcccactcc tgatttctgg aaaagagcta   3300
ggaaggacag gcaacttggc aaatcaaagc cctgggacta gggggttaaa atacagcttc   3360
ccctcttccc acccgcccca gtctctgtcc cttttgtagg agggacttag agaagggggtg   3420 ggcttgccct gtccagttaa tttctgacct ttactcctgc cctttgagtt tgatgatgct   3480
gagtgtacaa gcgttttctc cctaaagggt gcagctgagc taggcagcag caagcattcc   3540
tggggtggca tagtggggtg gtgaatacca tgtacaaagc ttgtgcccag actgtgggtg   3600
gcagtgcccc acatggccgc ttctcctgga agggcttcgt atgactgggg gtgttgggca   3660
gccctggagc cttcagttgc agccatgcct taagccaggc cagcctggca gggaagctca   3720
agggagataa aattcaacct cttgggcccct cctgggggta aggagatgct gcattcgccc   3780
tcttaatggg gaggtggcct agggctgctc acatattctg gaggagcctc ccctcctcat   3840
gccttcttgc ctcttgtctc ttaggcatgc aaaagagtcg aataagggcg acacaaaatt   3900
tattctaaat gcataataaa tactgataac atcttatagt ttgtattata ttttgtatta   3960
tcgttgacat gtataatttt gatatcaaaa actgattttc cctttattat tttcgagatt   4020
tattttctta attctctttta acaaactaga aatattgtat atacaaaaaa tcataaataa   4080
tagatgaata gtttaattat aggtgttcat caatcgaaaa agcaacgtat cttatttaaa   4140
gtgcgttgct tttttctcat ttataaggtt aaataattct catatatcaa gcaaagtgac   4200
aggcgccctt aaatattctg acaaatgctc tttccctaaa ctccccccat aaaaaaaccc   4260
gccgaagcgg gttttttacgt tatttgcgga ttaacgatta ctcgttatca gaaccgccca   4320
gggggcccga gcttaagact ggccgtcgtt ttacaacaca gaaagagttt gtagaaacgc   4380
aaaaaggcca tccgtcaggg gccttctgct tagtttgatg cctggcagtt ccctactctc   4440
gccttccgct tcctcgctca ctgactcgct gcgctcggtc gttcggctgc ggcgagcggt   4500
```

```
atcagctcac tcaaaggcgg taatacggtt atccacagaa tcaggggata acgcaggaaa    4560
gaacatgtga gcaaaaggcc agcaaaaggc caggaaccgt aaaaaggccg cgttgctggc    4620
gtttttccat aggctccgcc cccctgacga gcatcacaaa aatcgacgct caagtcagag    4680
gtggcgaaac ccgacaggac tataaagata ccaggcgttt ccccctggaa gctccctcgt    4740
gcgctctcct gttccgaccc tgccgcttac cggatacctg tccgcctttc tcccttcggg    4800
aagcgtggcg ctttctcata gctcacgctg taggtatctc agttcggtgt aggtcgttcg    4860
ctccaagctg ggctgtgtgc acgaaccccc cgttcagccc gaccgctgcg ccttatccgg    4920
taactatcgt cttgagtcca acccggtaag acacgactta tcgccactgg cagcagccac    4980
tggtaacagg attagcagag cgaggtatgt aggcggtgct acagagttct tgaagtggtg    5040
gcctaactac ggctacacta gaagaacagt atttggtatc tgcgctctgc tgaagccagt    5100
taccttcgga aaagagttg g gtagctcttg atccggcaaa caaaccaccg ctggtagcgg    5160
tggttttttt gtttgcaagc agcagattac gcgcagaaaa aaaggatctc aagaagatcc    5220
tttgatcttt tctacggggt ctgacgctca gtggaacgac gcgcgcgtaa ctcacgttaa    5280
gggattttgg tcatgagctt gcgccgtccc gtcaagtcag cgtaatgctc tgcttaggtg    5340
gcggtacttg ggtcgatatc aaagtgcatc acttcttccc gtatgcccaa ctttgtatag    5400
agagccactg cgggatcgtc accgtaatct gcttgcacgt agatcacata agcaccaagc    5460
gcgttggcct catgcttgag gagattgatg agcgcggtgg caatgccctg cctccggtgc    5520
tcgccggaga ctgcgagatc atagatatag atctcactac gcggctgctc aaacttgggc    5580
agaacgtaag ccgcgagagc gccaacaacc gcttcttggt cgaaggcagc aagcgcgatg    5640
aatgtcttac tacggagcaa gttcccgagg taatcggagt ccggctgatg ttgggagtag    5700
gtggctacgt caccgaactc acgaccgaaa agatcaagag cagcccgcat ggatttgact    5760
tggtcagggc cgagcctaca tgtgcgaatg atgcccatac ttgagccacc taactttgtt    5820
ttagggcgac tgccctgctg cgtaacatcg ttgctgctcc ataacatcaa acatcgaccc    5880
acggcgtaac gcgcttgctg cttggatgcc cgaggcatag actgtacaaa aaaacagtca    5940
taacaagcca tgaaaaccgc cactgcgccg ttaccaccgc tgcgttcggt caaggttctg    6000
gaccagttgc gtgagcgcat tttttttttcc tcctcggcgt ttacgccccg ccctgccact    6060
catcgcagta ctgttgtaat tcattaagca ttctgccgac atggaagcca tcacagacgg    6120
catgatgaac ctgaatcgcc agcggcatca gcaccttgtc gccttgcgta taatatttgc    6180
ccatagtgaa aacgggggcg aagaagttgt ccatattggc cacgtttaaa tcaaaactgg    6240
tgaaactcac ccagggattg gctgctgacga aaaacatatt ctcaataaac cctttaggga    6300
aataggccag ttttcaccg taacacgcca catcttgcga atatatgtgt agaaactgcc    6360
ggaaatcgtc gtgtgcactc atggaaaacg gtgtaacaag ggtgaacact atcccatatc    6420
accagctcac cgtctttcat tgccatacgg aactccggat gagcattcat caggcgggca    6480
agaatgtgaa taaaggccgg ataaaacttg tgcttatttt tctttacggt ctttaaaaag    6540
gccgtaatat ccagctgaac ggtctggtta taggtacatt gagcaactga ctgaaatgcc    6600
tcaaaatgtt ctttacgatg ccattgggat atatcaacgg tggtatatcc agtgattttt    6660
ttctccattt tttttttcctc ctttagaaaa actcatcgag catcaaatga aactgcaatt    6720
tattcatatc aggattatca ataccatatt tttgaaaaag ccgttctgt aatgaaggag    6780 aaaactcacc gaggcagttc cataggatgg caagatcctg gtatcggtct gcgattccga    6840
ctcgtccaac atcaatacaa cctattaatt tcccctcgtc aaaaataagg ttatcaagtg    6900
```

```
agaaatcacc atgagtgacg actgaatccg gtgagaatgg caaaagttta tgcatttctt    6960
tccagacttg ttcaacaggc cagccattac gctcgtcatc aaaatcactc gcatcaacca    7020
aaccgttatt cattcgtgat tgcgcctgag cgaggcgaaa tacgcgatcg ctgttaaaag    7080
gacaattaca aacaggaatc gagtgcaacc ggcgcaggaa cactgccagc gcatcaacaa    7140
tattttcacc tgaatcagga tattcttcta atacctggaa cgctgttttt ccggggatcg    7200
cagtggtgag taaccatgca tcatcaggag tacggataaa atgcttgatg gtcggaagtg    7260
gcataaattc cgtcagccag tttagtctga ccatctcatc tgtaacatca ttggcaacgc    7320
tacctttgcc atgtttcaga aacaactctg gcgcatcggg cttcccatac aagcgataga    7380
ttgtcgcacc tgattgcccg acattatcgc gagcccattt atacccatat aaatcagcat    7440
ccatgttgga atttaatcgc ggcctcgacg tttcccgttg aatatggctc attttttttt    7500
cctcctttac caatgcttaa tcagtgaggc acctatctca gcgatctgtc tatttcgttc    7560
atccatagtt gcctgactcc ccgtcgtgta gataactacg atacgggagg gcttaccatc    7620
tggccccagc gctgcgatga taccgcgaga accacgctca ccggctccgg atttatcagc    7680
aataaaccag ccagccggaa gggccgagcg cagaagtggt cctgcaactt tatccgcctc    7740
catccagtct attaattgtt gccgggaagc tagagtaagt agttcgccag ttaatagttt    7800
gcgcaacgtt gttgccatcg ctacaggcat cgtggtgtca cgctcgtcgt ttggtatggc    7860
ttcattcagc tccggttccc aacgatcaag gcgagttaca tgatccccca tgttgtgcac    7920
gttgtcagaa gtaagttggc cgcagtgtta tcactcatgg ttatggcagc actgcataat    7980
tctcttactg tcatgccatc cgtaagatgc ttttctgtga ctggtgagta ctcaaccaag    8040
tcattctgag aatagtgtat gcggcgaccg agttgctctt gcccggcgtc aatacgggat    8100
aataccgcgc cacatagcag aactttaaaa gtgctcatca ttggaaaacg ttcttcgggg    8160
cgaaaactct caaggatctt accgctgttg agatccagtt cgatgtaacc cactcgtgca    8220
cccaactgat cttcagcatc ttttactttc accagcgttt ctgggtgagc aaaaacagga    8280
aggcaaaatg ccgcaaaaaa gggaataagg gcgacacgga aatgttgaat actcatattc    8340
ttcctttttc aatattattg aagcatttat cagggttatt gtctcatgag cggatacata    8400
tttgaatgta tttagaaaaa taaacaaata ggggtcagtg ttacaaccaa ttaaccaatt    8460
ctgaacatta tcgcgagccc atttatacct gaatatggct cataacaccc cttgtttgcc    8520
tggcggcagt agcgcggtgg tcccacctga ccccatgccg aactcagaag tgaaacgccg    8580
tagcgccgat ggtagtgtgg ggactcccca tgcgagagta gggaactgcc aggcatcaaa    8640
taaaacgaaa ggctcagtcg aaagactggg cctttcgccc gggctaattg aggggtgtcg    8700
cccttattcg actcggggct cgag                                           8724
```

<210> SEQ ID NO 23
<211> LENGTH: 10271
<212> TYPE: DNA
<213> ORGANISM: Homo sapiens
<220> FEATURE:
<221> NAME/KEY: misc_feature
<222> LOCATION: (3486)..(3487)
<223> OTHER INFORMATION: n is a, c, g, or t
<220> FEATURE:
<221> NAME/KEY: n
<222> LOCATION: (4414)..(4414)
<223> OTHER INFORMATION: Any nucleic acid

<400> SEQUENCE: 23

```
cgcgttgtag ttaatgatta acccgccatg ctacttatct acgtagccat gctctaggaa        60
gatcggaatt cgcccttaag ctagcaggtt aattttttaaa aagcagtcaa aagtccaagt       120
ggcccttggc agcatttact ctctctgttt gctctggtta ataatctcag gagcacaaac       180
attccagatc caggttaatt tttaaaaagc agtcaaaagt ccaagtggcc cttggcagca       240
tttactctct ctgtttgctc tggttaataa tctcaggagc acaaacattc cagatccggc       300
gcgccagggc tggaagctac ctttgacatc atttcctctg cgaatgcatg tataatttct       360
acagaaccta ttagaaagga tcacccagcc tctgcttttg tacaactttc ccttaaaaaa       420
ctgccaattc cactgctgtt tggcccaata gtgagaactt tttcctgctg cctcttggtg       480
cttttgccta tggcccctat tctgcctgct gaagacactc ttgccagcat ggacttaaac       540
ccctccagct ctgacaatcc tctttctctt ttgttttaca tgaagggtct ggcagccaaa       600
gcaatcactc aaagttcaaa ccttatcatt ttttgctttg ttcctcttgg ccttggtttt       660
gtacatcagc tttgaaaata ccatcccagg gttaatgctg gggttaattt ataactaaga       720
gtgctctagt tttgcaatac aggacatgct ataaaaatgg aaagatgttg ctttctgaga       780
gactgcagaa gttggtcgtg aggcactggg caggtaagta tcaaggttac aagacaggtt       840
taaggagacc aatagaaact gggcttgtcg agacagagaa gactcttgcg tttctgatag       900
gcacctattg gtcttactga catccacttt gcctttctct ccacaggtgt ccaggcggcc       960
gcatgccccc gccccgcacc ggccgcggcc tgctgtggct gggcctggtg ctgagcagcg      1020
tgtgcgtggc cctgggcagc gagacccagg ccaacagcac caccgacgcc ctgaacgtgc      1080
tgctgatcat cgtggacgac ctgcgcccca gcctgggctg ctacggcgac aagctggtgc      1140
gcagccccaa catcgaccag ctggccagcc acagcctgct gttccagaac gccttcgccc      1200
agcaggccgt gtgcgccccc agccgcgtga gcttcctgac cggccgccgc cccgacacca      1260
cccgcctgta cgacttcaac agctactggc gcgtgcacgc cggcaacttc agcaccatcc      1320
cccagtactt caaggagaac ggctacgtga ccatgagcgt gggcaaggtg ttccaccccg      1380
gcatcagcag caaccacacc gacgacagcc cctacagctg gagcttcccc cctaccacc      1440 ccagcagcga aagtacgag aacaccaaga cctgccgcgg ccccgacggc gagctgcacg      1500
ccaacctgct gtgccccgtg gacgtgctgg acgtgcccga gggcaccctg cccgacaagc      1560
agagcaccga gcaggccatc cagctgctgg agaagatgaa gaccagcgcc agccccttct      1620
tcctggccgt gggctaccac aagccccaca tccccttccg ctaccccaag gagttccaga      1680
agctgtaccc cctggagaac atcacccctgg ccccgaccc cgaggtgccc gacggcctgc      1740
cccccgtggc ctacaacccc tggatggaca tccgccagcg cgaggacgtg caggccctga      1800
acatcagcgt gccctacggc cccatccccg tggacttcca gcgcaagatc cgccagagct      1860
acttcgccag cgtgagctac ctggacaccc aggtgggccg cctgctgagc gccctggacg      1920
acctgcagct ggccaacagc accatcatcg ccttccacca cgaccacggc tgggcctgg       1980 gcgagcacgg cgagtgggcc aagtacagca acttcgacgt ggccacccac gtgcccctga      2040
tcttctacgt gcccggccgc accgccagcc tgcccgaggc cggcgagaag ctgttcccct      2100
acctggaccc cttcgacagc gccagccagc tgatggagcc cggccgccag agcatggacc      2160
tggtggagct ggtgagcctg ttccccaccc tggccggcct ggccggcctg caggtgcccc      2220
cccgctgccc cgtgcccagc ttccacgtgg agctgtgccg cgagggcaag aacctgctga      2280
agcacttccg cttccgcgac ctggaggagg acccctacct gcccgcaac cccgcgagc       2340 tgatcgccta cagccagtac cccgccccca gcgacatccc ccagtggaac agcgacaagc      2400
```

-continued

```
ccagcctgaa ggacatcaag atcatgggct acagcatccg caccatcgac taccgctaca    2460
ccgtgtgggt gggcttcaac cccgacgagt tcctggccaa cttcagcgac atccacgccg    2520
gcgagctgta cttcgtggac agcgaccccc tgcaggacca caacatgtac aacgacagcc    2580
agggcggcga cctgttccag ctgctgatgc cctagaagcc tggatccaat caacctctgg    2640
attacaaaat ttgtgaaaga ttgactggta ttcttaacta tgttgctcct tttacgctat    2700
gtggatacgc tgctttaatg cctttgtatc atgctattgc ttcccgtatg gctttcattt    2760
tctcctcctt gtataaatcc tggttgctgt ctctttatga ggagttgtgg cccgttgtca    2820
ggcaacgtgg cgtggtgtgc actgtgtttg ctgacgcaac ccccactggt tggggcattg    2880
ccaccacctg tcagctcctt tccgggactt tcgctttccc cctccctatt gccacggcgg    2940
aactcatcgc cgcctgcctt gcccgctgct ggacaggggc tcggctgttg ggcactgaca    3000
attccgtggt gttgtcgggg aagctgacgt cctttccatg gctgctcgcc tgtgttgcca    3060
cctggattct gcgcgggacg tccttctgct acgtcccttc ggcccaat ccagcggacc     3120
ttccttcccg cggcctgctg ccggctctgc ggcctcttcc gcgtcttcga gatctgcctc    3180
gactgtgcct tctagttgcc agccatctgt tgtttgcccc tcccccgtgc cttccttgac    3240
cctggaaggt gccactccca ctgtcctttc ctaataaaat gaggaaattg catcgcattg    3300
tctgagtagg tgtcattcta ttctgggggg tggggtgggg caggacagca aggggaggag    3360
ttgggaagac aatagcaggc atgctgggga ctcgagttaa gggcgaattc ccgattagga    3420
tcttcctaga gcatggctac gtagataagt agcatggcgg gttaatcatt aactacagtt    3480
taaacnnatt taaataggaa cccctagtga tggagttggc cactccctct ctgcgcgctc    3540
gctcgctcac tgaggccggg cgaccaaagg tcgcccgacg cccgggcttt gcccgggcgg    3600
cctcagtgag cgagcgagcg cgcagagagt atacatcgat gtgagttcgc gggtggctgg    3660
ggggccctgg gctgcgaccg cccccgaacc gcgtctacga gccttgcggg ctccgggtct    3720
ttgcagtcgt atggggcag ggtagctgtt ccccgcaagg agagctcaag gtcagcgctc     3780
ggacctggcg gagccccgca cccaggctgt ggcgccctgt gcagctccgc ccttgcggcg    3840
ccatctgccc ggagcctcct tccctagtc cccagaaaca ggaggtccct actcccgccc     3900
gagatcccga cccggacccc taggtggggg acgctttctt ccttttcgcg ctctgcgggg    3960
tcacgtgtcg cagaggagcc cctccccac ggcctccggc accgcaggcc ccgggatgct     4020
agtgcgcagc gggtgcatcc ctgtccggat gctgcgcctg cggtagagcg gccgccatgt    4080
tgcaaccggg aaggaaatga atgggcagcc gttaggaaag cctgccggtg actaaccctg    4140
cgctcctgcc tcgatgggtg gagtcgcgtg tggcggggaa gtcaggtgga gcgaggctag    4200
ctggcccgat ttctcctccg ggtgatgctt ttcctagatt attctctggt aaatcaaaga    4260
agtgggttta tggaggtcct cttgtgtccc ctccccgcag aggtgtggtg gctgtggcat    4320
ggtgccaagc cggagaagc tgagtcatgg gtagttggaa aaggacattt ccaccgcaaa     4380
atggcccctc tggtggtggc cccttcctgc agcgccggct cacctcacgg ccccgccctt    4440
cccctgccag cctagcgttg acccgacccc aaaggccagg ctgtaaatgt caccgggagg    4500
attgggtgtc tgggcgcctc ggggaacctg cccttctccc cattccgtct tccggaaacc    4560
agatctccca ccgcaccctg gtctgaggtt aaatatagct gctgaccttt ctgtagctgg    4620
gggcctgggc tggggctctc tcccatccct tctccccaca cacatgcact tacctgtgct    4680
cccactcctg atttctggaa aagagctagg aaggacagga aacttggcaa atcaaagccc    4740
```

```
tgggactagg gggttaaaat acagcttccc ctcttcccac ccgccccagt ctctgtccct    4800
tttgtaggag ggacttagag aaggggtggg cttgccctgt ccagttaatt tctgaccttt    4860
actcctgccc tttgagtttg atgatgctga gtgtacaagc gttttctccc taaagggtgc    4920
agctgagcta ggcagcagca agcattcctg gggtggcata gtggggtggt gaataccatg    4980
tacaaagctt gtgcccagac tgtgggtggc agtgccccac atggccgctt ctcctggaag    5040
ggcttcgtat gactgggggt gttgggcagc cctggagcct tcagttgcag ccatgcctta    5100
agccaggcca gcctggcagg gaagctcaag ggagataaaa ttcaacctct tgggccctcc    5160
tgggggtaag gagatgctgc attcgccctc ttaatgggga ggtggcctag ggctgctcac    5220
atattctgga ggagcctccc ctcctcatgc cttcttgcct cttgtctctt aggcatgcaa    5280
aagagtcgaa taagggcgac acaaaattta ttctaaatgc ataataaata ctgataacat    5340
cttatagttt gtattatatt ttgtattatc gttgacatgt ataattttga tatcaaaaac    5400
tgattttccc tttattattt tcgagattta ttttcttaat tctctttaac aaactagaaa    5460
tattgtatat acaaaaaatc ataaataata gatgaatagt ttaattatag gtgttcatca    5520
atcgaaaaag caacgtatct tatttaaagt gcgttgcttt tttctcattt ataaggttaa    5580
ataattctca tatatcaagc aaagtgacag gcgcccttaa atattctgac aaatgctctt    5640
tccctaaact ccccccataa aaaaacccgc cgaagcgggt ttttacgtta tttgcggatt    5700
aacgattact cgttatcaga accgcccagg gggcccgagc ttaagactgg ccgtcgtttt    5760
acaacacaga aagagtttgt agaaacgcaa aaaggccatc cgtcagggc cttctgctta    5820 gtttgatgcc tggcagttcc ctactctcgc cttccgcttc ctcgctcact gactcgctgc    5880
gctcggtcgt tcggctgcgg cgagcggtat cagctcactc aaaggcggta atacggttat    5940
ccacagaatc aggggataac gcaggaaaga acatgtgagc aaaaggccag caaaaggcca    6000
ggaaccgtaa aaaggccgcg ttgctggcgt ttttccatag gctccgcccc cctgacgagc    6060
atcacaaaaa tcgacgctca agtcagaggt ggcgaaaccc gacaggacta taaagatacc    6120
aggcgtttcc ccctggaagc tccctcgtgc gctctcctgt tccgaccctg ccgcttaccg    6180
gatacctgtc cgcctttctc ccttcgggaa gcgtggcgct ttctcatagc tcacgctgta    6240
ggtatctcag ttcggtgtag gtcgttcgct ccaagctggg ctgtgtgcac gaaccccccg    6300
ttcagcccga ccgctgcgcc ttatccggta actatcgtct tgagtccaac ccggtaagac    6360
acgacttatc gccactggca gcagccactg gtaacaggat tagcagagcg aggtatgtag    6420
gcggtgctac agagttcttg aagtggtggg ctaactacgg ctacactaga agaacagtat    6480
ttggtatctg cgctctgctg aagccagtta ccttcggaaa aagagttggt agctcttgat    6540
ccggcaaaca aaccaccgct ggtagcggtg gtttttttgt ttgcaagcag cagattacgc    6600
gcagaaaaaa aggatctcaa gaagatcctt tgatcttttc tacggggtct gacgctcagt    6660
ggaacgacgc gcgcgtaact cacgttaagg gattttggtc atgagcttgc gccgtcccgt    6720
caagtcagcg taatgctctg cttaggtggc ggtacttggg tcgatatcaa agtgcatcac    6780
ttcttcccgt atgcccaact ttgtatagag agccactgcg ggatcgtcac cgtaatctgc    6840
ttgcacgtag atcacataag caccaagcgc gttggcctca tgcttgagga gattgatgag    6900
cgcggtggca atgccctgcc tccggtgctc gccggagact gcgagatcat agatatagat    6960
ctcactacgc ggctgctcaa acttgggcag aacgtaagcc gcgagagcgc caacaaccgc    7020
ttcttggtcg aaggcagcaa gcgcgatgaa tgtcttacta cggagcaagt tcccgaggta    7080
atcggagtcc ggctgatgtt gggagtaggt ggctacgtca ccgaactcac gaccgaaaag    7140
```

```
atcaagagca gcccgcatgg atttgacttg gtcagggccg agcctacatg tgcgaatgat    7200
gcccatactt gagccaccta actttgtttt agggcgactg ccctgctgcg taacatcgtt    7260
gctgctccat aacatcaaac atcgacccac ggcgtaacgc gcttgctgct tggatgcccg    7320
aggcatagac tgtacaaaaa aacagtcata acaagccatg aaaaccgcca ctgcgccgtt    7380
accaccgctg cgttcggtca aggttctgga ccagttgcgt gagcgcattt tttttttcctc    7440 ctcggcgttt acgccccgcc ctgccactca tcgcagtact gttgtaattc attaagcatt    7500
ctgccgacat ggaagccatc acagacggca tgatgaacct gaatcgccag cggcatcagc    7560
accttgtcgc cttgcgtata atatttgccc atagtgaaaa cggggggcgaa gaagttgtcc    7620 atattggcca cgtttaaatc aaaactggtg aaactcaccc agggattggc gctgacgaaa    7680
aacatattct caataaaccc tttagggaaa taggccaggt tttcaccgta acacgccaca    7740
tcttgcgaat atatgtgtag aaactgccgg aaatcgtcgt gtgcactcat ggaaaacggt    7800
gtaacaaggg tgaacactat cccatatcac cagctcaccg tctttcattg ccatacggaa    7860
ctccggatga gcattcatca ggcgggcaag aatgtgaata aaggccggat aaaacttgtg    7920 cttattttc tttacggtct ttaaaaaggc cgtaatatcc agctgaacgg tctggttata    7980
ggtacattga gcaactgact gaaatgcctc aaaatgttct ttacgatgcc attgggatat    8040
atcaacggtg gtatatccag tgattttttt ctccattttt ttttcctcct ttagaaaaac    8100
tcatcgagca tcaaatgaaa ctgcaattta ttcatatcag gattatcaat accatatttt    8160
tgaaaaagcc gtttctgtaa tgaaggagaa aactcaccga ggcagttcca taggatggca    8220
agatcctggt atcggtctgc gattccgact cgtccaacat caatacaacc tattaatttc    8280
ccctcgtcaa aaataaggtt atcaagtgag aaatcaccat gagtgacgac tgaatccggt    8340
gagaatggca aaagtttatg catttctttc cagacttgtt caacaggcca gccattacgc    8400
tcgtcatcaa aatcactcgc atcaaccaaa ccgttattca ttcgtgattg cgcctgagcg    8460
aggcgaaata cgcgatcgct gttaaaagga caattacaaa caggaatcga gtgcaaccgg    8520
cgcaggaaca ctgccagcgc atcaacaata ttttcacctg aatcaggata ttcttctaat    8580
acctggaacg ctgtttttcc ggggatcgca gtggtgagta accatgcatc atcaggagta    8640
cggataaaat gcttgatggt cggaagtggc ataaattccg tcagccagtt tagtctgacc    8700
atctcatctg taacatcatt ggcaacgcta cctttgccat gtttcagaaa caactctggc    8760
gcatcgggct tcccatacaa gcgatagatt gtcgcacctg attgcccgac attatcgcga    8820
gcccatttat acccatataa atcagcatcc atgttggaat ttaatcgcgg cctcgacgtt    8880
tcccgttgaa tatggctcat ttttttttcc tcctttacca atgcttaatc agtgaggcac    8940
ctatctcagc gatctgtcta tttcgttcat ccatagttgc ctgactcccc gtcgtgtaga    9000
taactacgat acgggagggc ttaccatctg gccccagcgc tgcgatgata ccgcgagaac    9060
cacgctcacc ggctccggat ttatcagcaa taaaccagcc agccggaagg gccgagcgca    9120
gaagtggtcc tgcaacttta tccgcctcca tccagtctat taattgttgc cgggaagcta    9180
gagtaagtag ttcgccagtt aatagtttgc gcaacgttgt tgccatcgct acaggcatcg    9240
tggtgtcacg ctcgtcgttt ggtatggctt cattcagctc cggttcccaa cgatcaaggc    9300
gagttacatg atcccccatg ttgtgcacgt tgtcagaagt aagttggccg cagtgttatc    9360
actcatggtt atggcagcac tgcataattc tcttactgtc atgccatccg taagatgctt    9420
ttctgtgact ggtgagtact caaccaagtc attctgagaa tagtgtatgc ggcgaccgag    9480
```

| | |
|---|---:|
| ttgctcttgc ccggcgtcaa tacgggataa taccgcgcca catagcagaa ctttaaaagt | 9540 |
| gctcatcatt ggaaaacgtt cttcggggcg aaaactctca aggatcttac cgctgttgag | 9600 |
| atccagttcg atgtaaccca ctcgtgcacc caactgatct tcagcatctt ttactttcac | 9660 |
| cagcgtttct gggtgagcaa aaacaggaag gcaaaatgcc gcaaaaaagg gaataagggc | 9720 |
| gacacggaaa tgttgaatac tcatattctt ccttttcaa tattattgaa gcatttatca | 9780 |
| gggttattgt ctcatgagcg gatacatatt tgaatgtatt tagaaaaata aacaaatagg | 9840 |
| ggtcagtgtt acaaccaatt aaccaattct gaacattatc gcgagcccat ttatacctga | 9900 |
| atatggctca taacacccct tgtttgcctg gcggcagtag cgcggtggtc ccacctgacc | 9960 |
| ccatgccgaa ctcagaagtg aaacgccgta gcgccgatgg tagtgtgggg actccccatg | 10020 |
| cgagagtagg gaactgccag gcatcaaata aaacgaaagg ctcagtcgaa agactgggcc | 10080 |
| tttcgcccgg gctaattgag gggtgtcgcc cttattcgac tcggggctcg agctgcgcgc | 10140 |
| tcgctcgctc actgaggccg cccgggcaaa gcccgggcgt cgggcgacct ttggtcgccc | 10200 |
| ggcctcagtg agcgagcgag cgcgcagaga gggagtggcc aactccatca ctaggggttc | 10260 |
| ctttaattaa a | 10271 |

<210> SEQ ID NO 24
<211> LENGTH: 9855
<212> TYPE: DNA
<213> ORGANISM: Homo sapiens
<220> FEATURE:
<221> NAME/KEY: n
<222> LOCATION: (3202)..(3202)
<223> OTHER INFORMATION: Any nucleic acid 1-20
<220> FEATURE:
<221> NAME/KEY: misc_feature
<222> LOCATION: (3202)..(3202)
<223> OTHER INFORMATION: n is a, c, g, or t

<400> SEQUENCE: 24

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct ttaattaaac gcgtggggga ggctgctggt gaatattaac caaggtcacc | 180 |
| ccagttatcg gaggagcaaa caggggctaa gtccaccggg ggaggctgct ggtgaatatt | 240 |
| aaccaaggtc accccagtta tcggaggagc aaacaggggc taagtccacc ggggaggct | 300 |
| gctggtgaat attaaccaag gtcaccccag ttatcggagg agcaaacagg ggctaagtcc | 360 |
| acactagtaa atgaccctatt aagaatattt catagaacga atgttccgat gctctaatct | 420 |
| ctctagacaa ggttcatatt tgtatgggtt acttattctc tctttgttga ctaagtcaat | 480 |
| aatcagaatc agcaggtttg cagtcagatt ggcagggata agcagcctag ctcaggagaa | 540 |
| gtgagtataa aagccccagg ctgggagcag ccatcacaga agtccactca ttcttggcag | 600 |
| gccgcggcta aggtaagttg gcgccgttta agggatggtt ggttggtggg gtattaatgt | 660 |
| ttaattacct tttttacagg cctgggcgcg ccgccaccat gccaccacct aggacaggca | 720 |
| ggggcctgct ttggcttgga ctggtgctga gctctgtctg tgttgccctg ggctccgaga | 780 |
| cccaagccaa ctctacaacc gatgctctca atgttctgct catcatagtg gatgacctgc | 840 |
| ggccctctct aggctgctat ggagacaagt tggtgcggag ccccaacata gaccagctag | 900 |
| cctctcactc cctgctgttc cagaatgcct cgcccagca agctgtgtgc gcccctcta | 960 |
| gagtgtcttt cctgacccgg gagaaggcctg atacaacaag gctgtatgac tttaacagct | 1020 |
| actggagggt gcacgcaggc aacttctcca ctatccccca atacttcaag gagaatggct | 1080 |

-continued

```
atgtgaccat gagcgtgggc aaggtcttcc accctggaat ctcctccaac cacactgatg    1140
atagtcccta ctcttggtct tttcctccct atcaccctag cagtgagaag tatgagaaca    1200
ccaaaacctg cagaggccct gatggggagc tgcatgctaa cctcctgtgt cctgtagatg    1260
tgctggacgt cccagagggc accttgccag ataagcagtc tactgagcag gctatccagc    1320
tgcttgagaa aatgaagact tctgcatctc ccttctttct ggctgttggc taccacaagc    1380
ctcacatccc cttcaggtac cctaaggagt tccaaaagct ctatcctctg aaaacatca    1440 cacttgcccc cgatcctgag gtccctgacg gcctcccacc agtagcctac aatccttgga    1500
tggacattag gcagagagag gatgtccagg ctctgaatat ttctgtgccc tatgggccca    1560
tcccggtgga cttccagcgc aaaatcagac agtcctactt tgcctctgtg agctatctgg    1620
acacccaggt tgggaggctc ctctccgccc ttgacgacct ccagttggcc aacagcacca    1680
ttatagcctt cacctctgac cacggctggg cactgggggga acacggggag tgggctaagt    1740
actctaactt tgatgtggcc acccacgtgc ccctcatctt ttatgtgcct ggcaggactg    1800
ccagcctgcc cgaagctggg gaaaaactgt ttccatacct ggaccctttt gacagtgctt    1860
ctcagctcat ggaacctggc cgtcagagca tggatctggt ggagctagtg tccctcttcc    1920
caaccttggc tggccttgct ggtctccagg tgcctcctag atgcccagtc cctccttcc    1980 atgttgaact ctgccgtgag gggaagaatc tgctgaagca cttcagattc agagacttgg    2040
aggaggaccc ctaccttcct gggaaccccca gggagttgat tgcatactcc cagtatccca    2100
ggccaagtga cattcccccag tggaactccg acaaaccaag tctgaaggac atcaagatca    2160
tggggtacag catcaggacc attgactaca gatacacagt gtgggttgga tttaacccag    2220
atgagttctt ggcaaacttt tctgacatcc atgcaagtca gttgtatttt gtggacagcg    2280
accctctgca ggatcacaac atgtacaatg acagccaggg tggggacctc tttcaactcc    2340
tcatgccata gcaattgaat caacctctgg attacaaaat ttgtgaaaga ttgactggta    2400
ttcttaactt tgttgctcct tttacgcttt gtggatacgc tgctttattg cctttgtatc    2460
ttgctattgc ttcccgtttg gctttcattt tctcctcctt gtataaatcc tggttgctgt    2520 ctcttttttga ggagttgtgg cccgttgtca ggcaacgtgg cgtggtgtgc actgtgtttg    2580
ctgacgcaac ccccactggt tggggcattg ccaccacctg tcagctcctt tccgggactt    2640
tcgctttccc cctccctatt gccacggcgg aactcatcgc cgcctgcctt gcccgctgct    2700
ggacaggggc tcggctgttg ggcactgaca attccgtggt gttgtcgggg aaatcatcgt    2760
cctttccttg gctgctcgcc tgtgttgcca cctggattct cgcgggacg tccttctgct    2820 acgtcccttc ggccctcaat ccagcggacc ttccttcccg cggcctgctg ccggctctgc    2880
ggcctcttcc gcgtcttcgc cttcgccctc agacgagtcg gatctccctt tgggccgcct    2940
ccccgcatcc aattggtcga ccctagagct cgctgatcag cctcgactgt gccttctagt    3000
tgccagccat ctgttgtttg ccctccccc gtgccttcct tgaccctgga aggtgccact    3060
cccactgtcc tttcctaata aaatgaggaa attgcatcgc attgtctgag taggtgtcat    3120
tctattctgg ggggtggggt ggggcaggac agcaaggggg aggattggga agacaatagc    3180
aggcatgctg gggaatctag angtttaaac atttaaatag gaaccccctag tgatggagtt    3240 ggccactccc tctctgcgcg ctcgctcgct cactgaggcc gggcgaccaa aggtcgcccg    3300
acgcccgggc tttgcccggg cggcctcagt gagcgagcga gcgcgcagag agtatacatc    3360
gatgtgagtt cgcgggtggc tgggggggccc tgggctgcga ccgcccccga accgcgtcta    3420
```

```
cgagccttgc gggctccggg tctttgcagt cgtatggggg cagggtagct gttccccgca    3480
aggagagctc aaggtcagcg ctcggacctg gcggagcccc gcacccaggc tgtggcgccc    3540
tgtgcagctc cgcccttgcg gcgccatctg cccggagcct ccttccccta gtccccagaa    3600
acaggaggtc cctactcccg cccgagatcc cgacccggac ccctaggtgg gggacgcttt    3660
ctttcctttc gcgctctgcg gggtcacgtg tcgcagagga gcccctcccc cacggcctcc    3720
ggcaccgcag gccccgggat gctagtgcgc agcgggtgca tccctgtccg gatgctgcgc    3780
ctgcggtaga gcggccgcca tgttgcaacc gggaaggaaa tgaatgggca gccgttagga    3840
aagcctgccg gtgactaacc ctgcgctcct gcctcgatgg gtggagtcgc gtgtggcggg    3900
gaagtcaggt ggagcgaggc tagctggccc gatttctcct ccgggtgatg cttttcctag    3960
attattctct ggtaaatcaa agaagtgggt ttatggaggt cctcttgtgt cccctccccg    4020
cagaggtgtg gtggctgtgg catggtgcca agccgggaga agctgagtca tgggtagttg    4080
gaaaaggaca tttccaccgc aaaatggccc ctctggtggt ggccccttcc tgcagcgccg    4140
gctcacctca cggccccgcc cttcccctgc cagcctagcg ttgacccgac cccaaaggcc    4200
aggctgtaaa tgtcaccggg aggattgggt gtctgggcgc ctcggggaac ctgcccttct    4260
ccccattccg tcttccggaa accagatctc ccaccgcacc ctggtctgag gttaaatata    4320
gctgctgacc tttctgtagc tgggggcctg ggctgggget ctctcccatc ccttctcccc    4380
acacacatgc acttacctgt gctcccactc ctgatttctg gaaagagct aggaaggaca    4440
ggcaacttgg caaatcaaag ccctgggact aggggggttaa aatacagctt cccctcttcc    4500
cacccgcccc agtctctgtc cctttttgtag gagggactta gagaaggggt gggcttgccc    4560
tgtccagtta atttctgacc tttactcctg ccctttgagt ttgatgatgc tgagtgtaca    4620
agcgttttct ccctaaaggg tgcagctgag ctaggcagca gcaagcattc ctggggtggc    4680
atagtggggt ggtgaatacc atgtacaaag cttgtgccca gactgtgggt ggcagtgccc    4740
cacatggccg cttctcctgg aagggcttcg tatgactggg ggtgttgggc agccctggag    4800
ccttcagttg cagccatgcc ttaagccagg ccagcctggc agggaagctc aagggagata    4860
aaattcaacc tcttgggccc tcctgggggt aaggagatgc tgcattcgcc ctcttaatgg    4920
ggaggtggcc tagggctgct cacatattct ggaggagcct cccctcctca tgccttcttg    4980
cctcttgtct cttaggcatg caaaagagtc gaataagggc gacacaaaat ttattctaaa    5040
tgcataataa atactgataa catcttatag tttgtattat attttgtatt atcgttgaca    5100
tgtataattt tgatatcaaa aactgatttt ccctttatta ttttcgagat ttattttctt    5160
aattctcttt aacaaactag aaatattgta tatacaaaaa atcataaata atagatgaat    5220
agtttaatta taggtgttca tcaatcgaaa aagcaacgta tcttatttaa agtgcgttgc    5280
tttttttctca tttataaggt taaataattc tcatatatca agcaaagtga caggcgccct    5340
taaatattct gacaaatgct ctttccctaa actccccccca taaaaaaacc cgccgaagcg    5400
ggttttttacg ttatttgcgg attaacgatt actcgttatc agaaccgccc aggggcccg    5460
agcttaagac tggccgtcgt tttacaacac agaaagagtt tgtagaaacg caaaaaggcc    5520
atccgtcagg ggccttctgc ttagtttgat gcctggcagt tccctactct cgccttccgc    5580
ttcctcgctc actgactcgc tgcgctcggt cgttcggctg cggcgagcgg tatcagctca    5640
ctcaaaggcg gtaatacggt tatccacaga atcaggggat aacgcaggaa agaacatgtg    5700
agcaaaaggc cagcaaaagg ccaggaaccg taaaaaggcc gcgttgctgg cgttttccca    5760
taggctccgc ccccctgacg agcatcacaa aaatcgacgc tcaagtcaga ggtggcgaaa    5820
```

```
cccgacagga ctataaagat accaggcgtt tccccctgga agctccctcg tgcgctctcc    5880
tgttccgacc ctgccgctta ccggatacct gtccgccttt ctcccttcgg gaagcgtggc    5940
gctttctcat agctcacgct gtaggtatct cagttcggtg taggtcgttc gctccaagct    6000
gggctgtgtg cacgaacccc ccgttcagcc cgaccgctgc gccttatccg gtaactatcg    6060
tcttgagtcc aacccggtaa gacacgactt atcgccactg gcagcagcca ctggtaacag    6120
gattagcaga gcgaggtatg taggcggtgc tacagagttc ttgaagtggt gggctaacta    6180
cggctacact agaagaacag tatttggtat ctgcgctctg ctgaagccag ttaccttcgg    6240
aaaaagagtt ggtagctctt gatccggcaa acaaaccacc gctggtagcg gtggtttttt    6300
tgtttgcaag cagcagatta cgcgcagaaa aaaaggatct caagaagatc ctttgatctt    6360
ttctacgggg tctgacgctc agtggaacga cgcgcgcgta actcacgtta agggattttg    6420
gtcatgagct tgcgccgtcc cgtcaagtca gcgtaatgct ctgcttaggt ggcggtactt    6480
gggtcgatat caaagtgcat cacttcttcc cgtatgccca actttgtata gagagccact    6540
gcgggatcgt caccgtaatc tgcttgcacg tagatcacat aagcaccaag cgcgttggcc    6600
tcatgcttga ggagattgat gagcgcggtg gcaatgccct gcctccggtg ctcgccggag    6660
actgcgagat catagatata gatctcacta cgcggctgct caaacttggg cagaacgtaa    6720
gccgcgagag cgccaacaac cgcttcttgg tcgaaggcag caagcgcgat gaatgtctta    6780
ctacggagca agttcccgag gtaatcggag tccggctgat gttgggagta ggtggctacg    6840
tcaccgaact cacgaccgaa aagatcaaga gcagcccgca tggatttgac ttggtcaggg    6900
ccgagcctac atgtgcgaat gatgcccata cttgagccac ctaactttgt tttagggcga    6960
ctgccctgct gcgtaacatc gttgctgctc cataacatca acatcgacc cacggcgtaa     7020 cgcgcttgct gcttggatgc ccgaggcata gactgtacaa aaaaacagtc ataacaagcc    7080
atgaaaaccg ccactgcgcc gttaccaccg ctgcgttcgg tcaaggttct ggaccagttg    7140
cgtgagcgca ttttttttttc ctcctcggcg tttacgcccc gccctgccac tcatcgcagt    7200
actgttgtaa ttcattaagc attctgccga catggaagcc atcacagacg gcatgatgaa    7260
cctgaatcgc cagcggcatc agcaccttgt cgccttgcgt ataatatttg cccatagtga    7320 aaacggggc gaagaagttg tccatattgg ccacgtttaa atcaaaactg gtgaaactca     7380
cccagggatt ggcgctgacg aaaaacatat tctcaataaa ccctttaggg aataggcca     7440 ggttttcacc gtaacacgcc acatcttgcg aatatatgtg tagaaactgc cggaaatcgt    7500
cgtgtgcact catggaaaac ggtgtaacaa gggtgaacac tatcccatat caccagctca    7560
ccgtctttca ttgccatacg gaactccgga tgagcattca tcaggcgggc aagaatgtga    7620
ataaaggccg gataaaactt gtgcttattt tctttacgg tctttaaaaa ggccgtaata    7680
tccagctgaa cggtctggtt ataggtacat tgagcaactg actgaaatgc ctcaaaatgt    7740
tctttacgat gccattggga tatatcaacg gtggtatatc cagtgatttt tttctccatt    7800
tttttttcct cctttagaaa aactcatcga gcatcaaatg aaactgcaat ttattcatat    7860
caggattatc aataccatat ttttgaaaaa gccgtttctg taatgaagga gaaaactcac    7920
cgaggcagtt ccataggatg gcaagatcct ggtatcggtc tgcgattccg actcgtccaa    7980
catcaataca acctattaat ttcccctcgt caaaaataag gttatcaagt gagaaatcac    8040
catgagtgac gactgaatcc ggtgagaatg gcaaaagttt atgcatttct ttccagactt    8100
gttcaacagg ccagccatta cgctcgtcat caaaatcact cgcatcaacc aaaccgttat    8160
```

```
tcattcgtga ttgcgcctga gcgaggcgaa atacgcgatc gctgttaaaa ggacaattac    8220
aaacaggaat cgagtgcaac cggcgcagga acactgccag cgcatcaaca atattttcac    8280
ctgaatcagg atattcttct aatacctgga acgctgtttt tccggggatc gcagtggtga    8340
gtaaccatgc atcatcagga gtacggataa aatgcttgat ggtcggaagt ggcataaatt    8400
ccgtcagcca gtttagtctg accatctcat ctgtaacatc attggcaacg ctacctttgc    8460
catgtttcag aaacaactct ggcgcatcgg gcttcccata caagcgatag attgtcgcac    8520
ctgattgccc gacattatcg cgagcccatt tatacccata taaatcagca tccatgttgg    8580
aatttaatcg cggcctcgac gtttcccgtt gaatatggct cattttttt tcctccttta    8640 ccaatgctta atcagtgagg cacctatctc agcgatctgt ctatttcgtt catccatagt    8700
tgcctgactc cccgtcgtgt agataactac gatacgggag ggcttaccat ctggccccag    8760
cgctgcgatg ataccgcgag aaccacgctc accggctccg gatttatcag caataaacca    8820
gccagccgga agggccgagc gcagaagtgg tcctgcaact ttatccgcct ccatccagtc    8880
tattaattgt tgccgggaag ctagagtaag tagttcgcca gttaatagtt tgcgcaacgt    8940
tgttgccatc gctacaggca tcgtggtgtc acgctcgtcg tttggtatgg cttcattcag    9000
ctccggttcc caacgatcaa ggcgagttac atgatccccc atgttgtgca cgttgtcaga    9060
agtaagttgg ccgcagtgtt atcactcatg gttatggcag cactgcataa ttctcttact    9120
gtcatgccat ccgtaagatg cttttctgtg actggtgagt actcaaccaa gtcattctga    9180
gaatagtgta tgcggcgacc gagttgctct tgcccggcgt caatacggga taataccgcg    9240
ccacatagca gaactttaaa agtgctcatc attggaaaac gttcttcggg gcgaaaactc    9300
tcaaggatct taccgctgtt gagatccagt tcgatgtaac ccactcgtgc acccaactga    9360
tcttcagcat cttttacttt caccagcgtt tctgggtgag caaaaacagg aaggcaaaat    9420
gccgcaaaaa agggaataag ggcgacacgg aaatgttgaa tactcatatt cttccttttt    9480
caatattatt gaagcattta tcagggttat tgtctcatga gcggatacat atttgaatgt    9540
atttagaaaa ataaacaaat aggggtcagt gttacaacca attaaccaat tctgaacatt    9600
atcgcgagcc catttatacc tgaatatggc tcataacacc ccttgtttgc ctggcggcag    9660
tagcgcggtg gtcccacctg accccatgcc gaactcagaa gtgaaacgcc gtagcgccga    9720
tggtagtgtg gggactcccc atgcgagagt agggaactgc caggcatcaa ataaaacgaa    9780
aggctcagtc gaaagactgg cctttcgcc cgggctaatt gaggggtgtc gcccttattc    9840
gactcggggc tcgag                                                     9855
```

ADENO ASSOCIATED VIRUS VECTORS FOR THE TREATMENT OF HUNTER DISEASE

CROSS-REFERENCE TO RELATED APPLICATIONS

This applications claims benefit of, and priority to, U.S. Ser. No. 62/945,920 filed on Dec. 10, 2019, the contents of which are incorporated herein.

INCORPORATION-BY-REFERENCE OF SEQUENCE LISTING

The contents of the file named "SHR-2011US1_ST25.txt," which was created on Jul. 14, 2021 and is 132,391 bytes in size are hereby incorporated by reference in their entirety.

BACKGROUND

Hunter syndrome, also known as mucopolysaccharidosis Type II (MPS II), is a lysosomal storage disease caused by deficiency or absence of iduronate-2-sulfatase (I2S) enzyme. Iduronate-2-sulfatase is involved in the break down and recycling of specific mucopolysaccharides, also known as glycosaminoglycans or GAG. As a result, in Hunter syndrome, GAG builds up in cells throughout the body, which in turn interferes with the normal function of various cells and organs in the body, resulting in a number of serious symptoms. In many cases of Hunter syndrome, there is a large buildup of GAGs in neurons and in the meninges of affected individuals, leading to various forms of central nervous system (CNS) symptoms, impaired cognitive performance and development delays.

Various treatment options have been used in the management of Hunter syndrome, including enzyme replacement therapy (ERT). Approved therapeutic ERT treatments include intravenous administration of recombinant I2S enzyme. However, intravenously administered I2S enzyme has various limitations, including poor distribution into the cells and tissues of the CNS and poor distribution into the cells of deep somatic tissues such as heart, lung, and bone. Treatment of Hunter syndrome remains a challenge.

The use of vectors that produce therapeutic proteins in vivo is desirable for the treatment of disease, but is limited by various factors including poor production of desired therapeutic proteins in vivo.

SUMMARY

The present invention provides efficient and robust recombinant adeno-associated virus (rAAV) vectors that encode I2S (referred to as I2S or IDS, throughout this application). The present invention is based in part on the surprising discovery that optimized rAAV vectors comprising I2S sequences result in robust I2S expression in vivo.

In some aspects, the present invention provides, a recombinant adeno-associated virus (rAAV) vector comprising an AAV8 capsid and a sequence encoding a human iduronate-2-sulfatase (I2S) enzyme.

In some aspects, the present invention provides, a recombinant adeno-associated virus (rAAV) vector comprising an AAV9 capsid and a sequence encoding human iduronate-2 sulfatase (I2S) enzyme.

In some embodiments, the rAAV encodes a codon-optimized human I2S enzyme. In some embodiments, the codon-optimized human I2S has a nucleotide sequence selected from SEQ ID NO: 11 or 12.

In some embodiments, the sequence encoding a human I2S enzyme comprises a sequence having at least about 70%, 75%, 80%, 85%, 90%, 95% or 99% identity to SEQ ID NO:6. In some embodiments, the human I2S enzyme is encoded by a nucleotide sequence at least about 70%, 75%, 80%, 85%, 90%, 95% or 99% identity to SEQ ID NO: 6. In some embodiments, the human I2S enzyme is encoded by a nucleotide sequence of SEQ ID NO: 6.

In some embodiments, the amino acid sequence of a human I2S enzyme comprises a sequence identical to SEQ ID NO: 1. In some embodiments, the amino acid sequence of a human I2S enzyme is the sequence identical to SEQ ID NO: 1.

In some embodiments, the amino acid sequence of a human I2S enzyme comprises a sequence having at least about 70%, 75%, 80%, 85%, 90%, 95% or 99% identity to SEQ ID NO: 2.

In some embodiments, the sequence encoding a human I2S enzyme comprises a sequence identical to SEQ ID NO: 2. In some embodiments, the amino acid sequence of a human I2S enzyme is the sequence identical to SEQ ID NO: 2.

In some embodiments, the codon-optimized sequence encoding a human I2S enzyme comprises a sequence having at least about 70%, 75%, 80%, 85%, 90%, 95% or 99% identity to SEQ ID NO: 11 or 12. In some embodiments, the codon-optimized sequence encoding a human I2S enzyme comprises a sequence identical to SEQ ID NO: 11 or 12.

In some embodiments, the vector further comprises a liver-specific promoter.

In some embodiments, the liver-specific promoter is transthyretin promoter (TTR).

In some embodiments, the vector further comprises a 5' and a 3' inverted terminal repeat (ITR), an intron upstream of the I2S sequence, and a cis-acting regulatory module (CRM).

In some embodiments, the vector further comprises a ubiquitous promoter.

In some embodiments, the vector further comprises a 5' and a 3' inverted terminal repeat, an intron upstream of the I2S sequence, and a cis-acting regulatory module (CRM).

In some embodiments, the rAAV vector comprises a sulfatase modifying factor 1 (SUMF1).

In some embodiments, the SUMF1 is preceded by an internal ribosome entry site (IRES).

In some embodiments, the vector further comprises a WPRE sequence. In some embodiments, the WPRE sequence is a variant WPRE sequence or an optimized WPRE sequence. In some embodiments, the WPRE sequence is encoded by a nucleotide sequence having at least about 70%, 75%, 80%, 85%, 90%, 95% or 99% identity to SEQ ID NO: 7. In some embodiments, the WPRE sequence is encoded by a nucleotide sequence having a SEQ ID NO: 7.

In some embodiments, the intron is a minute virus of mice (MVM) or SV40 intron. In some embodiments, the intron is a β-globin/IgG chimeric intron.

In some embodiments, the CRM is liver-specific CRM.

In some embodiments, the CRM is a neuronal-specific CRM. In some embodiments, the CRM is a muscle-specific CRM.

In some embodiments, the CRM is CRM8.

In some embodiments, the vector comprises at least three CRMs.

In some aspects, the present invention provides, a recombinant adeno-associated virus (rAAV) comprising an AAV8 capsid and an rAAV vector, said vector comprising: a) a 5' inverted terminal repeat (ITR); b.) a cis-acting regulatory module (CRM); c.) a liver specific promoter; d) a minute virus of mice (MVM); e. a sequence encoding a human iduronate-2-sulfatase (I2S) enzyme; f.) a woodchuck hepatitis virus posttranscriptional regulatory element (WPRE); and g.) a 3' ITR.

In some embodiments, the sequence encoding a human I2S enzyme is a wild type sequence or a codon-optimized sequence.

In some embodiments, the nucleotide sequence encoding a human I2S enzyme is a sequence having at least 70%, 75%, 80%, 85%, 90%, 95%, or 99% identity with SEQ ID NO: 6. In some embodiments, the nucleotide sequence encoding human I2S is identical to SEQ ID NO 6. In some embodiments, the nucleotide sequence encoding a human I2S enzyme is a sequence having at least 70%, 75%, 80%, 85%, 90%, 95%, or 99% identity with SEQ ID NO: 11 or 12. In some embodiments, the nucleotide sequence encoding a human I2S enzyme is a sequence identical to SEQ ID NO: 11 or 12.

In some embodiments, comprising a sequence encoding a sulfatase modifying factor 1 (SUMF1) and an internal ribosome entry site (IRES).

In some aspects, the present invention provides a recombinant adeno-associated virus (rAAV) comprising an AAV9 capsid and an rAAV vector, said vector comprising: a.) 5' inverted terminal repeat (ITR); b.) a cis-acting regulatory module (CRM); c) a ubiquitous promoter; d.) a minute virus of mice (MVM); e.) a sequence encoding a human iduronate-2-sulfatase (I2S) enzyme; f.) a woodchuck hepatitis virus posttranscriptional regulatory element (WPRE); and g.) a 3' ITR.

In some embodiments, the sequence encoding a human I2S enzyme is a wild type sequence or a codon-optimized sequence.

In some embodiments, comprising a sequence encoding a sulfatase modifying factor 1 (SUMF1) and an internal ribosome entry site (IRES).

In some embodiments, the rAAV vector does not comprise ApoB.

A method of treating a subject having Hunter syndrome (MPS II), comprising administering to the subject in need thereof an rAAV of any one of the preceding claims.

A method of treating a subject having Hunter syndrome (MPS II), comprising administering to the subject in need thereof a recombinant adeno-associated virus (rAAV) vector comprising an AAV8 or AAV9 capsid, and a promoter operably linked to a nucleic acid sequence that encodes iduronate-2-sulfatase (I2S), and wherein administering results in an increase in I2S enzymatic activity in the subject.

In some embodiments, the increase in I2S activity is detected in the serum of the subject.

In some embodiments, the increase in I2S activity is detected in the liver of the subject.

In some embodiments, the I2S activity is detected in the central nervous system (CNS).

In some embodiments, the increase in I2S activity is detected in the brain of the subject.

In some embodiments, the increase in I2S activity is detected in the hippocampus, thalamus, corpus callosum, cortex, cerebellum, or stratum of the brain.

In some embodiments, the increase of I2S activity is detected in the kidney etc. of the subject. In some embodiments, the increase in I2S activity is detected in the heart of the subject. In some embodiments, the increase in I2S activity is detected in the lung of the subject. In some embodiments, the increase in I2S activity is detected in the bone marrow of the subject. In some embodiments, the increase in I2S activity is detected in the kidney of the subject.

In some embodiments, the increase of I2S activity is maintained for at least 30, 60, 90, 120, 150, 180 days or more after a single administration.

In some embodiments, the level of I2S activity is measured by heparin sulfate assay.

In some embodiments, the level of I2S activity is measured by dermatan sulfate assay.

In some embodiments, the administering the AAV reduces the level of glycosaminoglycan (GAG) in the subject.

In some embodiments, the administering the AAV reduces the level of GAG in the serum of the subject.

In some embodiments, the administering the AAV reduces the level of GAG in the liver of the subject.

In some embodiments, the administering the AAV reduces the level of GAG in the kidney etc. of the subject. In some embodiments, the administering the AAV reduces the level of GAG in the heart of the subject. In some embodiments, the administering the AAV reduces the level of GAG in the lung of the subject. In some embodiments, the administering the AAV reduces the level of GAG in the bone marrow of the subject. In some embodiments, the administering the AAV reduces the level of GAG in the kidney of the subject.

In some embodiments, the administering the AAV reduces the level of GAG in the CNS of the subject.

In some embodiments, the administering the AAV reduces the level of GAG in the brain of the subject.

In some embodiments, the administering the AAV reduces the level of GAG in in the hippocampus, thalamus, corpus callosum, cortex, cerebellum, or stratum of the brain.

In some embodiments, the AAV is administered intravenously.

In some embodiments, the AAV is administered intrathecally.

In some embodiments, the AAV is administered at dose of about $5 \times 10^9$ vg.

In some embodiments, the administering of the rAAV does not elicit immune response.

Various aspects of the invention are described in detail in the following sections. The use of sections is not meant to limit the invention. Each section can apply to any aspect of the invention. In this application, the use of "or" means "and/or" unless stated otherwise. As used herein, the singular forms "a", "an", and "the" include both singular and plural referents unless the context clearly dictates otherwise.

BRIEF DESCRIPTION OF THE DRAWINGS

FIG. 1A is a schematic representation of the expression construct for hIDS expressing vector. FIG. 1B is a series of schematics that show the optimized expression constructs of hIDS-WPRE. ITR: inverted terminal repeat; pTBG: thyroid hormone-binding globulin promoter; hTTR: human transthyretin promoter; CRM: cis-acting regulatory module; MVM intron: minute virus of mice intron; WPRE: Woodchuck Hepatitis Virus (WHV) Posttranscriptional Regulatory Element; BGH pA: Bovine growth hormone terminator+polyA; COOLopt: codon-optimized by COOL (Codon Optimization Online) platform; AUSopt: codon-optimized by internal codon usage frequency table.

FIG. 2 is a series of schematics that show the optimized expression constructs of hIDS-IRES-SUMF1. ITR: inverted terminal repeat; pTBG: thyroid hormone-binding globulin promoter; hTTR: human transthyretin promoter; CRM: cis-acting regulatory module; MVM intron: minute virus of mice intron; WPRE: Woodchuck Hepatitis Virus (HWP) Posttranscriptional Regulatory Element; BGH pA: Bovine growth hormone terminator+polyA; COOLopt: codon-optimized by COOL (Codon Optimization Online) platform; AUSopt: codon-optimized by internal codon usage frequency table.

DEFINITIONS

Figure 3:
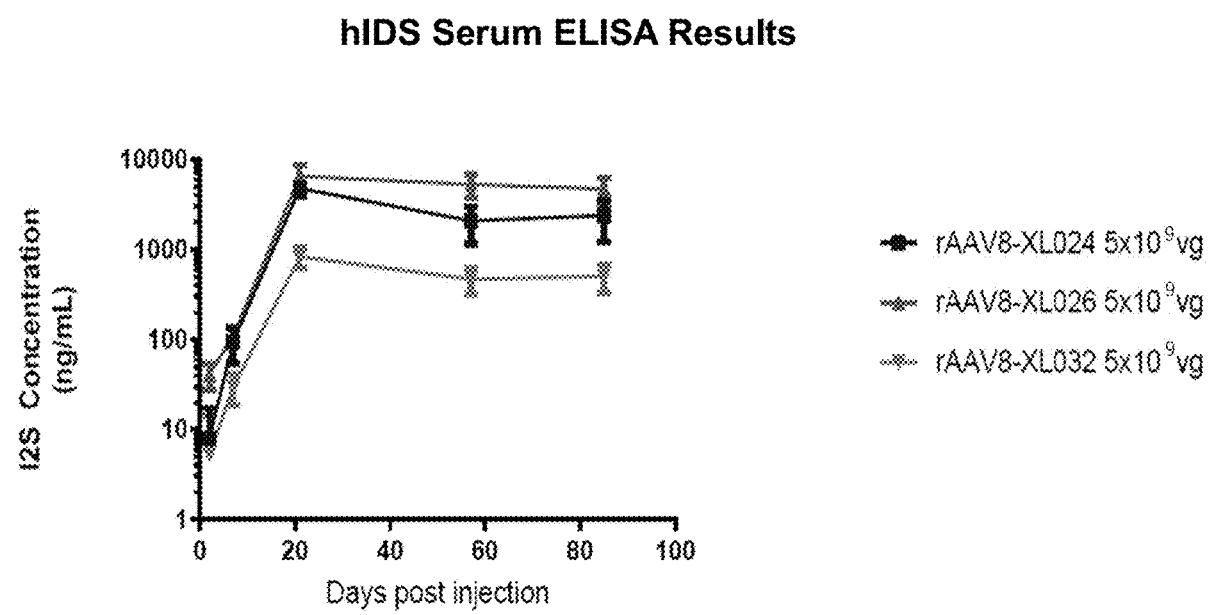
FIG. 3 is a graph that shows total I2S concentrations in mouse serum at day 0, day 2, day 7, day 21, week 8 and week 12 post injection of the identified rAAV vectors. The hI2S concentration was determined by ELISA.

Adeno-associated virus (AAV): As used herein, the terms "adeno-associated virus" or "AAV" or recombinant AAV ("rAAV") includes, but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV (see, e.g., Fields et al., Virology, volume 2, chapter 69 (4th ed., Lippincott-Raven Publishers); Gao et al., J. Virology 78:6381-6388 (2004); Mori et al., Virology 330:375-383 (2004)). Typically, AAV can infect both dividing and non-dividing cells and can be present in an extrachromosomal state without integrating into the genome of a host cell. AAV vectors are commonly used in gene therapy.

Administering: As used herein, the terms "administering," or "introducing" are used interchangeably in the context of delivering rAAV vectors encoding I2S into a subject, by a method or route which results in efficient delivery of the rAAV vector. Various methods are known in the art for administering rAAV vectors, including for example intravenously, subcutaneously or transdermally. Transdermal administration of rAAV vector can be performed by use of a "gene gun" or biolistic particle delivery system. In some embodiments, the rAAV vectors and/or the transgene expression cassette and/or the optimized IDS transgene sequences and/or any compositions of the gene expression cassette are administered via non-viral chemical particles such as lipid nanoparticles, non-viral biological molecules such as exosomes and/or extracellular vesicle.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

The recognized immunoglobulin polypeptides include the kappa and lambda light chains and the alpha, gamma (IgG1, IgG2, IgG3, IgG4), delta, epsilon and mu heavy chains or equivalents in other species. Full-length immunoglobulin "light chains" (of about 25 kDa or about 214 amino acids) comprise a variable region of about 110 amino acids at the NH2-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion.

Functional equivalent or derivative: As used herein, the term "functional equivalent" or "functional derivative" denotes, in the context of a functional derivative of an amino acid sequence, a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

IRES: As used herein, the term "IRES" refers to any suitable internal ribosome entry site sequence.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Polypeptide: The term, "polypeptide," as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Regulatory element: As used herein, the term "regulatory element" refers to transcriptional control elements, in particular non-coding cis-acting transcription control elements, capable of regulating and/or controlling transcription of a gene. Regulatory elements comprise at least one transcription factor binding site, for example at least one binding site for a tissue specific transcription factor. In embodiments described herein, regulatory elements have at least one binding site for a liver-specific transcription factor. Typically, regulatory elements increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. As is understood in the art, sequences regulating transcription may be situated either upstream (e.g., in the promoter region) or downstream (e.g., in the 3'UTR) of the gene that is regulated in vivo, and may be located in the immediate vicinity of the gene or further away. Regulatory elements can comprise either naturally occurring sequences, combinations of (parts of) such regulatory elements or several copies of a regulatory element, e.g., non-naturally occurring sequences. Accordingly, regulatory elements include naturally occurring and optimized or engineered regulatory elements to achieve a desired expression level.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, and/or condition has been diagnosed with or displays one or more symptoms of the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

The recitation of numerical ranges by endpoints herein includes all numbers and fractions subsumed within that range (e.g. 1 to 5 includes 1, 1.5, 2, 2.75, 3, 3.9, 4 and 5). It is also to be understood that all numbers and fractions thereof are presumed to be modified by the term "about."

Various aspects of the invention are described in detail in the following sections. The use of sections is not meant to limit the invention. Each section can apply to any aspect of the invention. In this application, the use of "or" means "and/or" unless stated otherwise. As used herein, the singular forms "a", "an", and "the" include both singular and plural referents unless the context clearly dictates otherwise.

Various aspects of the invention are described in detail in the following sections. The use of sections is not meant to limit the invention. Each section can apply to any aspect of the invention. In this application, the use of "or" means "and/or" unless stated otherwise.

DETAILED DESCRIPTION

The present disclosure describes efficient and robust recombinant adeno-associated virus (rAAV) vectors for the in vivo production of I2S for the treatment of diseases associated with an I2S deficiency, such as Hunter syndrome.

Mucopolysaccharidosis type II (MPS II, Hunter syndrome) is an X-chromosome-linked recessive lysosomal storage disorder that results from a deficiency in the enzyme iduronate-2-sulfatase (I2S). I2S cleaves the terminal 2-O-sulfate moieties from the glycosaminoglycans (GAG) dermatan sulfate and heparan sulfate. Due to the missing or defective I2S enzyme in patients with Hunter syndrome, GAG progressively accumulate in the lysosomes of a variety of cell types, leading to cellular engorgement, organomegaly, tissue destruction, and organ system dysfunction.

Generally, physical manifestations for people with Hunter syndrome include both somatic and neuronal symptoms. For example, in some cases of Hunter syndrome, central nervous system (CNS) involvement leads to developmental delays and nervous system problems. Symptoms such as neurodegeneration and mental retardation appear during childhood, and Hunter syndrome patients suffering from neuronal effects often die at an early age due to organ damage to the brain. Similarly, the accumulation of GAG can adversely affect the organ systems of the body. Manifesting initially as a thickening of the wall of the heart, lungs and airways, and abnormal enlargement of the liver, spleen and kidneys, these profound changes can ultimately lead to widespread catastrophic organ failure. As a result, Hunter syndrome is always severe, progressive, and life-limiting.

Enzyme replacement therapy (ERT) is an approved therapy for treating Hunter syndrome (MPS II), which involves administering exogenous replacement I2S enzyme to patients with Hunter syndrome. However, various drawbacks are associated with ERT, including, among these is for example limited distribution of I2S to various target organs.

The vectors described herein provide for robust expression of I2S in various organs, including for example liver, kidney, spleen, heart, lung, and the central nervous system. Accordingly, in some embodiments, the vectors described herein result in the expression of I2S in the liver. In some embodiments, the vectors described herein result in the expression of I2S in the kidney. In some embodiments, the vectors described herein result in the expression of I2S in the spleen. In some embodiments, the vectors described herein result in the expression of I2S in the heart. In some embodiments, the vectors described herein result in the expression of I2S in the lung. In some embodiments, the vectors described herein result in the expression of I2S in the central nervous system. In some embodiments, the vectors described herein result in the expression of I2S in the plasma.

rAAV I2S Vector Design

In some aspects, provided herewith is a recombinant adeno-associated virus (rAAV) vector encoding an iduronate-2-sulfatase (I2S) protein. A schematic that illustrates exemplary rAAV vectors of the present disclosure is illustrated in FIG. 1B. As shown in FIG. 1B, in some embodiments, an rAAV vector of the present disclosure comprises a liver specific promoter, a 5' and a 3' inverted terminal repeat (ITR), a cis-acting regulatory module (CRM), an intron, and a WPRE sequence.

In some embodiments, the vector also includes a sulfatase modifying factor 1 (SUMF) gene. In some embodiments, the vector comprises an internal ribosome entry site (IRES).

The iduronate-2-sulfatse (I2S) of the vector can be a wild-type or a codon-optimized variant. Accordingly, in some embodiments, the rAAV vector comprises a wild-type I2S nucleotide sequence. In some embodiments comprises a codon-optimized I2S sequence.

A suitable I2S for the present invention is any protein or a portion of a protein that can substitute for at least partial activity of naturally-occurring Iduronate-2-sulfatase (I2S) protein or rescue one or more phenotypes or symptoms associated with I2S-deficiency. As used herein, the terms "an I2S enzyme" and "an I2S protein", and grammatical equivalents, are used inter-changeably.

Typically, the human I2S protein is produced as a precursor form. The precursor form of human I2S contains a signal peptide (amino acid residues 1-25 of the full length precursor), a pro-peptide (amino acid residues 26-33 of the full length precursor), and a chain (residues 34-550 of the full length precursor) that may be further processed into the 42 kDa chain (residues 34-455 of the full length precursor) and the 14 kDa chain (residues 446-550 of the full length precursor). Typically, the precursor form is also referred to as full-length precursor or full-length I2S protein, which contains 550 amino acids. The amino acid sequences of the mature form (SEQ ID NO: 1) having the signal peptide removed and full-length precursor (SEQ ID NO:2) of a typical wild-type or naturally-occurring human I2S protein are shown in Table 1. The signal peptide is underlined.

TABLE 1

| Human Iduronate-2-sulfatase |
|---|
| Mature Form    SETQANSTTDALNVLLIIVDDLRPSLGCYGDKLVRSPNIDQL<br>ASHSLLFQNAFAQQAVCAPSRVSFLTGRRPDTTRLYDFNSY<br>WRVHAGNFSTIPQYFKENGYVTMSVGKVFHPGISSNHTDD<br>SPYSWSFPPYHPSSEKYENTKTCRGPDGELHANLLCPVDVL<br>DVPEGTLPDKQSTEQAIQLLEKMKTSASPFFLAVGYHKPHI<br>PFRYPKEFQKLYPLENITLAPDPEVPDGLPPVAYNPWMDIR<br>QREDVQALNISVPYGPIPVDFQRKIRQSYFASVSYLDTQVG<br>RLLSALDDLQLANSTIIAFTSDHGWALGEHGEWAKYSNFD |

TABLE 1-continued

Human Iduronate-2-sulfatase

| | |
|---|---|
| | VATHVPLIFYVPGRTASLPEAGEKLFPYLDPFDSASQLMEP<br>GRQSMDLVELVSLFPTLAGLAGLQVPPRCPVPSFHVELCRE<br>GKNLLKHFRFRDLEEDPYLPGNPRELIAYSQYPRPSDIPQW<br>NSDKPSLKDIKIMGYSIRTIDYRYTVWVGFNPDEFLANFSDI<br>HAGELYFVDSDPLQDHNMYNDSQGGDLFQLLMP (SEQ ID<br>NO: 1) |
| Full-Length<br>Precursor | MPPPRTGRGLLWLGLVLSSVCVALGSETQANSTTDALNVL<br>LIIVDDLRPSLGCYGDKLVRSPNIDQLASHSLLFQNAFAQQ<br>AVCAPSRVSFLTGRRPDTTRLYDFNSYWRVHAGNFSTIPQY<br>FKENGYVTMSVGKVFHPGISSNHTDDSPYSWSFPPYHPSSE<br>KYENTKTCRGPDGELHANLLCPVDVLDVPEGTLPDKQSTE<br>QAIQLLEKMKTSASPFFLAVGYHKPHIPFRYPKEFQKLYPL<br>ENITLAPDPEVPDGLPPVAYNPWMDIRQREDVQALNISVPY<br>GPIPVDFQRKIRQSYFASVSYLDTQVGRLLSALDDLQLANS<br>TIIAFTSDHGWALGEHGEWAKYSNFDVATHVPLIFYVPGRT<br>ASLPEAGEKLFPYLDPFDSASQLMEPGRQSMDLVELVSLFP<br>TLAGLAGLQVPPRCPVPSFHVELCREGKNLLKHFRFRDLEE<br>DPYLPGNPRELIAYSQYPRPSDIPQWNSDKPSLKDIKIMGYS<br>IRTIDYRYTVWVGFNPDEFLANFSDIHAGELYFVDSDPLQD<br>HNMYNDSQGGDLFQLLMP (SEQ ID NO: 2) |

Various kinds of promoters can be used in the rAAV vector described herein. These include, for example, ubiquitous, tissue-specific, and regulatable (e.g. inducible or repressible) promoters. In some embodiments, the promoter is a liver-specific promoter. Examples of liver-specific promoters are known in the art and include, for example, human transthyrethin promoter (TTR), α-Antitrypsin promoter, human factor IX pro/liver transcription factor-responsive oligomers, LSP, and the basic albumin promoter. Liver specific promoters are described, for example, in Zhijian Wu et al., *Molecular Therapy* vol 16, no 2, February 2008, the contents of which are incorporated herein by reference.

In some embodiments, the promotor is a ubiquitous promoter. In some embodiments, the promoter is a chicken beta actin promoter.

In some embodiments, the rAAV vector contains additional enhancer or regulatory elements to promote transcription and/or translation of the mRNA (e.g., enhancer sequences, Kozak sequences, polyadenylation sequences, transcriptional termination sequences, IRES and the like). In some embodiments, the vector comprises a 5' and a 3' inverted terminal repeat (ITR). In some embodiments, the vector comprises a one or more enhancer elements. In some embodiments, the vector comprises a poly(A) tail.

In some embodiments, the rAAV vector comprises one or more small elements, such as an intron. Various introns are known in the art. Suitable introns for the rAAV vector described herein include for example an MVM intron, a truncated F.IX intron, a chimeric β globin SD/immunoglobulin heavy chain SA intron, SV40 and/or an alpha globin 1$^{st}$ intron. In some embodiments, the rAAV vector comprises an MVM intron. In some embodiments, the rAAV vector comprises an SV40 intron.

In some embodiments, the rAAV vector comprises woodchuck hepatitis virus post-transcriptional control element (WPRE). Various optimized or variant forms of WPRE are known in the art, and include WPRE3, WPREmut6delATG among others. Other variant WPRE forms include, for example, WPRE2, WPRE_wt (GenBank accession no. J04514); WPRE_wt (GenBank accession no. J02442) and WPREmut6.

In some embodiments, the rAAV vector comprises a cis-actin regulatory module (CRM). Various kinds of CRM are suitable for use in the vectors described herein and include for example liver-specific CRM, neuronal-specific CRM. In some embodiments, the vectors described herein include a hepatocyte-specific CRM, for example, CRM8. In some embodiments, the vector includes more than one CRM. For example, in some embodiments, the vector comprises two, three, four, five or six CRM. In some embodiments, the vector comprises three CRM, for example three CRM8.

In some embodiments, the rAAV vector is sequence optimized to increase transcript stability, for more efficient translation, and to reduce immunogenicity. In some embodiments, the I2S is sequence optimized.

In some embodiments, the rAAV vector is an AAV1, AAV2, AAV3, AAV4, AAV5, AAV6, AAV7, AAV8, AAV9, AAV10, or AAV11 vector. In some embodiments, the rAAV vector is AAV1. In some embodiments, the rAAV vector is AAV2. In some embodiments, the rAAV vector is AAV3. In some embodiments, the rAAV vector is AAV4. In some embodiments, the rAAV vector is AAV5. In some embodiments, the rAAV vector is AAV 6. In some embodiments, the rAAV vector is AAV7. In some embodiments, the rAAV vector is AAV8. In some embodiments, the rAAV vector is AAV9. In some embodiments, the rAAV vector is AAV10. In some embodiments, the rAAV vector is AAV11.

Exemplary element sequences are shown in Table 2 below. In some embodiments, the rAAV vector comprises a rAAV vector element comprising a nucleotide sequence having at least 60%, 65%, 70%, 75%, 80%, 85%, 90%, 95% or 99% identity with a vector element sequence shown in Table 2. In some embodiments, the rAAV vector comprises a vector element nucleotide sequence identical to a vector element nucleotide sequence shown in Table 2. In the table, Xn (60-100) means DNA titer tag comprising 60-100 nucleotides.

TABLE 2

Exemplary I2S rAAV Element Sequences

3xCRM8 gggggaggctgctggtgaatattaaccaaggtcaccccagttatcggaggagcaaacaggggc
taagtccaccggggaggctgctggtgaatattaaccaaggtcaccccagttatcggaggagc
aaacaggggctaagtccaccggggaggctgctggtgaatattaaccaaggtcaccccagtta
tcggaggagcaaacaggggctaagtccac
(SEQ ID NO: 3)

hTTR promoter aaatgacctattaagaatatttcatagaacgaatgttccgatgctctaatctctctagacaag
gttcatatttgtatgggttacttattctctctttgttgactaagtcaataatcagaatcagca
ggtttgcagtcagattggcagggataagcagcctagctcaggagaagtgagtataaaagcccc
aggctgggagcagccatcacagaagtccactcattcttggcagg
(SEQ ID NO: 4)

MVM intron ctaaggtaagttggcgccgtttaagggatggttggttggtggggtattaatgtttaattacct
tttttacaggcctg
(SEQ ID NO: 5)

hIDS wt atgccgccaccccggaccggccgaggccttctctggctgggtctggttctgagctccgtctgc
gtcgccctcggatccgaaacgcaggccaactcgaccacagatgctctgaacgttcttctcatc
atcgtggatgacctgcgcccctccctgggctgttatggggataagctggtgaggtccccaaat
attgaccaactggcatcccacagcctcctcttccagaatgcctttgcgcagcaagcagtgtgc
gccccgagccgcgtttctttcctcactggcaggagacctgacaccacccgcctgtacgacttc
aactcctactggagggtgcacgctggaaacttctccaccatccccagtacttcaaggagaat
ggctatgtgaccatgtcggtggggaaaagtcttcaccctgggatatcttctaaccataccgat
gattctccgtatagctggtcttttccaccttatcatccttcctctgagaagtatgaaaacact
aagacatgtcgagggccagatggagaactccatgccaacctgcttttgccctgtggatgtgctg
gatgttcccgagggcaccttgcctgacaaacagagcactgagcaagccatacagttgttggaa
aagatgaaaacgtcagccagtcctttcttcctggccgttgggtatcataagccacacatcccc
ttcagatacccaaggaatttcagaagttgtatccccttggagaacatcaccctggcccccgat
cccgaggtccctgatggcctacccctgtggcctacaaccctggatggacatcaggcaacgg
gaagacgtccaagccttaaacatcagtgtgccgtatggtccaattcctgtggactttcagcgg
aaaatccgccagagctactttgcctctgtgtcatatttggatacacaggtcggccgcctcttg
agtgctttggacgatcttcagctggccaacagcaccatcattgcatttacctcggatcatggg
tgggctctaggtgaacatggagaatgggccaaatacagcaattttgatgttgctacccatgtt
cccctgatattctatgttcctggaaggacggcttcacttccggaggcaggcgagaagcttttc
ccttacctcgaccctttttgattccgcctcacagttgatggagccaggcaggcaatccatggac
cttgtggaacttgtgtctcttttccccacgctggctggacttgcaggactgcaggttccacct
cgctgccccgttccttcatttcacgttgagctgtgcagagaaggcaagaaccttctgaagcat
tttcgattccgtgacttggaagaggatccgtacctccctggtaatcccgtgaactgattgcc
tatagccagtatccccggccttcagacatccctcagtggaattctgacaagccgagtttaaaa
gatataaagatcatgggctattccatacgcaccatagactataggtatactgtgtgggttggc
ttcaatcctgatgaatttctagctaacttttctgacatccatgcaggggaactgtattttgtg
gattctgacccattgcaggatcacaatatgtataatgattcccaaggtggagatcttttccag
ttgttgatgccttga
(SEQ ID NO: 6)

WPREmut6delATG aatcaacctctggattacaaaatttgtgaaagattgactggtattcttaactttgttgctcct
tttacgctttgtggatacgctgctttattgcctttgtatcttgctattgcttcccgtttggct
ttcattttctcctccttgtataaatcctggttgctgtctcttttgaggagttgtggcccgtt
gtcaggcaacgtggcgtggtgtgcactgtgtttgctgacgcaaccccccactggttggggcatt
gccaccacctgtcagctccttccgggactttcgctttcccctcccattgccacggcggaa
ctcatcgccgcctgccttgcccgctgctggacaggggctcggctgttgggcactgacaattcc
gtggtgttgtcggggaaatcatcgtcctttccttggctgctcgcctgtgttgccacctggatt
ctgcgcgggacgtccttctgctacgtcccttcggccctcaatccagcggaccttccttcccgc
ggcctgctgccggctctgcggcctcttccgcgtcttcgccttcgccctcagacgagtcggatc
tcccttttgggccgcctccccgcatc
(SEQ ID NO: 7)

BGH pA cctagagctcgctgatcagcctcgactgtgccttctagttgccagccatctgttgtttgcccc
tccccgtgccttccttgaccctggaaggtgccactcccactgtcctttcctaataaaatgag
gaaattgcatcgcattgtctgagtaggtgtcattctattctggggggtggggtggggcaggac
agcaaggggaggattgggaagacaataagcaggcatgctggggaa
(SEQ ID NO: 8)

TABLE 2-continued

Exemplary I2S rAAV Element Sequences

3' ITR aggaaccctagtgatggagttggccactccctctctgcgcgctcgctcgctcactgaggccg
ggcgaccaaaggtcgcccgacgcccgggctttgcccgggcggcctcagtgagcgagcgagcgc
gcagaga
(SEQ ID NO: 9)

5' ITR ctgcgcgctcgctcgctcactgaggccgcccgggcaaagcccgggcgtcgggcgacctttggt
cgcccggcctcagtgagcgagcgagcgcgcagagagggagtggccaactccatcactaggggt
tcct
(SEQ ID NO: 10)

Codon Optimized human IDS (COOL opt)

atgccaccacctaggacaggcaggggcctgctttggcttggactggtgctgagctctgtctgt
gttgccctgggctccgagacccaagccaactctacaaccgatgctctcaatgttctgctcatc
atagtggatgacctgcggccctctctaggctgctatgggacaagttggtgcggagcccaac
atagaccagctagcctctcactccctgctgttccagaatgccttcgcccagcaagctgtgtgc
gccccctctagagtgtctttcctgaccgggagaaggcctgatacaacaaggctgtatgacttt
aacagctactggagggtgcacgcaggcaacttctccactatcccccaatacttcaaggagaat
ggctatgtgaccatgagcgtgggcaaggtcttccaccctggaatctcctccaaccacactgat
gatagtccctactcttggtcttttcctcccatcaccctagcagtgagaagtatgagaacacc
aaaacctgcagaggccctgatggggagctgcatgctaacctcctgtgtcctgtagatgtgctg
gacgtcccagagggcaccttgccagataagcagtctactgagcaggctatccagctgcttgag
aaaatgaagacttctgcatctcccttctttctggctgttggctaccacaagcctcacatcccc
ttcaggtaccctaaggagttccaaaagctctatcctctggaaaacatcacacttgccccgat
cctgaggtccctgacgcctcccaccagtagcctacaatccttggatggacattaggcagaga
gaggatgtccaggctctgaatatttctgtgccctatgggcccatcccggtggacttccagcgc
aaaatcagacagtcctactttgcctctgtgagctatctggacacccaggttggggaggctcctc
tccgcccttgacgacctccagttggccaacagcaccattatagccttcacctctgaccacggc
tgggcactggggaacacggggagtgggctaagtactctaactttgatgtggccacccacgtg
cccctcatctttatgtgcctggcaggactgccagcctgcccgaagctggggaaaaactgttt
ccatacctggacccttttgacagtgcttctcagctcatggaacctggccgtcagagcatggat
ctggtggagctagtgtgtccctcttcccaaccttggctggccttgctggtctccaggtgcctcct
agatgcccagtcccctccttccatgttgaactctgccgtgagggaagaatctgctgaagcac
ttcagattcagagacttggaggaggaccctaccttcctgggaaccccagggagttgattgca
tactcccagtatcccaggccaagtgacattccccagtggaactccgacaaaccaagtctgaag
gacatcaagatcatggggtacagcatcaggaccattgactacagatacacagtgtgggttgga
tttaacccagatgagttcttggcaaacttttctgacatccatgcaagtcagttgtattttgtg
gacagcgaccctctgcaggatcacaacatgtacaatgacagccagggtggggacctctttcaa
ctcctcatgccatag
(SEQ ID NO: 11)

Codon Optimized human IDS (AUS optimized)

atgccacccccccggaccgggagaggcctcttgtggttgggcctggtgctgagcagcgtgtgc
gtggccctgggcagtgagacccaggctaactctacaacagatgccttgaatgtgctgctgatc
attgtggatgacctgaggccaagtctgggctgctatggggacaaattggtgaggtccccaac
atcgaccagttggcctccactctctcctattccaaaatgctttcgcccagcaggcagtttgt
gccccctctagggtgagcttcctcactggcaggcgcctgacaccactagactgtatgactt
aacagctattggagggtgcacgcaggaaacttctccacaatccctcaatacttcaaggagaat
ggttatgtgacaatgtctgtgggcaaggtgttccaccctggcatcagcagcaaccacaccgat
gactcaccctatagttggtcttttcccccctaccatccttcatctgagaaatatgaaaacaca
aaaacctgccgaggcccagacgggaactgcatgccaacctactctgtcctgttgatgtactg
gacgtgcccgagggcaccctccctgataagcagtccacagaacaggccattcagctgcttgaa
aagatgaagacctccgcatccccttcttcttggctgtcggctaccacaagccccatatcccc
tttagataccccaaggaattccagaaactgtaccactggagaacatcacacttgctcctgac
cctgaagtgcctgacggactgcctccagtggcctataaccttggatggacatccggcagcgc
gaggatgtgcaggctctgaacattagtgtgccttatgggcccatccctgtgacttcagagg
aagattcgccagtcctactttgcctctgtatcctacctggacacacaggtgggacgcctgctg
tctgcccttgatgatctgcaactggccaacagcaccattatagctttcacatcagaccatggg
tgggctcttggggagcatggtgaatgggctaagtactccaacttcgatgtggcaacccatgtc
cctctgatcttctatgtgccaggaaggaccgcctctctgccagaggcaggtgagaagctgttc
ccctatctggacccttttgactccgccagccagtctgatggagccggccgacagtctatgac
ctggttgagctggtcagcctgtttcccacactcgctggactggctggcctgcaagtaccccca
cgctgccagtgccctccttccatgtggagctttgcaggagggaagaacctcctcaagcac
ttcaggttcagggacctagaggaggatccttatctgcctggaaaccccagagagcttattgct
tactcccagtatccaaggcctagtgacattcccaatggaactcagacaaaccaagcctgaaa
gacatcaagatcatgggatactctatcaggaccattggctacagatacacagtgtgggttggc
ttcaacccggatgagttcctggctaatttctctgacatacatgctggcgagctgtacttcgtg
gacagtgacccctgcaggatcacaacatgtacaatgattcccaggggggtgacctcttccag
cttctgatgccctaa
(SEQ ID NO: 12)

TABLE 2-continued

Exemplary I2S rAAV Element Sequences

IRES gcccctctccctccccccccctaacgttactggccgaagccgcttggaataaggccggtgtg
cgtttgtctatatgttattttccaccatattgccgtcttttggcaatgtgagggcccggaaac
ctggccctgtcttcttgacgagcattcctaggggtctttcccctctcgccaaaggaatgcaag
gtctgttgaatgtcgtgaaggaagcagttcctctggaagcttcttgaagacaaacaacgtctg
tagcgaccctttgcaggcagcggaaccccccacctggcgacaggtgcctctgcggccaaaagc
cacgtgtataagatacacctgcaaaggcggcacaaccccagtgccacgttgtgagttggatag
ttgtggaaagagtcaaatggctcacctcaagcgtattcaacaaggggctgaaggatgcccaga
aggtaccccattgtatgggatctgatctggggcctcggtgcacatgctttacatgtgtttagt
cgaggttaaaaaacgtctaggcccccccgaaccacggggacgtggttttcctttgaaaaacacg
atgataat
(SEQ ID NO: 13)

SUMF1 wild type atggctgcgcccgcactagggctggtgtgtggacgttgccctgagctgggtctcgtcctcttg
ctgctgctgctctcgctgctgtgtggagcggcagggagccaggaggccgggaccggtgcgggc
gcggggtcccttgcgggttcttgcggctgcggcacgcccagcgcctggcgcccatggcagt
tcggcagccgctcaccgatactcgcgggaggctaacgctccgggcccgtaccggagagcgg
caactcgcgcactcaaagatggtccccatccctgctggagtatttacaatgggcacagatgat
cctcagataaagcaggatggggaagcacctgcgaggagagttactattgatgccttttacatg
gatgcctatgaagtcagtaatactgaatttgagaagtttgtgaactcaactggctatttgaca
gaggctgagaagtttggcgactcctttgtctttgaaggcatgttgagtgagcaagtgaagacc
aatattcaacaggcagttgcagctgctccctggtggttacctgtgaaaggcgctaactggaga
cacccagaagggcctgactctactattctgcacaggccggatcatccagttctccatgtgtcc
tggaatgatgcggttgcctactgcacttgggcagggaagcggctgcccacggaagctgagtgg
gaatacagctgtcgaggaggcctgcataatagactttccctggggcaacaaactgcagccc
aaaggccagcattatgccaacatttggcagggcgagtttccggtgaccaacactggtgaggat
ggcttccaaggaactgcgcctgttgatgccttccctcccaatggttatggcttatacaacata
gtggggaacgcatgggaatggacttcagactggtggactgttcatcattctgttgaagaaacg
cttaacccaaaaggtccccttctgggaaagaccgagtgaagaaaggtggatcctacatgtgc
cataggtcttattgttacaggtatcgctgtgctgctcggagccagaacacacctgatagctct
gcttcgaatctgggattccgctgtgcagccgaccgcctgcccactatggactga
(SEQ ID NO: 14)

Codon Optimized SUMF-1 (COOL optimized)

atggctgctcctgccctggggctggtgtgtggaagatgtcctgaactgggcctggttctgtta
ctgcttctgctcagcctgctctgtggtgctgccggcagccaagaggcaggcactggcgctgga
gctggaagcctggctgggtcttgtggatgtggcacaccacagaggccaggggctcatggctcc
tctgctgcagctcataggtacagcagagaagccaatgctccaggcccagtgcctggagagaga
cagctggctcacagcaagatggtgcccatccctgctgggtgttcacaatgggaacagatgat
ccccagatcaagcaggatggggaggcgcctgccaggagggtgaccattgatgcattctatatg
gatgcctatgaggtgagcaatacagaatttgagaagtttgtgaactctactggctacctgact
gaggctgaaaaatttggagactcttttgtgtttaaggaatgcttagtgaacaggttaagacc
aacatccagcaggctgttgcagcagcccctggtggttgcctgtcaagggagctaactggagg
caccctgagggaccagattctacaatcctgcatagacctgatcatcctgttctgcatgtgtct
tggaatgatgctgtggcttactgtacctgggcaggaaaaaggctgccaacagaagctgagtgg
gaatactcttgcagaggaggcctgcacaatagactgttcccatggggcaacaagctgcaaccc
aagggccagcactatgctaacatctggcagggagaattccctgtgacaaacacaggagaggac
ggcttccagggaactgcccctgtagatgctttccctcctaatggctatgcctgtataacatt
gttggcaacgcctgggagtggacttctgattggtggacagtgcaccactctgttgaggagaca
ctgaatcctaagggggcacttctggaaaggatagagtgaagaagggggggaagctacatgtgc
cacaggtcttattgttacagatacaggtgcgctgctaggtctcagaacacccctgatagcagt
gctagcaatctgggcttcaggtgtgccgctgacagactgcctaccatggattaa
(SEQ ID NO: 15)

Codon Optimized SUMF-1 (AUS optimized)

atggctgcccctgctctgggattggtttgtggcagatgtcctgagcttggtctggtgctgttg
ctccttctgttgtctctgctgtgtggagcagctgggtctcaggaagctggcacaggcgctggg
gctggctctctggccgggtcatgtggctgtggaactcccagcggcctggagcccatggcagc
tctgccgcagcacacaggtattctagggaagccaatgcccaggccctgtgcctggggagaga
cagctagctcattctaagatggtgcctatcccagccggggttttacaatgggcactgatgat
cctcagattaagcaggatggagaggccccccgccagaagagtgaccattgatgctttctacatg
gatgcatatgaagtgtccaacacagagtttgagaaatttgtgaactctactggatacttgacc
gaggctgagaagtttggagattcctttgtctttgaaggcatgctgtctgagcaggtcaagacc
aacattcagcaagcagtggccgctgcaccttggtggcttcctgtgaagggccaactggaga
catccagaggggccagatagtaccatcctccacagacctgatcacccagtccttcatgtttcc
tggaatgatgcagttgcttactgcacttgggccggcaagaggctccctactgaggcagagtgg
gaatactcctgcagaggaggcctgcacaacagactgttcccttggggaacaagcttcagccc
aaaggccagcactatgctaacatctggcagggtgagtttccagtcaccaatacaggggaggac
ggattccagggaaccgcaccagtagatgccttccctcctaatggctatgcctgtataatatt TABLE 2-continued Exemplary I2S rAAV Element Sequences gtgggcaatgcatgggagtggacctctgactggtggactgtgcaccactcagtggaggaaacc
ctgaaccctaagggaccccttcaggcaaagatagagtcaaaaagggagggagctatatgtgt
cacagatcctattgctacagatatagatgtgcagccaggtcccagaacaccctgactcttct
gctagcaacctgggctttcggtgtgctgctgatagactgcccaccatggactaa
(SEQ ID NO: 16)

In some embodiments, the rAAV I2S vector comprises a nucleotide sequence having at least 60%, 65%, 70%, 75%, 80%, 85%, 90%, 95% or 99% identity with a nucleotide sequence shown in Table 3 below. In some embodiment, the rAAV I2S vector comprises a sequence identical to a nucleotide sequence shown in Table 3 below.

TABLE 3

Exemplary rAAV I2S vector nucleotide sequences pXL024

CTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGT
TCCTTTAATTAAACGCGTGGGGGAGGCTGCTGGTGAATATTAACCAAGGTCACCCCAGTTATC
GGAGGAGCAAACAGGGGCTAAGTCCACCGGGGGAGGCTGCTGGTGAATATTAACCAAGGTCAC
CCCAGTTATCGGAGGAGCAAACAGGGGCTAAGTCCACCGGGGGAGGCTGCTGGTGAATATTAA
CCAAGGTCACCCCAGTTATCGGAGGAGCAAACAGGGGCTAAGTCCACACTAGTAAATGACCTA
TTAAGAATATTTCATAGAACGAATGTTCCGATGCTCTAATCTCTCTAGACAAGGTTCATATTT
GTATGGGTTACTTATTCTCTCTTTGTTGACTAAGTCAATAATCAGAATCAGCAGGTTTGCAGT
CAGATTGGCAGGGATAAGCAGCCTAGCTCAGGAGAAGTGAGTATAAAAGCCCCAGGCTGGGAG
CAGCCATCACAGAAGTCCACTCATTCTTGGCAGGCCGCGGCTAAGGTAAGTTGGCGCCGTTTA
AGGGATGGTTGGTTGGTGGGGTATTAATGTTTAATTACCTTTTTTACAGGCCTGGGCGCGCCG
CCACCATGCCGCCACCCCGGACCGGCCGAGGCCTTCTCTGGCTGGGTCTGGTTCTGAGCTCCG
TCTGCGTCGCCCTCGGATCCGAAACGCAGGCCAACTCGACCACAGATGCTCTGAACGTTCTTC
TCATCATCGTGGATGACCTGCGCCCCTCCCTGGGCTGTTATGGGGATAAGCTGGTGAGGTCCC
CAAATATTGACCAACTGGCATCCCACAGCCTCCTCTTCCAGAATGCCTTTGCGCAGCAAGCAG
TGTGCGCCCCGAGCCGCGTTTCTTTCCTCACTGGCAGGAGACCTGACACCACCCGCCTGTACG
ACTTCAACTCCTACTGGAGGGTGCACGCTGGAAACTTCTCCACCATCCCCCAGTACTTCAAGG
AGAATGGCTATGTGACCATGTCGGTGGGAAAAGTCTTTCACCCTGGGATATCTTCTAACCATA
CCGATGATTCTCCGTATAGCTGGTCTTTTCCACCTTATCATCCTTCCTCTGAGAAGTATGAAA
ACACTAAGACATGTCGAGGGCCAGATGGAGAACTCCATGCCAACCTGCTTTGCCCTGTGGATG
TGCTGGATGTTCCCGAGGGCACCTTGCCTGACAAACAGAGCACTGAGCAAGCCATACAGTTGT
TGGAAAAGATGAAAACGTCAGCCAGTCCTTTCTTCCTGGCCGTTGGGTATCATAAGCCACACA
TCCCCTTCAGATACCCCAAGGAATTTCAGAAGTTGTATCCCTTGGAGAACATCACCCTGGCCC
CCGATCCCGAGGTCCCTGATGGCCTACCCCCTGTGGCCTACAACCCTGGATGGACATCAGGC
AACGGGAAGACGTCCAAGCCTTAAACATCAGTGTGCCGTATGGTCCAATTCCTGTGGACTTTC
AGCGGAAAATCCGCCAGAGCTACTTTGCCTCTGTGTCATATTTGGATACACAGGTCGGCCGCC
TCTTGAGTGCTTTGGACGATCTTCAGCTGGCCAACAGCACCATCATTGCATTTACCTCGGATC
ATGGGTGGGCTCTAGGTGAACATGGAGAATGGGCCAAATACAGCAATTTTGATGTTGCTACCC
ATGTTCCCCTGATATTCTATGTTCCTGGAAGGACGGCTTCACTTCCGGAGGCAGGCGAGAAGC
TTTTCCCTTACCTCGACCCTTTTGATTCCGCCTCACAGTTGATGGAGCCAGGCAGGCAATCCA
TGGACCTTGTGGAACTTGTGTCTCTTTTTCCCACGCTGGCTGGACTTGCAGGACTGCAGGTTC
CACCTCGCTGCCCCGTTCCTTCATTTCACGTTGAGCTGTGCAGAGAAGGCAAGAACCTTCTGA
AGCATTTTCGATTCCGTGACTTGGAAGAGGATCCGTACCTCCCTGGTAATCCCCGTGAACTGA
TTGCCTATAGCCAGTATCCCCGGCCTTCAGACATCCCTCAGTGGAATTCTGACAAGCCGAGTT
TAAAAGATATAAAGATCATGGGCTATTCCATACGCACCATAGACTATAGGTATACTGTGTGGG
TTGGCTTCAATCCTGATGAATTTCTAGCTAACTTTTCTGACATCCATGCAGGGGAACTGTATT
TTGTGGATTCTGACCCATTGCAGGATCACAATATGTATAATGATTCCCAAGGTGGAGATCTTT
TCCAGTTGTTGATGCCTTGAGGTACCAATCAACCTCTGGATTACAAAATTTGTGAAAGATTGA
CTGGTATTCTTAACTTTGTTGCTCCTTTTACGCTTTGTGGATACGCTGCTTTATTGCCTTTGT
ATCTTGCTATTGCTTCCCGTTTGGCTTTCATTTTCTCCTCCTTGTATAAATCCTGGTTGCTGT
CTCTTTTTGAGGAGTTGTGGCCCGTTGTCAGGCAACGTGGCGTGGTGTGCACTGTGTTTGCTG
ACGCAACCCCCACTGGTTGGGGCATTGCCACCACCTGTCAGCTCCTTTCCGGGACTTTCGCTT
TCCCCCTCCCTATTGCCACGGCGGAACTCATCGCCGCCTGCCTTGCCCGCTGCTGGACAGGGG
CTCGGCTGTTGGGCACTGACAATTCCGTGGTGTTGTCGGGGAAATCATCGTCCTTTCCTTGGC
TGCTCGCCTGTGTTGCCACCTGGATTCTGCGCGGGACGTCCTTCTGCTACGTCCCTTCGGCCC
TCAATCCAGCGGACCTTCCTTCCCGCGGCCTGCTGCCGGCTCTGCGGCCTCTTCCGCGTCTTC
GCCTTCGCCCTCAGACGAGTCGGATCTCCCTTTGGGCCGCCTCCCCGCATCGGTACCGTCGAC
CCTAGAGCTCGCTGATCAGCCTCGACTGTGCCTTCTAGTTGCCAGCCATCTGTTGTTTGCCCC
TCCCCCGTGCCTTCCTTGACCCTGGAAGGTGCCACTCCCACTGTCCTTTCCTAATAAAATGAG
GAAATTGCATCGCATTGTCTGAGTAGGTGTCATTCTATTCTGGGGGGTGGGGTGGGGCAGGAC
AGCAAGGGGGAGGATTGGGAAGACAATAGCAGGCATGCTGGGGAATCTAGA Xn(60-100)
GTTTAAACATTTAAATAGGAACCCCTAGTGATGGAGTTGGCCACTCCCTCTCTGCGCGCTCGC
TCGCTCACTGAGGCCGGGCGACCAAAGGTCGCCCGACGCCCGGGCTTTGCCCGGGCGGCCTCA
GTGAGCGAGCGAGCGCGCAGAGAGTATACATCGATGTGAGTTCGCGGGTGGCTGGGGGGCCCT
GGGCTGCGACCGCCCCCGAACCGCGTCTACGAGCCCTTGCGGGCTCCGGGTCTTTGCAGTCGTA
TGGGGGCAGGGTAGCTGTTCCCCGCAAGGAGAGCTCAAGGTCAGCGCTCGGACCTGGCGGAGC

TABLE 3-continued

Exemplary rAAV I2S vector nucleotide sequences

```
CCCGCACCCAGGCTGTGGCGCCCTGTGCAGCTCCGCCCTTGCGGCGCCATCTGCCCGGAGCCT
CCTTCCCCTAGTCCCCAGAAACAGGAGGTCCCTACTCCCGCCCAGATCCCGACCCGGACCCC
TAGGTGGGGGACGCTTTCTTTCCTTTCGCGCTCTGCGGGGTCACGTGTCGCAGAGGAGCCCCT
CCCCCACGGCCTCCGGCACCGCAGGCCCCGGGATGCTAGTGCGCAGCGGGTGCATCCCTGTCC
GGATGCTGCGCCTGCGGTAGAGCGGCCGCCATGTTGCAACCGGGAAGGAAATGAATGGGCAGC
CGTTAGGAAAGCCTGCCGGTGACTAACCCTGCGCTCCTGCCTCGATGGGTGGAGTCGCGTGTG
GCGGGGAAGTCAGGTGGAGCGAGGCTAGCTGGCCCGATTTCTCCTCCGGGTGATGCTTTTCCT
AGATTATTCTCTGGTAAATCAAAGAAGTGGGTTTATGGAGGTCCTCTTGTGTCCCCTCCCCGC
AGAGGTGTGGTGGCTGTGGCATGGTGCCAAGCCGGGAGAAGCTGAGTCATGGGTAGTTGGAAA
AGGACATTTCCACCGCAAAATGGCCCCTCTGGTGGTGGCCCCTTCCTGCAGCGCCGGCTCACC
TCACGGCCCCGCCCTTCCCCTGCCAGCCTAGCGTTGACCCGACCCCAAAGGCCAGGCTGTAAA
TGTCACCGGGAGGATTGGGTGTCTGGGCGCCTCGGGGAACCTGCCCTTCTCCCCATTCCGTCT
TCCGGAAACCAGATCTCCCACCGCACCCTGGTCTGAGGTTAAATATAGCTGCTGACCTTTCTG
TAGCTGGGGGCCTGGGCTGGGGCTCTCTCCCATCCCTTCTCCCCACACACATGCACTTACCTG
TGCTCCCACTCCTGATTTCTGGAAAAGAGCTAGGAAGGACAGGCAACTTGGCAATTCAAAGCC
CTGGGACTAGGGGGTTAAAATACAGCTTCCCCTCTTCCCACCCGCCCCAGTCTCTGTCCCTTT
TGTAGGAGGGACTTAGAGAAGGGGTGGGCTTGCCCTGTCCAGTTAATTTCTGACCTTTACTCC
TGCCCTTTGAGTTTGATGATGCTGAGTGTACAAGCGTTTTCTCCCTAAAGGGTGCAGCTGAGC
TAGGCAGCAGCAAGCATTCCTGGGGTGGCATAGTGGGGTGGTGAATACCATGTACAAAGCTTG
TGCCCAGACTGTGGGTGGCAGTGCCCCACATGGCCGCTTCTCCTGGAAGGGCTTCGTATGACT
GGGGGTGTTGGGCAGCCCTGGAGCCTTCAGTTGCAGCCATGCCTTAAGCCAGGCCAGCCTGGC
AGGGAAGCTCAAGGGAGATAAAATTCAACCTCTTGGGCCCTCCTGGGGGTAAGGAGATGCTGC
ATTCGCCCTCTTAATGGGGAGGTGGCCTAGGGCTGCTCACATATTCTGGAGGAGCCTCCCCTC
CTCATGCCTTCTTGCCTCTTGTCTCTTAGGCATGCAAAAGAGTCGAATAAGGGCGACACAAAA
TTTATTCTAAATGCATAATAAACTGATAACATCTTATAGTTTGTATTATATTTTGTATTAT
CGTTGACATGTATAATTTTGATATCAAAAACTGATTTTCCCTTTATTATTTTCGAGATTTATT
TTCTTAATTCTCTTTAACAAACTAGAAATATTGTATATACAAAAATCATAAATAATAGATGA
ATAGTTTAATTATAGGTGTTCATCAATCGAAAAAGCAACGTATCTTATTTAAAGTGCGTTGCT
TTTTTCTCATTTATAAGGTTAAATAATTCTCATATATCAAGCAAAGTGACAGGCGCCCTTAAA
TATTCTGACAAATGCTCTTTCCCTAAACTCCCCCCATAAAAAAACCCGCCGAAGCGGGTTTTT
ACGTTATTTGCGGATTAACGATTACTCGTTATCAGAACCGCCCAGGGGGCCCGAGCTTAAGAC
TGGCCGTCGTTTTACAACACAGAAAGAGTTTGTAGAAACGCAAAAAGGCCATCCGTCAGGGGC
CTTCTGCTTAGTTTGATGCCTGGCAGTTCCCTACTCTCGCCTTCCGCTTCCTCGCTCACTGAC
TCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTG
AAGTGGTGGCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGACGCGCGCGTAACTCACGTTAAGGGA
TTTTGGTCATGAGCTTGCGCCGTCCCGTCAAGTCAGCGTAATGCTCTGCTTAGGTGGCGGTAC
TTGGGTCGATATCAAAGTGCATCACTTCTTCCCGTATGCCCAACTTTGTATAGAGAGCCACTG
CGGGATCGTCACCGTAATCTGCTTGCACGTAGATCACATAAGCACCAAGCGCGTTGGCCTCAT
GCTTGAGGAGATTGATGAGCGCGGTGGCAATGCCCTGCCTCCGGTGCTCGCCGGAGACTGCGA
GATCATAGATATAGATCTCACTACGCGGCTGCTCAAACTTGGGCAGAACGTAAGCCGCGAGAG
CGCCAACAACCGCTTCTTGGTCGAAGGCAGCAAGCGCGATGAATGTCTTACTACGGAGCAAGT
TCCCGAGGTAATCGGAGTCCGGCTGATGTTGGGAGTAGGTGGCTACGTCACCGAACTCACGAC
CGAAAAGATCAAGAGCAGCCCGCATGGATTTGACTTGGTCAGGGCCGAGCCTACATGTGCGAA
TGATGCCCATACTTGAGCCACCTAACTTTGTTTTAGGGCGACTGCCCTGCTGCGTAACATCGT
TGCTGCTCCATAACATCAAACATCGACCCACGGCGTAACGCGCTTGCTGCTTGGATGCCCGAG
GCATAGACTGTACAAAAAAACAGTCATAACAAGCCATGAAAACCGCCACTGCGCCGTTACCAC
CGCTGCGTTCGGTCAAGGTTCTGGACCAGTTGCGTGAGCGCATTTTTTTTCCTCCTCGGCGT
TTACGCCCCGCCCTGCCACTCATCGCAGTACTGTTGTAATTCATTAAGCATTCTGCCGACATG
GAAGCCATCACAGACGGCATGATGAACCTGAATCGCCAGCGGCATCAGCACCTTGTCGCCTTG
CGTATAATATTTGCCCATAGTGAAAACGGGGGCGAAGAAGTTGTCCATATTGGCCACGTTTAA
ATCAAAACTGGTGAAACTCACCCAGGGATTGGCTGACGAAAAACATATTCTCAATAAACCC
TTTAGGGAAATAGGCCAGGTTTTCACCGTAACACGCCACATCTTGCGAATATATGTGTAGAAA
CTGCCGGAAATCGTCGTGTGCACTCATGGAAAACGGTGTAACAAGGGTGAACACTATCCCATA
TCACCAGCTCACCGTCTTTCATTGCCATACGAACTCCGGATGAGCATTCATCAGGCGGGCAA
GAATGTGAATAAAGGCCGGATAAAACTTGTGCTTATTTTTCTTTACGGTCTTTAAAAAGGCCG
TAATATCCAGCTGAACGGTCTGGTTATAGGTACATTGAGCAACTGACTGAAATGCCTCAAAAT
GTTCTTTACGATGCCATTGGGATATATCAACGGTGGTATATCCAGTGATTTTTTCTCCATTT
TTTTTCCTCCTTTAGAAAAACTCATCGAGCATCAAATGAAACTGCAATTTATTCATATCAGG
ATTATCAATACCATATTTTTGAAAAAGCCGTTTCTGTAATGAAGGAGAAAACTCACCGAGGCA
GTTCCATAGGATGGCAAGATCCTGGTATCGGTCTGCGATTCCGACTCGTCCAACATCAATACA
ACCTATTAATTTCCCCTCGTCAAAAATAAGGTTATCAAGTGAGAAATCACCATGAGTGACGAC
TGAATCCGGTGAGAATGGCAAAAGTTTATGCATTTCTTTCCAGACTTGTTCAACAGGCCAGCC
ATTACGCTCGTCATCAAAATCACTCGCATCAACCAAACCGTTATTCATTCGTGATTGCGCCTG
AGCGAGGCGAAATACGCGATCGCTGTTAAAAGGACAATTACAAACAGGAATCGAGTGCAACCG
GCGCAGGAACACTGCCAGCGCATCAACAATATTTTCACCTGAATCAGGATATTCTTCTAATAC
CTGGAACGCTGTTTTTCCGGGGATCGCAGTGGTGAGTAACCATGCATCATCAGGAGTACGGAT
AAAATGCTTGATGGTCGGAAGTGGCATAAATTCCGTCAGCCAGTTTAGTCTGACCATCTCATC
```

TABLE 3-continued

Exemplary rAAV I2S vector nucleotide sequences

```
TGTAACATCATTGGCAACGCTACCTTTGCCATGTTTCAGAAACAACTCTGGCGCATCGGCTT
CCCATACAAGCGATAGATTGTCGCACCTGATTGCCCGACATTATCGCGAGCCCATTTATACCC
ATATAAATCAGCATCCATGTTGGAATTTAATCGCGGCCTCGACGTTTCCCGTTGAATATGGCT
CATTTTTTTTTCCTCCTTTACCAATGCTTAATCAGTGAGGCACCTATCTCAGCGATCTGTCTA
TTTCGTTCATCCATAGTTGCCTGACTCCCCGTCGTGTAGATAACTACGATACGGGAGGGCTTA
CCATCTGGCCCCAGCGCTGCGATGATACCGCGAGAACCACGCTCACCGGCTCCGGATTTATCA
GCAATAAACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTTGCGC
AACGTTGTTGCCATCGCTACAGGCATCGTGGTGTCACGCTCGTCGTTTGGTATGGCTTCATTC
AGCTCCGGTTCCCAACGATCAAGGCGAGTTACATGATCCCCCATGTTGTGCACGTTGTCAGAA
GTAAGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAA
GGGCGACACGGAAATGTTGAATACTCATATTCTTCCTTTTTCAATATTATTGAAGCATTTATC
AGGGTTATTGTCTCATGAGCGGATACATATTTGAATGTATTTAGAAAAATAAACAAATAGGGG
TCAGTGTTACAACCAATTAACCAATTCTGAACATTATCGCGAGCCCATTTATACCTGAATATG
GCTCATAACACCCCTTGTTTGCCTGGCGGCAGTAGCGCGGTGGTCCCACCTGACCCCATGCCG
AACTCAGAAGTGAAACGCCGTAGCGCCGATGGTAGTGTGGGGACTCCCCATGCGAGAGTAGGG
AACTGCCAGGCATCAAATAAAACGAAAGGCTCAGTCGAAAGACTGGGCCTTTCGCCCGGGCTA
ATTGAGGGGTGTCGCCCTTATTCGACTCGGGGCTCGAG
(SEQ ID NO: 17)
``` pXL025

```
CTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGT
TCCTTTAATTAAACGCGTGGGGAGGCTGCTGGTGAATATTAACCAAGGTCACCCCAGTTATC
GGAGGAGCAAACAGGGGCTAAGTCCACCGGGGGAGGCTGCTGGTGAATATTAACCAAGGTCAC
CCCAGTTATCGGAGGAGCAAACAGGGGCTAAGTCCACACTAGTAAATGACCTA
TTAAGAATATTTCATAGAACGAATGTTCCGATGCTCTAATCTCTCTAGACAAGGTTCATATTT
GTATGGGTTACTTATTCTCTCTTTGTTGACTAAGTCAATAATCAGAATCAGCAGGTTTGCAGT
CAGATTGGCAGGGATAAGCAGCCTAGCTCAGGAGAAGTGAGTATAAAAGCCCCAGGCTGGGAG
CAGCCATCACAGAAGTCCACTCATTCTTGGCAGGCCGCGGCTAAGGTAAGTTGGCGCCGTTTA
AGGGATGGTTGGTTGGTGGGGTATTAATGTTTAATTACCTTTTTTACAGGCCTGGGCGCGCCG
CCACCATGCCACCACCTAGGACAGGCAGGGGCCTGCTTTGGCTTGGACTGGTGCTGAGCTCTG
TCTGTGTTGCCCTGGGCTCCGAGACCCAAGCCAACTCTACAACCGATGCTCTCAATGTTCTGC
TCATCATAGTGGATGACCTGCGGCCCTCTCTAGGCTGCTATGGAGCAAGTTGGTGCGGAGCC
CCAACATAGACCAGCTAGCCTCTCACTCCCTGCTGTTCCAGAATGCCTTCGCCCAGCAAGCTG
TGTGCGCCCCCTCTAGAGTGTCTTTCCTGACCGGGAGAAGGCCTGATACAACAAGGCTGTATG
ACTTTAACAGCTACTGGAGGGTGCACGCAGGCAACTTCTCCACTATCCCCCAATACTTCAAGG
AGAATGGCTATGTGACCATGAGCGTGGGCAAGGTCTTCCACCCTGGAATCTCCTCCAACCACA
CTGATGATAGTCCCTACTCTTGGTCTTTTCCTCCCTATCACCCTAGCAGTGAGAAGTATGAGA
ACACCAAAACCTGCAGAGGCCCTGATGGGGAGCTGCATGCTAACCTCCTGTGTCCTGTAGATG
TGCTGGACGTCCCAGAGGGCACCTTGCCAGATAAGCAGTCTACTGAGCAGGCTATCCAGCTGC
TTGAGAAAATGAAGACTTCTGCATCTCCCTTCTTTCTGGCTGTTGGCTACCACAAGCCTCACA
TCCCCTTCAGGTACCCTAAGGAGTTCCAAAAGCTCTATCCTCTGGAAAACATCACACTTGCCC
CCGATCCTGAGGTCCCTGACGGCCTCCCACCAGTAGCCTACAATCCTTGGATGGACATTAGGC
AGAGAGGATGTCCAGGCTCTGAATATTTCTGTGCCCTATGGGCCCATCCGGTGGACTTCC
AGCGCAAAATCAGACAGTCCTACTTTGCCTCTGTGAGCTATCTGGACACCCAGGTTGGGAGGC
TCCTCTCCGCCCTTGACGACCTCCAGTTGGCCAACAGCACCATTATAGCCTTCACCTCTGACC
ACGGCTGGGCACTGGGGGAACACGGGGAGTGGGCTAAGTACTCTAACTTTGATGTGGCCACCC
ACGTGCCCCTCATCTTTTATGTGCCTGGCAGGACTGCCAGCCTGCCCGAAGCTGGGGAAAAAC
TGTTTCCATACCTGGACCCTTTTGACAGTGCTTCTCAGCTCATGGAACCTGGCCGTCAGAGCA
TGGATCTGGTGGAGCTAGTGTCCCTCTTCCCAACCTTGGCTGGCCTTGCTGGTCTCCAGGTGC
CTCCTAGATGCCCAGTCCCCTCCTTCCATGTTGAACTCTGCCGTGAGGGGAAGAATCTGCTGA
AGCACTTCAGATTCAGAGACTTGGAGGAGGACCCCTACCTTCCTGGGAACCCCAGGGAGTTGA
TTGCATACTCCCAGTATCCCAGGCCAAGTGACATTCCCCAGTGGAATCCAGACAAAACCAAGTC
TGAAGGACATCAAGATCATGGGGTACAGCATCAGGACCATTGACTACAGATACACAGTGTGGG
TTGGATTTAACCCAGATGAGTTCTTGGCAAACTTTTCTGACATCCATGCAAGTCAGTTGTATT
TTGTGGACAGCGACCCTCTGCAGGATCACAACATGTACAATGACAGCCAGGGTGGGGACCTCT
TTCAACTCCTCATGCCATAGCAATTGAATCAACCTCTGGATTACAAAATTTGTGAAAGATTGA
CTGGTATTCTTAACTTTGTTGCTCCTTTTACGCTTTGTGGATACGCTGCTTTATTGCCTTTGT
ATCTTGCTATTGCTTCCCGTTTGGCTTTCATTTTCTCCTCCTTGTATAAATCCTGGTTGCTGT
CTCTTTTTGAGGAGTTGTGGCCCGTTGTCAGGCAACGTGGCGTGGTGTGCACTGTGTTTGCTG
ACGCAACCCCCACTGGTTGGGGCATTGCCACCACCTGTCAGCTCCTTTCCGGGACTTTCGCTT
TCCCCCTCCCTATTGCCACGGCGGAACTCATCGCCGCCTGCCTTGCCCGCTGCTGGACAGGGG
CTCGGCTGTTGGGCACTGACAATTCCGTGGTGTTGTCGGGGAAATCATCGTCCTTTCCTTGGC
TGCTCGCCTGTGTTGCCACCTGGATTCTGCGCGGGACGTCCTTCTGCTACGTCCCTTCGGCCC
TCAATCCAGCGGACCTTCCTTCCCGCGGCCTGCTGCCGGCTCTGCGGCCTCTTCCGCGTCTTC
GCCTTCGCCCTCAGACGAGTCGGATCTCCCTTTGGGCCGCCTCCCCGCATCGATACCGTCGAC
CTAGAGCTCGCTGATCAGCCTCGACTGTGCCTTCTAGTTGCCAGCCATCTGTTGTTTGCCCC
TCCCCCGTGCCTTCCTTGACCCTGGAAGGTGCCACTCCCACTGTCCTTTCCTAATAAAATGAG
GAAATTGCATCGCATTGTCTGAGTAGGTGTCATTCTATTCTGGGGGGTGGGGTGGGGCAGGAC
AGCAAGGGGGAGGATTGGGAAGACAATAGCAGGCATGCTGGGGAATCTAGA Xn(60-100)
```

TABLE 3-continued

Exemplary rAAV I2S vector nucleotide sequences

```
GTTTAAACATTTAAATAGGAACCCCTAGTGATGGAGTTGGCCACTCCCTCTCTGCGCGCTCGC
TCGCTCACTGAGGCCGGGCGACCAAAGGTCGCCCGACGCCCGGGCTTTGCCCGGGCGGCCTCA
GTGAGCGAGCGAGCGCGCAGAGAGTATACATCGATGTGAGTTGCGGGTGGCTGGGGGGCCCT
GGGCTGCGACCGCCCCCGAACCGCGTCTACGAGCCTTGCGGGCTCCGGGTCTTTGCAGTCGTA
TGGGGGCAGGGTAGCTGTTCCCCGCAAGGAGAGCTCAAGGTCAGCGCTCGGACCTGGCGGAGC
CCCGCACCCAGGCTGTGGCGCCCTGTGCAGCTCCGCCCTTGCGGCGCCATCTGCCCGGAGCCT
CCTTCCCCTAGTCCCCAGAAACAGGAGGTCCCTACTCCCGCCCGAGATCCCGACCCGGACCCC
TAGGTGGGGGACGCTTTCTTTCCTTTCGCGCTCTGCGGGGTCACGTGTCGCAGAGGAGCCCCT
CCCCCACGGCCTCCGGCACCGCAGGCCCCGGGATGCTAGTGCGCAGCGGGTGCATCCCTGTCC
GGATGCTGCGCCTGCGGTAGAGCGGCCGCCATGTTGCAACCGGGAAGGAAATGAATGGGCAGC
CGTTAGGAAAGCCTGCCGGTGACTAACCCTGCGCGTCCTGCCTCGATGGGTGGAGTCGCGTGTG
GCGGGGAAGTCAGGTGGAGCGAGGCTAGCTGGCCCGATTTCTCCTCCGGGTGATGCTTTTCCT
AGATTATTCTCTGGTAAATCAAAGAAGTGGGTTTATGGAGGTCCTCTTGTGTCCCCTCCCCGC
AGAGGTGTGGTGGCTGTGGCATGGTGCCAAGCCGGGAGAAGCTGAGTCATGGGTAGTTGGAAA
AGGACATTTCCACCGCAAAATGGCCCCTCTGGTGGTGGCCCCTTCCTGCAGCGCCGGCTCACC
TCACGGCCCCGCCCTTCCCCTGCCAGCCTAGCGTTGACCCGACCCCAAAGGCCAGGCTGTAAA
TGTCACCGGGAGGATTGGGTGTCTGGGCGCCTCGGGGAACCTGCCCTTCTCCCCATTCCGTCT
TCCGGAAACCAGATCTCCCACCGCACCCTGGTCTGAGGTTAAATATAGCTGCTGACCTTTCTG
TAGCTGGGGGCCTGGGCTGGGGCTCTCTCCCATCCCTTCTCCCCACACACATGCACTTACCTG
TGCTCCCACTCCTGATTTCTGAAAAGAGCTAGGAAGGACAGGCAACTTGGCAAATCAAAGCC
CTGGGACTAGGGGGTTAAAATACAGCTTCCCCTCTTCCCACCCGCCCCAGTCTCTGTCCCTTT
TGTAGGAGGGACTTAGAGAAGGGGTGGGCTTGCCCTGTCCAGTTAATTTCTGACCTTTACTCC
TGCCCTTTGAGTTTGATGATGCTGAGTGTACAAGCGTTTTCTCCCTAAAGGGTGCAGCTGAGC
TAGGCAGCAGCAAGCATTCCTGGGGTGGCATAGTGGGGTGGTGAATACCATGTACAAAGCTTG
TGCCCAGACTGTGGGTGGCAGTGCCCCACATGGCCGCTTCTCCTGGAAGGGCTTCGTATGACT
GGGGGTGTTGGGCAGCCCTGGAGCCTTCAGTTGCAGCCATGCCTTAAGCCAGGCCAGCCTGGC
AGGGAAGCTCAAGGGAGATAAAATTCAACCTCTTGGGCCCTCCTGGGGGTAAGGAGATGCTGC
ATTCGCCCTCTTAATGGGGAGGTGGCCTAGGGCTGCTCACATATTCTGGAGGAGCCTCCCCTC
CTCATGCCTTCTTGCCTCTTGTCTCTTAGGCATGCAAAAGAGTCGAATAAGGGCGACACAAAA
TTTATTCTAAATGCATAATAAATACTGATAACATCTTATAGTTTGTATTATATTTTGTATTAT
CGTTGACATGTATAATTTTGATATCAAAAACTGATTTTCCCTTTATTATTTTCGAGATTTATT
TTCTTAATTCTCTTTAACAAACTAGAAATATTGTATATACAAAAAATCATAAATAATAGATGA
ATAGTTTAATTATAGGTGTTCATCAATCGAAAAAGCAACGTATCTTATTTAAAGTGCGTTGCT
TTTTTCTCATTTATAAGGTTAAATAATTCTCATATATCAAGCAAAGTGACAGGCGCCCTTAAA
TATTCTGACAAATGCTCTTTCCCTAAACTCCCCCCATAAAAAAACCCGCCGAAGCGGGTTTTT
ACGTTATTTGCGGATTAACGATTACTCGTTATCAGAACCGCCCAGGGGGCCGAGCTTAAGAC
TGGCCGTCGTTTTACAACACAGAAAGAGTTTGTAGAAACGCAAAAGGCCATCCGTCAGGGGC
CTTCTGCTTAGTTTGATGCCTGGCAGTTCCCTACTCTCGCCTTCCGCTTCCTCGCTCACTGAC
TCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTG
AAGTGGTGGCCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGACGCGCGTAACTCACGTTAAGGGA
TTTTGGTCATGAGCTTGCGCCGTCCCGTCAAGTCAGCGTAATGCTCTGCTTAGGTGGCGGTAC
TTGGGTCGATATCAAAGTGCATCACTTCTTCCCGTATGCCCAACTTTGTATAGAGAGCCACTG
CGGGATCGTCACCGTAATCTGCTTGCACGTAGATCACATAAGCACCAAGCGCGTTGGCCTCAT
GCTTGAGGAGATTGATGAGCGCGGTGGCAATGCCCTGCCTCCGGTGCTCGCCGGAGACTGCGA
GATCATAGATATAGATCTCACTACGCGGCTGCTCAAACTTGGGCAGAACGTAAGCCGCGAGAG
CGCCAACAACCGCTTCTTGGTCGAAGGCAGCAAGCGCGATGAATGTCTTACTACGGAGCAAGT
TCCCGAGGTAATCGGAGTCCGGCTGATGTTGGGAGTAGGTGGCTACGTCACCGAACTCACGAC
CGAAAAGATCAAGAGCAGCCCGCATGGATTTGACTTGGTCAGGGCCGAGCCTACATGTGCGAA
TGATGCCCATACTTGAGCCACCTAACTTTGTTTTAGGGCGACTGCCCTGCTGCGTAACATCGT
TGCTGCTCCATAACATCAAACATCGACCCACGGCGTAACGCGCTTGCTGCTTGGATGCCCGAG
GCATAGACTGTACAAAAAAACAGTCATAACAAGCCATGAAAACCGCCACTGCGCCGTTACCAC
CGCTGCGTTCGGTCAAGGTTCTGGACCAGTTGCGTGAGCGCATTTTTTTTCCTCCTCGGCGT
TTACGCCCCGCCCTGCCACTCATCGCAGTACTGTTGTAATTCATTAAGCATTCTGCCGACATG
GAAGCCATCACAGACGGCATGATGAACCTGAATCGCCAGCGGCATCAGCACCTTGTCGCCTTG
CGTATAATATTTGCCCATAGTGAAAACGGGGGCGAAGAAGTTGTCCATATTGGCCACGTTTAA
ATCAAAACTGGTGAAACTCACCCAGGGATTGGCGCTGACGAAAAACATATTCTCAATAAACCC
TTTAGGGAAATAGGCCAGGTTTTCACCGTAACACGCCACATCTTGCGAATATATGTGTAGAAA
CTGCCGGAAATCGTCGTGTGCACTCATGGAAAACGGTGTAACAAGGGTGAACACTATCCATA
TCACCAGCTCACCGTCTTTCATTGCCATACGGAACTCCGGATGAGCATTCATCAGGCGGGCAA
GAATGTGAATAAAGGCCGGATAAAACTTGTGCTTATTTTTCTTTACGGTCTTTAAAAAGGCCG
TAATATCCAGCTGAACGGTCTGGTTATAGGTACATTGAGCAACTGACTGAAATGCCTCAAAAT
GTTCTTTACGATGCCATTGGGATATATCAACGGTGGTATATCCAGTGATTTTTTTCTCCATTT
TTTTTTCCTCCTTTAGAAAACTCATCGAGCATCAAATGAAACTGCAATTTATTCATATCAGG
ATTATCAATACCATATTTTGAAAAAGCCGTTTCTGTAATGAAGGAGAAAACTCACCGAGGCA
GTTCCATAGGATGGCAAGATCCTGGTATCGGTCTGCGATTCCGACTCGTCCAACATCAATACA
ACCTATTAATTTCCCCTCGTCAAAAATAAGGTTATCAAGTGAGAAATCACCATGAGTGACGAC
TGAATCCGGTGAGAATGGCAAAAGTTTATGCATTTCTTTCCAGACTTGTTCAACAGGCCAGCC
```

TABLE 3-continued

Exemplary rAAV I2S vector nucleotide sequences

ATTACGCTCGTCATCAAAATCACTCGCATCAACCAAACCGTTATTCATTCGTGATTGCGCCTG
AGCGAGGCGAAATACGCGATCGCTGTTAAAAGGACAATTACAAACAGGAATCGAGTGCAACCG
GCGCAGGAACACTGCCAGCGCATCAACAATATTTTCACCTGAATCAGGATATTCTTCTAATAC
CTGGAACGCTGTTTTTCCGGGGATCGCAGTGGTGAGTAACCATGCATCATCAGGAGTACGGAT
AAAATGCTTGATGGTCGGAAGTGGCATAAATTCCGTCAGCCAGTTTAGTCTGACCATCTCATC
TGTAACATCATTGGCAACGCTACCTTTGCCATGTTTCAGAAACAACTCTGGCGCATCGGGCTT
CCCATACAAGCGATAGATTGTCGCACCTGATTGCCCGACATTATCGCGAGCCCATTTATACCC
ATATAAATCAGCATCCATGTTGGAATTTAATCGCGGCCTCGACGTTTCCCGTTGAATATGGCT
CATTTTTTTTCCTCCTTTACCAATGCTTAATCAGTGAGGCACCTATCTCAGCGATCTGTCTA
TTTCGTTCATCCATAGTTGCCTGACTCCCCGTCGTGTAGATAACTACGATACGGGAGGGCTTA
CCATCTGGCCCCAGCGCTGCGATGATACCGCGAGAACCACGCTCACCGGCTCCGGATTTATCA
GCAATAAACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTTGCGC
AACGTTGTTGCCATCGCTACAGGCATCGTGGTGTCACGCTCGTCGTTTGGTATGGCTTCATTC
AGCTCCGGTTCCCAACGATCAAGGCGAGTTACATGATCCCCCATGTTGTGCACGTTGTCAGAA
GTAAGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAA
GGGCGACACGGAAATGTTGAATACTCATATTCTTCCTTTTTCAATATTATTGAAGCATTTATC
AGGGTTATTGTCTCATGAGCGGATACATATTTGAATGTATTTAGAAAAATAAACAAATAGGGG
TCAGTGTTACAACCAATTAACCAATTCTGAACATTATCGCGAGCCCATTTATACCTGAATATG
GCTCATAACACCCCTTGTTTGCCTGGCGGCAGTAGCGCGGTGGTCCCACCTGACCCCATGCCG
AACTCAGAAGTGAAACGCCGTAGCGCCGATGGTAGTGTGGGGACTCCCCATGCGAGAGTAGGG
AACTGCCAGGCATCAAATAAAACGAAAGGCTCAGTCGAAAGACTGGGCCTTTCGCCCGGGCTA
ATTGAGGGGTGTCGCCCTTATTCGACTCGGGGCTCGAG (SEQ ID NO: 24)

pXL026

CTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGT
TCCTTTAATTAAACGCGTGGGGGAGGCTGCTGGTGAATATTAACCAAGGTCACCCCAGTTATC
GGAGGAGCAAACAGGGGCTAAGTCCACCGGGGGAGGCTGCTGGTGAATATTAACCAAGGTCAC
CCCAGTTATCGGAGGAGCAAACAGGGGCTAAGTCCACCGGGGAGGCTGCTGGTGAATATTAA
CCAAGGTCACCCCAGTTATCGGAGGAGCAAACAGGGGCTAAGTCCACACTAGTAAATGACCTA
TTAAGAATATTTCATAGAACGAATGTTCCGATGCTCTAATCTCTCTAGACAAGGTTCATATTT
GTATGGGTTACTTATTCTCTCTTTGTTGACTAAGTCAATAATCAGAATCAGCAGGTTTGCAGT
CAGATTGGCAGGGATAAGCAGCCTAGCTCAGGAGAAGTAGATATAAAAGCCCCAGGCTGGGAG
CAGCCATCACAGAAGTCCACTCATTCTTGGCAGGCCGCGGCTAAGGTAAGTTGGCGCCGTTTA
AGGGATGGTTGGTTGGTGGGTATTAATGTTTAATTACCTTTTTTTACAGGCCTGGGCGCGCCG
CCACCATGCCACCCCCCCGGACCGGGAGAGGCCTCTTGTGGTTGGGCCTGGTGCTGAGCAGCG
TGTGCGTGGCCCTGGGCAGTGAGACCCAGGCTAACTCTACAACAGATGCCTTGAATGTGCTGC
TGATCATTGTGGATGACCTGAGGCCAAGTCTGGGCTGCTATGGGGACAAATTGGTGAGGTCCC
CCAACATCGACCAGTTGGCCTCCCACTCTCCTATTCCAAAATGCTTTCGCCCAGCAGGCAG
TTTGTGCCCCTCTAGGGTGAGCTTCCTCACTGGCAGGCGCCCTGACACCACTAGACTGTATG
ACTTTAACAGCTATTGGAGGGTGCACGCAGGAAACTTCTCCACAATCCCTCAATACTTCAAGG
AGAATGGTTATGTGACAATGTCTGTGGGCAAGGTGTTCCACCCTGGCATCAGCAGCAACCACA
CCGATGACTCACCCTATAGTTGGTCTTTTCCCCCCTACCATCCTTCATCTGAGAAATATGAAA
ACACAAAAACCTGCCGAGGCCCAGACGGGGAACTGCATGCCAACCTACTCTGTCCTGTTGATG
TACTGGACGTGCCCGAGGGCACCCTCCCTGATAAGCAGTCCACAGAACAGGCCATTCAGCTGC
TTGAAAAGATGAAGACCTCCGCATCCCCCTTCTTCTTGGCTGTCGGTACCACAAGCCCCATA
TCCCCTTTAGATACCCCAAGGAATTCCAGAAACTGTACCCACTGGAGAACATCACACTTGCTC
CTGACCCTGAAGTGCCTGACGGACTGCCTCCAGTGGCCTATAACCCTTGGATGGACATCCGGC
AGCGCGAGGATGTGCAGGCTCTGAACATTAGTGTGCCTTATGGGCCCATCCCTGTGGACTTTC
AGAGGAAGATTCGCCAGTCCTACTTTGCCTCTGTATCCTACCTGGACACACAGGTGGGACGCC
TGCTGTCTGCCCTTGATGATCTGCAACTGGCCAACAGCACCATTATAGCTTTCACATCAGACC
ATGGGTGGGCTCTTGGGGAGCATGGTGAATGGGCTAAGTACTCCAACTTCGATGTGGCAACCC
ATGTCCCTCTGATCTTCTATGTGCCAGGAAGGACCGCCTCTCTGCCAGAGGCAGGTGAGAAGC
TGTTCCCCTATCTGGACCCTTTTGACTCCGCCAGCCAGTTGATGGAGCCTGGCCGACAGTCTA
TGGACCTGGTTGAGCTGGTCAGCCTGTTTCCCACACTCGCTGGACTGGCTGGCCTGCAAGTAC
CCCACGCTGCCCAGTGCCCTCCTTCCATGTGGAGCTTTGCAGGGAGGGGAAGAACCTCCTCA
AGCACTTCAGGTTCAGGGACCTAGAGGAGGATCCTTATCTGCCTGGAAACCCAGAGAGCTTA
TTGCTTACTCCCAGTATCCAAGGCCTAGTGACATTCCCCAATGGAACTCAGACAAACCAAGCC
TGAAAGACATCAAGATCATGGGATACTCTATCAGGACCATTGACTACAGGTACACTGTGTGGG
TTGGCTTCAACCCGGATGAGTTCCTGGCTAATTTCTCTGACATACATGCTGGCGAGCTGTACT
TCGTGGACAGTGACCCCCTGCAGGATCACAACATGTACAATGATTCCCAGGGGGTGACCTCT
TCCAGCTTCTGATGCCCTAAGGTACCAATCAACCTCTGGATTACAAAATTTGTGAAAGATTGA
CTGGTATTCTTAACTTTGTTGCTCCTTTTACGCTTTGTGGATACGCTGCTTTATTGCCTTTGT
ATCTTGCTATTGCTTCCCGTTTGGCTTTCATTTTCTCCTCCTTGTATAAATCCTGGTTGCTGT
CTCTTTTTGAGGAGTTGTGGCCCGTTGTCAGGCAACGTGGCGTGGTGTGCACTGTGTTTGCTG
ACGCAACCCCCACTGGTTGGGGCATTGCCACCACCTGTCAGCTCCTTTCCGGGACTTTCGCTT
TCCCCCTCCCTATTGCCACGGCGGAACTCATCGCCGCCTGCCTTGCCCGCTGCTGGACAGGGG
CTCGGCTGTTGGGCACTGACAATTCCGTGGTGTTGTCGGGGAAATCATCGTCCTTTCCTTGGC
TGCTCGCCTGTGTTGCCACCTGGATTCTGCGCGGGACGTCCTTCTGCTACGTCCCTTCGGCCC
TCAATCCAGCGGACCTTCCTTCCCGCGGCCTGCTGCCGGCTCTGCGGCCTCTTCCGCGTCTTC
GCCTTCGCCCTCAGACGAGTCGGATCTCCCTTTGGGCCGCCTCCCCGCATCGGTACCGTCGAC

TABLE 3-continued

Exemplary rAAV I2S vector nucleotide sequences

```
CCTAGAGCTCGCTGATCAGCCTCGACTGTGCCTTCTAGTTGCCAGCCATCTGTTGTTTGCCCC
TCCCCCGTGCCTTCCTTGACCCTGGAAGGTGCCACTCCCACTGTCCTTTCCTAATAAAATGAG
GAAATTGCATCGCATTGTCTGAGTAGGTGTCATTCTATTCTGGGGGGTGGGGTGGGGCAGGAC
AGCAAGGGGGAGGATTGGGAAGACAATAGCAGGCATGCTGGGGAATCTAGA Xn(60-100)
GTTTAAACATTTAAATAGGAACCCCTAGTGATGGAGTTGGCCACTCCCTCTCTGCGCGCTCGC
TCGCTCACTGAGGCCGGGCGACCAAAGGTCGCCCGACGCCCGGGCTTTGCCCGGGCGGCCTCA
GTGAGCGAGCGAGCGCGCAGAGAGTATACATCGATGTGAGTTCGCGGGTGGCTGGGGGGCCCT
GGGCTGCGACCGCCCCCGAACCGCGTCTACGAGCCTTGCGGGCTCCGGGTCTTTGCAGTCGTA
TGGGGGCAGGGTAGCTGTTCCCCGCAAGGAGAGCTCAAGGTCAGCGCTCGGACCTGGCGGAGC
CCCGCACCCAGGCTGTGGCGCCCTGTGCAGCTCCGCCCTTGCGGCGCCATCTGCCCGGAGCCT
CCTTCCCCTAGTCCCCAGAAACAGGAGGTCCCTACTCCCGCCCGAGATCCCGACCCGGACCCC
TAGGTGGGGGACGCTTTCTTTCCTTTCGCGCTCTGCGGGGTCACGTGTCGCAGAGGAGCCCCT
CCCCCACGGCCTCCGGCACCGCAGGCCCCGGGATGCTAGTGCGCAGCGGGTGCATCCTGTCC
GGATGCTGCGCCTGCGGTAGAGCGGCCGCCATGTTGCAACCGGGAAGGAAATGAATGGGCAGC
CGTTAGGAAAGCCTGCCGGTGACTAACCCTGCGCTCCTGCCTCGATGGGTGGAGTCGCGTGTG
GCGGGGAAGTCAGGTGGAGCGAGGCTAGCTGGCCCGATTTCTCCTCCGGGTGATGCTTTTCCT
AGATTATTCTCTGGTAAATCAAAGAAGTGGGTTTATGGAGGTCCTCTTGTGTCCCCTCCCCGC
AGAGGTGTGGTGGCTGTGGCATGGTGCCAAGCCGGGAGAAGCTGAGTCATGGGTAGTTGGAAA
AGGACATTTCCACCGCAAAATGGCCCCTCTGGTGGTGGCCCCTTCCTGCAGCGCCGGCTCACC
TCACGGCCCCGCCCTTCCCCTGCCAGCCTAGCGTTGACCCGACCCCAAAGGCCAGGCTGTAAA
TGTCACCGGGAGGATTGGGTGTCTGGGCGCCTCGGGGAACCTGCCCTTCTCCCCATTCCGTCT
TCCGGAAACCAGATCTCCCACCGCACCCTGGTCTGAGGTTAAATATAGCTGCTGACCTTTCTG
TAGCTGGGGGCCTGGGCTGGGGCTCTCTCCCATCCCTTCTCCCCACACACATGCACTTACCTG
TGCTCCCACTCCTGATTTCTGGAAAAGAGCTAGGAAGGACAGGCAACTTGGCAAATCAAAGCC
CTGGGACTAGGGGGTTAAAATACAGCTTCCCTCTTCCCACCCGCCCCAGTCTCTGTCCCTTT
TGTAGGAGGGACTTAGAGAAGGGGTGGGCTTGCCCTGTCCAGTTAATTTCTGACCTTTACTCC
TGCCCTTTGAGTTTGATGATGCTGAGTGTACAAGCGTTTTCTCCCTAAAGGGTGCAGCTGAGC
TAGGCAGCAGCAAGCATTCCTGGGGTGGCATAGTGGGGTGGTGAATACCATGTACAAAGCTTG
TGCCCAGACTGTGGGTGGCAGTGCCCCACATGGCCGCTTCTCCTGGAAGGGCTTCGTATGACT
GGGGGTGTTGGGCAGCCCTGGAGCCTTCAGTTGCAGCCATGCCTTAAGCCAGGCCAGCCTGGC
AGGGAAGCTCAAGGGAGATAAAATTCAACCTCTTGGGCCCTCCTGGGGGTAAGGAGATGCTGC
ATTCGCCCTCTTAATGGGGAGGTGGCCTAGGGCTGCTCACATATTCTGGAGGAGCCTCCCCTC
CTCATGCCTTCTTGCCTCTTGTCTCTTAGGCATGCAAAAGAGTCGAATAAGGGCGACACAAAA
TTTATTCTAAATGCATAATAAATACTGATAACATCTTATAGTTTGTATTATATTTTGTATTAT
CGTTGACATGTATAATTTTGATATCAAAAACTGATTTTCCCTTTATTATTTTCGAGATTTATT
TTCTTAATTCTCTTTAACAAACTAGAAATATTGTATATACAAAAAATCATAAATAATAGATGA
ATAGTTTAATTATAGGTGTTCATCAATCGAAAAAGCAACGTATCTTATTTAAAGTGCGTTGCT
TTTTTCTCATTTATAAGGTTAAATAATTCTCATATATCAAGCAAAGTGACAGGCGCCCTTAAA
TATTCTGACAAATGCTCTTTCCCTAAACTCCCCCCATAAAAAAACCCGCCGAAGCGGGTTTTT
ACGTTATTTGCGGATTAACGATTACTCGTTATCAGAACCGCCCAGGGGGCCCGAGCTTAAGAC
TGGCCGTCGTTTTACAACACAGAAAGAGTTTGTAGAAACGCAAAAAGGCCATCCGTCAGGGGC
CTTCTGCTTAGTTTGATGCCTGGCAGTTCCCTACTCTCGCCTTCCGCTTCCTCGCTCACTGAC
TCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTG
AAGTGGTGGGCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGACGCGCGCGTAACTCACGTTAAGGGA
TTTTGGTCATGAGCTTGCGCCGTCCCGTCAAGTCAGCGTAATGCTCTGCTTAGGTGGCGGTAC
TTGGGTCGATATCAAAGTGCATCACTTCTTCCCGTATGCCCAACTTTGTATAGAGAGCCACTG
CGGGATCGTCACCGTAATCTGCTTGCACGTAGATCACATAAGCACCAAGCGCGTTGGCCTCAT
GCTTGAGGAGATTGATGAGCGCGGTGGCAATGCCCTGCCTCCGGTGCTCGCCGGAGACTGCGA
GATCATAGATATAGATCTCACTACGCGGCTGCTCAAACTTGGGCAGAACGTAAGCCGCGAGAG
CGCCAACAACCGCTTCTTGGTCGAAGGCAGCAAGCGCGATGAATGTCTTACTACGGAGCAAGT
TCCCGAGGTAATCGGAGTCCGGCTGATGTTGGGAGTAGGTGGCTACGTCACCGAACTCACGAC
CGAAAAGATCAAGAGCAGCCCGCATGGATTTGACTTGGTCAGGGCCGAGCCTACATGTGCGAA
TGATGCCCATACTTGAGCCACCTAACTTTGTTTTAGGGCGACTGCCCTGCTGCGTAACATCGT
TGCTGCTCCATAACATCAAACATCGACCCACGGCGTAACGCCTTGTCGCTTGGATGCCCGAG
GCATAGACTGTACAAAAAAACAGTCATAACAAGCCATGAAAACCGCCACTGCGCCGTTACCAC
CGCTGCGTTCGGTCAAGGTTCTGGACCAGTTGCGTGAGCGCATTTTTTTTCCTCCTCGGCGT
TTACGCCCCGCCCTGCCACTCATCGCAGTACTGTTGTAATTCATTAAGCATTCTGCCGACATG
GAAGCCATCACAGACGGCATGATGAACCTGAATCGCCAGCGGCATCAGCACCTTGTCGCCTTG
CGTATAATATTTGCCCATAGTGAAAACGGGGGCGAAGAAGTTGTCCATATTGGCCACGTTTAA
ATCAAAACTGGTGAAACTCACCCAGGGATTGGCTGACGAAAAACATATTCTCAATAAACCC
TTTAGGGAAATAGGCCAGGTTTTCACCGTAACACGCCACATCTTGCGAATATATGTGTAGAAA
CTGCCGGAAATCGTCGTGGCACTCATGGAAAACGGTGTAACACTGGGAACACTATCCATA
TCACCAGCTCACCGTCTTTCATTGCCATACGGAACTCCGGATGAGCATTCATCAGGCGGGCAA
GAATGTGAATAAAGGCCGGATAAAACTTGTGCTTATTTTTCTTTACGGTCTTTAAAAGGCCG
TAATATCCAGCTGAACGGTCTGGTTATAGGTACATTGAGCAACTGACTGAAATGCCTCAAAAT
GTTCTTTACGATGCCATTGGGATATATCAACGGTGGTATATCCAGTGATTTTTTTCTCCATTT
TTTTTTCCTCCTTTAGAAAAACTCATCGAGCATCAAATGAAACTGCAATTTATTCATATCAGG
```

TABLE 3-continued

Exemplary rAAV I2S vector nucleotide sequences

ATTATCAATACCATATTTTTGAAAAAGCCGTTTCTGTAATGAAGGAGAAAACTCACCGAGGCA
GTTCCATAGGATGGCAAGATCCTGGTATCGGTCTGCGATTCCGACTCGTCCAACATCAATACA
ACCTATTAATTTCCCCTCGTCAAAAATAAGGTTATCAAGTGAGAAATCACCCATGAGTGACGAC
TGAATCCGGTGAGAATGGCAAAAGTTTATGCATTTCTTTCCAGACTTGTTCAACAGGCCAGCC
ATTACGCTCGTCATCAAAATCACTCGCATCAACCAAACCGTTATTCATTCGTGATTGCGCCTG
AGCGAGGCGAAATACGCGATCGCTGTTAAAAGGACAATTACAAACAGGAATCGAGTGCAACCG
GCGCAGGAACACTGCCAGCGCATCAACAATATTTTCACCTGAATCAGGATATTCTTCTAATAC
CTGGAACGCTGTTTTTCCGGGGATCGCAGTGGTGAGTAACCATGCATCATCAGGAGTACGGAT
AAAATGCTTGATGGTCGGAAGTGGCATAAATTCCGTCAGCCAGTTTAGTCTGACCATCTCATC
TGTAACATCATTGGCAACGCTACCTTTGCCATGTTTCAGAAACAACTCTGGCGCATCGGGCTT
CCCATACAAGCGATAGATTGTCGCACCTGATTGCCCGACATTATCGCGAGCCCATTTATACCC
ATATAAATCAGCATCCATGTTGGAATTTAATCGCGGCCTCGACGTTTCCCGTTGAATATGGCT
CATTTTTTTTTCCTCCTTTACCAATGCTTAATCAGTGAGGCACCTATCTCAGCGATCTGTCTA
TTTCGTTCATCCATAGTTGCCTGACTCCCCGTCGTGTAGATAACTACGATACGGGAGGGCTTA
CCATCTGGCCCCAGCGCTGCGATGATACCGCGAGAACCACGCTCACCGGCTCCGGATTTATCA
GCAATAAACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTTGCGC
AACGTTGTTGCCATCGCTACAGGCATCGTGGTGTCACGCTCGTCGTTTGGTATGGCTTCATTC
AGCTCCGGTTCCCAACGATCAAGGCGAGTTACATGATCCCCCATGTTGTGCACGTTGTCAGAA
GTAAGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAA
GGGCGACACGGAAATGTTGAATACTCATATTCTTCCTTTTTCAATATTATTGAAGCATTTATC
AGGGTTATTGTCTCATGAGCGGATACATATTTGAATGTATTTAGAAAAATAAACAAATAGGGG
TCAGTGTTACAACCAATTAACCAATTCTGAACATTATCGCGAGCCCATTTATACCTGAATATG
GCTCATAACACCCCTTGTTTGCCTGGCGGCAGTAGCGCGGTGGTCCCACCTGACCCCATGCCG
AACTCAGAAGTGAAACGCCGTAGCGCCGATGGTAGTGTGGGGACTCCCCATGCGAGAGTAGGG
AACTGCCAGGCATCAAATAAAACGAAAGGCTCAGTCGAAAGACTGGGCCTTTCGCCCGGGCTA
ATTGAGGGGTGTCGCCCTTATTCGACTCGGGGCTCGAG
(SEQ ID NO: 18)

pXL027

CTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGT
TCCTTTAATTAAACGCGTGGGGAGGCTGCTGGTGAATATTAACCAAGGTCACCCCAGTTATC
GGAGGAGCAAACAGGGGCTAAGTCCACCGGGGAGGCTGCTGGTGAATATTAACCAAGGTCAC
CCCAGTTATCGGAGGAGCAAACAGGGGCTAAGTCCACCGGGGAGGCTGCTGGTGAATATTAA
CCAAGGTCACCCCAGTTATCGGAGGAGCAAACAGGGGCTAAGTCCACACTAGTAAATGACCTA
TTAAGAATATTTCATAGAACGAATGTTCCGATGCTCTAATCTCTCTAGACAAGGTTCATATTT
GTATGGGTTACTTATTCTCTCTTTGTTGACTAAGTCAATAATCAGAATTCAGCAGGTTTGCAGT
CAGATTGGCAGGGATAAGCAGCCTAGCTCAGGAGAAGTGAGTATAAAAGCCCCAGGCTGGGAG
CAGCCATCACAGAAGTCCACTCATTCTTGGCAGGCCGCGGCTAAGGTAAGTTGGCGCCGTTTA
AGGGATGGTTGGTTGGTGGGGTATTAATGTTTAATTACCTTTTTTACAGGCCTGGGCGCGCCG
CCACCATGCCGCCACCCCGGACCGGCCGAGGCCTTCTCTGGCTGGGTCTGGTTCTGAGCTCCG
TCTGCGTCGCCCTCGGATCCGAAACGCAGGCCAACTCGACCACAGATGCTCTGAACGTTCTTC
TCATCATCGTGGATGACCTGCGCCCCTCCCTGGGCTGTTATGGGGATAAGCTGGTGAGGTCCC
CAAATATTGACCAACTGGCATCCCACAGCCTCCTCTTCCAGAATGCCTTTGCGCAGCAAGCAG
TGTGCGCCCCGAGCCGCGTTTCTTTCCTCACTGGCAGGAGACCTGACACCACCCGCCTGTACG
ACTTCAACTCCTACTGGAGGGTGCACGCTGGAAACTTCTCCACCATCCCCCAGTACTTCAAGG
AGAATGGCTATGTGACCATGTCGGTGGGAAAAGTCTTTCACCCTGGGATATCTTCTAACCATA
CCGATGATTCTCCGTATAGCTGGTCTTTTCCACCTTATCATCCTTCCTCTGAGAAGTATGAAA
ACACTAAGACATGTCGAGGGCCAGATGGAGAACTCCATGCCAACCTGCTTTGCCCTGTGGATG
TGCTGGATGTTCCCGAGGGCACCTTGCCTGACAAACAGAGCACTGAGCAAGCCATACAGTTGT
TGGAAAAGATGAAAACGTCAGCCAGTCCTTTCTTCCTGGCCGTTGGGTATCATAAGCCACACA
TCCCCTTCAGATACCCCAAGGAATTTCAGAAGTTGTATCCCTTGGAGAACATCACCCTGGCCC
CCGATCCCGAGGTCCCTGATGGCCTACCCCCTGTGGCCTACAACCCCTGGATGGACATCAGGC
AACGGGAAGACGTCCAAGCCTTAAACATCAGTGTGCCGTATGGTCCAATTCCTGTGGACTTTC
AGCGGAAAATCCGCCAGAGCTACTTTGCCTCTGTGTCATATTTGGATACACAGGTCGGCCGCC
TCTTGAGTGCTTTGGACGATCTTCAGCTGGCCAACAGCACCATCATTGCATTTACCTCGGATC
ATGGGTGGGCTCTAGGTGAACATGGAGAATGGGCAAATACAGCAATTTTGATGTTGCTACCC
ATGTTCCCTGATATTCTATGTTCCTGGAAGGACGGCTTCACTTCCGGAGGCAGGCAGAAGC
TTTTCCCTTACCTCGACCCTTTTGATTCCGCCTCACAGTTGATGGACAGGCAGGCAATCCA
TGGACCTTGTGGAACTTGTGTCTCTTTTTCCCACGCTGGCTGGACTTGCAGGACTGCAGGTTC
CACCTCGCTGCCCCGTTCCTTCATTTCACGTTGAGCTGTGCAGAGAAGGCAAGAACCTTCTGA
AGCATTTTCGATTCCGTGACTTGGAAGAGGATCCGTACCTCCCTGGTAATCCCGTGAACTGA
TTGCCTATAGCCAGTATCCCCGGCCTTCAGACATCCCTCAGTGGAATTCTGACAAGCCGAGTT
TAAAAGATATAAAGATCATGGGCTATTCCATACGCACCATAGACTATAGGTATACTGTGTGGG
TTGGCTTCAATCCTGATGAATTTCTAGCTAACTTTTCTGACATCCATGCAGGGGAACTGTATT
TTGTGGATTCTGACCCATTGCAGGATCACAATATGTATAATGATTCCCAAGGTGGAGATCTTT
TCCAGTTGTTGATGCCTTGACAATTGGCCCCTCTCCCTCCCCCCCCCTAACGTTACTGGCCG
AAGCCGCTTGGAATAAGGCCGGTGTGCGTTTGTCTATATGTTATTTTCCACCATATTGCCGTC
TTTTGGCAATGTGAGGGCCCGGAAACCTGGCCCTGTCTTCTTGACGAGCATTCCTAGGGGTCT
TTCCCCTCTCGCCAAAGGAATGCAAGGTCTGTTGAATGTCGTGAAGGAAGCAGTTCCTCTGGA
AGCTTCTTGAAGACAAACAACGTCTGTAGCGACCCTTTGCAGGCAGCGGAACCCCCCACCTGG

TABLE 3-continued

Exemplary rAAV I2S vector nucleotide sequences

CGACAGGTGCCTCTGCGGCCAAAAGCCACGTGTATAAGATACACCTGCAAAGGCGGCACAACC
CCAGTGCCACGTTGTGAGTTGGATAGTTGTGGAAAGAGTCAAATGGCTCACCTCAAGCGTATT
CAACAAGGGGCTGAAGGATGCCCAGAAGGTACCCCATTGTATGGGATCTGATCTGGGGCCTCG
GTGCACATGCTTTACATGTGTTTAGTCGAGGTTAAAAAACGTCTAGGCCCCCCGAACCACGGG
GACGTGGTTTTCCTTTGAAAAACACGATGATAATCATATGGCCACCATGGCTGCGCCCGCACT
AGGGCTGGTGTGTGGACGTTGCCCTGAGCTGGGTCTCGTCGTTGCTGCTGCTGCTCTTGCGCT
GCTGTGTGGAGCGGCAGGGAGCCAGGAGGCCGGGACCGGTGCGGGCGCGGGGTCCCTTGCGGG
TTCTTGCGGCTGCGGCACGCCCCAGCGGCCTGGCGCCCATGGCAGTTCGGCAGCCGCTCACCG
ATACTCGCGGGAGGCTAACGCTCCGGGCCCCGTACCCGGAGAGCGGCAACTCGCGCACTCAAA
GATGGTCCCCATCCCTGCTGGAGTATTTACAATGGGCACAGATGATCCTCAGATAAAGCAGGA
TGGGGAAGCACCTGCGAGGAGAGTTACTATTGATGCCTTTTACATGGATGCCTATGAAGTCAG
TAATACTGAATTTGAGAAGTTTGTGAACTCAACTGGCTATTTGACAGAGGCTGAGAAGTTTGG
CGACTCCTTTGTCTTTGAAGGCATGTTGAGTGAGCAAGTGAAGACCAATATTCAACAGGCAGT
TGCAGCTGCTCCCTGGTGGTTACCTGTGAAAGGCGCTAACTGGAGACACCCAGAAGGGCCTGA
CTCTACTATTCTGCACAGGCCGGATCATCCAGTTCTCCATGTGTCCTGGAATGATGCGGTTGC
CTACTGCACTTGGGCAGGGAAGCGGCTGCCCACGGAAGCTGAGTGGGAATACAGCTGTCGAGG
AGGCCTGCATAATAGACTTTTCCCCTGGGGCAACAAACTGCAGCCCAAAGGCCAGCATTATGC
CAACATTTGGCAGGGCGAGTTTCCGGTGACCAACACTGGTGAGGATGGCTTCCAAGGAACTGC
GCCTGTTGATGCCTTCCCTCCCAATGGTTATGGCTTATACAACATAGTGGGGAACGCATGGGA
ATGGACTTCAGACTGGTGGACTGTTCATCATTCTGTTGAAGAAACGCTTAACCCAAAAGGTCC
CCCTTCTGGGAAAGACCGAGTGAAGAAGGTGGATCCTACATGTGCCATAGGTCTTATTGTTA
CAGGTATCGCTGTGCTGCTCGGAGCCAGAACACACCTGATAGCTCTGCTTCGAATCTGGGATT
CCGCTGTGCAGCCGACCGCCTGCCCACTATGGACTGAGTCGACCCTAGAGCTCGCTGATCAGC
CTCGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGTCT
GAGTAGGTGTCATTCTATTCTGGGGGGTGGGGTGGGGCAGGACAGCAAGGGGGAGGATTGGGA
AGACAATAGCAGGCATGCTGGGGAATCTAGA Xn(60-100)
GTTTAAACATTTAAATAGGAACCCCTAGTGATGGAGTTGGCCACTCCCTCTCTGCGCGCTCGC
TCGCTCACTGAGGCCGGGCGACCAAAGGTCGCCCGACGCCCGGGCTTTGCCCGGGCGGCCTCA
GTGAGCGAGCGAGCGCGCAGAGAGTATACATCGATGTGAGTTCGCGGGTGGCTGGGGGGCCCT
GGGCTGCGACCGCCCCCGAACCGCGTCTACGAGCCTTGCGGGCTCCGGGTCTTTGCAGTCGTA
TGGGGGCAGGGTAGCTGTTCCCCGCAAGGAGAGCTCAAGGTCAGCGCTCGGACCTGGCGGAGC
CCCGCACCCAGGCTGTGGCGCCCTGTGCAGCTCCGCCCTTGCGGCGCCATCTGCCCGGAGCCT
CCTTCCCCTAGTCCCCAGAAACAGGAGGTCCCTACTCCCGCCCGAGATCCCGACCCGGACCCC
TAGGTGGGGGACGCTTTCTTTCCTTTCGCGCTCTGCGGGGTCACGTGTCGCAGAGGAGCCCCT
CCCCCACGGCCTCCGGCACCGCAGGCCCCGGGATGCTAGTGCGCAGCGGGTGCATCCCTGTCC
GGATGCTGCGCCTGCGGTAGAGCGGCCGCCATGTTGCAACCGGGAAGGAAATGAATGGGCAGC
CGTTAGGAAAGCCTGCCGGTGACTAACCCTGCGCTCCTGCCTCGATGGGTGGAGTCGCGTGTG
GCGGGGAAGTCAGGTGGAGCGAGGCTAGCTGGCCCGATTTCTCCTCCGGGTGATGCTTTTCCT
AGATTATTCTCTGGTAAATCAAAGAAGTGGGTTTATGGAGGTCCTCTTGTGTCCCCTCCCCGC
AGAGGTGTGGTGGCTGTGGCATGGTGCCAAGCCGGGAGAAGCTGAGTCATGGGTAGTTGGAAA
AGGACATTTCCACCGCAAAATGGCCCCTCTGGTGGTGGCCCCTTCCTGCAGCGCCGGCTCACC
TCACGGCCCCGCCCTTCCCCTGCCAGCCTAGCGTTGACCCGACCCCAAAGGCCAGGCTGTAAA
TGTCACCGGGAGGATTGGGTGTCTGGGCGCCTCGGGGAACCTGCCCTTCTCCCCATTCCGTCT
TCCGGAAACCAGATCTCCCACCGCACCCTGGTCTGAGGTTAAATATAGCTGCTGACCTTTCTG
TAGCTGGGGGCCTGGGCTGGGGCTCTCTCCCATCCCTTCTCCCCACACACATGCACTTACCTG
TGCTCCCACTCCTGATTTCTGGAAAAGAGCTAGGAAGGACAGGCAACTTGGCAAATCAAAGCC
CTGGGACTAGGGGGTTAAAATACAGCTTCCCTCTTCCCACCCGCCCCAGTCTCTGTCCCTTT
TGTAGGAGGGACTTAGAGAAGGGGTGGGCTTGCCCTGTCCAGTTAATTTCTGACCTTTACTCC
TGCCCTTTGAGTTTGATGATGCTGAGTGTACAAGCGTTTTCTCCCTAAAGGGTGCAGCTGAGC
TAGGCAGCAGCAAGCATTCCTGGGGTGGCATAGTGGGGTGGTGAATACCATGTACAAAGCTTG
TGCCCAGACTGTGGGTGGCAGTGCCCCACATGGCCGCTTCTCCTGGAAGGGCTTCGTATGACT
GGGGGTGTTGGGCAGCCCTGGAGCCTTCAGTTGCAGCCATGCCTTAAGCCAGGCCAGCCTGGC
AGGGAAGCTCAAGGGAGATAAAATTCAACCTCTTGGGCCCTCCTGGGGGTAAGGAGATGCTGC
ATTCGCCCTCTTAATGGGGAGGTGGCCTAGGGCTGCTCACATATTCTGGAGGAGCCTCCCCTC
CTCATGCCTTCTTGCCTCTTGTCTCTTAGGCATGCAAAAGAGTCGAATAAGGGCGACACAAAA
TTTATTCTAAATGCATAATAAATACTGATAACATCTTATAGTTTGTATTATATTTTGTATTAT
CGTTGACATGTATAATTTTGATATCAAAAACTGATTTTCCCTTTATTATTTTCGAGATTTATT
TTCTTAATTCTCTTTAACAAACTAGAAATATTGTATATACAAAAAATCATAAATAATAGATGA
ATAGTTTAATTATAGGTGTTCATCAATCGAAAAAGCAACGTATCTATTTATTTAAAGTGCGTTGCT
TTTTTCTCATTTATAAGGTTAAATAATTCTCATATATCAAGCAAAGTGACAGGCGCCCTTAAA
TATTCTGACAAATGCTCTTTCCCTAAACTCCCCCCATAAAAAAACCCGCCGAAGCGGGTTTTT
ACGTTATTTGCGGATTAACGATTACTCGTTATCAGAACCGCCCAGGGGGCCCGAGCTTAAGAC
TGGCCGTCGTTTTACAACACAGAAAGAGTTTGTAGAAACGCAAAAAGGCCATCCGTCAGGGGC
CTTCTGCTTAGTTTGATGCCTGGCAGTTCCCTACTCTCGCCTTCCGCTTCCTCGCTCACTGAC
TCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCG
TTTCCCCCTGGAAGCTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCTGTAGGTATCTCAGT
TCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTG
AAGTGGTGGCCTAACTACGGCTACACTAGAAGAACAGTATTTGGTATCTGCGCTCTGCTGAAG
CCAGTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAGAAGATCCT
TTGATCTTTTCTACGGGGTCTGACGCTCAGTGGAACGACGCGCGCGTAACTCACGTTAAGGGA

TABLE 3-continued

Exemplary rAAV I2S vector nucleotide sequences

TTTTGGTCATGAGCTTGCGCCGTCCCGTCAAGTCAGCGTAATGCTCTGCTTAGGTGGCGGTAC
TTGGGTCGATATCAAAGTGCATCACTTCTTCCCGTATGCCCAACTTTGTATAGAGAGCCACTG
CGGGATCGTCACCGTAATCTGCTTGCACGTAGATCACATAAGCACCAAGCGCGTTGGCCTCAT
GCTTGAGGAGATTGATGAGCGCGGTGGCAATGCCCTGCCTCCGGTGCTCGCCGGAGACTGCGA
GATCATAGATATAGATCTCACTACGCGGCTGCTCAAACTTGGGCAGAACGTAAGCCGCGAGAG
CGCCAACAACCGCTTCTTGGTCGAAGGCAGCAAGCGCGATGAATGTCTTACTACGGAGCAAGT
TCCCGAGGTAATCGGAGTCCGGCTGATGTTGGGAGTAGGTGGCTACGTCACCGAACTCACGAC
CGAAAAGATCAAGAGCAGCCCGCATGGATTTGACTTGGTCAGGGCCGAGCCTACATGTGCGAA
TGATGCCCATACTTGAGCCACCTAACTTTGTTTTAGGGCGACTGCCCTGCTGCGTAACATCGT
TGCTGCTCCATAACATCAAACATCGACCCACGGCGTAACGCGCTTGCTGCTTGGATGCCCGAG
GCATAGACTGTACAAAAAAACAGTCATAACAAGCCATGAAAACCGCCACTGCGCCGTTACCAC
CGCTGCGTTCGGTCAAGGTTCTGGACCAGTTGCGTGAGCGCATTTTTTTTTCCTCCTCGGCGT
TTACGCCCCGCCCTGCCACTCATCGCAGTACTGTTGTAATTCATTAAGCATTCTGCCGACATG
GAAGCCATCACAGACGGCATGATGAACCTGAATCGCCAGCGGCATCAGCACCTTGTCGCCTTG
CGTATAATATTTGCCCATAGTGAAAACGGGGGCGAAGAAGTTGTCCATATTGGCCACGTTTAA
ATCAAAACTGGTGAAACTCACCCAGGGATTGGCGCTGACGAAAAACATATTCTCAATAAACCC
TTTAGGGAAATAGGCCAGGTTTTCACCGTAACACGCCACATCTTGCGAATATATGTGTAGAAA
CTGCCGGAAATCGTCGTGTGCACTCATGGAAAACGGTGTAACAAGGGTGAACACTATCCCATA
TCACCAGCTCACCGTCTTTCATTGCCATACGGAACTCCGGATGAGCATTCATCAGGCGGGCAA
GAATGTGAATAAAGGCCGGATAAAACTTGTGCTTATTTTTCTTTACGGTCTTTAAAAAGGCCG
TAATATCCAGCTGAACGGTCTGGTTATAGGTACATTGAGCAACTGACTGAAATGCCTCAAAAT
GTTCTTTACGATGCCATTGGGATATATCAACGGTGGTATATCCAGTGATTTTTTCTCCATTT
TTTTTTCCTCCTTTAGAAAAACTCATCGAGCATCAAATGAAACTGCAATTTATTCATATCAGG
ATTATCAATACCATATTTTTGAAAAAGCCGTTTCTGTAATGAAGGAGAAAACTCACCGAGGCA
GTTCCATAGGATGGCAAGATCCTGGTATCGGTCTGCGATTCCGACTCGTCCAACATCAATACA
ACCTATTAATTTCCCCTCGTCAAAAATAAGGTTATCAAGTGAGAAATCACCATGAGTGACGAC
TGAATCCGGTGAGAATGGCAAAAGTTTATGCATTTCTTTCCAGACTTGTTCAACAGGCCAGCC
ATTACGCTCGTCATCAAAATCACTCGCATCAACCAAACCGTTATTCATTCGTGATTGCGCCTG
AGCGAGGCGAAATACGCGATCGCTGTTAAAGGACAATTACAAACAGGAATCGAGTGCAACCG
GCGCAGGAACACTGCCAGCGCATCAACAATATTTTCACCTGAATCAGGATATTCTTCTAATAC
CTGGAACGCTGTTTTTCCGGGGATCGCAGTGGTGAGTAACCATGCATCATCAGGAGTACGGAT
AAAATGCTTGATGGTCGGAAGTGGCATAAATTCCGTCAGCCAGTTTAGTCTGACCATCTCATC
TGTAACATCATTGGCAACGCTACCTTTGCCATGTTTCAGAAACAACTCTGGCGCATCGGGCTT
CCCATACAAGCGATAGATTGTCGCACCTGATTGCCCGACATTATCGCGAGCCCATTTATACCC
ATATAAATCAGCATCCATGTTGGAATTTAATCGCGGCCTCGACGTTTCCCGTTGAATATGGCT
CATTTTTTTTCCTCCTTTACCAATGCTTAATCAGTGAGGCACCTATCTCAGCGATCTGTCTA
TTTCGTTCATCCATAGTTGCCTGACTCCCCGTCGTGTAGATAACTACGATACGGGAGGGCTTA
CCATCTGGCCCCAGCGCTGCGATGATACCGCGAGAACCACGCTCACCGGCTCCGGATTTATCA
GCAATAAACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTTGCGC
AACGTTGTTGCCATCGCTACAGGCATCGTGGTGTCACGCTCGTCGTTTGGTATGGCTTCATTC
AGCTCCGGTTCCCAACGATCAAGGCGAGTTACATGATCCCCCATGTTGTGCACGTTGTCAGAA
GTAAGTTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAGAATAGT
GTATGCGGCGACCGAGTTGCTCTTGCCCGGCGTCAATACGGGATAATACCGCGCCACATAGCA
GAACTTTAAAAGTGCTCATCATTGGAAAACGTTCTTCGGGGCGAAAACTCTCAAGGATCTTAC
CGCTGTTGAGATCCAGTTCGATGTAACCCACTCGTGCACCCAACTGATCTTCAGCATCTTTTA
CTTTCACCAGCGTTTCTGGGTGAGCAAAAACAGGAAGGCAAAATGCCGCAAAAAAGGGAATAA
GGGCGACACGGAAATGTTGAATACTCATATTCTTCCTTTTTCAATATTATTGAAGCATTTATC
AGGGTTATTGTCTCATGAGCGGATACATATTTGAATGTATTTAGAAAAATAAACAAATAGGGG
TCAGTGTTACAACCAATTAACCAATTCTGAACATTATCGCGAGCCCATTTATACCTGAATATG
GCTCATAACACCCCTTGTTTGCCTGGCGGCAGTAGCGCGGTGGTCCCACCTGACCCCATGCCG
AACTCAGAAGTGAAACGCCGTAGCGCCGATGGTAGTGTGGGGACTCCCCATGCGAGAGTAGGG
AACTGCCAGGCATCAAATAAAACGAAAGGCTCAGTCGAAAGACTGGGCCTTTCGCCCGGGCTA
ATTGAGGGGTGTCGCCCTTATTCGACTCGGGGCTCGAG
(SEQ ID NO: 19)

pXL028

CTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGT
TCCTTTAATTAAACGCGTGGGGGAGGCTGCTGGTGAATATTAACCAAGGTCACCCCAGTTATC
GGAGGAGCAAACAGGGGCTAAGTCCACCGGGGGAGGCTGCTGGTGAATATTAACCAAGGTCAC
CCCAGTTATCGGAGGAGCAAACAGGGGCTAAGTCCACCGGGGAGGCTGCTGGTGAATATTAA
CCAAGGTCACCCCAGTTATCGGAGGAGCAAACAGGGGCTAAGTCCACCACTAGTAAATGACCTA
TTAAGAATATTTCATAGAACGAATGTTCCGATGCTCTAATCTCTCTAGACAAGGTTCATATTT
GTATGGGTTACTTATTCTCTCTTTGTTGACTAAGTCAATAATCAGAATCAGCAGGTTTGCAGT
CAGATTGGCAGGGATAAGCAGCCTAGCTCAGGAGAAGTGAGTATAAAAGCCCCAGGCTGGGAG
CAGCCATCACAGAAGTCCACTCATTCTTGGCAGGCCGCGGCTAAGGTAAGTTGGCGCCGTTTA
AGGGATGGTTGGTTGGTGGGGTATTAATGTTTAATTACCTTTTTTACAGGCCTGGGCGCGCCG
CCACCATGCCACCACCTAGGACAGGCAGGGGCCTGCTTTGGCTTGGACTGGTGCTGAGCTCTG
TCTGTGTTGCCCTGGGCTCCGAGACCCAAGCCAACTCTACAACCGATGCTCTCAATGTTCTGC
TCATCATAGTGGATGACCTGCGGCCCTCTCTAGGCTGCTATGGAGACAAGTTGGTGCGGAGCC
CCAACATAGACCAGCTAGCCTCTCACTCCCTGCTGTTCCAGAATGCCTTCGCCCAGCAAGCTG
TGTGCGCCCCCTCTAGAGTGTCTTTCCTGACCGGGAGAAGGCCTGATACAACAAGGCTGTATG
ACTTTAACAGCTACTGGAGGGTGCACGCAGGCAACTTCTCCACTATCCCCCAATACTTCAAGG
AGAATGGCTATGTGACCATGAGCGTGGGCAAGGTCTTCCACCCTGGAATCTCCTCCAACCACA
CTGATGATAGTCCCTACTCTTGGTCTTTTCCTCCCTATCACCCTAGCAGTGAGAAGTATGAGA

TABLE 3-continued

Exemplary rAAV I2S vector nucleotide sequences

ACACCAAAACCTGCAGAGGCCCTGATGGGGAGCTGCATGCTAACCTCCTGTGTCCTGTAGATG
TGCTGGACGTCCCAGAGGGCACCTTGCCAGATAAGCAGTCTACTGAGCAGGCTATCCAGCTGC
TTGAGAAAATGAAGACTTCTGCATCTCCCTTCTTTCTGGCTGTTGGCTACCACAAGCCTCACA
TCCCCTTCAGGTACCCTAAGGAGTTCCAAAAGCTCTATCCTCTGGAAAACATCACACTTGCCC
CCGATCCTGAGGTCCCTGACGGCCTCCCACCAGTAGCCTACAATCCTTGGATGGACATTAGGC
AGAGAGAGGATGTCCAGGCTCTGAATATTTCTGTGCCCTATGGGCCCATCCCGGTGGACTTCC
AGCGCAAAATCAGACAGTCCTACTTTGCCTCTGTGAGCTATCTGGACACCCAGGTTGGGAGGC
TCCTCTCCGCCCTTGACGACCTCCAGTTGGCCAACAGCACCATTATAGCCTTCACCTCTGACC
ACGGCTGGGCACTGGGGGAACACGGGGAGTGGGCTAAGTACTCTAACTTTGATGTGGCCACCC
ACGTGCCCCTCATCTTTTATGTGCCTGGCAGGACTGCCAGCCTGCCCGAAGCTGGGGAAAAAC
TGTTTCCATACCTGGACCCTTTTGACAGTGCTTCTCAGCTCATGGAACCTGGCCGTCAGAGCA
TGGATCTGGTGGAGCTAGTGTCCCTCTTCCCAACCTTGGCTGGCCTTGCTGGTCTCCAGGTGC
CTCCTAGATGCCCAGTCCCCTCCTTCCATGTTGAACTCTGCCGTGAGGGGAAGAATCTGCTGA
AGCACTTCAGATTCAGAGACTTGGAGGAGGACCCCTACCTTCCTGGGAACCCCAGGGAGTTGA
TTGCATACTCCCAGTATCCCAGGCCAAGTGACATTCCCAGTGGAACTCCGACAAACCAAGTC
TGAAGGACATCAAGATCATGGGGTACAGCATCAGGACCATTGACTACAGATACACAGTGTGGG
TTGGATTTAACCCAGATGAGTTCTTGGCAAACTTTTCTGACATCCATGCAAGTCAGTTGTATT
TTGTGGACAGCGACCCTCTGCAGGATCACAACATGTACAATGACAGCCAGGGTGGGGACCTCT
TTCAACTCCTCATGCCATAGCAATTGGCCCCTCTCCCTCCCCCCCCTAACGTTACTGGCCG
AAGCCGCTTGGAATAAGGCCGGTGTGCGTTTGTCTATATGTTATTTTCCACCATATTGCCGTC
TTTTGGCAATGTGAGGGCCCGGAAACCTGGCCCTGTCTTCTTTGACGAGCATTCCTAGGGGTCT
TTCCCCTCTCGCCAAAGGAATGCAAGGTCTGTTGAATGTCGTGAAGGAAGCAGTTCCTCTGGA
AGCTTCTTGAAGACAAACAACGTCTGTAGCGACCCTTTGCAGGCAGCGGAACCCCCCAACCTGG
CGACAGGTGCCTCTGCGGCCAAAAGCCACGTGTATAAGATACACCTGCAAAGGCGGCACAACC
CCAGTGCCACGTTGTGAGTTGGATAGTTGTGGAAAGAGTCAAATGGCTCACCTCAAGCGTATT
CAACAAGGGGCTGAAGGATGCCCAGAAGGTACCCCATTGTATGGGATCTGATCTGGGGCCTCG
GTGCACATGCTTTACATGTGTTTAGTCGAGGTTAAAAAACGTCTAGGCCCCCCGAACCACGGG
GACGTGGTTTTCCTTTGAAAAACACGATGATAATCATATGGCCACCATGGCTGCTCCTGCCCT
GGGGCTGGTGTGTGGAAGATGTCCTGAACTGGGCCTGGTTCTGTTACTGCTTCTGCTCAGCCT
GCTCTGTGGTGCTGCCGGCAGCCAAGAGGCAGGCACTGGCGCTGGAGCTGGAAGCCTGGCTGG
GTCTTGTGGATGTGGCACACCACAGAGGCCAGGGGCTCATGGCTCCTCTGCTGCAGCTCATAG
GTACAGCAGAGAAGCCAATGCTCCAGGCCCAGTGCCTGGAGAGAGACAGCTGGCTCACAGCAA
GATGGTGCCCATCCCTGCTGGGGTGTTCACAATGGGAACAGATGATCCCCAGATCAAGCAGGA
TGGGGAGGCGCCTGCCAGGAGGGTGACCATTGATGCATTCTATATGGATGCCTATGAGGTGAG
CAATACAGAATTTGAGAAGTTTGTGAACTCTACTGGCTACCTGACTGAGGCTGAAAAATTTGG
AGACTCTTTTGTGTTTGAAGGAATGCTTAGTGAACAGGTTAAGACCAACATCCAGCAGGCTGT
TGCAGCAGCCCCTGGTGGTTGCCTGTCAAGGGAGCTAACTGGAGGCACCCTGAGGGACCAGA
TTCTACAATCCTGCATAGACCTGATCATCCTGTTCTGCATGTGTCTTGGAATGATGCTGTGGC
TTACTGTACCTGGGCAGGAAAAAGGCTGCCAACAGAAGCTGAGTGGGAATACTCTTGCAGAGG
AGGCCTGCACAATAGACTGTTCCCATGGGGCAACAAGCTGCAACCCAAGGGCCAGCACTATGC
TAACATCTGGCAGGGAGAATTCCCTGTGACAAACACAGGAGAGGACGGCTTCCAGGGAACTGC
CCCTGTAGATGCTTTCCCTCCTAATGGCTATGGCCTGTATAACATTGTTGGCAACGCCTGGGA
GTGGACTTCTGATTGGTGGACAGTGCACCACTCTGTTGAGGAGACACTGAATCCTAAGGGGCC
ACCTTCTGGAAAGGATAGAGTGAAGAAGGGGGGAAGCTACATGTGCCACAGGTCTTATTGTTA
CAGATACAGGTGCGCTGCTAGGTCTCAGAACACCCCTGATAGCAGTGCTAGCAATCTGGGCTT
CAGGTGTGCCGCTGACAGACTGCCTACCATGGATTAAGTCGACCCTAGAGCTCGCTGATCAGC
CTCGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGTCT
GAGTAGGTGTCATTCTATTCTGGGGGGTGGGGTGGGGCAGGACAGCAAGGGGGAGGATTGGGA
AGACAATAGCAGGCATGCTGGGGAATCTAGA Xn(60-
100)GTTTAAACATTTAAATAGGAACCCCTAGTGATGGAGTTGGCCACTCCCTCTCTGCGCGC
TCGCTCGCTCACTGAGGCCGGGCGACCAAAGGTCGCCCGACGCCCGGGCTTTGCCGGGCGGC
CTCAGTGAGCGAGCGAGCGCGCAGAGAGTATACATCGATGTGAGTTCGCGGGTGGCTGGGGGG
CCCTGGGCTGCGACCGCCCCCGAACCGCGTCTACGAGCCTTGCGGGCTCCGGTCTTTGCAGT
CGTATGGGGGCAGGGTAGCTGTTCCCCGCAAGGAGAGCTCAAGGTCAGCGCTCGGACCTGGCG
GAGCCCCGCACCCAGGCTGTGGCGCCCTGTGCAGCTCCGCCCTTGCGGCGCCATCTGCCCGGA
GCCTCCTTCCCCTAGTCCCCAGAAACAGGAGGTCCCTACTCCCGCCCGAGATCCCGACCCGGA
CCCCTAGGTGGGGGACGCTTTCTTTCCTTTCGCGCTCTGCGGGTCACGTGTCGCAGAGGAGC
CCCTCCCCCACGGCCTCCGGCACCGCAGGCCCCGGGATGCTAGTGCGCAGCGGGTGCATCCCT
GTCCGGATGCTGCGCCTGCGGTAGACGGCCGCCATGTTGCAACCGGGAAGGAAATGAATGGG
CAGCCGTTAGGAAAGCCTGCCGGTGACTAACCCTGCGCTCCTGCCTCGATGGGTGGAGTCGCG
TGTGGCGGGGAAGTCAGGTGGAGCGAGGCTAGCTGGCCCGATTTCTCCTCCGGGTGATGCTTT
TCCTAGATTATTCTCTGGTAAATCAAAGAAGTGGGTTTATGGAGGTCCTCTTTGTGTCCCCTCC
CCGCAGAGGTGTGGTGGCTGTGGCATGGTGCCAAGCCGGGAGAAGCTGAGTCATGGGTAGTTG
GAAAAGGACATTTCCACCGCAAAATGGCCCCTCTGGTGGTGGCCCCTTCCTGCAGCGCCGGCT
CACCTCACGGCCCCGCCCTTCCCCTGCCAGCCTAGCGTTGACCCGACCCCAAAGGCCAGGCTG
TAAATGTCACCGGGAGGATTGGGTGTCTGGGCGCCTGGGGAACCTGCCCTTCTCCCCATTCC
GTCTTCCGGAAACCAGATCTCCCACCGCACCCTGGTCTGAGGTTAAATATAGCTGCTGACCTT
TCTGTAGCTGGGGCCTCTGGGCTGGGGCTCTCTCCCATCCCTTTCTCCCCACACACATGCACTTA
CCTGTGCTCCCACTCCTGATTTCTGGAAAAGAGCTAGGAAGGACAGGCAACTTGGCAAATCAA
AGCCCTGGGACTAGGGGGTTAAATACAGCTTCCCCTCTTCCCACCCGCCCCAGTCTCTGTCC
CTTTTGTAGGAGGGACTTAGAGAAGGGTGGGCTTGCCCTGTCCAGTTAATTTCTGACCTTTA
CTCCTGCCCTTTGAGTTTGATGATGCTGAGTGTACAAGCGTTTTCTCCCTAAAGGGTGCAGCT
GAGCTAGGCAGCAGCAAGCATTCCTGGGGTGGCATAGTGGGGTGGTGAATACCATGTACAAAG
CTTGTGCCCAGACTGTGGGTGGCAGTGCCCCACATGGCCGCTTCTCCTGGAAGGGCTTCGTAT
GACTGGGGGTGTTGGGCAGCCCTGGAGCCTTCAGTTGCAGCCATGCCTTAAGCCAGGCCAGCC
TGGCAGGGAAGCTCAAGGGAGATAAAATTCAACCTCTTGGGCCCTCCTGGGGGTAAGGAGATG
CTGCATTCGCCCTCTTAATGGGGAGGTGGCCTAGGGCTGCTCACATATTCTGGAGGAGCCTCC

TABLE 3-continued

Exemplary rAAV I2S vector nucleotide sequences

```
CCTCCTCATGCCTTCTTGCCTCTTGTCTCTTAGGCATGCAAAAGAGTCGAATAAGGGCGACAC
AAAATTTATTCTAAATGCATAATAAATACTGATAACATCTTATAGTTTGTATTATATTTTGTA
TTATCGTTGACATGTATAATTTTGATATCAAAAACTGATTTTCCCTTTATTATTTTCGAGATT
TATTTTCTTAATTCTCTTTAACAAACTAGAAATATTGTATATACAAAAAATCATAAATAATAG
ATGAATAGTTTAATTATAGGTGTTCATCAATCGAAAAAGCAACGTATCTTATTTAAAGTGCGT
TGCTTTTTTCTCATTTATAAGGTTAAATAATTCTCATATATCAAGCAAAGTGACAGGCGCCT
TAAATATTCTGACAAATGCTCTTTCCCTAAACTCCCCCCATAAAAAAACCCGCCGAAGCGGGT
TTTTACGTTATTTGCGGATTAACGATTACTCGTTATCAGAACCGCCCAGGGGGCCCGAGCTTA
AGACTGGCCGTCGTTTTACAACACAGAAAGAGTTTGTAGAAACGCAAAAAGGCCATCCGTCAG
GGGCCTTCTGCTTAGTTTGATGCCTGGCAGTTCCCTACTCTCGCCTTCCGCTTCCTCGCTCAC
TGACTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTACAGAGTT
CTTGAAGTGGTGGGCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGACGCGCGCGTAACTCACGTTAA
GGGATTTTGGTCATGAGCTTGCGCCGTCCCGTCAAGTCAGCGTAATGCTCTGCTTAGGTGGCG
GTACTTGGGTCGATATCAAAGTGCATCACTTCTTCCCGTATGCCCAACTTTGTATAGAGAGCC
ACTGCGGGATCGTCACCGTAATCTGCTTGCACGTAGATCACATAAGCACCAAGCGCGTTGGCC
TCATGCTTGAGGAGATTGATGAGCGCGGTGGCAATGCCCTGCCTCCGGTGCTCGCCGGAGACT
GCGAGATCATAGATATAGATCTCACTACGCGGCTGCTCAAACTTGGGCAGAACGTAAGCCGCG
AGAGCGCCAACAACCGCTTCTTGGTCGAAGGCAGCAAGCGCGATGAATGTCTTACTACGGAGC
AAGTTCCCGAGGTAATCGGAGTCCGGCTGATGTTGGGAGTAGGTGGCTACGTCACCGAACTCA
CGACCGAAAAGATCAAGAGCAGCCCGCATGGATTTGACTTGGTCAGGGCCGAGCCTACATGTG
CGAATGATGCCCATACTTGAGCCACCTAACTTTGTTTTAGGGCGACTGCCCTGCTGCGTAACA
TCGTTGCTGCTCCATAACATCAAACATCGACCCACGGCGTAACGCGCTTGCTGCTTGGATGCC
CGAGGCATAGACTGTACAAAAAAACAGTCATAACAAGCCATGAAAACCGCCACTGCGCCGTTA
CCACCGCTGCGTTCGGTCAAGGTTCTGGACCAGTTGCGTGAGCGCATTTTTTTTCCTCCTCG
GCGTTTACGCCCCGCCCTGCCACTCATCGCAGTACTGTTGTAATTCATTAAGCATTCTGCCGA
CATGGAAGCCATCACAGACGGCATGATGAACCTGAATCGCCAGCGGCATCAGCACCTTGTCGC
CTTGCGTATAATATTTGCCCATAGTGAAAACGGGGGCGAAGAAGTTGTCCATATTGGCCACGT
TTAAATCAAAACTGGTGAAACTCACCCAGGGATTGGCGCTGACGAAAAACATATTCTCAATAA
ACCCTTTAGGGAAATAGGCCAGGTTTTCACCGTAACACGCCACATCTTGCGAATATATGTGTA
GAAACTGCCGGAAATCGTCGTGTGCACTCATGGAAAACGGTGTAACAAGGGTGAACACTATCC
CATATCACCAGCTCACCGTCTTTCATTGCCATACGGAACTCCGGATGAGCATTCATCAGGCGG
GCAAGAATGTGAATAAAGGCCGGATAAAACTTGTGCTTATTTTTCTTTACGGTCTTTAAAAAG
GCCGTAATATCCAGCTGAACGGTCTGGTTATAGGTACATTGAGCAACTGACTGAAATGCCTCA
AAATGTTCTTTACGATGCCATTGGGATATATCAACGGTGGTATATCCAGTGATTTTTTTCTCC
ATTTTTTTTTCCTCCTTTAGAAAAACTCATCGAGCATCAAATGAAACTGCAATTTATTCATAT
CAGGATTATCAATACCATATTTTTGAAAAAGCCGTTTCTGTAATGAAGGAGAAAACTCACCGA
GGCAGTTCCATAGGATGGCAAGATCCTGGTATCGGTCTGCGATTCCGACTCGTCCAACATCAA
TACAACCTATTAATTTCCCCTCGTCAAAAATAAGGTTATCAAGTGAGAAATCACCATGAGTGA
CGACTGAATCCGGTGAGAATGGCAAAAGTTTATGCATTTCTTTCCAGACTTGTTCAACAGGCC
AGCCATTACGCTCGTCATCAAAATCACTCGCATCAACCAAACCGTTATTCATTCGTGATTGCG
CCTGAGCGAGGCGAAATACGCGATCGCTGTTAAAAGGACAATTACAAACAGGAATCGAGTGCA
ACCGGCGCAGGAACACTGCCAGCGCATCAACAATATTTTCACCTGAATCAGGATATTCTTCTA
ATACCTGGAACGCTGTTTTTCCGGGGATCGCAGTGGTGAGTAACCATGCATCATCAGGAGTAC
GGATAAAATGCTTGATGGTCGGAAGTGGCATAAATTCCGTCAGCCAGTTTAGTCTGACCATCT
CATCTGTAACATCATTGGCAACGCTACCTTTGCCATGTTTCAGAAACAACTCTGGCGCATCGG
GCTTCCCATACAAGCGATAGATTGTCGCACCTGATTGCCCGACATTATCGCGAGCCCATTTAT
ACCCATATAAATCAGCATCCATGTTGGAATTTAATCGCGGCCTCGAGTTTCCCGTTGAATAT
GGCTCATTTTTTTTCCTCCTTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGG
CTTACCATCTGGCCCCAGCGCTGCGATGATACCGCGAGAACCACGCTCACCGGCTCCGGATTT
ATCAGCAATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAATAGTTT
GCGCAACGTTGTTGCCATCGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCACGTTGTC
AGAAGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCACAT
AGCAGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGA
ATAAGGGCGACACGGAAATGTTGAATACTCATATTCTTCCTTTTTCAATATTATTGAAGCATT
TATCAGGGTTATTGTCTCATGAGCGGATACATATTTGAATGTATTTAGAAAAATAAACAAATA
GGGGTCAGTGTTACAACCAATTAACCAATTCTGAACATTATCGCGAGCCCATTTATACCTGAA
```

TABLE 3-continued

Exemplary rAAV I2S vector nucleotide sequences

```
TATGGCTCATAACACCCCTTGTTTGCCTGGCGGCAGTAGCGCGGTGGTCCCACCTGACCCCAT
GCCGAACTCAGAAGTGAAACGCCGTAGCGCCGATGGTAGTGTGGGGACTCCCCATGCGAGAGT
AGGGAACTGCCAGGCATCAAATAAAACGAAAGGCTCAGTCGAAAGACTGGGCCTTTCGCCCGG
GCTAATTGAGGGGTGTCGCCCTTATTCGACTCGGGGCTCGAG
(SEQ ID NO: 20)
``` pXL029

```
CTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGT
TCCTTTAATTAAACGCGTGGGGAGGCTGCTGGTGAATATTAACCAAGGTCACCCCAGTTATC
GGAGGAGCAAACAGGGGCTAAGTCCACCGGGGGAGGCTGCTGGTGAATATTAACCAAGGTCAC
CCCAGTTATCGGAGGAGCAAACAGGGGCTAAGTCCACCGGGGGAGGCTGCTGGTGAATATTAA
CCAAGGTCACCCCAGTTATCGGAGGAGCAAACAGGGGCTAAGTCCACACTAGTAAATGACCTA
TTAAGAATATTTCATAGAACGAATGTTCCGATGCTCTAATCTCTCTAGACAAGGTTCATATTT
GTATGGGTTACTTATTCTCTCTTTGTTGACTAAGTCAATAATCAGAATCAGCAGGTTTGCAGT
CAGATTGGCAGGGATAAGCAGCCTAGCTCAGGAGAAGTGAGTATAAAAGCCCCAGGCTGGGAG
CAGCCATCACAGAAGTCCACTCATTCTTGGCAGGCCGCGGCTAAGGTAAGTTGGCGCCGTTTA
AGGGATGGTTGGTTGGTGGGTATTAATGTTTAATTACCTTTTTTACAGGCCTGGGCGCGCCG
CCACCATGCCACCCCCCGGACCGGGAGAGGCCTCTTGTGGTTGGGCCTGGTGCTGAGCAGCG
TGTGCGTGGCCCTGGGCAGTGAGACCCAGGCTAACTCTACAACAGATGCCTTGAATGTGCTGC
TGATCATTGTGGATGACCTGAGGCCAAGTCTGGGCTGCTATGGGGACAAATTGGTGAGGTCCC
CCAACATCGACCAGTTGGCCTCCCACTCTCTCCTATTCCAAAATGCTTTCGCCCAGCAGGCAG
TTTGTGCCCCCTCTAGGGTGAGCTTCCTCACTGGCAGGCGCCCTGACACCACTAGACTGTATG
ACTTTAACAGCTATTGGAGGGTGCACGCAGGAAACTTCTCCACAATCCCTCAATACTTCAAGG
AGAATGGTTATGTGACAATGTCTGTGGGCAAGGTGTTCCACCCTGGCATCAGCAGCAACCACA
CCGATGACTCACCCTATAGTTGGTCTTTTCCCCCCTACCATCCTTCATCTGAGAAATATGAAA
ACACAAAAACCTGCCGAGGCCCAGACGGGGAACTGCATGCCAACCTACTCTGTCCTGTTGATG
TACTGGACGTGCCCGAGGGCACCCTCCCTGATAAGCAGTCCACAGAACAGGCCATTCAGCTGC
TTGAAAAGATGAAGACCTCCGCATCCCCCTTCTTCTTGGCTGTCGGCTACCACAAGCCCCATA
TCCCCCTTTAGATACCCCAAGGAATTCCAGAAACTGTACCCACTGGAGAACATCACACTTGCTC
CTGACCCTGAAGTGCCTGACGGACTGCCTCCAGTGGCCTATAACCCTTGGATGGACATCCGGC
AGCGCGAGGATGTGCAGGCTCTGAACATTAGTGTGCCTTATGGGCCCATCCCTGTGGACTTTC
AGAGGAAGATTCGCCAGTCCTACTTTGCCTCTGTATCCTACCTGGACACACAGGTGGGACGCC
TGCTGTCTGCCCTTGATGATCTGCAACTGGCCAACAGCACCATTATAGCTTTCACATCAGACC
ATGGGTGGGCTCTTGGGGAGCATGGTGAATGGGCTAAGTACTCCAACTTCGATGTGGCAACCC
ATGTCCCTCTGATCTTCTATGTGCCAGGAAGGACCGCCTCTCTGCCCAGAGGCAGGTGAGAAGC
TGTTCCCCTATCTGGACCCTTTTGACTCCGCCAGCCAGCTGATGGAGCCTGGCCGACAGTCTA
TGGACCTGGTTGAGCTGGTCAGCCTGTTTCCCACACTCGCTGGACTGGCTGGCCTGCAAGTAC
CCCCACGCTGCCCAGTGCCCTCCTTCCATGTGGAGCTTTGCAGGGAGGGGAAGAACCTCCTCA
AGCACTTCAGGTTCAGGGACCTAGAGGAGGATCCTTATCTGCCTGGAAACCCCAGAGAGCTTA
TTGCTTACTCCCAGTATCCAAGGCCTAGTGACATTCCCCAATGGAACTCAGACAAACCAAGCC
TGAAAGACATCAAGATCATGGGATACTCTATCAGGACCATTGACTACAGGTACACTGTGTGGG
TTGGCTTCAACCCGGATGAGTTCCTGGCTAATTTCTCTGACATACATGCTGGCGAGCTGTACT
TCGTGGACAGTGACCCCCTGCAGGATCACAACATGTACAATGATTCCCAGGGGGTGACCTCT
TCCAGCTTCTGATGCCCTAACAATTGGCCCCTCTCCCTCCCCCCCCCCTAACGTTACTGGCCG
AAGCCGCTTGGAATAAGGCCGGTGTGCGTTTGTCTATATGTTATTTTCCACCATATTGCCGTC
TTTTGGCAATGTGAGGGCCCGGAAACCTGGCCCTGTCTTCTTGACGAGCATTCCTAGGGGTCT
TTCCCCTCTCGCCAAAGGAATGCAAGGTCTGTTGAATGTCGTGAAGGAAGCAGTTCCTCTGGA
AGCTTCTTGAAGACAAACAACGTCTGTAGCGACCCTTTGCAGGCAGCGGAACCCCCCACCTGG
CGACAGGTGCCTCTGCGGCCAAAAGCCACGTGTATAAGATACACCTGCAAAGGCGGCACAACC
CCAGTGCCACGTTGTGAGTTGGATAGTTGTGGAAAGAGTCAAATGGCTCACCTCAAGCGTATT
CAACAAGGGCTGAAGGATGCCCAGAAGGTACCCCATTGTATGGGATCTGATCTGGGGCCTCG
GTGCACATGCTTTACATGTGTTTAGTCGAGGTTAAAAAACGTCTAGGCCCCCCGAACCACGGG
GACGTGGTTTTCCTTTGAAAAACACGATGATAATACCGGTGCCACCATGGCTGCCCCTGCTCT
GGGATTGGTTTGTGGCAGATGTCCTGAGCTTGGTCTGGTGCTGTTGCTCCTTCTGTTGTCTCT
GCTGTGTGGAGCAGCTGGGTCTCAGGAAGCTGGCACAGGCGCTGGGGCTGGCTCTCTGGCCGG
GTCATGTGGCTGTGGAACTCCCCAGCGGCCTGGAGCCCATGGCAGCTCTGCGCAGCACACAG
GTATTCTAGGGAAGCCAATGCCCCAGGCCCTGTGCCTGGGGAGAGACAGCTAGCTCATTCTAA
GATGGTGCCTATCCCAGCCGGGGTTTTTACAATGGGCACTGATGATCCTCAGATTAAGCAGGA
TGGAGAGGCCCCCGCCAGAAGAGTGACCATTGATGCTTTCTACATGGATGCATATGAAGTGTC
CAACACAGAGTTTGAGAAATTTGTGAACTCTACTGGATACTTGACCGAGGCTGAGAAGTTTGG
AGATTCCTTTGTCTTTGAAGGCATGCTGTCTGAGCAGGTCAAGACCAACATTCAGCAAGCAGT
GGCCGCTGCACCTTGGTGGCTTCCTGTGAAGGGCGCCAACTGGAGACATCCAGAGGGGCCAGA
TAGTACCATCCTCCACAGACCTGATCACCCAGTCCTTCATGTTTCCTGGAATGATGCAGTTGC
TTACTGCACTTGGGCCGGCAAGAGGCTCCCTACTGAGGCAGAGTGGGAATACTCCTGCAGAGG
AGGCCTGCACAACAGACTGTTCCCTTGGGGGAACAAGCTTCAGCCCAAAGGCCAGCACTATGC
TAACATCTGGCAGGGTGAGTTTCCAGTCACCAATAGAGGAGGACGGATTCCAGGGAACCGC
ACCAGTAGATGCCTTCCCTCCTAATGGCTATGGCCTGTATAATATTGTGGGCAATGCATGGGA
GTGGACCTCTGACTGGTGGACTGTGCACCACTCAGTGGAGGAAACCCTGAACCCTAAGGGACC
CCCCTTCAGGCAAAGATAGAGTCAAAAAGGGAGGGAGCTATATGTGTCACAGATCCTATTGCTA
CAGATATAGATGTGCAGCCAGGTCCCAGAACACCCCTGACTCTTCTGCTAGCAACCTGGGCTT
TCGGTGTGCTGCTGATAGACTGCCCACCATGGACTAAGTCGACCCTAGAGCTCGCTGATCAGC
CTCGACTGTGCCTTCTAGTTGCCAGCCATCTGTTGTTTGCCCCTCCCCCGTGCCTTCCTTGAC
```

TABLE 3-continued

Exemplary rAAV I2S vector nucleotide sequences

```
CCTGGAAGGTGCCACTCCCACTGTCCTTTCCTAATAAAATGAGGAAATTGCATCGCATTGTCT
GAGTAGGTGTCATTCTATTCTGGGGGGTGGGGTGGGGCAGGACAGCAAGGGGGAGGATTGGGA
AGACAATAGCAGGCATGCTGGGGAATCTAGA Xn(60-
100)GTTTAAACATTTAAATAGGAACCCCTAGTGATGGAGTTGGCCACTCCCTCTCTGCGCGC
TCGCTCGCTCACTGAGGCCGGGCGACCAAAGGTCGCCCGACGCCCGGGCTTTGCCCGGGCGGC
CTCAGTGAGCGAGCGAGCGCGCAGAGAGTATACATCGATGTGAGTTGCGGGTGGCTGGGGGG
CCCTGGGCTGCGACCGCCCCCGAACCGCGTCTACGAGCCTTGCGGGCTCCGGGTCTTTGCAGT
CGTATGGGGCAGGGTAGCTGTTCCCCGCAAGGAGAGCTCAAGGTCAGCGCTCGGACCTGGCG
GAGCCCCGCACCCAGGCTGTGGCGCCCTGTGCAGCTCCGCCCTTGCGGCGCCATCTGCCCGGA
GCCTCCTTCCCCTAGTCCCCAGAAACAGGAGGTCCCTACTCCCGCCCGAGATCCCGACCCGGA
CCCCTAGGTGGGGGACGCTTTCTTTCCTTTCGCGCTCTGCGGGGTCACGTGTCGCAGAGGAGC
CCCTCCCCCACGGCCTCCGGCACCGCAGGCCCCGGGATGCTAGTGCGCAGCGGGTGCATCCCT
GTCCGGATGCTGCGCCTGCGGTAGAGCGGCCGCCATGTTGCAACCGGGAAGGAAATGAATGGG
CAGCCGTTAGGAAAGCCTGCCGGTGACTAACCCTGCGCTCCTGCCTCGATGGGTGGAGTCGCG
TGTGGCGGGGAAGTCAGGTGGAGCGAGGCTAGCTGGCCCGATTTCTCCTCCGGGTGATGCTTT
TCCTAGATTATTCTCTGGTAAATCAAAGAAGTGGGTTTATGGAGGTCCTCTTGTGTCCCCTCC
CCGCAGAGGTGTGGTGGCTGTGGCATGGTGCCAAGCCGGGAGAAGCTGAGTCATGGGTAGTTG
GAAAAGGACATTTCCACCGCAAAATGGCCCCTCTGGTGGTGGCCCCTTCCTGCAGCGCCGGCT
CACCTCACGGCCCCGCCCTTCCCCTGCCAGCCTAGCGTTGACCCGACCCCAAAGGCCAGGCTG
TAAATGTCACCGGGAGGATTGGGTGTCTGGGCGCCTCGGGGAACCTGCCCTTCTCCCCATTCC
GTCTTCCGGAAACCAGATCTCCCACCGCACCCTGGTCTGAGGTTAAATATAGCTGCTGACCTT
TCTGTAGCTGGGGGCCTGGGCTGGGCTCTCTCCCATCCCTTCTCCCCACACACATGCACTTA
CCTGTGCTCCCACTCCTGATTTCTGGAAAAGAGCTAGGAAGGACAGGCAACTTGGCAAATCAA
AGCCCTGGGACTAGGGGGTTAAAATACAGCTTCCCCTCTTCCCACCCGCCCCAGTCTCTGTCC
CTTTTGTAGGAGGGACTTAGAGAAGGGGTGGGCTTGCCCTGTCCAGTTAATTTCTGACCTTTA
CTCCTGCCCTTTGAGTTTGATGATGCTGAGTGTACAAGCGTTTTCTCCCTAAAGGGTGCAGCT
GAGCTAGGCAGCAGCAAGCATTCCTGGGGTGGCATAGTGGGGTGGTGAATACCATGTACAAAG
CTTGTGCCCAGACTGTGGGTGGCAGTGCCCCACATGGCCGCTTCTCCTGGAAGGGCTTCGTAT
GACTGGGGGTGTTGGGCAGCCCTGGAGCCTTCAGTTGCAGCCATGCCTTAAGCCAGGCCAGCC
TGGCAGGGAAGCTCAAGGGAGATAAAATTCAACCTCTTGGGCCCTCCTGGGGGTAAGGAGATG
CTGCATTCGCCCTCTTAATGGGGAGGTGGCCTAGGGCTGCTCACATATTCTGGAGGAGCCTCC
CCTCCTCATGCCTTCTTGCCTCTTGTCTCTTAGGCATGCAAAAGAGTCGAATAAGGGCGACAC
AAAATTTATTCTAAATGCATAATAAATACTGATAACATCTTATAGTTTGTATTATATTTTGTA
TTTATCGTTGACATGTATAATTTTGATATCAAAAACTGATTTTCCCTTTATTATTTTCGAGATT
TATTTTCTTAATTCTCTTTAACAAACTAGAAATATTGTATATACAAAAAATCATAAATAATAG
ATGAATAGTTTAATTATAGGTGTTCATCAATCGAAAAAGCAACGTATCTTATTTAAAGTGCGT
TGCTTTTTTCTCATTTATAAGGTTAAATAATTCTCATATATCAAGCAAAGTGACAGGCGCCCT
TAAATATTCTGACAAATGCTCTTTCCCTAAACTCCCCCCATAAAAAAACCCGCCGAAGCGGGT
TTTTACGTTATTTGCGGATTAACGATTACTCGTTATCAGAACCGCCCAGGGGGCCCGAGCTTA
AGACTGGCCGTCGTTTTACAACACAGAAAGAGTTTGTAGAAACGCAAAAAGGCCATCCGTCAG
GGGCCTTCTGCTTAGTTTGATGCCTGGCAGTTCCCTACTCTCGCCTTCCGCTTCCTCGCTCAC
TGACTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTACAGAGTT
CTTGAAGTGGTGGGCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGACGCGCGTAACTCACGTTAA
GGGATTTTGGTCATGAGCTTGCGCCGTCCCGTCAAGTCAGCGTAATGCTCTGCTTAGGTGGCG
GTACTTGGGTCGATATCAAAGTGCATCACTTCTTCCCGTATGCCCAACTTTGTATAGAGACC
ACTGCGGGATCGTCACCGTAATCTGCTTGCACGTAGATCACATAAGCACCAAGCGCGTTGGCC
TCATGCTTGAGGAGATTGATGAGCGCGGTGGCAATGCCCTGCCTCCGGTGCTCGCCGGAGACT
GCGAGATCATAGATATAGATCTCACTACGCGGCTGCTCAAACTTGGGCAGAACGTAAGCCGCG
AGAGCGCCAACAACCGCTTCTTGGTCGAAGGCAGCAAGCGCGATGAATGTCTTACTACGGAGC
AAGTTCCCGAGGTAATCGGAGTCCGGCTGATGTTGGGAGTAGGTGGCTACGTCACCGAACTCA
CGACCGAAAAGATCAAGAGCAGCCCGCATGGATTTGACTTGGTCAGGGCCGAGCCTACATGTG
CGAATGATGCCCATACTTGAGCCACCTAACTTTGTTTTAGGGCGACTGCCCTGCTGCGTAACA
TCGTTGCTGCTCCATAACATCAAACATCGACCCACGGCGTAACGCGCTTGCTGCTTGGATGCC
CGAGGCATAGACTGTACAAAAAACAGTCATAACAAGCCATGAAAACCGCCACTGCGCCGTTA
CCACCGCTGCGTTCGGTCAAGGTTCTGGACCAGTTGCGTGAGCGCATTTTTTTTCCTCCTCG
GCGTTTACGCCCCGCCCTGCCACTCATCGCAGTACTGTTGTAATTCATTAAGCATTCTGCCGA
CATGGAAGCCATCACAGACGGCATGATGAACCTGAATCGCCAGCGGCATCAGCACCTTGTCGC
CTTGCGTATAATATTTGCCCATAGTGAAAACGGGGGCGAAGAAGTTGTCCATATTGGCCACGT
TTAAATCAAAACTGGTGAAACTCACCCAGGGATTGGCGCTGACGAAAAACATATTCTCAATAA
ACCCTTTAGGGAAATAGGCCAGGTTTTCACCGTAACACGCCACATCTTGCGAATATATGTGTA
GAAACTGCCGGAAATCGTCGTGTGCACTCATGGAAACGGTGTAACAAGGGTGAACACTATCC
CATATCACCAGCTCACCGTCTTTCATTGCCATACGGAACTCCGGATGAGCATTCATCAGGCGG
GCAAGAATGTGAATAAAGGCCGGATAAAACTTGTGCTTATTTTTCTTTACGGTCTTTAAAAAG
GCCGTAATATCCAGCTGAACGGTCTGGTTATAGGTACATTGAGCAACTGACTGAAATGCCTCA
AAATGTTCTTTACGATGCCATTGGGATATATCAACGGTGGTATATCCAGTGATTTTTTTCTCC
ATTTTTTTTTCCTCCTTTAGAAAAACTCATCGAGCATCAAATGAAACTGCAATTTATTCATAT
CAGGATTATCAATACCATATTTTTGAAAAAGCCGTTTCTGTAATGAAGGAGAAAACTCACCGA
```

TABLE 3-continued

Exemplary rAAV I2S vector nucleotide sequences

```
GGCAGTTCCATAGGATGGCAAGATCCTGGTATCGGTCTGCGATTCCGACTCGTCCAACATCAA
TACAACCTATTAATTTCCCCTCGTCAAAAATAAGGTTATCAAGTGAGAAATCACCATGAGTGA
CGACTGAATCCGGTGAGAATGGCAAAAGTTTATGCATTTCTTTCCAGACTTGTTCAACAGGCC
AGCCATTACGCTCGTCATCAAAATCACTCGCATCAACCAAACCGTTATTCATTCGTGATTGCG
CCTGAGCGAGGCGAAATACGCGATCGCTGTTAAAAGGACAATTACAAACAGGAATCGAGTGCA
ACCGGCGCAGGAACACTGCCAGCGCATCAACAATATTTTCACCTGAATCAGGATATTCTTCTA
ATACCTGGAACGCTGTTTTTCCGGGGATCGCAGTGGTGAGTAACCATGCATCATCAGGAGTAC
GGATAAAATGCTTGATGGTCGGAAGTGGCATAAATTCCGTCAGCCAGTTTAGTCTGACCATCT
CATCTGTAACATCATTGGCAACGCTACCTTTGCCATGTTTCAGAAACAACTCTGGCGCATCGG
GCTTCCCATACAAGCGATAGATTGTCGCACCTGATTGCCCGACATTATCGCGAGCCCATTTAT
ACCCATATAAATCAGCATCCATGTTGGAATTTAATCGCGGCCTCGACGTTTCCCGTTGAATAT
GGCTCATTTTTTTTCCTCCTTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGG
CTTACCATCTGGCCCCAGCGCTGCGATGATACCGCGAGAACCACGCTCACCGGCTCCGGATTT
ATCAGCAATAAACCAGCCAGCCGGAAGGGCCGAGCGCAGAAGTGGTCCTGCAACTTTATCGC
CTCCATCCAGTCTATTAATTGTTGCCGGGAAGCTAGAGTAAGTAGTTCGCCAGTTAATAGTTT
GCGCAACGTTGTTGCCATCGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCACGTTGTC
AGAAGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCACAT
AGCAGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGA
ATAAGGGCGACACGGAAATGTTGAATACTCATATTCTTCCTTTTTCAATATTATTGAAGCATT
TATCAGGGTTATTGTCTCATGAGCGGATACATATTTGAATGTATTTAGAAAAATAAACAAATA
GGGGTCAGTGTTACAACCAATTAACCAATTCTGAACATTATCGCGAGCCCATTTATACCTGAA
TATGGCTCATAACACCCCTTGTTTGCCTGGCGGCAGTAGCGCGGTGGTCCCACCTGACCCCAT
GCCGAACTCAGAAGTGAAACGCCGTAGCGCCGATGGTAGTGTGGGGACTCCCCATGCGAGAGT
AGGGAACTGCCAGGCATCAAATAAAACGAAAGGCTCAGTCGAAAGACTGGGCCTTTCGCCCGG
GCTAATTGAGGGGTGTCGCCCTTATTCGACTCGGGGCTCGAG
(SEQ ID NO: 21)
``` pXL030

```
CTGCGCGCTCGCTCGCTCACTGAGGCCGCCCGGGCAAAGCCCGGGCGTCGGGCGACCTTTGGT
CGCCCGGCCTCAGTGAGCGAGCGAGCGCGCAGAGAGGGAGTGGCCAACTCCATCACTAGGGGT
TCCTTTAATTAAACGCGTGGGGAGGCTGCTGGTGAATATTAACCAAGGTCACCCCAGTTATC
GGAGGAGCAAACAGGGGCTAAGTCCACCGGGGGAGGCTGCTGGTGAATATTAACCAAGGTCAC
CCCAGTTATCGGAGGAGCAAACAGGGGCTAAGTCCACCGGGGGAGGCTGCTGGTGAATATTAA
CCAAGGTCACCCCAGTTATCGGAGGAGCAAACAGGGGCTAAGTCCACACTAGTAAATGACCTA
TTAAGAATATTTCATAGAACGAATGTTCCGATGCTCTAATCTCTAGACAAGGTTCATATTT
GTATGGGTTACTTATTCTCTCTTTGTTGACTAAGTCAATAATCAGAATCAGCAGGTTTGCAGT
CAGATTGGCAGGGATAAGCAGCCTAGCTCAGGAGAAGTGAGTATAAAAGCCCCAGGCTGGGAG
CAGCCATCACAGAAGTCCACTCATTCTTGGCAGGCCGCGGCTAAGGTAAGTTGGCGCCGTTTA
AGGGATGGTTGGTTGGTGGGTATTAATGTTTAATTACCTTTTTTTACAGGCCTGGGCGCGCCG
CCACCATGGCTGCGCCCGCACTAGGGCTGGTGTGTGGACGTTGCCCTGAGCTGGGTCTCGTCC
TCTTGCTGCTGCTGCTCTCGCTGCTGTGTGGAGCGGCAGGGAGCCAGGAGGCCCGGGACCGGTG
CGGGCGCGGGGTCCCTTGCGGGTTCTTGCGGCTGCGGCACGCCCCAGCGGCCTGGCGCCCATG
GCAGTTCGGCAGCCGCTCACCGATACTCGCGGGAGGCTAACGCTCCGGGCCCCGTACCCGGAG
AGCGGCAACTCGCGCACTCAAAGATGGTCCCCATCCCTGCTGGAGTATTTACAATGGGCACAG
ATGATCCTCAGATAAAGCAGGATGGGGAAGCACCTGCGAGGAGGTTACTATTGATGCCTTTT
ACATGGATGCCTATGAAGTCAGTAATACTGAATTTGAGAAGTTTGTGAACTCAACTGGCTATT
TGACAGAGGCTGAGAAGTTTGGCGACTCCTTTGTCTTTGAAGGCATGTTGAGTGAGCAAGTGA
AGACCAATATTCAACAGGCAGTTGCAGCTGCTCCCTGGTGGTTACCTGTGAAAGGCGCTAACT
GGGAGACACCCAGAAGGGCCTGACTCTACTATTCTGCACAGGCCGGATCATCCAGTTCTCCATA
TGTCCTGGAATGATGCGGTTGCCTACTGCACTTGGGCAGGGAAGCGGCTGCCACGGAAGCTG
AGTGGGAATACAGCTGTCGAGGAGGCCTGCATAATAGACTTTTCCCCTGGGGCAACAAACTGC
AGCCCAAAGGCCAGCATTATGCCAACATTTGGCAGGGCGAGTTTCCGGTGACCAACACTGGTG
AGGATGGCTTCAAGGAACTGCGCCTGTTGATGCCTTCCCTCCCAATGGTTAGCTTATACA
ACATAGTGGGGAACGCATGGGAATGGACTTCAGACTGGTGGACTGTTCATCATTCTGTTGAAG
AAACGCTGGAACCCAAAAGGTCCCCCTTCTGGGAAAGACCGAGTGAAGAAAGGTGGATCCTACA
TGTGCCATAGGTCTTATTGTTACAGGTATCGCTGTGCTGCTGGAGCCAGAACACACCTGATA
GCTCTGCTTCGAATCTGGGATTCCGCTGTGCAGCCGACCGCCTGCCCACTATGGACTGAGTCG
ACCCTAGAGCTCGCTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTTTCCTAATAAAATG
AGGAAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGCTGGGGAATCTAGA Xn(60-
100) GTTTAAACATTTAAATAGGAACCCCTAGTGATGGAGTTGGCCACTCCCTCTCTGCGCGC
TCGCTCGCTCACTGAGGCCGGGCGACCAAAGGTCGCCCGACGCCCGGGCTTTGCCCGGGCGGC
CTCAGTGAGCGAGCGAGCGCGCAGAGAGTATACATCGATGTGAGTTCGCGGGTGGCTGGGGGG
CCCTGGGCTGCGACCGCCCCCGAACCGCGTCTACGAGCCTTGCGGGCTCCGGGTCTTTGCAGT
CGTATGGGGCAGGGTAGCTGTTCCCCGCAAGGAGAGCTCAAGGTCAGCGCTCGGAGCCTGGCG
GAGCCCCGCACCCCAGGCTGTGGCGCCCTGTGCAGCTCCGCCCTTGCGGCGCCATCTGCCCGGA
GCCTCCTTCCCCTAGTCCCCAGAAACAGGAGGTCCCTACTCCCGCCCGAGATCCCGACCCGGA
CCCCTAGGTGGGGGACGCTTTCTTTCCTTTCGCGCTCTGCGGGGTCACGTGTCGCAGAGGAGC
CCCTCCCCCACGGCCTCCGGCACCGCAGGCCCCGGGATGCTAGTGCGCAGCGGGTGCATCCCT
GTCCGGATGCTGCGCCTGCGGTAGAGCGGCCGCCATGTTGCAACCGGGAAGGAAATGAATGGG
```

TABLE 3-continued

Exemplary rAAV I2S vector nucleotide sequences

```
CAGCCGTTAGGAAAGCCTGCCGGTGACTAACCCTGCGCTCCTGCCTCGATGGGTGGAGTCGCG
TGTGGCGGGGAAGTCAGGTGGAGCGAGGCTAGCTGGCCCGATTTCTCCTCCGGGTGATGCTTT
TCCTAGATTATTCTCTGGTAAATCAAAGAAGTGGGTTTATGGAGGTCCTCTTGTGTCCCCTCC
CCGCAGAGGTGTGGTGGCTGTGGCATGGTGCCAAGCCGGGAGAAGCTGAGTCATGGGTAGTTG
GAAAAGGACATTTCCACCGCAAAATGGCCCCTCTGGTGGTGGCCCCTTCCTGCAGCGCCGGCT
CACCTCACGGCCCCGCCCTTCCCCTGCCAGCCTAGCGTTGACCCGACCCCAAAGGCCAGGCTG
TAAATGTCACCGGGAGGATTGGGTGTCTGGGCGCCTCGGGGAACCTGCCCTTCTCCCCATTCC
GTCTTCCGGAAACCAGATCTCCCACCGCACCCTGGTCTGAGGTTAAATATAGCTGCTGACCTT
TCTGTAGCTGGGGGCCTGGGCTGGGGCTCTCTCCCATCCCTTCTCCCCACACACATGCACTTA
CCTGTGCTCCCACTCCTGATTTCTGGAAAAGAGCTAGGAAGGACAGGCAACTTGGCAAATCAA
AGCCCTGGGACTAGGGGGTTAAAATACAGCTTCCCCTCTTCCCACCCGCCCCAGTCTCTGTCC
CTTTTGTAGGAGGGACTTAGAGAAGGGGTGGGCTTGCCCTGTCCAGTTAATTTCTGACCTTTA
CTCCTGCCCTTTGAGTTTGATGATGCTGAGTGTACAAGCGTTTTCTCCCTAAAGGGTGCAGCT
GAGCTAGGCAGCAGCAAGCATTCCTGGGGTGGCATAGTGGGGTGGTGAATACCATGTACAAAG
CTTGTGCCCAGACTGTGGGTGGCAGTGCCCCACATGGCCGCTTCTCCTGGAAGGGCTTCGTAT
GACTGGGGGTGTTGGGCAGCCCTGGAGCCTTCAGTTGCAGCCATGCCTTAAGCCAGGCCAGCC
TGGCAGGGAAGCTCAAGGGAGATAAAATTCAACCTCTTGGGCCCTCCTGGGGGTAAGGAGATG
CTGCATTCGCCCTCTTAATGGGGAGGTGGCCTAGGGCTGCTCACATATTCTGGAGGAGCCTCC
CCTCCTCATGCCTTCTTGCCTCTTGTCTCTTAGGCATGCAAAAGAGTCGAATAAGGGCGACAC
AAAATTTATTCTAAATGCATAATAAATACTGATAACATCTTATAGTTTGTATTATATTTTGTA
TTATCGTTGACATGTATAATTTTGATATCAAAAACTGATTTTCCCTTTATTATTTTCGAGATT
TATTTTCTTAATTCTCTTTAACAAACTAGAAATATTGTATATACAAAAAATCATAAATAATAG
ATGAATAGTTTAATTATAGGTGTTCATCAATCGAAAAAGCAACGTATCTTATTTAAAGTGCGT
TGCTTTTTTCTCATTTATAAGGTTAAATAATTCTCATATATCAAGCAAAGTGACAGGCGCCCT
TAAATATTCTGACAAATGCTCTTTCCCTAAACTCCCCCCATAAAAAAACCCGCCGAAGCGGGT
TTTTACGTTATTTGCGGATTAACGATTACTCGTTATCAGAACCGCCCAGGGGGCCCGAGCTTA
AGACTGGCCGTCGTTTTACAACACAGAAAGAGTTTGTAGAAACGCAAAAAGGCCATCCGTCAG
GGGCCTTCTGCTTAGTTTGATGCCTGGCAGTTCCCTACTCTCGCCTTCCGCTTCCTCGCTCAC
TGACTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACTATAAAGATACCA
GGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGCC
ACTGGCAGCAGCCACTGGTAACAGGATTAGCAGAGCGAGGTATGTAGGCGGTGCTACAGAGTT
CTTGAAGTGGTGGCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGACGCGCGCGTAACTCACGTTAA
GGGATTTTGGTCATGAGCTTGCGCCGTCCCGTCAAGTCAGCGTAATGCTCTGCTTAGGTGGCG
GTACTTGGGTCGATATCAAAGTGCATCACTTCTTCCCGTATGCCCAACTTTGTATAGAGAGCC
ACTGCGGGATCGTCACCGTAATCTGCTTGCACGTAGATCACATAAGCACCAAGCGCGTTGGC
TCATGCTTGAGGAGATTGATGAGCGCGGTGGCAATGCCCTGCCTCCGGTGCTCGCCGGAGACT
GCGAGATCATAGATATAGATCTCACTACGCGGCTGCTCAAACTTGGGCAGAACGTAAGCCGCG
AGAGCGCCAACAACCGCTTCTTGGTCGAAGGCAGCAAGCGCGATGAATGTCTTACTACGGAGC
AAGTTCCCGAGGTAATCGGAGTCCGGCTGATGTTGGGAGTAGGTGGCTACGTCACCGAACTCA
CGACCGAAAAGATCAAGAGCAGCCCGCATGGATTTGACTTGGTCAGGGCCGAGCCTACATGTG
CGAATGATGCCCATACTTGAGCCACCTAACTTTGTTTTAGGGCGACTGCCCTGCTGCGTAACA
TCGTTGCTGCTCCATAACATCAAACATCGACCCACGCGTAACGCGCTTGCTGCTTGGATGCC
CGAGGCATAGACTGTACAAAAAAACAGTCATAACAAGCCATGAAAACCGCCACTGCGCCGTTA
CCACCGCTGCGTTCGGTCAAGGTTCTGGACCAGTTGCGTGAGCGCATTTTTTTTTCCTCCTCG
GCGTTTACGCCCGCCCTGCCACTCATCGCAGTACTGTTGTAATTCATTAAGCATTCTGCCGA
CATGGAAGCCATCACAGACGGCATGATGAACCTGAATCGCCAGCGGCATCAGCACCTTGTCGC
CTTGCGTATAATATTTGCCCATAGTGAAAACGGGGCGAAGAAGTTGTCCATATTGGCCACGT
TTAAATCAAAACTGGTGAAACTCACCCAGGGATTGGCGCTGACGAAAAACATATTCTCAATAA
ACCCTTTAGGGAAATAGGCCAGGTTTTCACCGTAACACGCCACATCTTGCGAATATATGTGTA
GAAACTGCCGGAAATCGTCGTGTGCACTCATGGAAAACGGTGTAACAAGGGTGAACACTATCC
CATATCACCAGCTCACCGTCTTTCATTGCCATACGGAACTCCGGATGAGCATTCATCAGGCGG
GCAAGAATGTGAATAAAGGCCGGATAAAACTTGTGCTTATTTTTCTTTACGGTCTTTAAAAAG
GCCGTAATATCCAGCTGAACGGTCTGGTTATAGGTACATTGAGCAACTGACTGAAATGCCTCA
AAATGTTCTTTACGATGCCATTGGGATATATCAACGGTGGTATATCCAGTGATTTTTTTCTCC
ATTTTTTTTCCTCCTTTAGAAAAACTCATCGAGCATCAAATGAAACTGCAATTTATTCATAT
CAGGATTATCAATACCATATTTTTGAAAAAGCCGTTTCTGTAATGAAGGAGAAAACTCACCGA
GGCAGTTCCATAGGATGGCAAGATCCTGGTATCGGTCTGCGATTCCGACTCGTCCAACATCAA
TACAACCTATTAATTTCCCCTCGTCAAAAATAAGGTTATCAAGTGAGAAATCACCATGAGTGA
CGACTGAATCCGGTGAGAATGGCAAAAGTTTATGCATTTCTTTCCAGACTTGTTCAACAGGCC
AGCCATTACGCTCGTCATCAAAATCACTCGCATCAACCAAACCGTTATTCATTCGTGATTGCG
CCTGAGCGAGGCGAAATACGCGATCGCTGTTAAAAGGACAATTACAAACAGGAATCGAGTGCA
ACCGGCGCAGGAACACTGCCAGCGCATCAACAATATTTTCACCTGAATCAGGATATTCTTCTA
ATACCTGGAACGCTGTTTTTCCGGGGATCGCAGTGGTGAGTAACCATGCATCATCAGGAGTAC
GGATAAAATGCTTGATGGTCGGAAGTGGCATAAATTCCGTCAGCCAGTTTAGTCTGACCATCT
CATCTGTAACATCATTGGCAACGCTACCTTTGCCATGTTTCAGAAACAACTCTGGCGCATCGG
GCTTCCCATACAAGCGATAGATTGTCGCACCTGATTGCCCGACATTATCGCGAGCCCATTTAT
ACCCATATAAATCAGCATCCATGTTGGAATTTAATCGCGGCCTCGACGTTTCCCGTTGAATAT
GGCTCATTTTTTTTCCTCCTTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGG
```

TABLE 3-continued

Exemplary rAAV I2S vector nucleotide sequences

CTTACCATCTGGCCCCAGCGCTGCGATGATACCGCGAGAACCACGCTCACCGGCTCCGGATTT
ATCAGCAATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAATAGTTT
GCGCAACGTTGTTGCCATCGCTACAGGCATCGTGGTGTCACGCTCGTCGTTTGGTATGGCTTC
ATTCAGCTCCGGTTCCCAACGATCAAGGCGAGTTACATGATCCCCCATGTTGTGCACGTTGTC
AGAAGTAAGTTGGCCGCAGTGTTATCACTCATGGTTATGGCAGCACTGCATAATTCTCTTACT
GTCATGCCATCCGTAAGATGCTTTTCTGTGACTGGTGAGTACTCAACCAAGTCATTCTGAGAA
TAGTGTATGCGGCGACCGAGTTGCTCTTGCCCGGCGTCAATACGGGATAATACCGCGCCACAT
AGCAGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGA
ATAAGGGCGACACGGAAATGTTGAATACTCATATTCTTCCTTTTTCAATATTATTGAAGCATT
TATCAGGGTTATTGTCTCATGAGCGGATACATATTTGAATGTATTTAGAAAAATAAACAAATA
GGGGTCAGTGTTACAACCAATTAACCAATTCTGAACATTATCGCGAGCCCATTTATACCTGAA
TATGGCTCATAACACCCCTTGTTTGCCTGGCGGCAGTAGCGCGGTGGTCCCACCTGACCCCAT
GCCGAACTCAGAAGTGAAACGCCGTAGCGCCGATGGTAGTGTGGGGACTCCCCATGCGAGAGT
AGGGAACTGCCAGGCATCAAATAAAACGAAAGGCTCAGTCGAAAGACTGGGCCTTTCGCCCGG
GCTAATTGAGGGGTGTCGCCCTTATTCGACTCGGGGCTCGAG
(SEQ ID NO: 22)

pXL032

CGCGTTGTAGTTAATGATTAACCCGCCATGCTACTTATCTACGTAGCCATGCTCTAGGAAGAT
CGGAATTCGCCCTTAAGCTAGCAGGTTAATTTTTAAAAAGCAGTCAAAAGTCCAAGTGGCCCT
TGGCAGCATTTACTCTCTCTGTTTGCTCTGGTTAATAATCTCAGGAGCACAAACATTCCAGAT
CCAGGTTAATTTTTAAAAAGCAGTCAAAAGTCCAAGTGGCCCTTGGCAGCATTTACTCTCTCT
GTTTGCTCTGGTTAATAATCTCAGGAGCACAAACATTCCAGATCCGGCGCGCCAGGGCTGGAA
GCTACCTTTGACATCATTTCCTCTGCGAATGCATGTATAATTTCTACAGAACCTATTAGAAAG
GATCACCCAGCCTCTGCTTTTGTACAACTTTCCCTTAAAAAACTGCCAATTCCACTGCTGTTT
GGCCCAATAGTGAGAACTTTTTCCTGCTGCCTCTTGGTGCTTTTGCCTATGGCCCCTATTCTG
CCTGCTGAAGACACTCTTGCCAGCATGGACTTAAACCCCTCCAGCTCTGACAATCCTCTTTCT
CTTTTGTTTTACATGAAGGGTCTGGCAGCCAAAGCAATCACTCAAAGTTCAAACCTTATCATT
TTTTGCTTTGTTCCTCTTGGCCTTGGTTTTGTACATCAGCTTTGAAAATACCATCCCAGGGTT
AATGCTGGGGTTAATTTATAACTAAGAGTGCTCTAGTTTTGCAATACAGGACATGCTATAAAA
ATGGAAAGATGTTGCTTTCTGAGAGACTGCAGAAGTTGGTCGTGAGGCACTGGGCAGGTAAGT
ATCAAGGTTACAAGACAGGTTTAAGGAGACCAATAGAAACTGGGCTTGTCGAGACAGAGAAGA
CTCTTGCGTTTCTGATAGGCACCTATTGGTCTTACTGACATCCACTTTGCCTTTCTCTCCACA
GGTGTCCAGGCGGCCGCATGCCCCGCCCCGCACCGGCCGCGGCCTGCTGTGGCTGGGCCTGG
TGCTGAGCAGCGTGTGCGTGGCCCTGGGCAGCGAGACCCAGGCCAACAGCACCACCGACGCCC
TGAACGTGCTGCTGATCATCGTGGACGACCTGCGCCCCAGCCTGGGCTGCTACGGCGACAAGC
TGGTGCGCAGCCCCAACATCGACCAGCTGGCCAGCCACAGCCTGCTGTTCCAGAACGCCTTCG
CCCAGCAGGCCGTGTGCGCCCCCAGCCGCGTGAGCTTCCTGACCGGCCGCCGCCCCGACACCA
CCCGCCTGTACGACTTCAACAGCTACTGGCGCGTGCACGCCGGCAACTTCAGCACCATCCCCC
AGTACTTCAAGGAGAACGGCTACGTGACCATGAGCGTGGGCAAGGTGTTCCACCCCGGCATCA
GCAGCAACCACACCGACGACAGCCCCTACAGCTGGAGCTTCCCCCCCTACCACCCCAGCAGCG
AGAAGTACGAGAACACCAAGACCTGCCGCGGCCCCGACGGCGAGCTGCACGCCAACCTGCTGT
GCCCCGTGGACGTGCTGGACGTGCCCGAGGGCACCCTGCCCGACAAGCAGAGCACCGAGCAGG
CCATCCAGCTGCTGGAGAAGATGAAGACCAGCGCCAGCCCCTTCTTCCTGGCCGTGGGCTACC
ACAAGCCCCACATCCCCTTCCGCTACCCCAAGGAGTTCCAGAAGCTGTACCCCCTGGAGAACA
TCACCCTGGCCCCCGACCCCGAGGTGCCCGACGGCCTGCCCCCCGTGGCCTACAACCCCTGGA
TGGACATCCGCCAGCGCGAGGACGTGCAGGCCCTGAACATCAGCGTGCCCTACGGCCCCATCC
CCGTGGACTTCCAGCGCAAGATCCGCCAGAGCTACTTCGCCAGCGTGAGCTACCTGGACACCC
AGGTGGGCCGCCTGCTGAGCGCCCTGGACGACCTGCAGCTGGCCAACAGCACCATCATCGCCT
TCACCAGCGACCACGGCTGGGCCCTGGGCGAGCACGGCGAGTGGGCCAAGTACAGCAACTTCG
ACGTGGCCACCCACGTGCCCCTGATCTTCTACGTGCCCGGCCGCACCGCCAGCCTGCCCGAGG
CCGGCGAGAAGCTGTTCCCCTACCTGGACCCCTTCGACAGCGCCAGCCAGCTGATGGAGCCCG
GCCGCCAGAGCATGGACCTGGTGGAGCTGGTGAGCCTGTTCCCCACCCTGGCCGGCCTGGCCG
GCCTGCAGGTGCCCCCCCGCTGCCCCGTGCCCAGCTTCCACGTGGAGCTGTGCCGCGAGGGCA
AGAACCTGCTGAAGCACTTCCGCTTCCGCGACCTGGAGGAGGACCCCTACCTGCCCGGCAACC
CCCGCGAGCTGATCGCCTACAGCCAGTACCCCCGCCCCAGCGACATCCCCCAGTGGAACAGCG
ACAAGCCCAGCCTGAAGGACATCAAGATCATGGGCTACAGCATCCGCACCATCGACTACCGCT
ACACCGTGTGGGTGGGCTTCAACCCCGACGAGTTCCTGGCCAACTTCAGCGACATCCACGCCG
GCGAGCTGTACTTCGTGGACAGCGACCCCCTGCAGGACCACAACATGTACAACGACAGCCAGG
GCGGCGACCTGTTCCAGCTGCTGATGCCCTAGAAGCCTGGATCCAATCAACCTCTGGATTACA
AAATTTGTGAAAGATTGACTGGTATTCTTAACTATGTTGCTCCTTTTACGCTATGTGGATACG
CTGCTTTAATGCCTTTGTATCATGCTATTGCTTCCCGTATGGCTTTCATTTTCTCCTCCTTGT
ATAAATCCTGGTTGCTGTCTCTTTATGAGGAGTTGTGGCCCGTTGTCAGGCAACGTGGCGTGG
TGTGCACTGTGTTTGCTGACGCAACCCCCACTGGTTGGGGCATTGCCACCACCTGTCAGCTCC
TTTCCGGGACTTTCGCTTTCCCCCTCCCTATTGCCACGGCGGAACTCATCGCCGCCTGCCTTG
CCCGCTGCTGGACAGGGGCTCGGCTGTTGGGCACTGACAATTCCGTGGTGTTGTCGGGGAAGC
TGACGTCCTTTCCATGGCTGCTCGCCTGTGTTGCCACCTGGATTCTGCGCGGGACGTCCTTCT
GCTACGTCCCTTCGGCCCTCAATCCAGCGGACCTTCCTTCCCGCGGCCTGCTGCCGGCTCTGC
GGCCTCTTCCGCGTCTTCGAGATCTGCCTCGACTGTGCCTTCTAGTTGCCAGCCATCTGTTGT
TTGCCCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGGGTGGG
GCAGGACAGCAAGGGGGAGGATTGGGAAGACAATAGCAGGCATGCTGGGGACTCGAGTTAAGG
GCGAATTCCCGATTAGGATCTTCCTAGAGCATGGCTACGTAGATAAGTAGCATGGCGGGTTAA
TCATTAACTACAGTTTAAAC Xn(60-

TABLE 3-continued

Exemplary rAAV I2S vector nucleotide sequences

100)ATTTAAATAGGAACCCCTAGTGATGGAGTTGGCCACTCCCTCTCTGCGCGCTCGCTCGC
TCACTGAGGCCGGGCGACCAAAGGTCGCCCGACGCCCGGGCTTTGCCCGGGCGGCCTCAGTGA
GCGAGCGAGCGCGCAGAGAGTATACATCGATGTGAGTTCGCGGGTGGCTGGGGGGCCCTGGGC
TGCGACCGCCCCCGAACCGCGTCTACGAGCCTTGCGGGCTCCGGGTCTTTGCAGTCGTATGGG
GGCAGGGTAGCTGTTCCCCGCAAGGAGAGCTCAAGGTCAGCGCTCGGACCTGGCGGAGCCCCG
CACCCAGGCTGTGGCGCCCTGTGCAGCTCCGCCCTTGCGGCGCCATCTGCCCGGAGCCTCCTT
CCCCTAGTCCCCAGAAACAGGAGGTCCCTACTCCCGCCCGAGATCCCGACCCGGACCCCTAGG
TGGGGGACGCTTTCTTTCCTTTCGCGCTCTGCGGGGTCACGTGTCGCAGAGGAGCCCCTCCCC
CACGGCCTCCGGCACCGCAGGCCCCGGGATGCTAGTGCGCAGCGGGTGCATCCCTGTCCGGAT
GCTGCGCCTGCGGTAGAGCGGCCGCCATGTTGCAACCGGGAAGGAAATGAATGGGCAGCCGTT
AGGAAAGCCTGCCGGTGACTAACCCTGCGCTCCTGCCTCGATGGGTGGAGTCGCGTGTGGCGG
GGAAGTCAGGTGGAGCGAGGCTAGCTGGCCCGATTTCTCCTCCGGGTGATGCTTTTCCTAGAT
TATTCTCTGGTAAATCAAAGAAGTGGGTTTATGGAGGTCCTCTTGTGTCCCCTCCCCGCAGAG
GTGTGGTGGCTGTGGCATGGTGCCAAGCCGGGAGAAGCTGAGTCATGGGTAGTTGGAAAAGGA
CATTTCCACCGCAAAATGGCCCTCTGGTGGTGGCCCCTTCCTGCAGCGCCGGCTCACCTCAC
GGCCCCGCCCTTCCCCTGCCAGCCTAGCGTTGACCCGACCCCAAAGGCCAGGCTGTAAATGTC
ACCGGGAGGATTGGGTGTCTGGGCGCCTCGGGGAACCTGCCCTTCTCCCCATTCCGTCTTCCG
GAAACCAGATCTCCCACCGCACCCTGGTCTGAGGTTAAATATAGCTGCTGACCTTTCTGTAGC
TGGGGGCCTGGGCTGGGGCTCTCTCCCATCCCTTCTCCCCACACACATGCACTTACCTGTGCT
CCCACTCCTGATTTCTGGAAAAGAGCTAGGAAGGACAGGCAACTTGGCAAATCAAAGCCCTGG
GACTAGGGGGTTAAAATACAGCTTCCCCTCTTCCCACCCGCCCCAGTCTCTGTCCCTTTTGTA
GGAGGGACTTAGAGAAGGGGTGGGCTTGCCCTGTCCAGTTAATTTCTGACCTTTACTCCTGCC
CTTTGAGTTTGATGATGCTGAGTGTACAAGCGTTTTCTCCCTAAAGGGTGCAGCTGAGCTAGG
CAGCAGCAAGCATTCCTGGGGTGGCATAGTGGGGTGGTGAATACCATGTACAAAGCTTGTGCC
CAGACTGTGGGTGGCAGTGCCCCACATGGCCGCTTCTCCTGGAAGGGCTTCGTATGACTGGGG
GTGTTGGGCAGCCCTGGAGCCTTCAGTTGCAGCCATGCCTTAAGCCAGGCCAGCCTGGCAGGG
AAGCTCAAGGGAGATAAAATTCAACCTCTTGGGCCCTCCTGGGGGTAAGGAGATGCTGCATTC
GCCCTCTTAATGGGGAGGTGGCCTAGGGCTGCTCACATATTCTGGAGGAGCCTCCCCTCCTCA
TGCCTTCTTGCCTCTTGTCTCTTAGGCATGCAAAAGAGTCGAATAAGGGCGACACAAAATTTA
TTCTAAATGCATAATAAATACTGATAACATCTTATAGTTTGTATTATATTTTGTATTATCGTT
GACATGTATAATTTTGATATCAAAAACTGATTTTCCCTTTATTATTTTCGAGATTTATTTTCT
TAATTCTCTTTAACAAACTAGAAATATTGTATATACAAAAAATCATAAATAATAGATGAATAG
TTTAATTATAGGTGTTCATCAATCGAAAAAGCAACGTATCTTATTTAAAGTGCGTTGCTTTTT
TCTCATTTATAAGGTTAAATAATTCTCATATATCAAGCAAAGTGACAGGCGCCCTTAAATATT
CTGACAAATGCTCTTTCCCTAAACTCCCCCCATAAAAAAACCCGCCGAAGCGGGTTTTTACGT
TATTTGCGGATTAACGATTACTCGTTATCAGAACCGCCCAGGGGGCCCGAGCTTAAGACTGGC
CGTCGTTTTACAACACAGAAAGAGTTTGTAGAAACGCAAAAAGGCCATCCGTCAGGGGCCTTC
TGCTTAGTTTGATGCCTGGCAGTTCCCTACTCTCGCCTTCCGCTTCCTCGCTCACTGACTCGC
TGCGCTCGGTCGTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGCAAAAGGCCAGGA
ACCGTAAAAAGGCCGCGTTGCTGGCGTTTTTCCATAGGCTCCGCCCCCCTGACGAGCATCACA
AAAATCGACGCTCAAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGG
TGTAGGTCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCACTGGCAG
CAGCCACTGGTAACAGGATTAGCAGAGCGAGGTATGTAGGCGGTGCTACAGAGTTCTTGAAGT
GGTGGCTAACTACGGCTACACTAGAAGAACAGTATTTGGTATCTGCGCTCTGCTGAAGCCAG
TTACCTTCGGAAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGA
TCTTTTCTACGGGGTCTGACGCTCAGTGGAACGACGCGCGCGTAACTCACGTTAAGGGATTTT
GGTCATGAGCTTGCGCCGTCCCGTCAAGTCAGCGTAATGCTCTGCTTAGGTGGCGGTACTTGG
GTCGATATCAAAGTGCATCACTTCTTCCCGTATGCCCAACTTTGTATAGAGAGCCACTGCGGG
ATCGTCACCGTAATCTGCTTGCACGTAGATCACATAAGCACCAAGCGCGTTGGCCTCATGCTT
GAGGAGATTGATGAGCGCGGTGGCAATGCCCTGCCTCCGGTGCTCGCCGGAGACTGCGAGATC
ATAGATATAGATCTCACTACGCGGCTGCTCAAACTTGGGCAGAACGTAAGCCGCGAGAGCGCC
AACAACCGCTTCTTGGTCGAAGGCAGCAAGCGCGATGAATGTCTTACTACGGAGCAAGTTCCC
GAGGTAATCGGAGTCCGGCTGATGTTGGGAGTAGGTGGCTACGTCACCGAACTCACGACCGAA
AAGATCAAGAGCAGCCCGCATGGATTTGACTTGGTCAGGGCCGAGCCTACATGTGCGAATGAT
GCCCATACTTGAGCCACCTAACTTTGTTTTAGGGCGACTGCCCTGCTGCGTAACATCGTTGCT
GCTCCATAACATCAAACATCGACCCACGGCGTAACGCGCTTGCTGCTTGGATGCCCGAGGCAT
AGACTGTACAAAAAAACAGTCATAACAAGCCATGAAAACCGCCACTGCGCCGTTACCACCGCT
GCGTTCGGTCAAGGTTCTGGACCAGTTGCGTGAGCGCATTTTTTTTCCTCCTCGGCGTTTAC
GCCCCGCCCTGCCACTCATCGCAGTACTGTTGTAATTCATTAAGCATTCTGCCGACATGGAAG
CCATCACAGACGGCATGATGAACCTGAATCGCCAGCGGCATCAGCACCTTGTCGCCTTGCGTA
TAATATTTGCCCATAGTGAAAACGGGGGCGAAGAAGTTGTCCATATTGGCCACGTTTAAATCA
AAACTGGTGAAACTCACCCAGGGATTGGCGCTGACGAAAACATATTCTCAATAAACCCTTTA
GGGAAATAGGCCAGGTTTTCACCGTAACACGCCACATCTTGCGAATATATGTGTAGAAACTGC
CGGAAATCGTCGTGTGCACTCATGGAAAACGGTGTAACAAGGGTGAACACTATCCCATATCAC
CAGCTCACCGTCTTTCATTGCCATACGGAACTCCGGATGAGCATTCATCAGGCGGGCAAGAAT
GTGAATAAAGGCCGGATAAAACTTGTGCTTATTTTTCTTTACGGTCTTTAAAAAGGCCGTAAT
ATCCAGCTGAACGGTCTGGTTATAGGTACATTGAGCAACTGACTGAAATGCCTCAAAATGTTC
TTTACGATGCCATTGGGATATATCAACGGTGGTATATCCAGTGATTTTTTTCTCCATTTTTT
TTCCTCCTTTAGAAAAACTCATCGAGCATCAAATGAAACTGCAATTTATTCATATCAGGATTA
TCAATACCATATTTTTGAAAAAGCCGTTTCTGTAATGAAGGAGAAAACTCACCGAGGCAGTTC
CATAGGATGGCAAGATCCTGGTATCGGTCTGCGATTCCGACTCGTCCAACATCAATACAACCT
ATTAATTTCCCCTCGTCAAAAATAAGGTTATCAAGTGAGAAATCACCATGAGTGACGACTGAA
TCCGGTGAGAATGGCAAAAGTTTATGCATTTCTTTCCAGACTTGTTCAACAGGCCAGCCATTA

TABLE 3-continued

Exemplary rAAV I2S vector nucleotide sequences

```
CGCTCGTCATCAAAATCACTCGCATCAACCAAACCGTTATTCATTCGTGATTGCGCCTGAGCG
AGGCGAAATACGCGATCGCTGTTAAAAGGACAATTACAAACAGGAATCGAGTGCAACCGGCGC
AGGAACACTGCCAGCGCATCAACAATATTTTCACCTGAATCAGGATATTCTTCTAATACCTGG
AACGCTGTTTTTCCGGGGATCGCAGTGGTGAGTAACCATGCATCATCAGGAGTACGGATAAAA
TGCTTGATGGTCGGAAGTGGCATAAATTCCGTCAGCCAGTTTAGTCTGACCATCTCATCTGTA
ACATCATTGGCAACGCTACCTTTGCCATGTTTCAGAAACAACTCTGGCGCATCGGGCTTCCCA
TACAAGCGATAGATTGTCGCACCTGATTGCCCGACATTATCGCGAGCCCATTTATACCCATAT
AAATCAGCATCCATGTTGGAATTTAATCGCGGCCTCGACGTTTCCCGTTGAATATGGCTCATT
TTTTTTTCCTCCTTTACCAATGCTTAATCAGTGAGGCACCTATCTCAGCGATCTGTCTATTTC
GTTCATCCATAGTTGCCTGACTCCCCGTCGTGTAGATAACTACGATACGGGAGGGCTTACCAT
CTGGCCCCAGCGCTGCGATGATACCGCGAGAACCACGCTCACCGGCTCCGGATTTATCAGCAA
TAAACCAGCCAGCCGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTTAATAGTTTGCGCAACG
TTGTTGCCATCGCTACAGGCATCGTGGTGTCACGCTCGTCGTTTGGTATGGCTTCATTCAGCT
CCGGTTCCCAACGATCAAGGCGAGTTACATGATCCCCCATGTTGTGCACGTTGTCAGAAGTAA
GTTGGCCGCAGTGTTATCACTCATGGTTATGGCAGCACTGCATAATTCTCTTACTGTCATGCC
ATCCGTAAGATGCTTTTCTGTGACTGGTGAGTACTCAACCAAGTCATTCTGAGAATAGTGTAT
GCGGCGACCGAGTTGCTCTTGCCCGGCGTCAATACGGGATAATACCGCGCCACATAGCAGAAC
TTTAAAAGTGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCTTTTACTTT
CACCAGCGTTTCTGGGTGAGCAAAAACAGGAAGGCAAAATGCCGCAAAAAAGGGAATAAGGGC
GACACGGAAATGTTGAATACTCATATTCTTCCTTTTTCAATATTATTGAAGCATTTATCAGGG
TTATTGTCTCATGAGCGGATACATATTTGAATGTATTTAGAAAAATAAACAAATAGGGGTCAG
TGTTACAACCAATTAACCAATTCTGAACATTATCGCGAGCCCATTTATACCTGAATATGGCTC
ATAACACCCCTTGTTTGCCTGGCGGCAGTAGCGCGGTGGTCCCACCTGACCCCATGCCGAACT
CAGAAGTGAAACGCCGTAGCGCCGATGGTAGTGTGGGGACTCCCCATGCGAGAGTAGGGAACT
GCCAGGCATCAAATAAAACGAAAGGCTCAGTCGAAAGACTGGGCCTTTCGCCCGGGCTAATTG
AGGGGTGTCGCCCTTATTCGACTCGGGGCTCGAGCTGCGCGCTCGCTCGCTCACTGAGGCCGC
CCGGGCAAAGCCCGGGCGTCGGGCGACCTTTGGTCGCCCGGCCTCAGTGAGCGAGCGAGCGCG
CAGAGAGGGAGTGGCCAACTCCATCACTAGGGGTTCCTTTAATTAAA
(SEQ ID NO: 23)
```

Xn(60-100) is denoted by n which represents any nucleic acid (A, T, G, C) in the corresponding Sequence Listing.

Use of rAAV Vectors That Encode I2S for Treatment of Disease

Described herein are methods of treating a disease associated with I2S enzyme deficiency. Accordingly, in some embodiments, the rAAV vectors described herein are suitable for treating a subject that has an I2S deficiency, such as Hunter syndrome (MPSII). The method of treating includes administering to the subject in need thereof a recombinant adeno-associated virus (rAAV) vector as described herein.

The rAAV vector described herein can be used to treat any disease associated with I2S deficiency or disorder.

In some embodiments, the rAAV vector remains episomal following administration to a subject in need thereof. In some embodiments, the rAAV vector does not remain episomal following administration to a subject in need thereof. For example, in some embodiments, the rAAV vector integrates into the genome of the subject. Such integration can be achieved, for example, by using various gene-editing technologies, such as, zinc finger nucleases (ZFNs), Transcription activator-like effector nucleases (TALENS), ARCUS genome editing, and/or CRISPR-Cas systems.

In some embodiments, a pharmaceutical composition comprising an rAAV vector described herein is used to treat subjects in need thereof. The pharmaceutical composition containing an rAAV vector or particle of the invention contains a pharmaceutically acceptable excipient, diluent or carrier. Examples of suitable pharmaceutical carriers are well known in the art and include phosphate buffered saline solutions, water, emulsions, such as oil/water emulsions, various types of wetting agents, sterile solutions and the like. Such carriers can be formulated by conventional methods and are administered to the subject at a therapeutically effective amount.

The rAAV vector is administered to a subject in need thereof via a suitable route. In embodiments, the rAAV vector is administered by intravenous, intraperitoneal, subcutaneous, or intradermal administration. In embodiments, the rAAV vector is administered intravenously. In embodiments, the intradermal administration comprises administration by use of a "gene gun" or biolistic particle delivery system. In some embodiments, the rAAV vector is administered via a non-viral lipid nanoparticle. For example, a composition comprising the rAAV vector may comprise one or more diluents, buffers, liposomes, a lipid, a lipid complex. In some embodiments, the rAAV vector is comprised within a microsphere or a nanoparticle, such as a lipid nanoparticle. In some embodiments, the rAAV vectors and/or the transgene expression cassette and/or the optimized IDS transgene sequences and/or any compositions of the gene expression cassette are administered via non-viral chemical particles such as lipid nanoparticles, non-viral biological molecules such as exosomes and/or extracellular vesicle.

In some embodiments, functional I2S is detectable in plasma or serum of the subject at about 2 to 6 weeks post administration of the rAAV vector. In some embodiments, functional I2S is detectable in plasma or serum of the subject at about 2 weeks. In some embodiments, functional I2S is detectable in plasma or serum of the subject at about 3 weeks. In some embodiments, functional I2S is detectable in plasma or serum of the subject at about 4 weeks. In some embodiments, functional I2S is detectable in plasma or serum of the subject at about 5 weeks. In some embodiments, functional I2S is detectable in plasma or serum of the subject at about 6 weeks. In some embodiments, functional I2S is detectable in hepatocytes of the subject at about 2 to 6 weeks post administration of the rAAV vector.

In some embodiments, functional I2S is detectable in plasma of the subject at least 3 months, 6 months, 12 months, 2 years, 3 years, 4 years, 5 years, 6 years, 7 years, 8 years, 9 years, or 10 years after administration of the rAAV vector. Accordingly, in some embodiments, functional I2S is detectable in plasma or serum of the subject at least 3 months after administration of the rAAV vector. In some embodiments, functional I2S is detectable in plasma or serum of the subject at least 6 months after administration of the rAAV vector. In some embodiments, functional I2S is detectable in plasma or serum of the subject at least 12 months after administration of the rAAV vector. In some embodiments, functional I2S is detectable in plasma or serum of the subject at least 2 years after administration of the rAAV vector. In some embodiments, functional I2S is detectable in plasma or serum of the subject at least 3 years after administration of the rAAV vector. In some embodiments, functional I2S is detectable in plasma or serum of the subject at least 4 years after administration of the rAAV vector. In some embodiments, functional I2S is detectable in plasma or serum of the subject at least 5 years after administration of the rAAV vector. In some embodiments, functional I2S is detectable in plasma or serum of the subject at least 6 years after administration of the rAAV vector. In some embodiments, functional I2S is detectable in plasma or serum of the subject at least 7 years after administration of the rAAV vector. In some embodiments, functional I2S is detectable in plasma or serum of the subject at least 8 years after administration of the rAAV vector. In some embodiments, functional I2S is detectable in plasma or serum of the subject at least 9 years after administration of the rAAV vector. In some embodiments, functional I2S is detectable in plasma or serum of the subject at least 10 years after administration of the rAAV vector. In some embodiments, functional I2S is detectable in plasma or serum of the subject for the remainder of the subject's life following administration of the rAAV vector.

In some embodiments, the administered rAAV comprising I2S results in the production of active I2S to the same extent as found following administration of purified I2S protein delivered intravenously. In some embodiments, the administered rAAV comprising I2S results in production of a greater amount of active I2S as compared to administration of purified I2S protein delivered intravenously.

In some embodiments, the administered rAAV comprising I2S results in the reduction of glycosaminoglycan (GAG) in the subject. In some embodiments, the administered rAAV comprising I2S reduces GAG in the subject by about 95%, 90%, 85%, 80%, 75%, 70%, 65%, 60%, 55%, 50%, 45%, 40%, 35%, 30%, 25%, 20%, 15%, or about 10% in comparison to the subject's baseline GAG level prior to administering the rAAV comprising I2S. Accordingly, in some embodiments, the administered rAAV comprising I2S reduces GAG in the subject by about 95%. In some embodiments, the administered rAAV comprising I2S reduces GAG in the subject by about 90%. In some embodiments, the administered rAAV comprising I2S reduces GAG in the subject by about 85%. In some embodiments, the administered rAAV comprising I2S reduces GAG in the subject by about 80%. In some embodiments, the administered rAAV comprising I2S reduces GAG in the subject by about 75%. In some embodiments, the administered rAAV comprising I2S reduces GAG in the subject by about 70%. In some embodiments, the administered rAAV comprising I2S reduces GAG in the subject by about 65%. In some embodiments, the administered rAAV comprising I2S reduces GAG in the subject by about 60%. In some embodiments, the administered rAAV comprising I2S reduces GAG in the subject by about 55%. In some embodiments, the administered rAAV comprising I2S reduces GAG in the subject by about 50%. In some embodiments, the administered rAAV comprising I2S reduces GAG in the subject by about 45%. In some embodiments, the administered rAAV comprising I2S reduces GAG in the subject by about 40%. In some embodiments, the administered rAAV comprising I2S reduces GAG in the subject by about 35%. In some embodiments, the administered rAAV comprising I2S reduces GAG in the subject by about 30%. In some embodiments, the administered rAAV comprising I2S reduces GAG in the subject by about 25%. In some embodiments, the administered rAAV comprising I2S reduces GAG in the subject by about 20%. In some embodiments, the administered rAAV comprising I2S reduces GAG in the subject by about 15%. In some embodiments, the administered rAAV comprising I2S reduces GAG in the subject by about 10%.

In some embodiments, the administered rAAV comprising I2S reduces GAG in the subject for at least about 2 weeks, 1 month, 2 months, 3 months, 4 months, 5 months, 6 months, 12 months, 1 year, 2 years, 3 years, 4 years, 5 years, or more than 5 years.

In some embodiments, following administration of the AAV vector to the subject the levels of functional I2S detectable in the circulation are between about 2 and 10 times greater than the amount of functional I2S detectable in the subject before administration of the rAAV comprising I2S.

In some embodiments, following administration of the AAV vector to the subject the levels of detectable active I2S meets or exceeds human therapeutic level. In some embodiments, the levels of active I2S post administration of the rAAV vector is about between 2 and 35 times the human therapeutic level. In some embodiments, the levels of active I2S post administration is about 2 times the human therapeutic level. In some embodiments, the levels of active I2S post administration is about 3 times the human therapeutic level. In some embodiments, the levels of active I2S post administration is about 4 times the human therapeutic level. In some embodiments, the levels of active I2S post administration is about 5 times the human therapeutic level. In some embodiments, the levels of active I2S post administration is about 6 times the human therapeutic level. In some embodiments, the levels of active I2S post administration is about 6 times the human therapeutic level. In some embodiments, the levels of active I2S post administration is about 7 times the human therapeutic level. In some embodiments, the levels of active I2S post administration is about 8 times the human therapeutic level. In some embodiments, the levels of active I2S post administration is about 9 times the human therapeutic level. In some embodiments, the levels of active I2S post administration is about 10 times the human therapeutic level. In some embodiments, the levels of active I2S post administration is about 15 times the human therapeutic level. In some embodiments, the levels of active I2S post administration is about 20 times the human therapeutic level. In some embodiments, the levels of active I2S post administration is about 25 times the human therapeutic level. In some embodiments, the levels of active I2S post administration is about 30 times the human therapeutic level. In some embodiments, the levels of ac active I2S post administration is about 35 times the human therapeutic level.

Thus, administration of rAAV vector comprising the I2S results in sustained robust expression in comparison to a single administration of purified I2S to a subject in need.

In some embodiments, the rAAV I2S vector is delivered as a single dose per subject. In some embodiments, the subject is delivered the minimal effective dose (MED). As used herein, MED refers to the rAAV I2S vector dose required to achieve I2S activity resulting in reduced GAG levels in a subject.

The vector titer is determined on the basis of the DNA content of the vector preparation. In some embodiments, quantitative PCR or optimized quantitative PCR is used to determine the DNA content of the rAAV I2S vector preparations. In one embodiment, the dosage is about $1\times10^{11}$ vector genome (vg)/kg body weight to about $1\times10^{13}$ vg/kg, inclusive of endpoints.

In one embodiment, the dosage is selected in the range of $1\times10^9$ vg/kg to $3\times10^{15}$ vg/kg (for example, $1\times10^9$ vg/kg, $3\times10^9$ vg/kg, $1\times10^{10}$ vg/kg, $3\times10^{10}$ vg/kg, $1\times10^{11}$ vg/kg, $3\times10^{11}$ vg/kg, $1\times10^{12}$ vg/kg, $3\times10^{12}$ vg/kg, $1\times10^{13}$ vg/kg, $3\times10^{13}$ vg/kg, $1\times10^{14}$ vg/kg, $3\times10^{14}$ vg/kg, $1\times10^{15}$ vg/kg, $3\times10^{15}$ vg/kg). In some embodiments, the dosage is $5\times10^{13}$ vg/kg. In another embodiment, the dosage is $5\times10^{12}$ vg/kg In specific embodiments, the dose of rAAV administered to a subject is at least $5\times10^{11}$ vg/kg, $1\times10^{12}$ vg/kg, $1.5\times10^{12}$ vg/kg, $2.0\times10^{12}$ vg/kg, $2.5\times10^{12}$ vg/kg, $3.0\times10^{12}$ vg/kg, $3.5\times10^{12}$ vg/kg, $4.0\times10^{12}$ vg/kg, $4.5\times10^{12}$ vg/kg, $5.0\times10^{12}$ vg/kg, $5.5\times10^{12}$ vg/kg, $6.0\times10^{12}$ vg/kg, $6.5\times10^{12}$ vg/kg, $7.0\times10^{12}$ vg/kg, or $7.5\times10^{12}$ vg/kg.

In some embodiments, the rAAV I2S vector compositions can be formulated in dosage units to contain an amount of replication-defective virus that is in the range of about $1.0\times10^9$ vg to about $1.0\times10^{15}$ vg. As used herein, the term "dosage" can refer to the total dosage delivered to the subject in the course of treatment, or the amount delivered in a single (of multiple) administration.

In some embodiments, the dosage is sufficient to decrease plasma GAG levels in the patient by 25% or more. In some embodiments, rAAV I2S is administered in combination with one or more therapies for the treatment of Hunter syndrome.

Production of rAAV Viral Vectors

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/1 10689; and U.S. Pat. No. 7,588,772 B2. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

In some embodiments, the expression cassette flanked by ITRs and rep/cap genes are introduced into a desired cell or cell line by infection with baculovirus-based vectors.

In some embodiments, the expression cassette flanked by ITRs and rep/cap genes are introduced into insect cells by infection with baculovirus-based vectors. For reviews on these production systems, see generally, e.g., Zhang et al, 2009, "Adenovirus-adeno-associated virus hybrid for large-scale recombinant adeno-associated virus production," *Human Gene Therapy* 20:922-929, the contents of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," *Adv. Biochem. Engin/Biotechnol.* 99: 119-145; Buning et al, 2008, "Recent developments in adeno-associated virus vector technology," *J. Gene Med* 10:717-733; and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol, 70:520-532 and U.S. Pat. No. 5,478,745.

Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

In one embodiment, the production plasmid is that described herein, or as described in WO2012/158757, which is incorporated herein by reference. Various plasmids are known in the art for use in producing rAAV vectors, and are useful herein. The production plasmids are cultured in the host cells which express the AAV cap and/or rep proteins. In the host cells, each rAAV genome is rescued and packaged into the capsid protein or envelope protein to form an infectious viral particle.

In certain embodiments, the rAAV expression cassette, the vector (such as rAAV vector), the virus (such as rAAV), the production plasmid comprises AAV inverted terminal repeat sequences, a codon optimized nucleic acid sequence that encodes IDS and/or SUMF-1, and expression control sequences that direct expression of the encoded proteins in a host cell. In other embodiments, the rAAV expression cassette, the virus, the vector (such as rAAV vector), the production plasmid further comprise one or more of an intron, a Kozak sequence, a polyA, posttranscriptional regulatory elements and others. In one embodiment, the posttranscriptional regulatory element is Woodchuck Hepatitis Virus (WHP) Posttranscriptional Regulatory Element (WPRE).

Various methods are known in the art relating to the production and purification of AAV vectors. See, e.g., Mizukami, Hiroaki, et al. A Protocol for AAV vector production and purification; U.S. Patent Publication Numbers US20070015238 and US20120322861. For example, a plasmid comprising a gene of interest may be combined with one or more helper plasmids, e.g., that contain a rep gene (e.g., encoding Rep78, Rep68, Rep52 and Rep40) and a cap gene (encoding VP1, VP2, and VP3, including a modified VP2 region as described herein), and transfected into a recombinant cells such that the rAAV can be packaged and subsequently purified.

In some embodiments, the packaging is performed in a helper cell or producer cell, such as a mammalian cell or an insect cell. Exemplary mammalian cells include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect cells include, but are not limited to Sf9 cells (see, e.g., ATCC® CRL-1711™). The helper cell may comprises rep and/or cap genes that encode the Rep protein and/or Cap proteins for use in a method described herein. In some embodiments, the packaging is performed in vitro.

In some embodiments, a plasmid containing comprising the gene of interest is combined with one or more helper plasmids, e.g., that contain a rep gene of a first serotype and a cap gene of the same serotype or a different serotype, and transfected into helper cells such that the rAAV is packaged.

In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. In some embodiments, the cap gene is modified such that one or more of the proteins VP1, VP2 and VP3 do not get expressed. In some embodiments, the cap gene is modified such that VP2 does not get expressed. Methods for making such modifications are known in the art (Lux et al. (2005), *J Virology,* 79: 11776-87).

Helper plasmids, and methods of making such plasmids, are generally known in the art and generally commercially available (see, e.g., pDF6, pRep, pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, *Human Gene Therapy,* Vol. 9, 2745-2760; Kem, A. et al. (2003), Identification of a Heparin-Binding Motif on Adeno-Associated Virus Type 2 Capsids, *Journal of Virology,* Vol. 77, 11072-11081; Grimm et al. (2003), Helper Virus-Free, Optically Controllable, and Two-Plasmid-Based Production of Adeno-associated Virus Vectors of Serotypes 1 to 6, *Molecular Therapy,* Vol. 7, 839-850; Kronenberg et al. (2005).

EXAMPLES

Other features, objects, and advantages of the present invention are apparent in the examples that follow. It should be understood, however, that the examples, while indicating embodiments of the present invention, are given by way of illustration only, not limitation. Various changes and modifications within the scope of the invention will become apparent to those skilled in the art from the examples.

Example 1

Vector Design

Exemplary methods and designs of generating rAAV expression constructs (rAAV vectors) comprising coding sequences of human iduronate 2-sulfatase (IDS or I2S) and variations of the same are provided in this Example. In this study, recombinant AAV vector (rAAV8) was used. The basic design of an rAAV vector comprises an expression cassette flanked by inverted terminal repeats (ITRs): a 5'-ITR and a 3'-ITR. These ITRs mediate the replication and packaging of the vector genome by the AAV replication protein Rep and associated factors in vector producer cells. Typically, an expression cassette contains a promoter, a coding sequence, a polyA tail and/or a tag, as shown in FIG. 1A. An expression construct encoding human IDS (hIDS) was designed and prepared using standard molecular biology techniques. The coding sequence for the hIDS was inserted downstream of a promoter, hTTR (human transthyrethin promoter). Additionally, liver-specific cis-acting regulatory module (CRM) was inserted upstream of the promoter, and a minute virus of mice (MVM) intron sequence was inserted downstream of the promoter. This regulatory and promoter combination was tested for high transduction level, as shown in the examples that follow. Furthermore, the WPRE sequence was inserted downstream of the coding region. Without wishing to be bound by theory, this element creates a tertiary structure that increases the mRNA stability. Other mechanisms of function have been described for WPRE including, for example, improving transcript termination and facilitating mRNA nuclear export. FIG. 1B shows schematic representations of the expression constructs described above. The expression construct was then cloned into an AAV plasmid backbone and confirmed by sequencing. Vectors were packaged in viral particles and stored.

Any number of variations of the above scheme can be performed. Alternative constructs can be obtained by replacing the WPRE sequence with a SUMF1 (sulfatase-modifying factor 1) coding sequence preceded by an internal ribosomal entry site (IRES), as shown in FIG. 2. Based on published data (Fraldi A et al. 2007. Biochem J. 403:305-312), the presence of SUMF1 increases I2S activities when tested in in vitro cell-based assays. Additional in vivo data published in the same study demonstrated more significant improvement of sulfamidase (SGSH) activity in the presence of SUMF1. Provided that SUMF1 is required to activate the Formyl glycine catalytic residue of its substrate, including IDS, in the endoplasmic reticulum, co-expression of IDS and SUMF1 from the same vector can ensure that there is increased amount of SUMF1 to process the increased amount of IDS at a cellular level, therefore increasing the probability of activated IDS to be processed prior to trafficking to the lysosome, or exiting the cells to travel to other cells for update.

Codon Optimization

Additionally, the coding sequences for the IDS or SUMF1 were codon-optimized based on multiple parameters, such as codon adaptation index (CAI), CpG site count, GC content, and repetitious base sequences. High CAI was preferred to utilize more frequently used codons and to potentially increase transgene product expression level from the vector. CpG sites, which can elicit immune response, were reduced. Repetitious bases were also removed. A web-based multi-objective optimization platform for synthetic gene design called COOL (Codon Optimization Online) and internal codon usage frequency table were used for this purpose. Additionally, potential splicing sites were manually removed. The characteristics of the optimized hIDS and SUMF1 coding sequences are summarized in Table 4, and the schematics for the representative constructs of hIDS-WPRE and hIDS-IRES-SUMF1 are shown in FIG. 1B and FIG. 2, respectively. Any number of variations of the above scheme can be performed. For example, more than one promoter may be used, and/or an IRES sequence may be introduced upstream of the coding region. Additionally, different combinations of regulatory region, promotor, and intron can be contemplated.

TABLE 4

Exemplary characteristics of optimized hIDS and SUMF1 coding sequences

| Coding sequence | CpG | CAI | CG % | Repeats |
|---|---|---|---|---|
| hIDS WT | 56 | 0.7645 | 51.97 | 896 |
| hIDS COOLopt | 24 | 0.8403 | 54.14 | 0 |
| hIDS AUSopt | 30 | 0.8519 | 54.51 | 0 |
| SUMF1 WT | 49 | 0.75 | 55.91 | 455 |
| SUMF1 COOLopt | 7 | 0.9038 | 54.04 | 0 |
| SUMF1 AUSopt | 13 | 0.8572 | 54.58 | 0 |

Example 2

Expression of rAAV-Driven hIDS-WPRE Expression In Vivo

This example illustrates the potency of the optimized constructs for rAAV-driven IDS expression in vivo. Mice were injected with control vector (rAAV-XL032) (Group A); or test samples rAAV-XL024 (hIDS wt-WPRE) construct (Group B) or rAAV-XL026 (hIDS-AUSopt-WPRE) construct (Group C), as depicted in FIG. 1A and FIG. 1B. Mice of six weeks of age received $5 \times 10^9$ vg of vectors in a volume of 200 µl via the tail vain, and serum samples were collected at 2 days, 7 days, 21 days, 8 weeks, and 12 weeks post injection. Mice were sacrificed at 12 weeks, and the tissue samples were harvested. A group of age-matched wild-type mice and a group of the age-matched, untreated IDS-KO mice were used as positive and negative controls, respectively. The experimental design is summarized in Table 5, below.

TABLE 5

Exemplary in vivo study using rAAV vectors that encode hIDS

| Group | Condition | Treatment | Volume | Dose | N/group |
|---|---|---|---|---|---|
| A | Control vector | rAAV-XL032 (hIDS wt-WPRE) | 200 µl | $5 \times 10^9$ vg | 8 |
| B | Test | rAAV-XL024 (hIDS wt-WPRE) | 200 µl | $5 \times 10^9$ vg | 8 |
| C | Test | rAAV-XL026 (hIDS AUSopt-WPRE) | 200 µl | $5 \times 10^9$ vg | 8 |
| D | Positive Control | WT; Uninjected | — | — | 6 |
| E | Negative Control | IDS-KO; Uninjected | — | — | 6 |
| F | Positive Control | IDS Enzyme (Intrathecal to KO mice) | 10 µl | 250 µg/dose | 5 |

Vector-mediated expression quantity was determined by ELISA using B85 antibody. Results are depicted in FIG. 3. Mice injected with rAAV vectors of the optimized constructs, rAAV-XL024 (Group B) and rAAV-XL026 (Group C) showed higher hIDS concentration in serum compared to mice injected with the control vector, rAAV-XL032 (Group A) which is a vector that encodes a codon-optimized hIDS by a different algorithm that does not reduce CpG sites and a shortened version of wild type WPRE sequence. For all groups injected with vectors (Groups A-C), the hIDS concentration increased until day 21, and the hIDS level was maintained up to 12 weeks (84 days) after a single injection. hIDS was not detected for all WT and IDS-KO groups as they do not express human IDS.

Figure 4A:
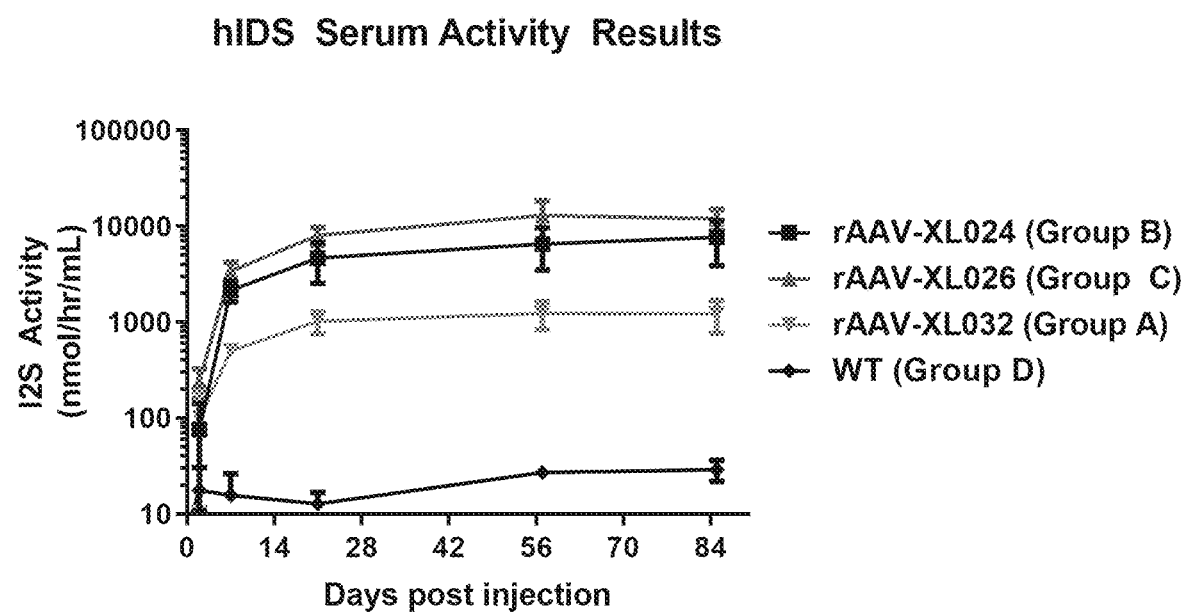
FIG. 4A is a graph that shows I2S activity in mouse serum at day 0, day 2, day 7, day 21, week 8 and week 12 post injection of the identified rAAV vectors.

Similar results were obtained when the level of hIDS activity was tested as shown in FIG. 4A. For all groups injected with vectors (Groups A-C), the activity levels increase until day 21. Similar to the expression results, the hIDS activity in mouse groups injected with rAAV vectors of optimized constructs (Group B and Group C) was higher than in mouse group with the control vector rAAV-XL032 (Group A). The hIDS activity level of WT mouse group was relatively stable throughout the study period. The rAAV vector used in this example was rAAV8.

Figure 4B:
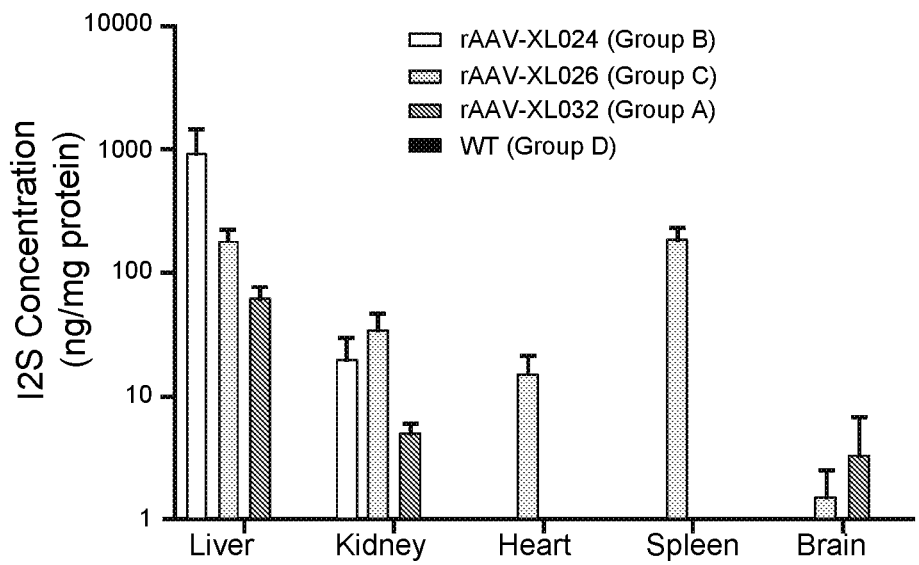
FIG. 4B is a graph that shows I2S concentration in mouse tissues.

In tissues, hI2S was measured using ELISA as shown in FIG. 4B. For rAAV-XL024 (Group B), hI2S was detectable in liver and kidney but not brain. Heart and spleen were not analyzed for this group. For rAAV-XL026 (Group C), hI2S was detectable in liver, kidney, heart, spleen, and brain. For rAAV-XL032 (Group A), hI2S was detectable in liver, kidney, and brain. Heart and spleen were not analyzed for this group.

Figure 4C:
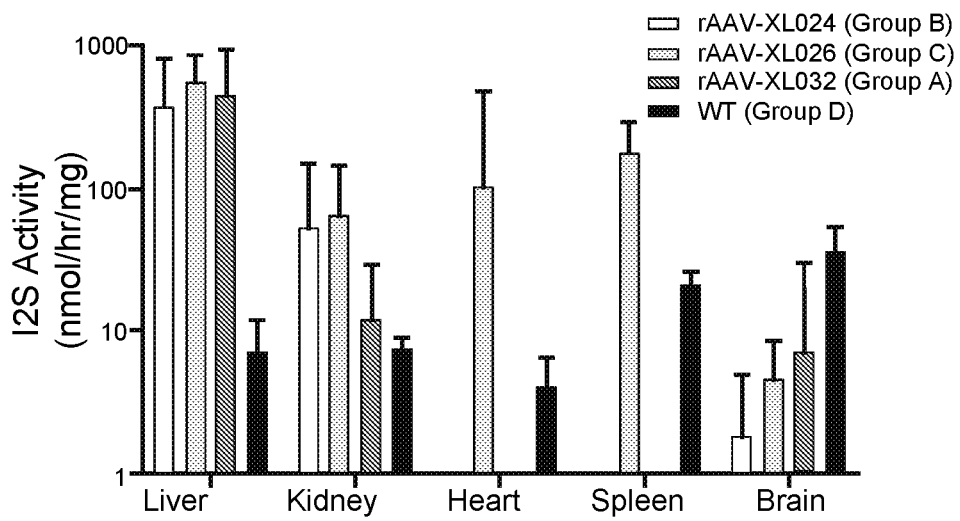
FIG. 4C is a graph that shows I2S activity in mouse tissues.
Figure 4D:
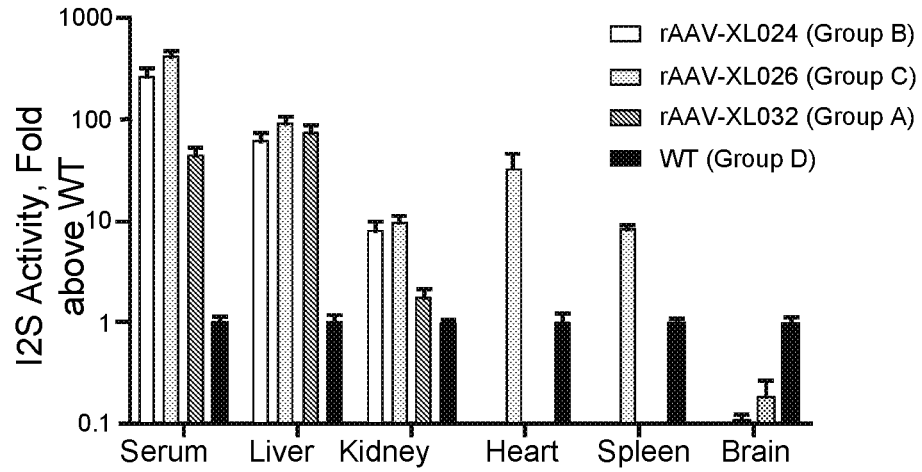
FIG. 4D is a graph that shows relative I2S activity in animals administered hIDS expressing vector relative to wild-type.

In tissues, hI2S was measured using activity as shown in FIG. 4C. For rAAV-XL024 (Group B), hI2S activity was detectable in liver, kidney, and brain. Heart and spleen were not analyzed for this group. For rAAV-XL026 (Group C), hI2S was detectable in liver, kidney, heart, spleen, and brain. For rAAV-XL032 (Group A), hI2S was detectable in liver, kidney, and brain. Heart and spleen were not analyzed for this group. Enzyme activity levels were compared to the WT group as shown in FIG. 4D. In serum and somatic tissues, all vector dosed groups contained levels of activity greater than WT. In brain, levels of rAAV-XL026 and rAAV-XL032 were less than WT.

Example 3

GAG Clearance by Gene Therapy With hIDS-WPRE Constructs

The enzyme iduronate-2-sulfatase (IDS) removes the sulfate group from the glycosaminoglycans (GAGs), dermatan and heparan sulfates, and its absence or inactivity results in mucopolysaccharidosis type II (MPSII), or Hunter syndrome, a lysosomal storage disorder. Therefore, GAG clearance was measured to evaluate the potency of hIDS expressed by the optimized rAAV constructs. Brain, liver, and kidney tissues were extracted from mouse groups shown in Table 5 at week 12, and the GAG level in each tissue was measured.

Figure 5A:
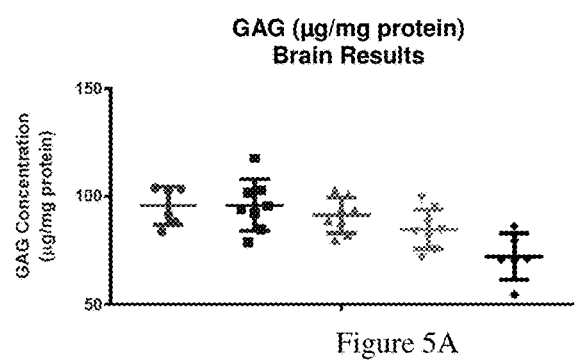
FIG. 5A is a graph that shows the GAG level in mouse brain.
Figure 5B:
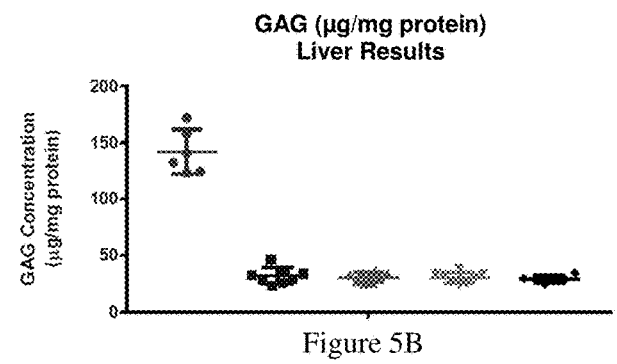
FIG. 5B is a graph that shows the GAG level in mouse liver.
Figure 5C:
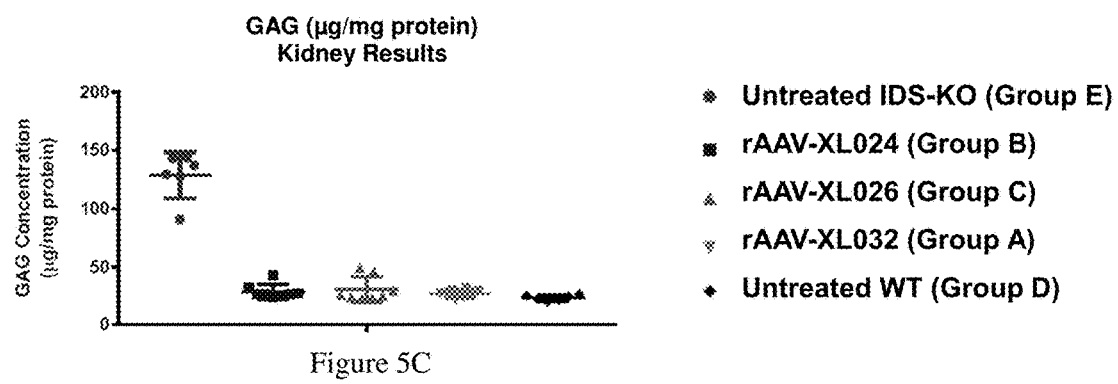
FIG. 5C is a graph that shows the GAG level in mouse kidney at week 12 post injection of the identified rAAV vectors.

As shown in FIG. 5A, in the brain the GAG level was slightly reduced for rAAV-XL026 (Group C) and rAAV-XL032 (Group A) compared to untreated IDS-KO mice. As shown in FIG. 5B and FIG. 5C, the GAG level was significantly reduced in liver and kidney when the mice were injected with rAAV vectors encoding hIDS. The GAG level was similar to the GAG level found in untreated WT mice.

Example 4

Reduction in Heparin Sulfate (HS) and Dermatan Sulfate (DS) by Gene Therapy With hIDS-WPRE Constructs This example illustrates the reduction in heparan sulfate and dermatan sulfate levels by expression of hIDS in mice.

The enzyme iduronate-2-sulfatase (IDS) removes the sulfate group from the glycosaminoglycans (GAGs), dermatan and heparan sulfate, and its absence or inactivity results in accumulation of GAGs resulting in mucopolysaccharidosis type II (MPSII), or Hunter syndrome, a lysosomal storage disorder.

In order to evaluate the potency of hI2S expressed by optimized rAAV constructs, GAG clearance was measured.

Figure 6A:
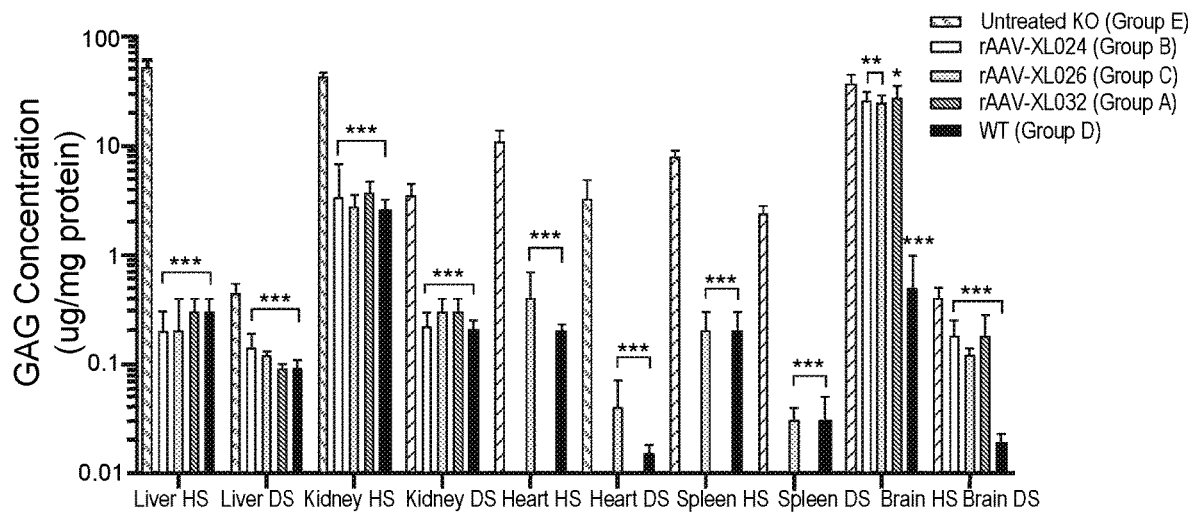
FIG. 6A is a graph that shows the heparan sulfate (HS) and dermatan sulfate (DS) GAG levels in liver and kidney etc. of mice at week 12 post injection of the identified rAAV vectors. One-way ANOVA was carried out relative to untreated knockout animals with multiple comparisons using Dunnett method. P<0.01, *P<0.001.

Glycosaminoglycans (GAGs) were measured using a liquid chromatography-mass spectrometry (LC/MS) assay that can detect heparan sulfate (HS) and dermatan sulfate (DS) in liver, kidney, heart, spleen, and brain tissues extracted at week 12 from the mouse groups shown in Table 5. The results are shown in FIG. 6A-B.

For rAAV-XL024 (Group B), HS and DS GAGs were reduced compared to untreated KO (Group E) in liver and kidney, and to a lesser extent in brain. Heart and spleen were not analyzed for this group. For rAAV-XL026 (Group C), HS and DS GAGs were reduced compared to untreated KO (Group E) liver, kidney, heart, spleen, and to a lesser extent in brain. For rAAV-XL032 (Group A), HS and DS GAGs were reduced compared to untreated KO (Group E) in liver and kidney, and to a lesser extent in brain.

Figure 6B:
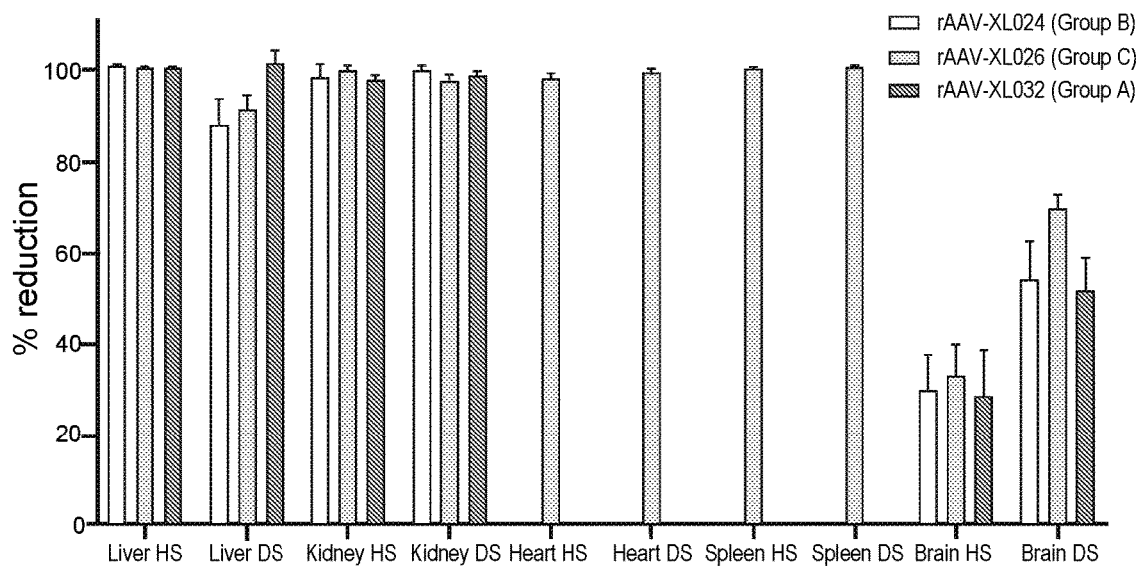
FIG. 6B is a graph that shows the percent reduction of heparan sulfate (HS) and dermatan sulfate (DS) levels in liver and kidney etc. relative to control animals at week 12 post injection of the identified rAAV vectors.

The HS and DS GAG levels were normalized to untreated IKO=0% reduction and WT=100% reduction as shown in FIG. 6B.

Overall, all vector dosed groups showed % reduction in HS and DS GAGs in somatic tissues and % GAG reduction in brain HS and DS GAGs. The results showed that expression of I2S resulted in reduced GAG levels in mouse tissue.

Example 5

Reduction in Lysosomal Storage Compartment by Gene Therapy With hIDS-WPRE Constructs in Mice This example illustrates a reduction in lysosomal storage compartment as detected by LAMP1 staining upon enzyme replacement therapy with hIDS-WPRE constructs in mice, for example, in treatment of Mucopolysaccharidosis (MPSII).

Briefly, LAMP1 staining was used to measure the lysosomal storage compartment in mice. Various tissues such as liver and brain hippocampus, thalamus, corpus callosum, cortex, cerebellum and stratum were stained. In this example, a control mouse group was administered with I2S enzyme intrathecally (IT) five times during the experimental period, at day 0, day 7, day 14, day 21 and day 28 (Group F in Table 5). Reduced LAMP1 staining indicates substrate reduction, an improvement in the pathology of the KO mice.

Figure 7A:
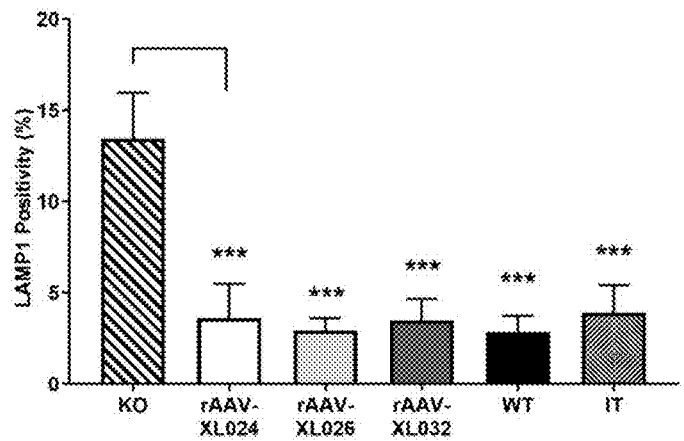
FIG. 7A is a graph that shows the LAMP1 level in the liver determined by LAMP1 immunohistochemistry staining, which serves as a biomarker of detection of reduced lysosomal storage compartment. One-way ANOVA was carried out relative to untreated knockout animals with multiple comparisons using Dunnett method. *** indicated P<0.001.
Figure 7B:
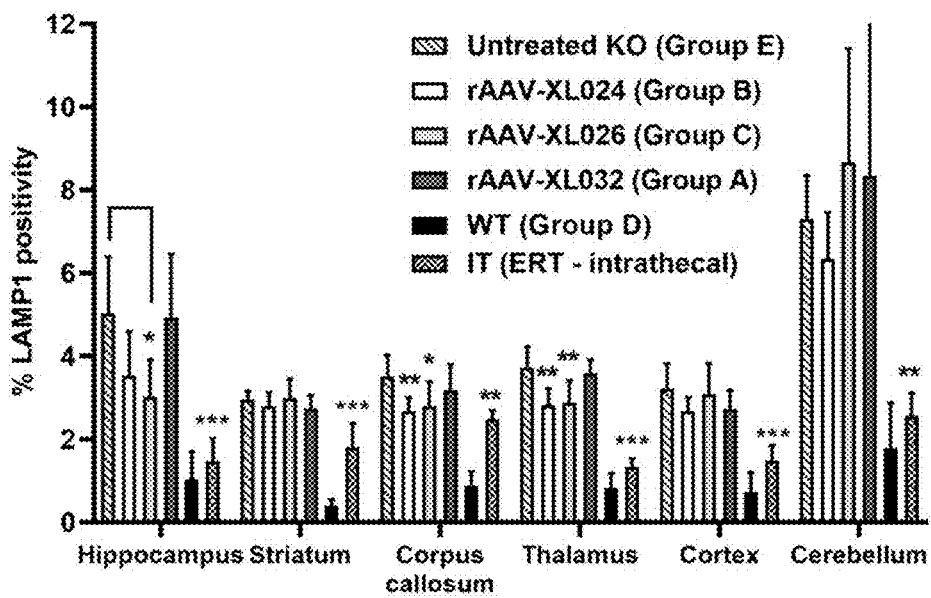
FIG. 7B is a graph that shows the LAMP1 level in the brain determined by LAMP1 immunohistochemistry staining, which serves as a biomarker of detection of reduced lysosomal storage compartment. One-way ANOVA was carried out relative to untreated knockout animals with multiple comparisons using Dunnett method. *P<0.05, P<0.01, *P<0.001.

The results are shown in FIG. 7A and FIG. 7B. Significant reduction in LAMP1 was observed in liver tissues of mice injected with vectors as seen in FIG. 7A. The effect in liver was comparable to WT mice, and mouse group treated with ERT.

Brain is shown in FIG. 7B. Compared to the untreated KO (Group E), reductions in LAMP1 staining positivity reached statistical significance in hippocampus with rAAV-XL026, corpus callosum with rAAV-XL024 and rAAV-XL026, and thalamus with rAAV-XL024 and rAAV-XL026.

Overall, the results showed that in mouse liver and brain tissues, administration of IDS resulted in reduced lysosomal storage compartment as measured by LAMP1 staining.

Example 6

Expression of rAAV-Driven hIDS-IRES-SUMF1 Expression In Vivo

This example compares the in vivo expression and activity of hIDS from administration of hIDS-IRES-SUMF1 vectors relative to hIDS-WPRE vectors in mice.

SUMF1 is required to activate the FGly catalytic residue of IDS, so a comparison was performed using vectors that expressed hIDS and SUMF1 relative to vectors that expressed hIDS-WPRE.

Mice were injected with rAAV vectors expressing hIDS AUSopt-WPRE construct (rAAV-XL026; Group C), hIDS-IRES-SUMF1 constructs (rAAV-XL027; Group G, and XL029; Group H), or SUMF1 construct (rAAV-XL030; Group I) as a negative control. The schematics for these constructs are depicted in FIG. 1B and FIG. 2.

Mice of six weeks of age received $5 \times 10^9$ vg of vectors in a volume of 200 µl via the tail vain, and serum samples were collected at 2 days, 7 days and 21 days post injection. A group of age-matched wild-type mice were used as positive and negative controls, respectively. The exemplary in vivo study is summarized in Table 6.

TABLE 6

Exemplary in vivo study using rAAV vectors that encode hIDS and SUMF1 relative to hIDS and WPRE

| Group | Condition | Treatment | Volume | Dose |
|---|---|---|---|---|
| C | Control | rAAV-XL026 (hIDS AUSopt-WPRE) | 200 µl | $5 \times 10^9$ vg |
| D | Positive Control | WT; Uninjected | — | — |
| G | Test | rAAV-XL027 (hIDS wt-IRES-SUMF1 wt) | 200 µl | 200 µl |
| H | Test | rAAV-XL029 (hIDS AUSopt-IRES-SUMF1AUSopt) | 200 µl | 200 µl |
| I | Negative Control | rAAV-XL030 (SUMF1 wt) | 200 µl | 200 µl |

Figure 8:
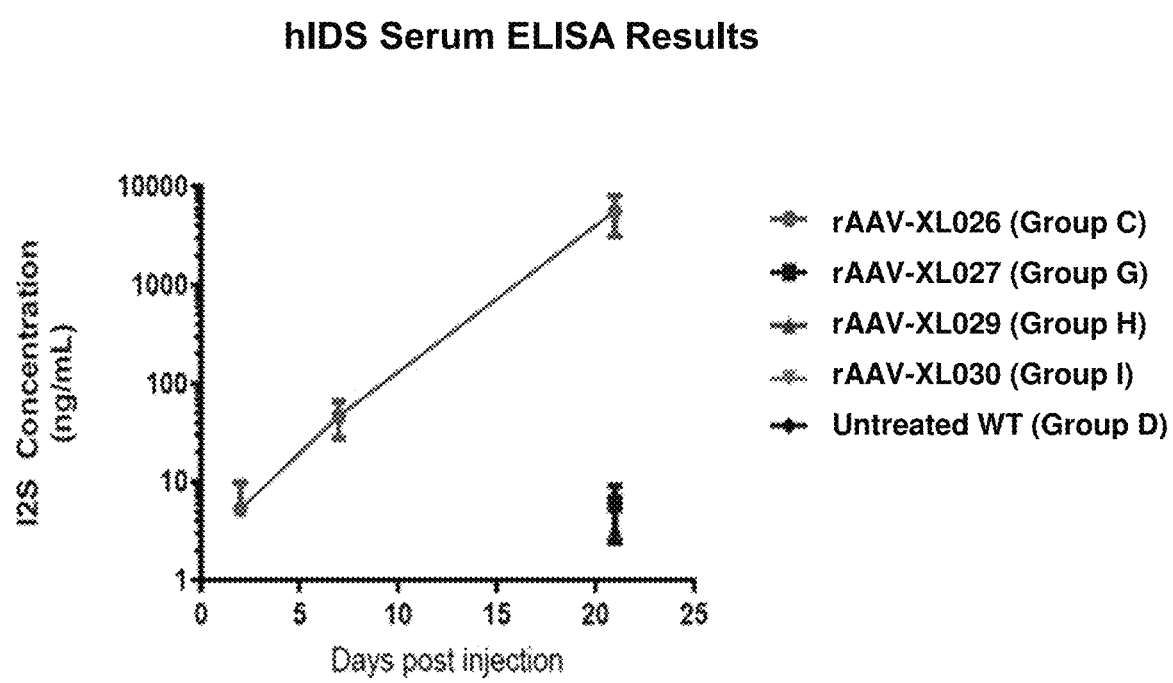
FIG. 8 is a graph that shows total hI2S concentrations in mouse serum at day 2, day 7, and day 21 post injection with vectors expressing hI2S and SUMF1.

Expression levels of IDS in serum was quantified by ELISA. Results are depicted in FIG. 8. Unexpectedly, mice injected with rAAV-XL027 and rAAV-XL029 expressing both hIDS and SUMF1 showed lower hI2S concentration in serum at day 21 compared to mice injected with the rAAV-XL026 vector (Group C), which expresses only the hIDS.

Figure 9:
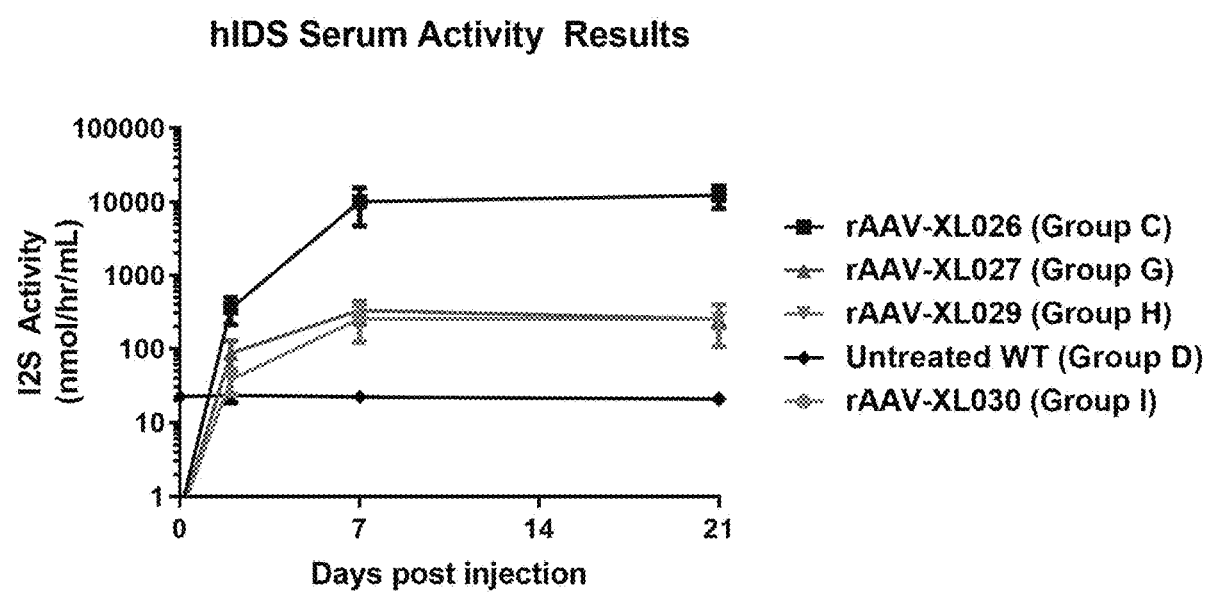
FIG. 9 is a graph that shows hI2S activity in mouse serum at day 0, day 2, day 7, and day 21 post injection of the identified rAAV vectors.

Similar results were obtained when the level of hI2S activity was tested as shown in FIG. 9. For all groups injected with vectors expressing both hIDS and SUMF1 (Groups G-H), the activity level was lower than the group injected with vector expressing hIDS-WPRE (Group C). Without wishing to be bound by a particular theory, it is believed that the WPRE element in rAAV-XL026 vector creates a tertiary structure that increase the mRNA stability and subsequently yields higher protein expression and therefore increased activity. Other mechanisms of function have been described for WPRE including, for example, improving transcript termination and facilitating mRNA nuclear export. SUMF1, on the other hand, creates more active forms of hIDS, but the quantity of hIDS expressed with WPRE element is significantly higher. The rAAV vector used in this example is rAAV8.

The results showed that IDS enzyme levels and activity were higher upon expression of hIDS-WPRE vectors relative to hIDS-IRES-SUMF1 vectors.

Example 7

Long-Term Expression of rAAV-Driven hIDS-WPRE in Serum and Tissue In Vivo in Mice This example compares the in vivo expression and activity of hIDS in mice administered one of three doses of hIDS-WPRE. Expression levels and activity were evaluated over about 12-13 months in serum and tissues.

Mice were injected with rAAV vectors expressing hIDS AUSopt-WPRE construct (rAAV-XL026) at doses of $5 \times 10^9$ vg (Group D), $2.5 \times 10^{10}$ vg (Group E), $1.25 \times 10^{11}$ vg (Group F), null vector construct rAAV-MY011 at a dose of $1.25 \times 10^{11}$ vg (Group G) as a negative control. The schematics for these constructs are depicted in FIG. 1B and FIG. 2.

Five- to seven-week-old mice received vectors in a volume of 200 μl via the tail vein, and serum samples were collected at days 7, 14, 28, 56, 84, 112, 140, 168, 196, 224, 252, 280, 308, 336, and 364 post injection. A group of age-matched wild-type mice and a group of the age-matched, untreated IDS-KO mice were used as positive and negative controls, respectively. An exemplary in vivo study is summarized in Table 7.

TABLE 7

Exemplary in vivo study using rAAV vectors and monitored for 12 months

| Group | Condition | Treatment | Volume | Dose | N/group |
|---|---|---|---|---|---|
| D | Test | rAAV-XL026 (hIDS AUSopt-WPRE) | 200 μl | $5 \times 10^9$ vg | 12 |
| E | Test | rAAV-XL026 (hIDS AUSopt-WPRE) | 200 μl | $2.5 \times 10^{10}$ vg | 12 |
| F | Test | rAAV-XL026 (hIDS AUSopt-WPRE) | 200 μl | $1.25 \times 10^{11}$ vg | 12 |
| G | Negative Control | rAAV-MY011 (null vector) | 200 μl | $1.25 \times 10^{11}$ vg | 11 |
| H | Negative Control | IDS-KO; Uninjected | — | — | 9 |
| I | Positive Control | WT; Uninjected | — | — | 6 |

Figure 10:
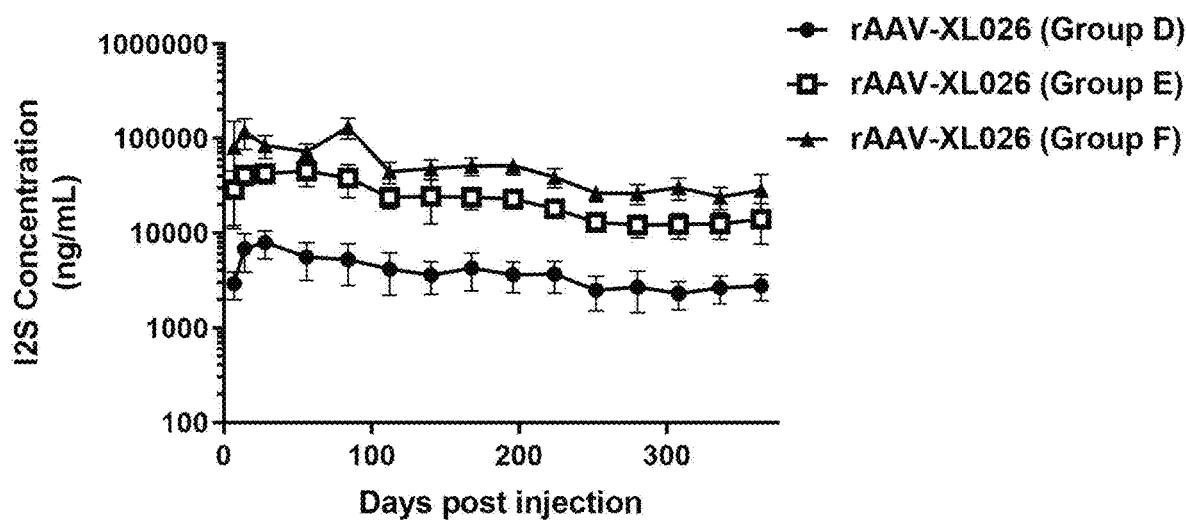
FIG. 10 is a graph that shows I2S concentration up to 364 days post-injection.

Serum hI2S levels and activity: Expression levels of serum hI2S was determined by ELISA. Results are depicted in FIG. 10. Concentrations of hI2S increased with increasing doses of the rAAV-XL026 vector (Groups D, E, F), and hI2S remained detectable until the final timepoint of 364 days post-injection. The rAAV vector used in this example is rAAV8.

Figure 11:
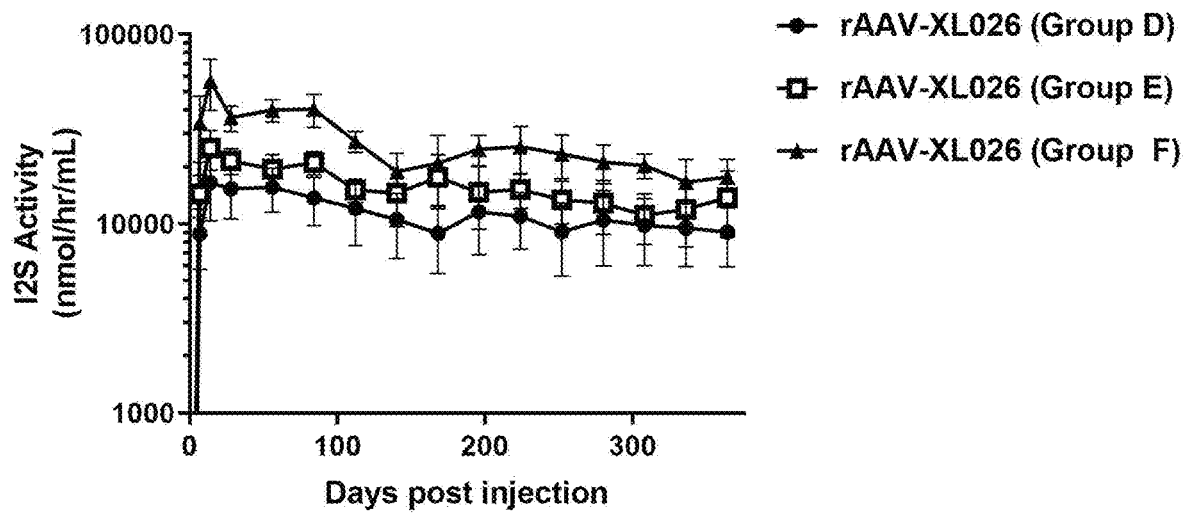
FIG. 11 is a graph that shows I2S concentration up to 364 days post-injection.

Similar results were obtained when the level of hI2S activity was tested as shown in FIG. 11. Concentrations of hI2S activity increased with increasing doses of the rAAV-XL026 vector (Groups D, E, F), and hI2S activity remained detectable until the final timepoint of 364 days post-injection.

Figure 12A:
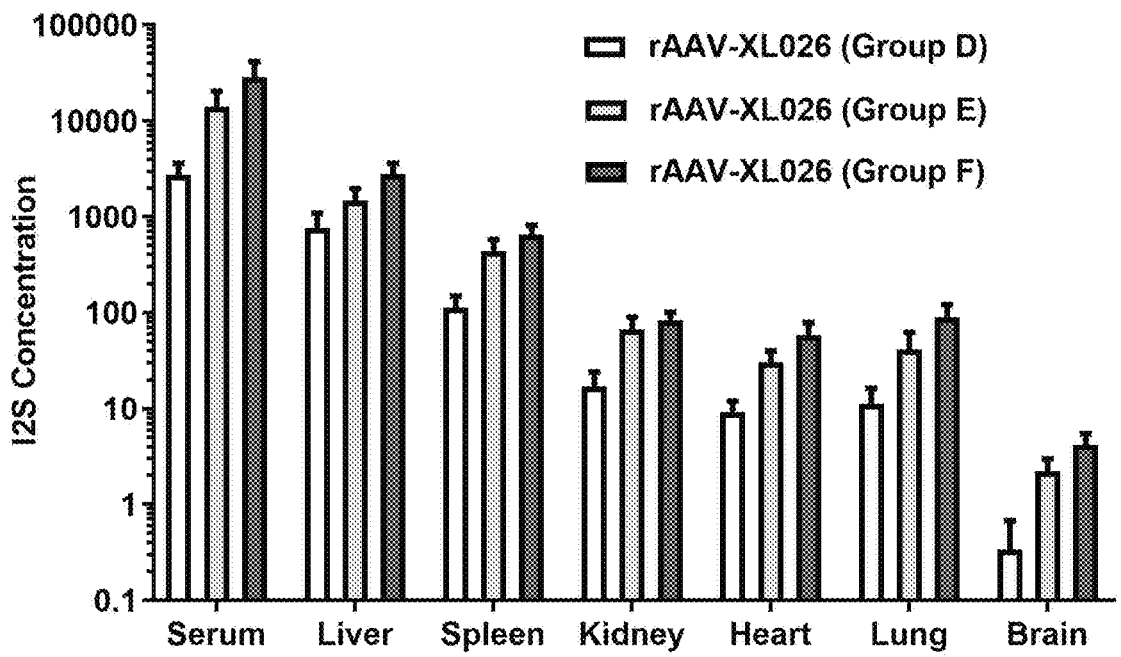
FIG. 12A is a graph of I2S concentration in mice administered hI2S as measured by ELISA in serum and tissue over 12 months.

Tissue hI2S levels and activity: In tissues, hI2S was measured using ELISA as shown in FIG. 12A. For rAAV-XL026 (Group D, E, F), hI2S was detectable in liver, spleen, kidney, heart, lung, and brain and increased with increasing doses.

Figure 12B:
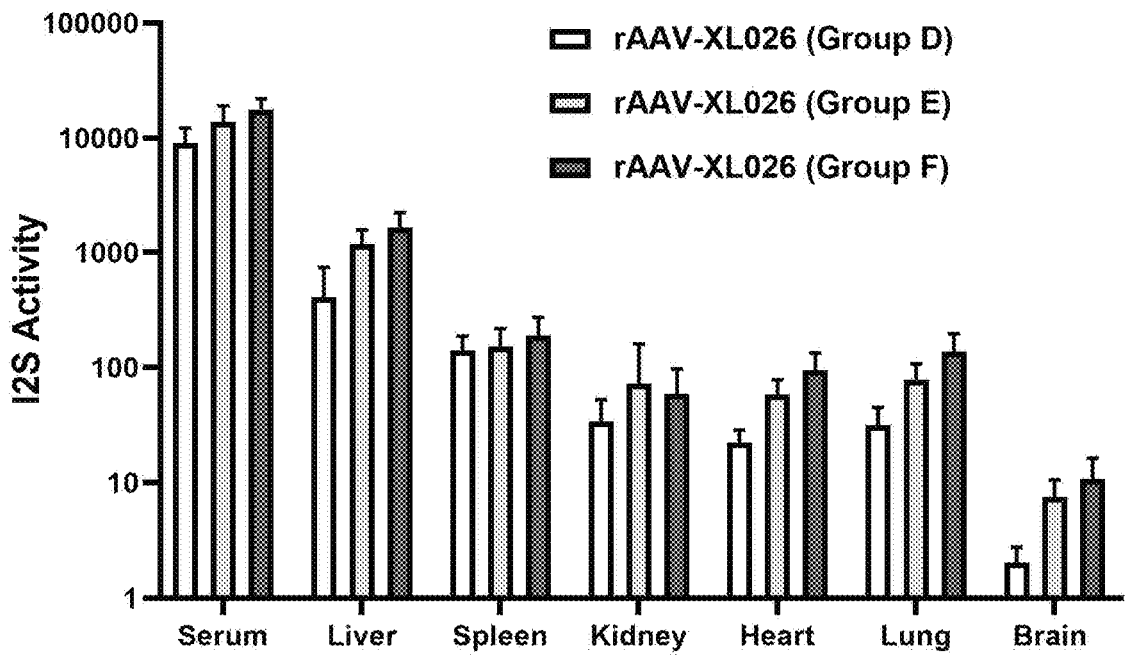
FIG. 12B is a graph of I2S activity in serum and mouse tissue.

In tissues, hI2S activity was measured as shown in FIG. 12B. rAAV-XL026 (Group D, E, F), hI2S activity was detectable in liver, spleen, kidney, heart, lung, and brain and increased with increasing doses.

Figure 12C:
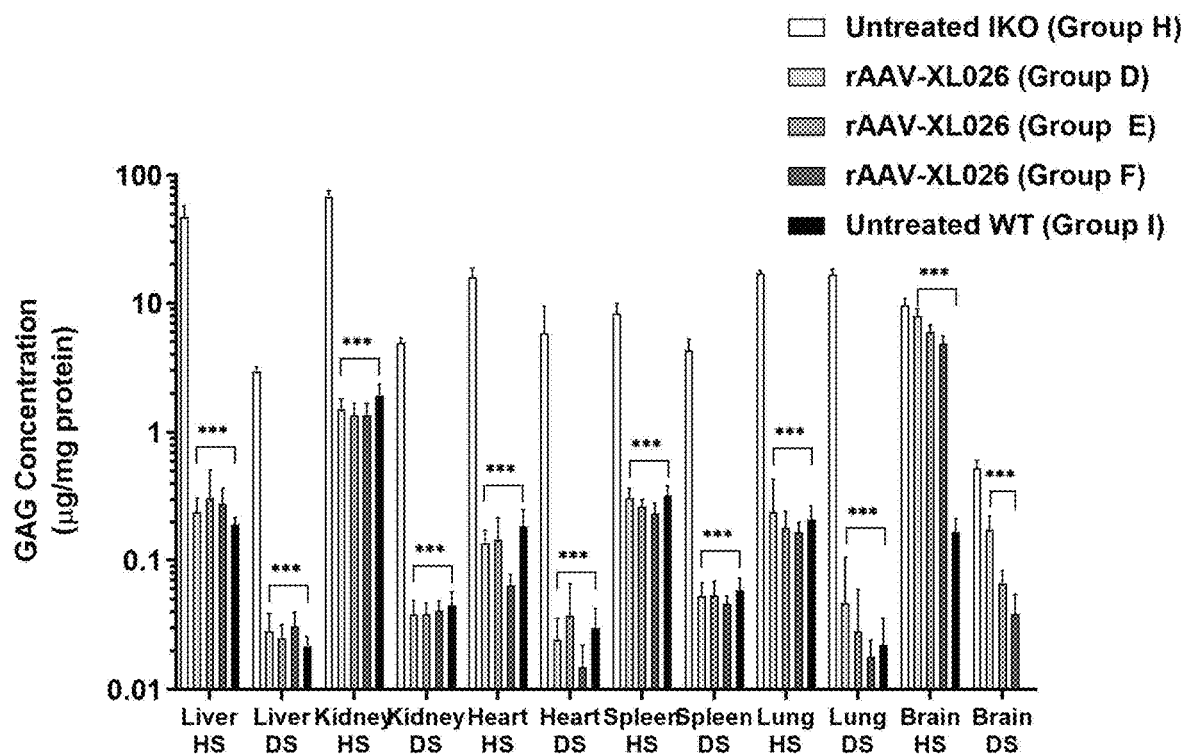
FIG. 12C is a graph of GAG levels in mouse tissues.

Glycosaminoglycans (GAGs) were measured using a liquid chromatography-mass spectrometry (LC/MS) assay that can detect heparan sulfate (HS) and dermatan sulfate (DS) in liver, kidney, heart, spleen, lung, and brain tissues extracted at day 364 from the mouse groups shown in Table 7. The results are shown in FIG. 12C.

Figure 12D:
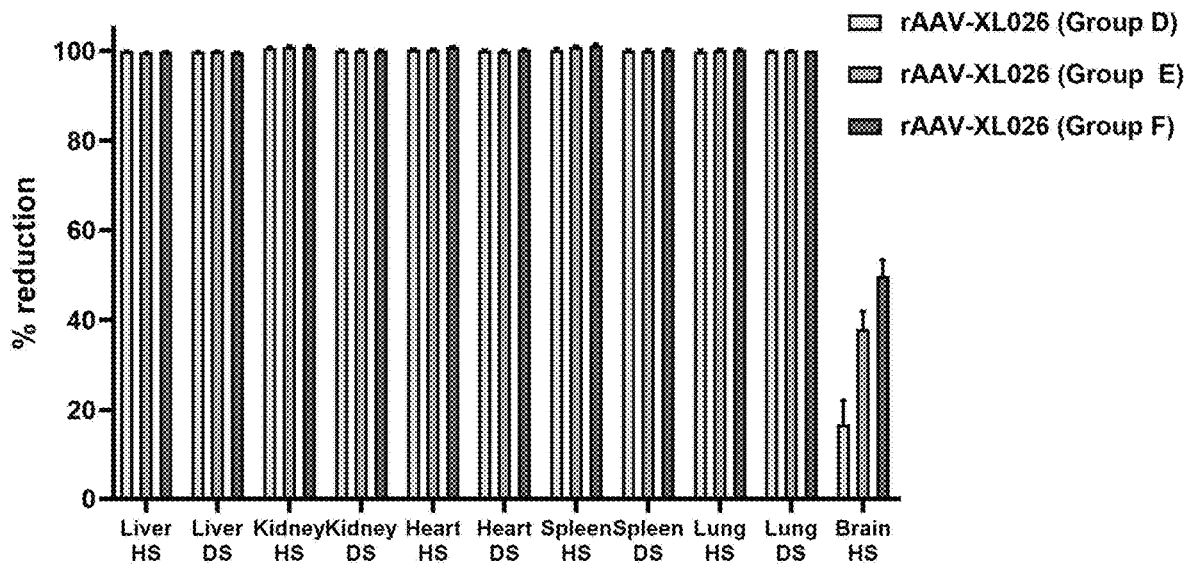
FIG. 12D is a graph of percent reduction in GAG levels in mouse tissues.

In the somatic tissues, rAAV-XL026 at all doses (Group D, E, F) greatly reduced HS and DS GAG levels. The HS and DS GAG levels were normalized to untreated IKO=0% reduction and WT=100% reduction as shown in FIG. 12D. All three doses of rAAV-XL026 (Group D, E, F) showed 100% reductions in HS and DS GAGs in somatic tissues. In brain HS, GAGs were decreased by 17% for rAAV-XL026 Group D, 38% for rAAV-XL026 Group E, and 50% for rAAV-XL026 Group F.

Figure 12E:
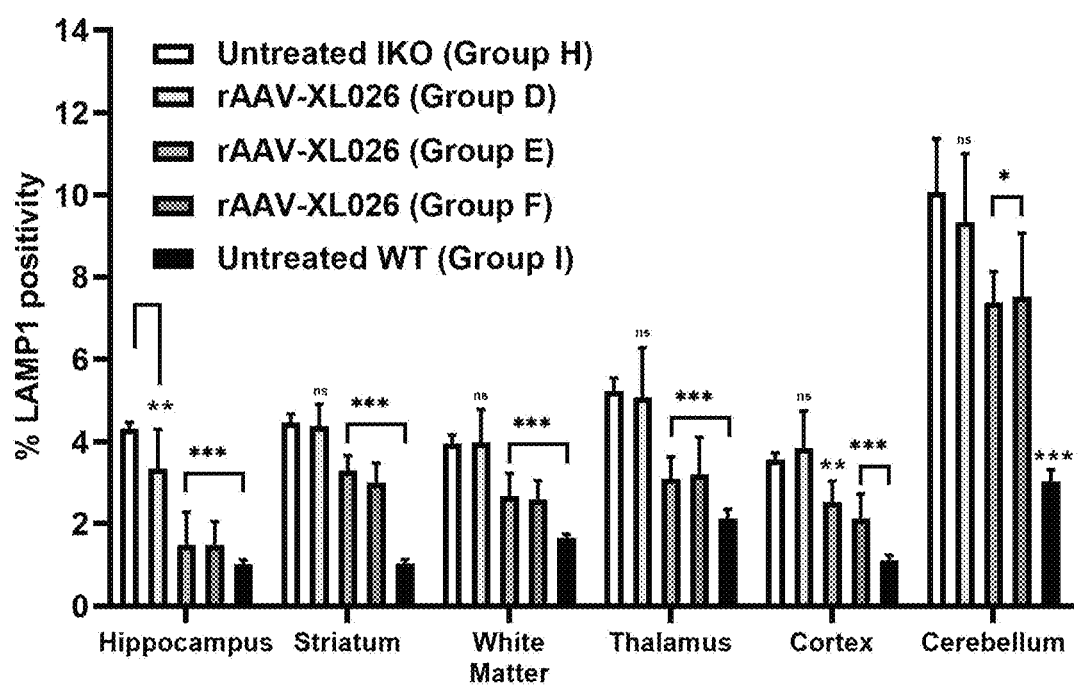
FIG. 12E is a graph of LAMP1 staining, which is a biomarker of lysosomal storage compartment. Statistics were performed using one-way ANOVA relative to untreated knockout animals with multiple comparisons using Dunnett method. *P<0.05, P<0.01, *P<0.001, ns=not significant.

Various tissues such as liver and brain hippocampus, thalamus, white matter, cortex, cerebellum and striatum were stained for LAMP1. Brain is shown in FIG. 12E. Compared to the untreated KO (Group H), reductions in LAMP1 staining positivity reached statistical significance in hippocampus with rAAV-XL026 Group D, Group E, and Group F, in striatum with rAAV-XL026 Group E and Group F, in white matter with rAAV-XL026 Group E and Group F, in thalamus with rAAV-XL026 Group E and Group F, in cortex with rAAV-XL026 Group E and Group F, and in cerebellum with rAAV-XL026 Group E and Group F.

Bone volume: Body structure was investigated using micro-computed tomography (micro-CT). Bone volume was measured over time at mouse ages 7, 9, 11, and 13 months using micro-CT as shown in FIG. 13A and FIG. 13B.

Figures 13A, 13B:
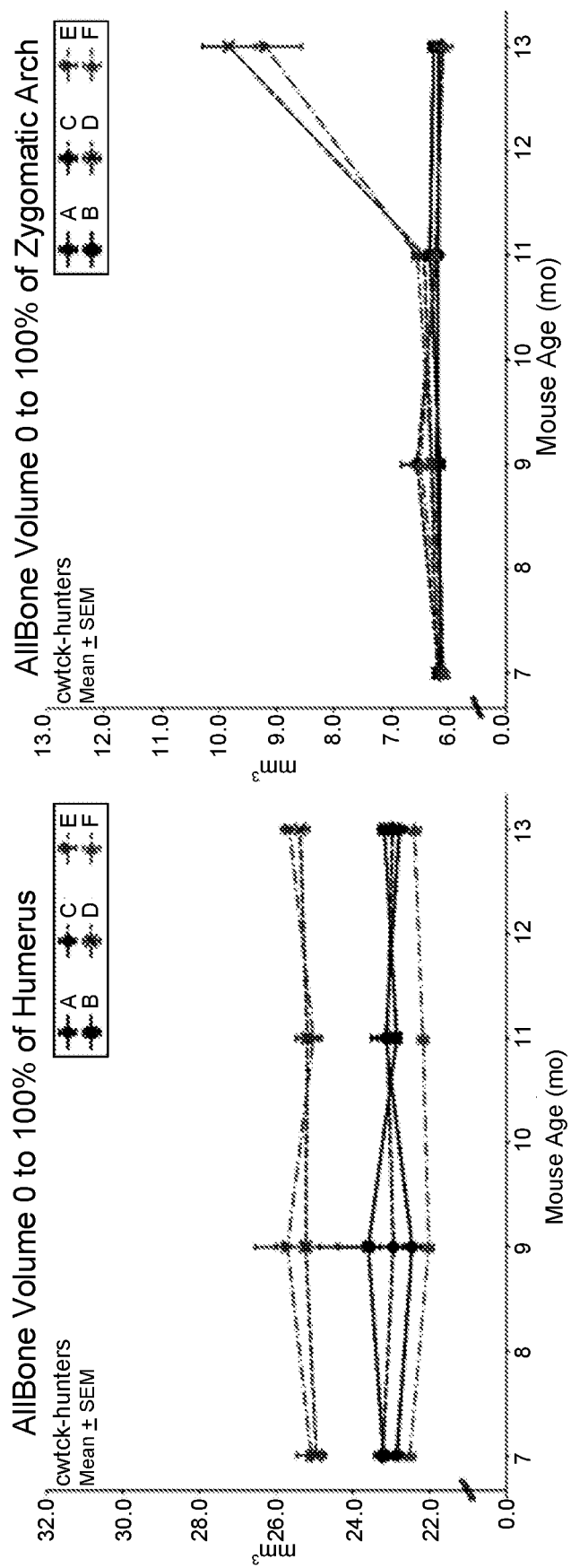
FIG. 13A shows a graph of bone volume in the humerus.
FIG. 13B shows a graph of bone volume in the zygomatic arch as measured by microCT in mice administered I2S relative to control animals.

In FIG. 13A and FIG. 13B, line A corresponds to rAAV-XL026 Group D, line B to rAAV-XL026 Group E, line C to rAAV-XL026 Group F, line D to rAAV-MY011 Group G negative control, line E to untreated IDS-KO Group H negative control, and line F to untreated wild-type Group I positive control.

In the humerus (FIG. 13A), the measurements of bone volumes for rAAV-XL026 Group D, Group E, and Group F overlay with the positive control wild-type Group I and volumes for these groups are lower than the negative controls rAAV-MY011 Group G and untreated IDS-KO Group H.

In the zygomatic arch of the cranium (FIG. 13B) at 13 months, measurements of bone volumes for rAAV-XL026 Group D, Group E, and Group F overlay with the positive control wild-type Group I and volumes for these groups are lower than the negative controls rAAV-MY011 Group G and untreated IDS-KO Group H.

These results showed lower bone volume in the humerus and zygomatic arch bone upon expression of I2S, which was maintained over 13 months.

Overall, the results showed that serum and tissue I2S expression and activity levels and resultant effects on bone volume were maintained over about 12-13 months.

Example 8

Monitoring of rAAV-Driven hIDS-WPRE Expression In Vivo for 3 Months After Low-Dose Administration in Mice This example illustrates the in vivo expression and activity of hI2S in mice administered hI2S over 3 months at a dose of between $5 \times 10^6 - 5 \times 10^9$ vg.

Mice were injected with rAAV vectors expressing hIDS AUSopt-WPRE construct (rAAV-XL026) at doses of $5 \times 10^6$ vg (Group C), $5 \times 10^7$ vg (Group D), $5 \times 10^8$ vg (Group E), $5 \times 10^9$ vg (Group F), null vector construct rAAV-MY011 at a dose of $5 \times 10^9$ vg (Group B) as a negative control.

Five- to seven-week-old mice were administered 200 µl of vector via the tail vain, and serum samples were collected at days 14, 28, 56, and 84 post injection. A group of age-matched wild-type mice and a group of the age-matched, untreated IDS-KO mice were used as positive and negative controls, respectively. The exemplary in vivo study is summarized in Table 8.

TABLE 8

Exemplary in vivo study using rAAV vectors and monitored for 3 months

| Group | Condition | Treatment | Volume | Dose | N/group |
|---|---|---|---|---|---|
| A | Negative Control | IDS-KO; Uninjected | — | — | 8 |
| B | Negative Control | rAAV-MY011 (null vector) | 200 µl | $2.5 \times 10^9$ vg | 8 |
| C | Test | rAAV-XL026 (hIDS AUSopt-WPRE) | 200 µl | $5 \times 10^6$ vg | 8 |
| D | Test | rAAV-XL026 (hIDS AUSopt-WPRE) | 200 µl | $5 \times 10^7$ vg | 8 |
| E | Test | rAAV-XL026 (hIDS AUSopt-WPRE) | 200 µl | $5 \times 10^8$ vg | 8 |
| F | Test | rAAV-XL026 (hIDS AUSopt-WPRE) | 200 µl | $5 \times 10^9$ vg | 8 |
| G | Positive Control | WT; Uninjected | — | — | 5 |

Figure 14A:
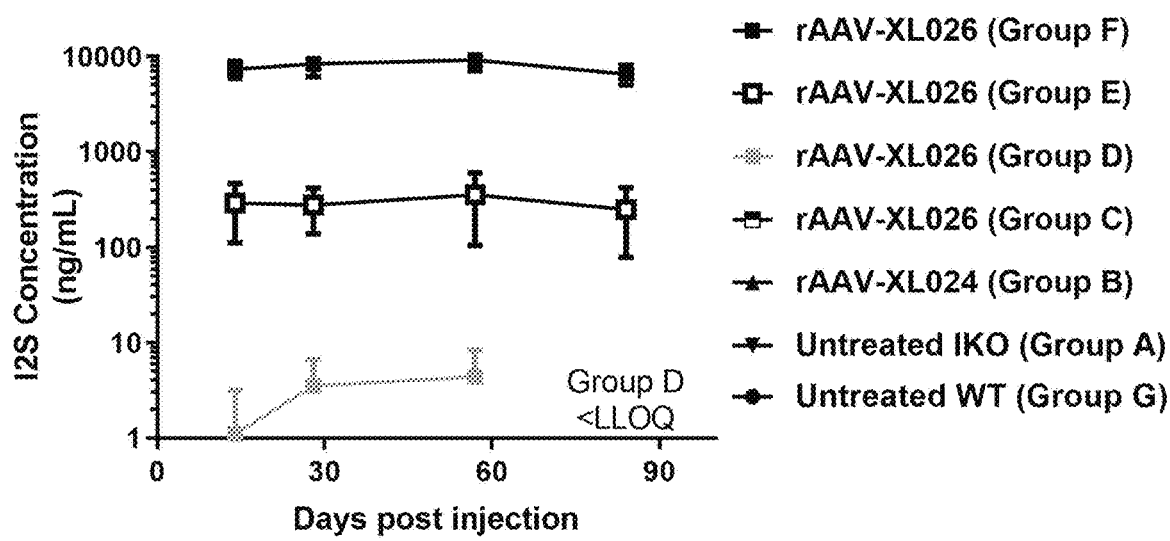
FIG. 14A shows a graph of I2S concentration in mice administered low dose hI2S as measured by ELISA in serum over 90 days.

Serum IDS levels and activity: Expression levels of hIDS in serum of mice administered low doses of the hIDS-WPRE vector was determined by ELISA, and shown in FIG. 14A. Concentrations of hI2S decreased with decreasing doses of the rAAV-XL026 vector for Groups D, E, F, and hI2S was undetectable for group C. The rAAV vector used in this example is rAAV8.

Figure 14B:
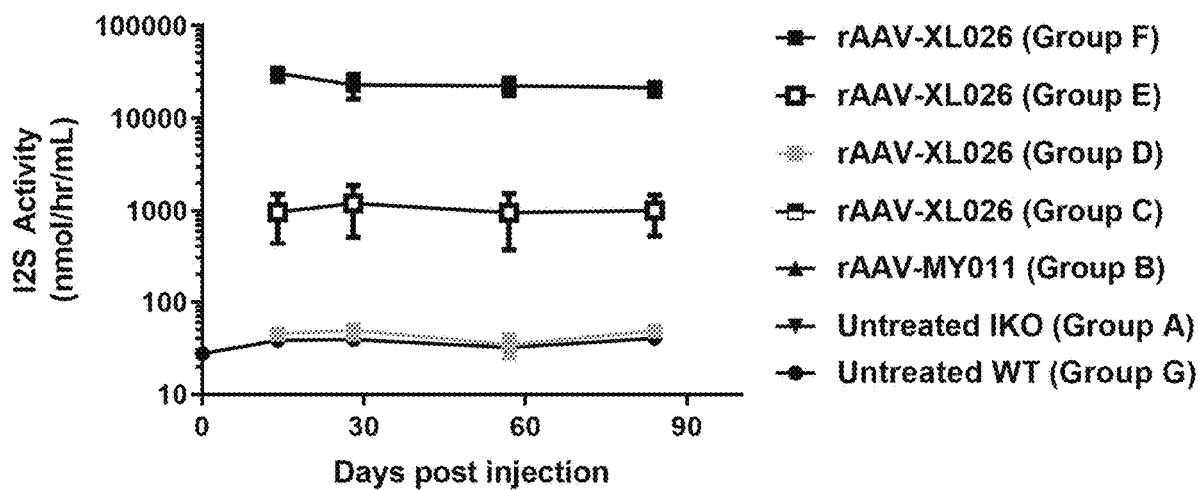
FIG. 14B is a graph of I2S activity in serum.

Serum I2S activity levels were measured as in FIG. 14B. Concentrations of hI2S decreased with decreasing doses of the rAAV-XL026 vector for Groups D, E, F, and hI2S was undetectable for group C.

Overall, Groups D and E administered $5 \times 10^8$ vg and $5 \times 10^9$ vg doses respectively, showed an increase in I2S expression and activity over untreated mice, and levels and activity of I2S were maintained over 84 days or 3 months.

Figure 14C:
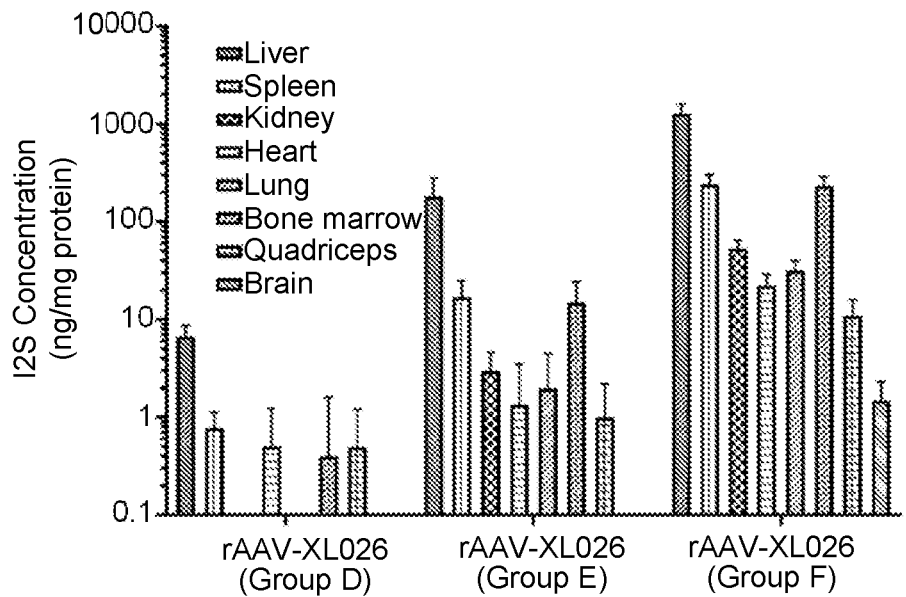
FIG. 14C is a graph of I2S concentration in mouse tissue.

Tissue I2S levels and activity: In liver, spleen, kidney, heart, lung, bone marrow, quadriceps, and brain, as measured by ELISA, the untreated KO (Group A) and untreated WT (Group J) and negative control rAAV-MY011 (Group B) groups did not contain detectable human I2S (hI2S) protein (FIG. 14C). From $5 \times 10^7$ vg to $5 \times 10^9$ vg, the rAAV-XL026 Groups D, E, and F contained increasing concentrations of hI2S in tissues with increasing dose.

Figure 14D:
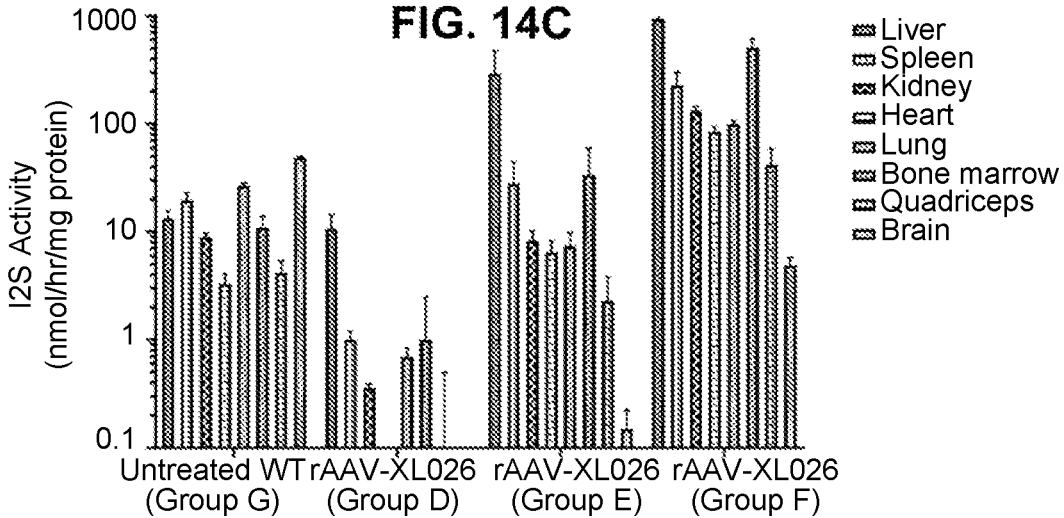
FIG. 14D is a graph of I2S activity in mouse tissue.
Figure 14E:
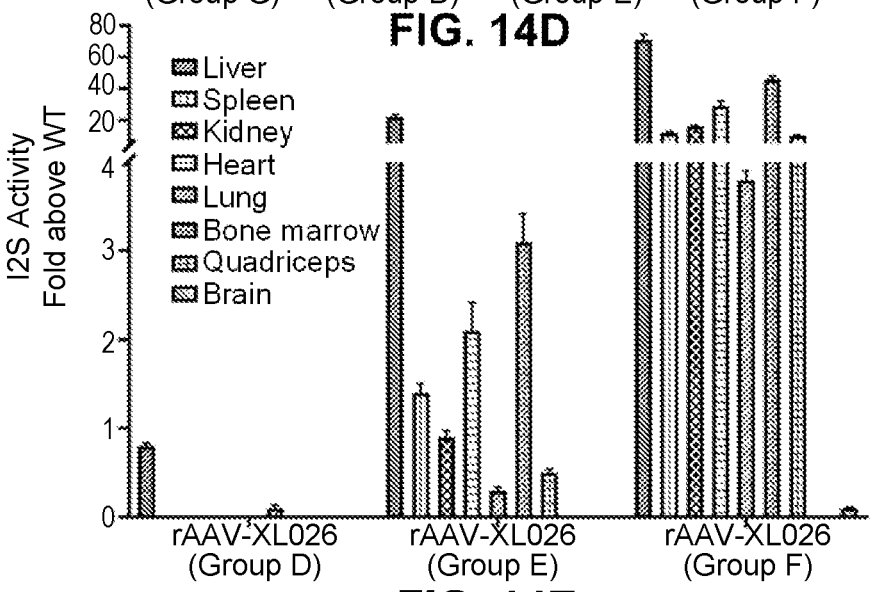
FIG. 14E is a graph of relative I2S activity in animals administered a low dose of hI2S relative to wild-type animals.

I2S activity was measured in liver, spleen, kidney, heart, lung, bone marrow, quadriceps, and brain as shown in FIG. 14D. The rAAV-MY011 (Group B) contained I2S activity in all tissues that was similar to untreated KO (Group A). From $5 \times 10^7$ vg to $5 \times 10^9$ vg, the rAAV-XL026 Groups D, E, and F contained increasing concentrations of I2S activity in tissues with increasing dose. I2S activity levels in each tissue of the dosed KO mice can be compared to the untreated WT levels as shown in FIG. 14E.

Tissue levels and activity of I2S were increased in a dose-dependent manner in mice administered low doses of rAAV vector comprising hI2S-WPRE.

Tissue GAG levels: Glycosaminoglycans (GAGs) were measured using a liquid chromatography-mass spectrometry (LC/MS) assay that can detect heparan sulfate (HS) and dermatan sulfate (DS) in liver, spleen, kidney, heart, lung, bone marrow, quadriceps, skin, and brain tissues extracted at day 84 from the mouse groups shown in Table 8. The HS and DS GAG levels were normalized to untreated IKO=0% reduction and WT=100% reduction as shown in Table 9 and Table 10.

The $5 \times 10^8$ vg rAAV-XL026 Group E reduced HS and GAG levels by >90% in all somatic tissues measured. In brain, the $5 \times 10^8$ vg rAAV-XL026 Group E reduced HS and GAG levels in brain by 8.8% and 41%, respectively. The $5 \times 10^9$ vg rAAV-XL026 Group F reduced HS and GAG levels by >95% in all somatic tissues measured. In brain, the $5 \times 10^9$ vg rAAV-XL026 Group F reduced HS and GAG levels in brain by 39% and 78%, respectively.

HS and GAG levels were reduced in somatic tissues and brain upon administration of $5 \times 10^7$, $5 \times 10^8$ or $5 \times 10^9$ vg rAAV comprising IDS-WPRE.

TABLE 9

Normalized HS GAG reduction

| Tissue | rAAV-XL026 $5 \times 10^7$ vg | rAAV-XL026 $5 \times 10^8$ vg | rAAV-XL026 $5 \times 10^9$ vg |
|---|---|---|---|
| Liver | 99% | 100% | 100% |
| Spleen | 79% | 98% | 100% |
| Kidney | 37% | 91% | 101% |
| Heart | 20% | 97% | 99% |
| Lung | 50% | 97% | 100% |
| Bone marrow | 92% | 99% | 100% |
| Quadriceps | 59% | 99% | 102% |
| Skin | 62% | 94% | 100% |
| Brain | 11% | 8.8% | 39% |

TABLE 10

Normalized DS GAG reduction

| Tissue | rAAV-XL026 $5 \times 10^7$ vg | rAAV-XL026 $5 \times 10^8$ vg | rAAV-XL026 $5 \times 10^9$ vg |
|---|---|---|---|
| Liver | 92% | 99% | 99% |
| Spleen | 66% | 95% | 100% |
| Kidney | 22% | 97% | 100% |
| Heart | 43% | 99% | 99% |
| Lung | 32% | 100% | 100% |
| Bone marrow | 88% | 101% | 101% |
| Quadriceps | 86% | 100% | 100% |
| Skin | 92% | 94% | 106% |
| Brain | 17% | 41% | 78% |

Figure 14F:
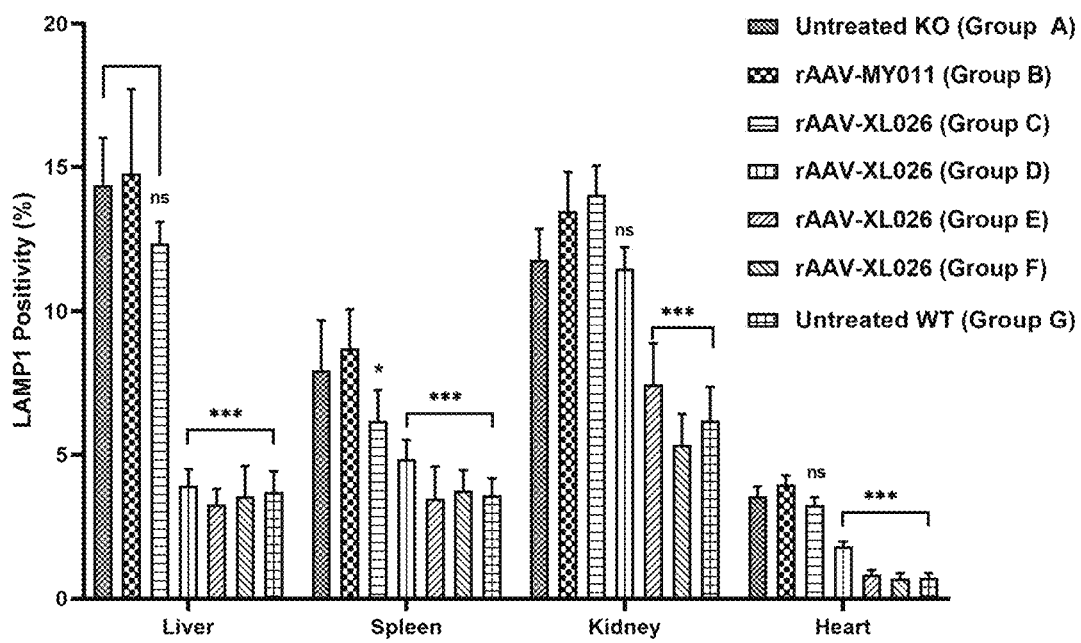
FIG. 14F is a graph that shows levels of LAMP1 staining in mice administered hI2S in somatic tissues including liver, spleen, heart and kidney.

Lysosomal storage: Various tissues such as liver, spleen, kidney, heart, and brain hippocampus, thalamus, white matter, cortex, cerebellum and striatum were stained for LAMP1. Somatic tissues are shown in FIG. 14F. In the somatic tissues including liver, spleen, and heart, LAMP1 IHC staining positivity was significantly reduced compared to the naïve KO control for rAAV-XL026 $5 \times 10^7$ vg dose Group D, $5 \times 10^8$ vg dose Group E, and $5 \times 10^9$ vg dose Group F. In the kidney, LAMP1 staining positivity was significantly reduced compared to the naïve KO control for rAAV-XL026 $5 \times 10^8$ vg dose Group E, and $5 \times 10^9$ vg dose Group F.

Figure 14G:
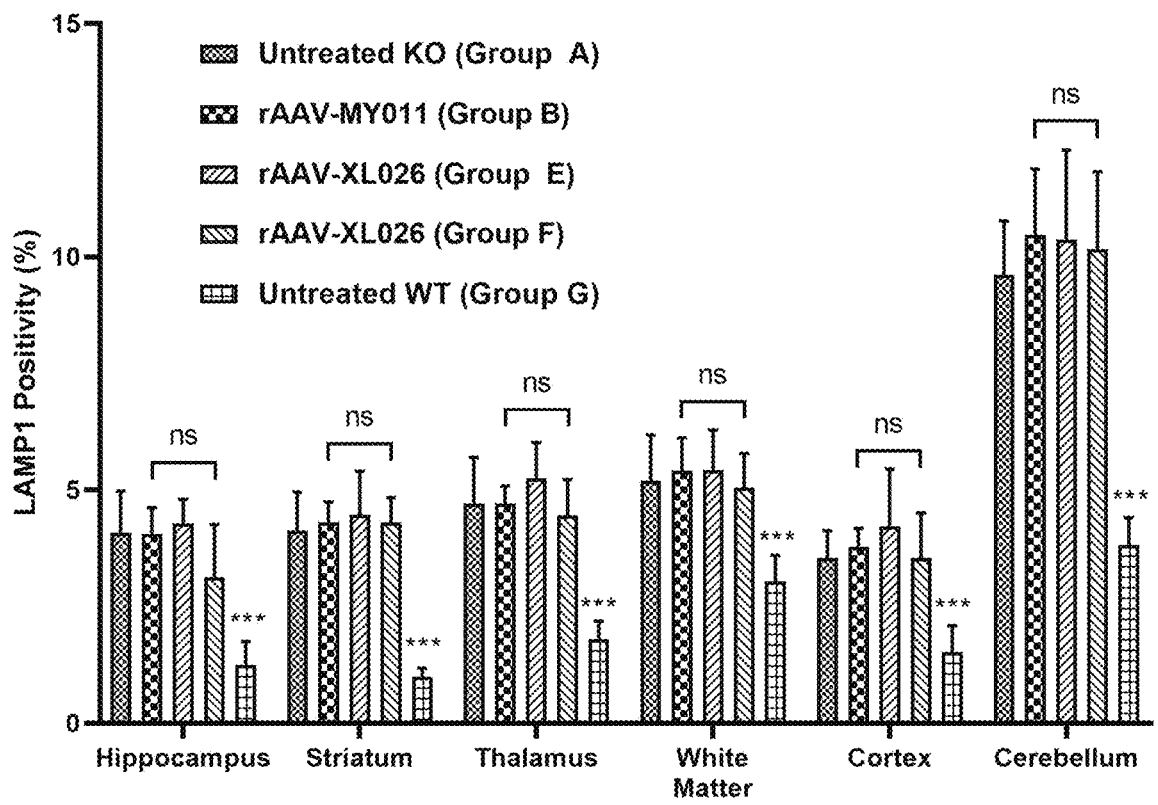
FIG. 14G is a graph that shows levels of LAMP1 staining in the brain.

LAMP1 IHC staining in brain regions is shown in FIG. 14G. In the brain, LAMP1 positivity staining was measured in hippocampus, striatum, thalamus, white matter, cortex, and cerebellum. In all of these regions the LAMP1 staining positivity for the rAAV-XL026 dose Groups C, D, E, and F was not significantly different from the untreated KO control Group A.

The results showed that lysosomal storage was decreased in somatic tissues upon administration of low doses of IDS-WPRE, but not significantly in the brain.

Overall, the results showed that upon administration of low doses of rAAV comprising hIDS-WPRE in mice, serum and tissue I2S expression and activity was maintained over about three months, and lysosomal storage was decreased in somatic tissues as determined by LAMP.

Example 9

Serum Expression Levels of hI2S Transgene Product in Non-Human Primates (NHPs

This example illustrates an exemplary PK/distribution study in non-human primates administered a hI2S transgene product.

Non-human male primates between about 1.8 to 2 years of age were administered the hI2S product via intravenous infusion. Low dose cohort animals received a low dose of hI2S of $1.25 \times 10^{12}$ vg/kg (n=3) and high dose cohort animals received a higher dose of hI2S of $6.25 \times 10^{12}$ vg/kg (n=6). Control animals received only formulation buffer.

Serum samples were collected at various time-points, starting from pre-dose, prior to administration of hI2S transgene, followed by sampling every 20 days up to 240 days. Three animals each from the low dose cohort and the high dose cohort, respectively, were sacrificed at 3 months.

Figure 15A:
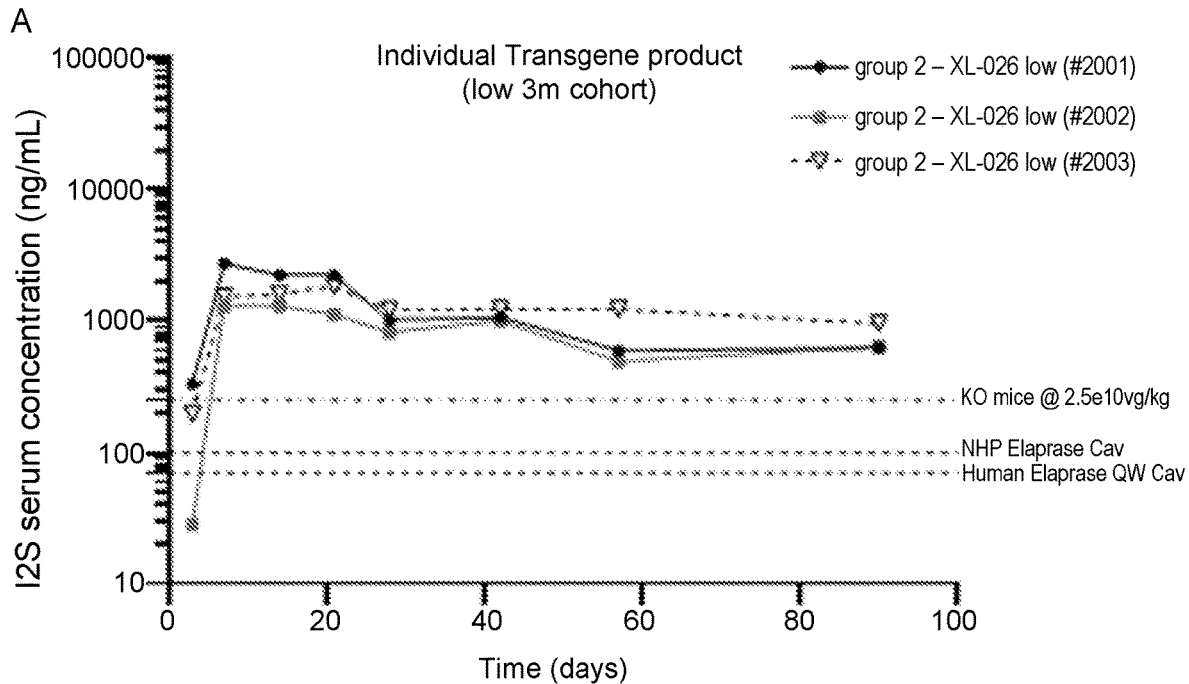
FIG. 15A is a graph that shows I2S serum concentration in non-human primates that received a low dose of I2S.

FIG. 15A demonstrates the hI2S transgene product serum concentration from the low dose cohort in NHP serum post-dose day 1- to 3-month necropsy. Sustained hI2S transgene product concentration was observed at $1.25 \times 12$ vg/kg (low dose).

Figure 15B:
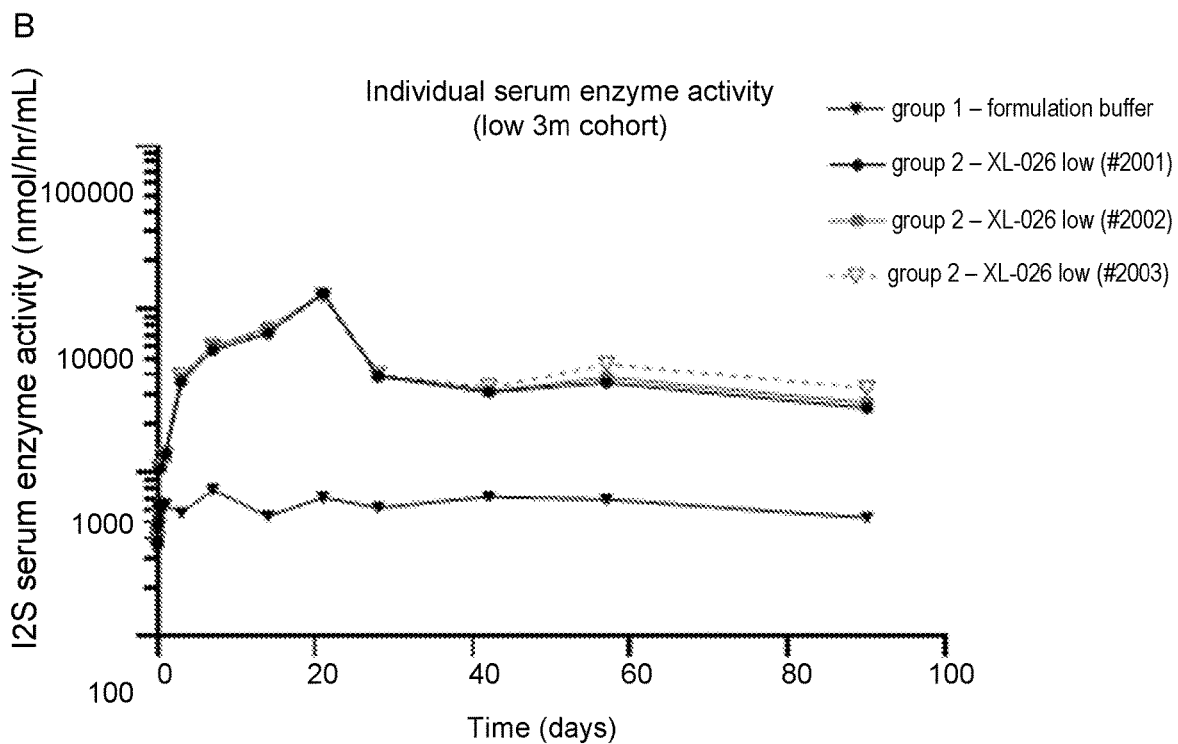
FIG. 15B is a graph that shows I2S serum activity in non-human primates that received a low dose of I2S.

Correspondingly, in FIG. 15B, the hI2S transgene product enzyme activity in serum showed sustained levels up to 3 months. At 3 months, about 5-fold higher levels of I2S enzyme activity was observed relative to the NHP endogenous I2S activity levels measured in control animals that received only formulation buffer.

Figure 15C:
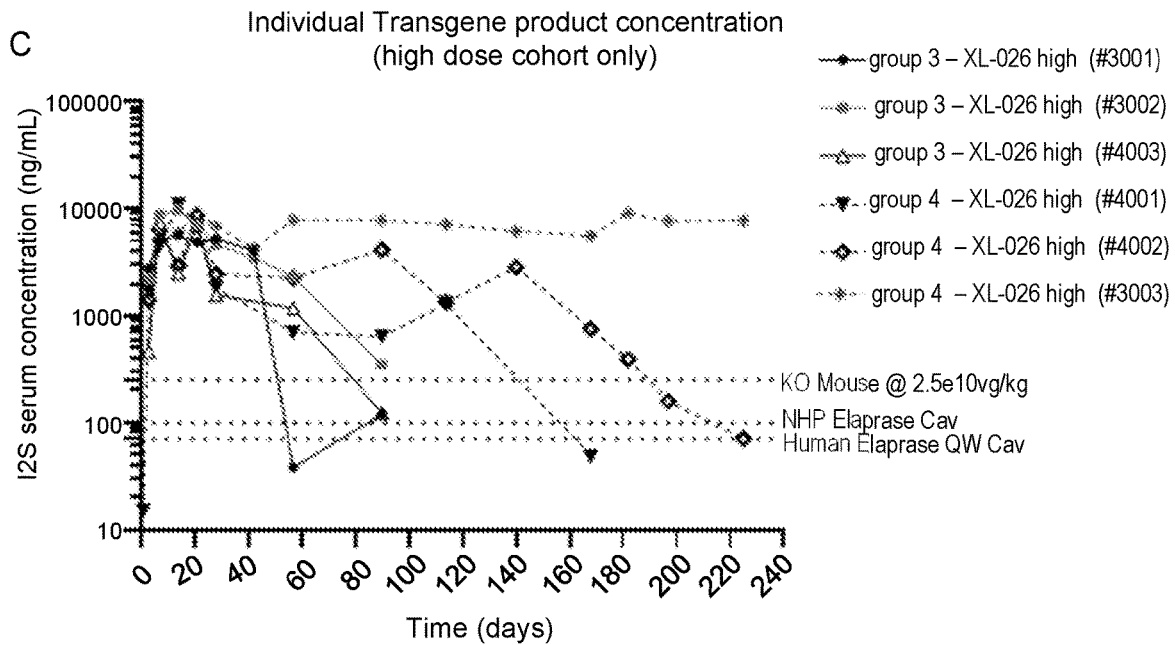
FIG. 15C is a graph that shows I2S serum concentration in non-human primates that received a high dose of I2S.

FIG. 15C demonstrates the hI2S transgene product serum concentrations from high dose cohorts in three NHP post-dose day 1 to about 90 days or 3-months necropsy, and remaining three high-dose animals from post-dose day 1 to about 240 days or 8 months.

Figure 15D:
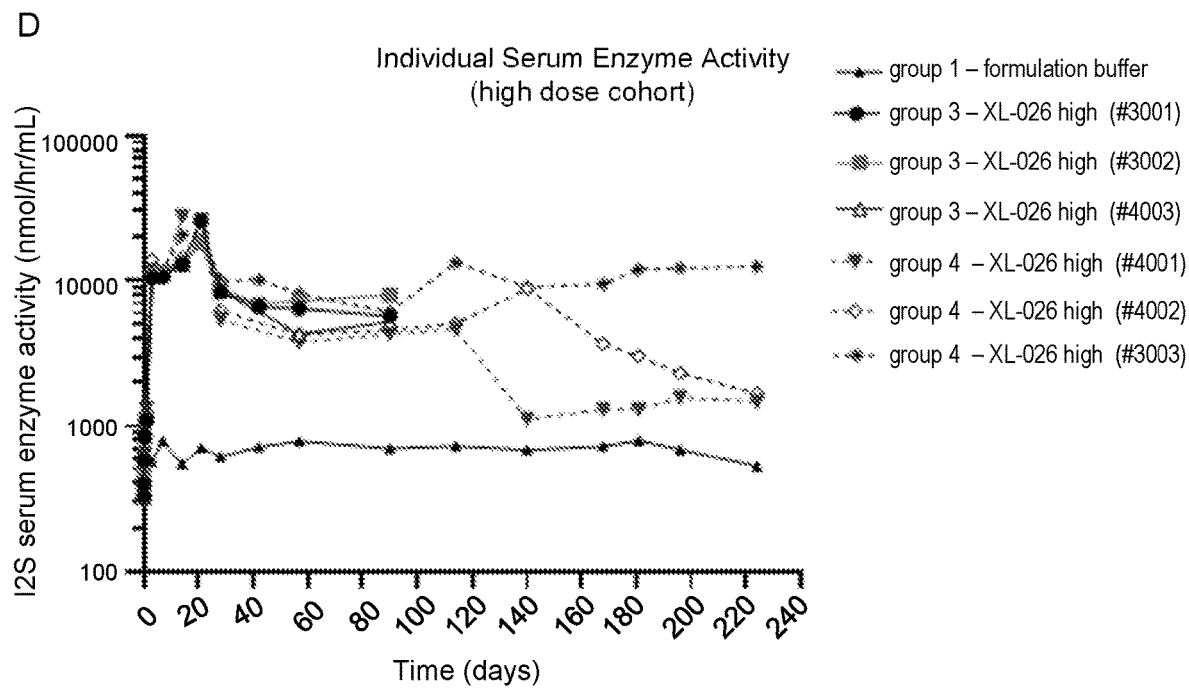
FIG. 15D is a graph that shows I2S serum activity in non-human primates that received a high dose of I2S.

The individual animals showed a variable profile of hI2S transgene product and variability was observed in the initial maximum serum concentration level achieved. A rapid decline in hI2S transgene product serum concentration was observed in the animals that were followed until 3-month necropsy. The corresponding hI2S enzyme activity in serum showed an increase then a decline after day 21 to a plateau level of about 5200-7500 nmol/hr/mL) (FIG. 15D), demonstrating sustained hI2S enzyme activity in serum even though the I2S transgene product concentration was reduced in the three animals that were terminated at 3 months.

The animals where serum hI2S transgene product concentration and serum I2S activity was followed to about 240 days (8 months) showed variability in their hI2S transgene product concentration profile. Two animals showed a decline in I2S transgene product concentration to about 100 ng/mL or below by about 8 months. This was also associated with an observed decline in hI2S enzyme activity to about endogenous levels (formulation buffer) by about 8 months. One of the animals in this study showed sustained hI2S transgene product concentration and enzyme activity out to about 8 months.

Overall, the data demonstrated that even in the absence of immunosuppressants, sustained expression of the hI2S transgene product was achieved in non-human primates.

Example 10

Comparison of Serum Concentrations of hI2S Transgene Product and I2S Enzyme Activity in Low and High Dose Non-Human Primates Relative to Anti-Transgene Product Antibody (a.k.a. Anti-hI2S ADA (Anti-Drug Antibody)) and Anti-AAV8 ADA Titration This example illustrates a comparison between anti-hI2S ADA and anti-AAV8 ADA data from individual non-human primates plotted with hI2S transgene product concentration and enzyme activity.

Figure 16:
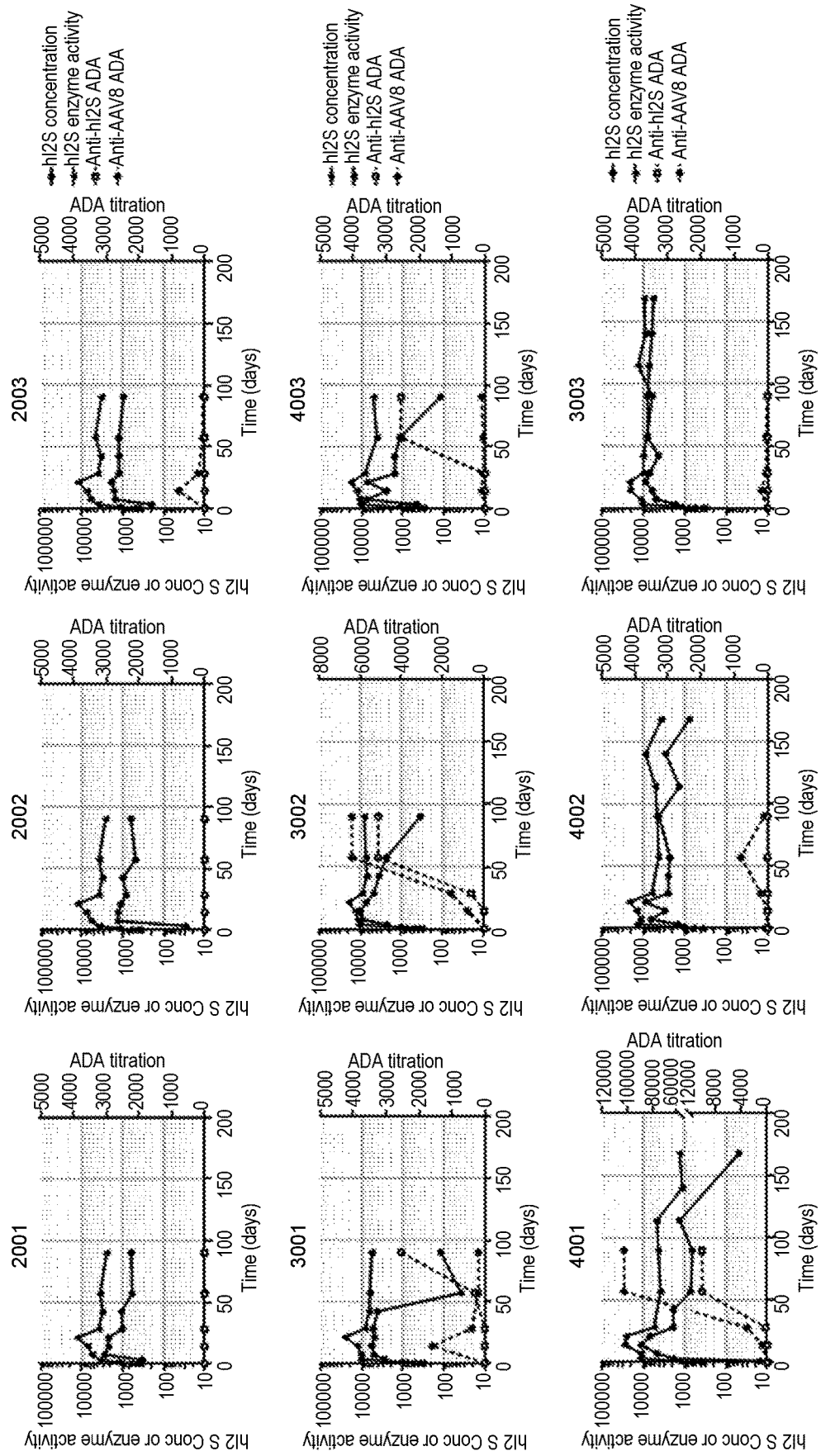
FIG. 16 shows I2S concentration and enzyme activity profiles in individual non-human primates and anti-I2S ADA activity profiles in the same animals.

Anti-hI2S ADA and anti-AAV8 ADA data from individual animals were plotted against hI2S transgene product concentration and enzyme activity (FIG. 16). Only up to 3 months of ADA data were illustrated in these graphs. An initial decline in hI2S level was observed within the first month in the absence of anti-hI2S ADA in some animals (2001, 3002, 4003, 4001 and 4002). The decline in hI2S levels was not dose dependent. The initial decline of hI2S transgene product concentration in NHP serum (within the first month) varied from animal to animal (10%-80%).

The decline in hI2S transgene product in serum after the equilibrium state was correlated with the presence of anti-hI2S ADA in the cohort that received a high dose of hI2S. "Equilibrium state" or "re-established state" refers to "steady state" or plateau levels of I2S enzyme or I2S enzyme activity. The presence of anti-AAV8 ADA in some animals (3002 and 4001) may prevent re-dosing. None of the animals in the low dose cohort showed the presence of anti-hI2S ADA in serum.

The results showed that the decline in serum I2S levels was correlated with the presence of anti-hI2S ADA in non-human primates that received a high dose of rAAV-XL026 comprising hIDS-WPRE.

Example 11

Individual Non-Human Primate Liver hI2S Transgene Product Concentration Profile

This example illustrates the hI2S transgene product concentration profile in the liver of non-human primates.

Figure 17A:
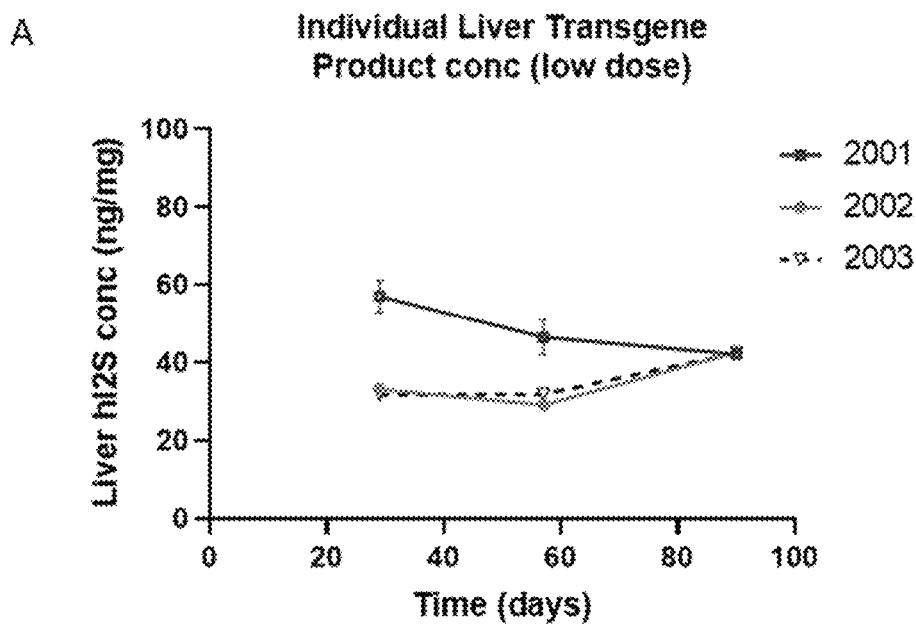
FIG. 17A shows hI2S concentration in the liver of individual non-human primates administered a low dose of hI2S.
Figure 17B:
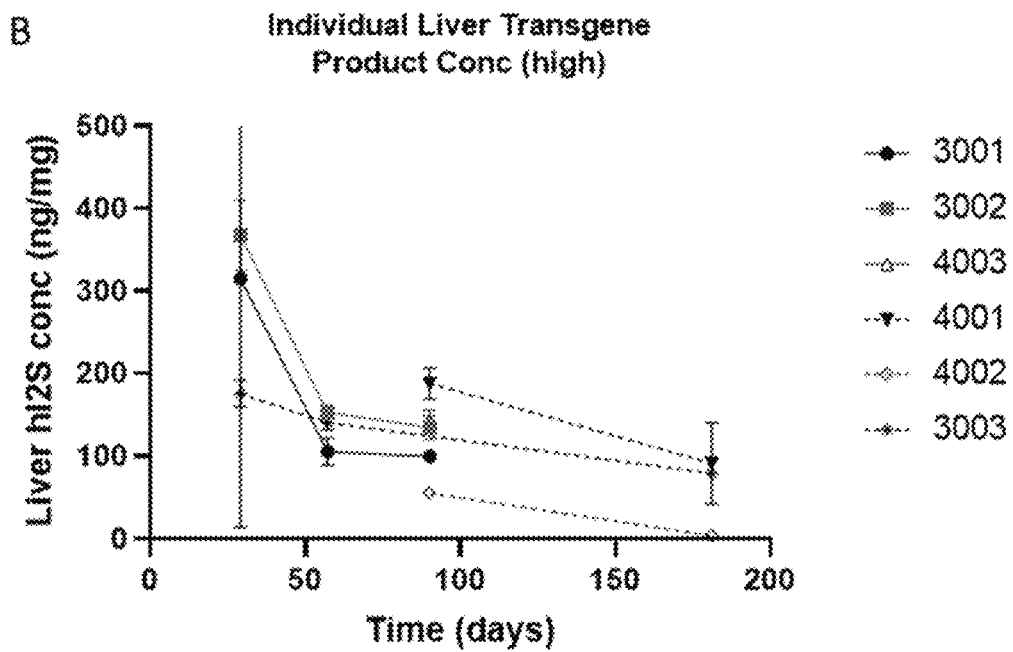
FIG. 17B shows hI2S concentration in the liver of individual non-human primates administered a high dose of hI2S.

Liver biopsies were carried out from both low dose (FIG. 17A) and high dose (FIG. 17B) animals at 1 month and 2 months and terminal liver samples were collected at 3 months. The three animals from high dose cohort that were intended for 12 months necropsy had a biopsy at 3 months and 6 months.

Each biopsy was taken from left and right lobes. The average hI2S transgene product concentration between the left and right lobes in the liver from low dose cohort ranged from an average of 38.2 ng/mL to 42.5 ng/mL between 1 month and 3 months.

The hI2S transgene product concentration in the liver from high dose cohort ranged from 175.1 ng/mL to 367.6 ng/mL at 1 month. One of the animals (animal 3001) showed a large difference between the left (101.8 ng/mL) and right (528.3 ng/mL) lobes.

At 2 months, two animals (animal 3001 and animal 3002) showed a rapid decline of liver hI2S transgene product concentration from 1 month to 2 months. Other animals also showed decline from 2 months to 6 months, including animal 3003, but to a lesser extent.

Overall, these results showed individual concentration profiles of I2S transgene product in non-human primate tissues from 1 to 3 months post-administration of rAAV-XL026.

Example 12

Comparative Concentration Profile of hI2S Transgene Product in Non-Human Primate Tissues This example illustrates a comparative concentration profile of hI2S transgene product in non-human primate tissues.

Tissue necropsy was performed on animals from the low dose cohort and 3 animals from the high dose cohort at 3 months.

Figure 18A:
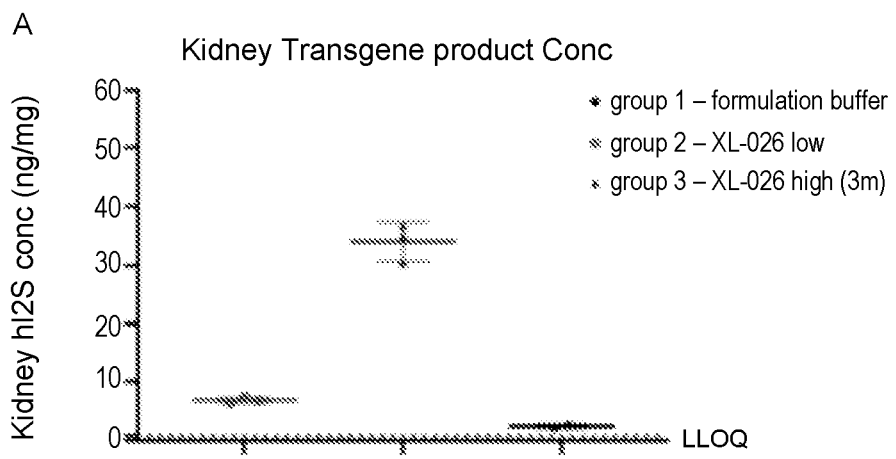
FIG. 18A shows hI2S concentration in the kidney of non-human primates administered high and low doses of I2S.
Figure 18B:
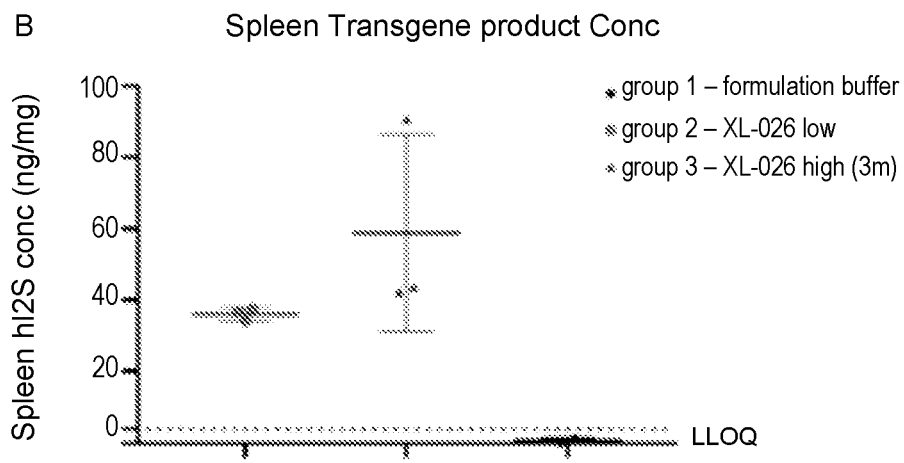
FIG. 18B shows hI2S concentration in the spleen of non-human primates administered high and low doses of I2S.

The hI2S transgene product concentration was measured by ELISA in tissue homogenate from various organs including kidney, spleen, lung, heart and bone marrow. Although the hI2S transgene product concentration in serum from high dose cohort at 3 months showed a significant lower level (<250 ng/mL) in the presence of anti-hI2S ADA when compared to those of low dose cohort (>640 ng/mL), the average hI2S concentration in kidney (FIG. 18A) and spleen (FIG. 18B) showed a higher level in the high dose cohort than that of lower dose.

Figure 18C:
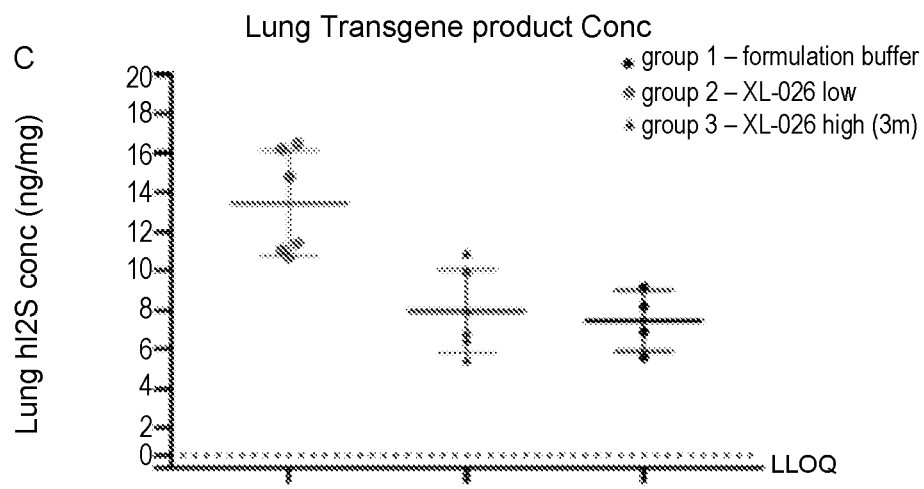
FIG. 18C shows hI2S concentration in the lung of non-human primates administered high and low doses of I2S.
Figure 18D:
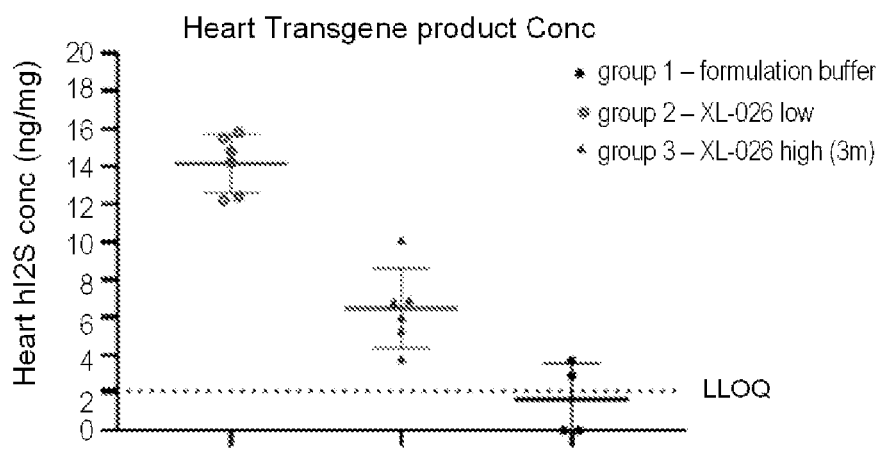
FIG. 18D shows hI2S concentration in the heart of non-human primates administered high and low doses of I2S.
Figure 18E:
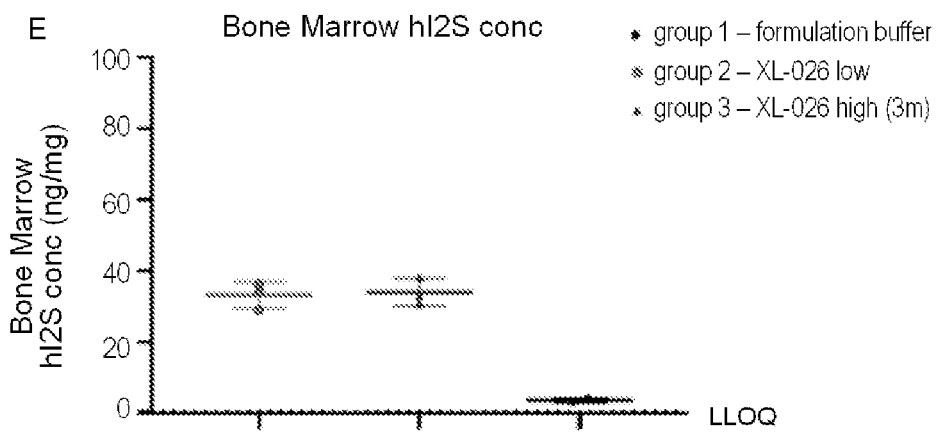
FIG. 18E shows hI2S concentration in the bone marrow of non-human primates administered high and low doses of I2S.

In the presence of anti-hI2S ADA, the 3 animals from the high dose cohort showed lower hI2S transgene product concentration in the lung (FIG. 18C) and heart (FIG. 18D), whereas in the bone marrow (FIG. 18E), hI2S tissue concentration was comparable between animals in the high and low dose cohort. Since the tissues were from healthy NHP, endogenous I2S is detected, for example, in the formulation buffer group in the lung.

The results showed the comparative concentration profile of I2S in different non-human primate tissues post-treatment of rAAV-XL026.

Example 13

Comparative hI2S Tissue Exposure in Non-Human Primates Relative to IDS Knockout Mice This example illustrates the comparative I2S concentration and enzyme activity in various target tissues between non-human primates and IDS KO mice.

The hI2S tissue enzyme activity and corresponding percentage of HS GAG reduction from $2.5 \times 10^{11}$ vg/kg and $2.5 \times 10^{10}$ vg/kg in IDS KO mice are shown in Table 11.

In mice, greater than 95% HS GAG reduction was observed at a dose of about $2.5 \times 10^{10}$ vg/kg for most tissues except for the kidney, where a reduction of about 91% was observed. In the heart and bone marrow, data from the low dose cohort of non-human primates showed higher hI2S tissue concentration and enzyme activity than those of IDS KO mice at $2.5 \times 10^{10}$ vg/kg.

In lung tissue, in IDS KO mice, there was only 30% of WT I2S enzyme activity yet this level showed HS GAG reduction of 97%. In non-human primates, administered a low dose of hI2S, enzyme activity in the lung showed a greater % of WT hI2S enzyme activity at 40%. By administering rAAV-XL026 via IV infusion at $1.25 \times 10^{12}$ vg/kg to NHP, sufficient hI2S transgene production exposure in the lung was achieved that can result in a reduction of HS GAG to ≥95% in a disease model.

TABLE 11

Comparison of hI2S concentration and enzyme activity and GAG reduction in knock-out mice and non-human primates.

| | hI2S concentration in NHP tissues at 3 months necropsy above vehicle control | hI2S concentration (at $2.5 \times 10^{10}$ vg/kg) in KO mouse tissues at 3 months necropsy. | NHP tissue hI2S enzyme activity expressed as a % of WT | KO mouse tissue hI2S enzyme activity (at $2.5 \times 10^{10}$ vg/kg) expressed as % of WT | KO mouse tissue HS GAG reduction (at $2.5 \times 10^{10}$ vg/kg) expressed as % of the KO vehicle | KO mouse hI2S enzyme activity (at $2.5 \times 10^{11}$ vg/kg) expressed as % of WT | KO mouse tissue HS GAG reduction (at $2.5 \times 10^{11}$ vg/kg) expressed as % of the KO vehicle. |
|---|---|---|---|---|---|---|---|
| Lung (low) | 7.1 ng/mg | 2 ng/mg | 40% | 30% | ~97% | 270% | 100% |
| Lung (high) | 0.9 ng/mg | | 20% | | | | |
| Heart (low) | 12.5 ng/mg | 1.4 ng/mg | 232% | 210% | ~97% | 2480% | 100% |
| Heart (high) | 4.8 ng/mg | | 174% | | | | |
| Bone marrow (low) | 29.6 ng/mg | 15.1 ng/mg | 210% | 310% (10% at $2.5 \times 10^9$ vg/kg) | 100% (92% at $2.5 \times 10^9$ vg/kg) | 46,000% | 100% |
| Bone marrow (high) | 30.4 ng/mg | | 170% | | | | |
| Kidney (low) | 4.5 ng/mg | 3 ng/mg | 10% | 90% | ~91% | 1380% | 100% |
| Kidney (high) | 31.6 ng/mg | | 180% | | | | |
| Spleen (low) | 36.2 ng/mg | 17 ng/mg | 100% | 140% | ~95% | 1170% | 100% |
| Spleen (high) | 58.4 ng/mg | | 190% | | | | |

Equivalents and Scope

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

We claim:

1. A recombinant adeno-associated virus (rAAV) vector comprising an AAV8 capsid or an AAV9 capsid, and a nucleotide sequence encoding an iduronate-2-sulfatase (I2S) enzyme,
wherein the nucleotide sequence encoding the IS2 enzyme comprises a sequence having at least 80% identity to SEQ ID NO: 12.

2. The rAAV vector of claim 1, wherein the nucleotide sequence encoding an I2S enzyme comprises a sequence identical to SEQ ID NO: 12.

3. The rAAV vector of claim 1, wherein the vector further comprises a liver-specific promoter and wherein the liver-specific promoter is transthyretin promoter (TTR).

4. The rAAV vector of claim 3, wherein the vector further comprises a 5' and a 3' inverted terminal repeat (ITR), an intron upstream of the I2S sequence, and a cis-acting regulatory module (CRM).

5. A recombinant adeno-associated virus (rAAV) comprising an AAV8 or AAV9 capsid and an rAAV vector, said vector comprising:
  (a) a 5' inverted terminal repeat (ITR);
  (b) a cis-acting regulatory module (CRM);
  (c) a promoter;
  (d) a minute virus of mice (MVM) intron sequence;
  (e) a nucleotide sequence encoding an iduronate-2-sulfatase (I2S) enzyme;
  (f) a woodchuck hepatitis virus posttranscriptional regulatory element (WPRE); and
  (g) a 3' ITR, wherein the nucleotide sequence encoding the IS2 enzyme comprises a sequence having at least 80% identity to SEQ ID NO: 12.

6. A method of treating a subject having Hunter syndrome (MPS II), comprising administering to the subject in need thereof the rAAV of claim 1.

7. A method of treating a subject having Hunter syndrome (MPS II), comprising administering to the subject in need thereof a recombinant adeno-associated virus (rAAV) vector comprising an AAV8 or AAV9 capsid, and a promoter operably linked to a nucleotide sequence that encodes iduronate-2-sulfatase (I2S), wherein administering results in an increase in I2S enzymatic activity in the subject and wherein the nucleotide sequence encoding the IS2 comprises a sequence having at least 80% identity to SEQ ID NO: 12.

8. The method of claim 7, wherein the increase in I2S activity is detected in the serum, liver, kidney or central nervous system of the subject.

9. The method of claim 7, wherein the administering the AAV reduces the level of glycosaminoglycan (GAG) in the serum, liver, kidney, CNS or brain of the subject.

10. The method of claim 7, wherein the AAV is administered intravenously.

11. The method of claim 7, wherein the AAV is administered at dose of about $5\times10^9$ vg.

12. The rAAV vector of claim 1, wherein the nucleotide sequence encoding an I2S enzyme comprises a sequence at least 95% identical to SEQ ID NO: 12.

13. The rAAV vector of claim 1, wherein the nucleotide sequence encoding an I2S enzyme comprises a sequence identical to SEQ ID NO: 11.

14. The rAAV of claim 5, wherein the sequence encoding an I2S enzyme is identical to SEQ ID NO: 12.

15. The rAAV of claim 5, wherein the sequence encoding an I2S enzyme is identical to SEQ ID NO: 11.

16. The method of claim 7, wherein the nucleotide sequence encoding the IS2 comprises a sequence identical to SEQ ID NO: 12.

17. The method of claim 7, wherein the nucleotide sequence encoding the IS2 comprises a sequence identical to SEQ ID NO: 11.

* * * * *

UNITED STATES PATENT AND TRADEMARK OFFICE
CERTIFICATE OF CORRECTION

| | |
|---|---|
| PATENT NO. | : 11,981,912 B2 |
| APPLICATION NO. | : 17/116098 |
| DATED | : May 14, 2024 |
| INVENTOR(S) | : Choi et al. |

It is certified that error appears in the above-identified patent and that said Letters Patent is hereby corrected as shown below:

On the Title Page

Item (73), delete "Pharma ceutical" and insert -- Pharmaceutical --, therefor.

In the Claims

In Column 165, Claim 7, Line 13, delete "subject and wherein" and insert -- subject, and wherein --, therefor.

Signed and Sealed this
Seventeenth Day of September, 2024

Katherine Kelly Vidal
*Director of the United States Patent and Trademark Office*